(12) United States Patent  
Golding et al.

(10) Patent No.: US 8,618,158 B2  
(45) Date of Patent: Dec. 31, 2013

(54) THERAPEUTIC AGENTS

(75) Inventors: Bernard Thomas Golding, Newcastle upon Tyne (GB); Christiane Riedinger, Cambridge (GB); Roger John Griffin, Northumberland (GB); Ian Robert Hardcastle, Hexham (GB); Eric Valeur, Vieux-Ferrette (FR); Anna Frances Watson, Cambridge (GB); Martin Noble, Oxford (GB)

(73) Assignee: Cancer Research Technology Limited, London (GB)

( * ) Notice: Subject to any disclaimer, the term of this patent is extended or adjusted under 35 U.S.C. 154(b) by 115 days.

(21) Appl. No.: 13/001,372

(22) PCT Filed: Jun. 25, 2009

(86) PCT No.: PCT/GB2009/001599  
§ 371 (c)(1),  
(2), (4) Date: May 31, 2011

(87) PCT Pub. No.: WO2009/156735  
PCT Pub. Date: Dec. 30, 2009

(65) Prior Publication Data  
US 2011/0224274 A1 Sep. 15, 2011

(30) Foreign Application Priority Data  
Jun. 25, 2008 (GB) .................. 0811643.6

(51) Int. Cl.  
*A61K 31/4035* (2006.01)  
*C07D 207/46* (2006.01)

(52) U.S. Cl.  
USPC ............ 514/415; 514/416; 548/452; 548/472

(58) Field of Classification Search  
USPC ................................. 548/452, 472  
See application file for complete search history.

(56) References Cited

U.S. PATENT DOCUMENTS

| | | | |
|---|---|---|---|
| 3,466,298 | A | 9/1969 | Sulkowski et al. |
| 3,763,178 | A | 10/1973 | Sulkowski |
| 4,001,271 | A | 1/1977 | Cotrel et al. |
| 4,200,759 | A | 4/1980 | Dickinson |
| 4,244,966 | A | 1/1981 | Lippman et al. |
| 4,331,600 | A | 5/1982 | Golec, Jr. |
| 4,505,921 | A | 3/1985 | Beregi et al. |
| 6,344,468 | B1 | 2/2002 | Schindler |

FOREIGN PATENT DOCUMENTS

| | | | |
|---|---|---|---|
| CH | 374071 | A | 12/1963 |
| CH | 374071 | A1 | 12/1963 |
| DE | 2313227 | A1 | 9/1973 |
| EP | 1199306 | A1 | 4/2002 |
| GB | 1325065 | A1 | 8/1973 |
| GB | 1601701 | A | 11/1981 |
| JP | 2000506163 | A | 5/2000 |
| JP | 2004217591 | A | 8/2004 |
| JP | 2005217591 | A | 8/2005 |
| JP | 2005255660 | A | 9/2005 |
| WO | 0132928 | A2 | 5/2001 |
| WO | WO 03/051359 | A1 | 6/2003 |
| WO | 2006024837 | A1 | 3/2006 |

OTHER PUBLICATIONS

Cancer and Metastasis Reviews (1998), 17(1), 91-106.*  
Science (1999), vol. 286, 531-537.*  
Cancer [online], [retrieved on Jul. 6, 2007]. Retrieved from the internet, URL http://www.nlm.nih.gov/medlineplus/cancer.html>.*  
Cancer [online], [retrieved on Jul. 6, 2007]. Retrieved from the internet, URL; http://en.wikipedia.orglwikilCancer.*  
Straub, et al. Document No. 138:137167, retrieved from CAPLUS; Jan. 30, 2003.*  
Anderson, et al. Document No. 116:128972, retrieved from CAPLIS; Dec. 11, 1991.*  
Toyooka, et al. Document No. 141:38525, retrieved from CAPLUS; Jun. 10, 2004.*  
Yoshikatsu Ito, "Solid-State and Solution Photolyses of Tetracyanobenzene with Benzyl Cyanides or Benzyl Alcohols," Tetrahedron 56 (2006), Elsevier Science Publishers, Amsterdam, NL., pp. 7139-7152.  
Uri Golik, "The Synthesis of Some 2,4-Benzodiazepin-1-ones, Potent C.N.S. Agents (1)," vol. 12, Oct. 1, 1975, Journal of Heterocyclic Chemistry, Provo, US, pp. 908-908.  
M. Vivekananda Bhatt, et al., "Aspects of Tautomerism, Part V.† Solvent, Substituent, and Steric Effects on the Ring-Chain Tautomerism of o-Benzoylbenzamides," Journal of the Chemical Society, Perkin Transactions II, (1973), Letchworth, GB, pp. 1160-1166.

(Continued)

*Primary Examiner* — Shawquia Young  
(74) *Attorney, Agent, or Firm* — Pillsbury Winthrop Shaw Pittman LLP

(57) ABSTRACT

A compound of formula (I) or a compound of formula (II) or pharmaceutically acceptable salts thereof, wherein R1-R7 and X are as defined in the description, and the use of these compounds in therapy, in particular in treating cancer or as an inhibitor of the interaction of the MDM2 protein with p53.

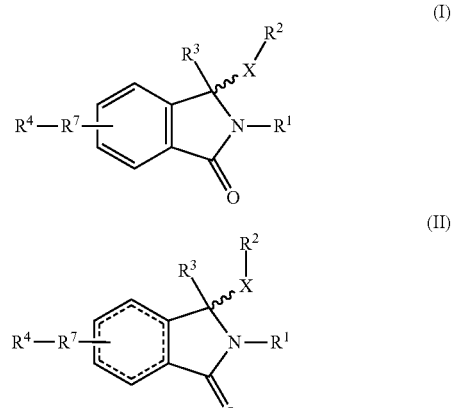

19 Claims, 9 Drawing Sheets

(56) References Cited

OTHER PUBLICATIONS

John G. Topliss, et al., Antihypertensive Agents. III. 3-Hydroxy-3-phenylphthalimidines, Journal of Medicinal Chemistry, vol. 7, (1964), Pennsylvania, US, pp. 453-456.

E. H. Charlesworth, et al., Fluoranthene Studies, III. A Synthesis of 3-bromo-6-nitrofluorenone; Canadian Journal of Chemistry, vol. 46, 1(968), pp. 463-465.

R. Valters, et al., "Ring-chain transformations involving the carbonyl group. XI. Acid chlorides and amides of 2-benzoyl-3-, 4-,5-, and 6-nitrobenzoic acids," Rizh. Politekh, Inst., Riga, USSR; Latvijas PSR Zinatnu Akademijas Vesitis, Kimijas Serija (1972), (1), 61-5.

International Search Report for PCT/GB2009/001599m mailed Jun. 10, 2010.

H.D. Bartfeld, 3-0xo-Isoindole, Tetrahedron Letters No. 10 757-760, 1970.

I. Lencbergs, 3-Hydroxy-3-(a-aminobenzyl)-2-substituted 1-isoindolinones, Document 95:150329 retrieved from CAPLUS on May 21, 2010.

J. Rebek, et al., Olefin Expoxidation With a-Substituted Hydroperoxides, Document 93:220149 retrieved from CAPLUS on May 21, 2010.

Jan Epsztajn et al., Application of Organolithium and Related Reagents in Synthesis, Tetrahedron 56 (2000) 4837-4844.

Jonathan Griffiths, et al., Model Studies for Damage to Nucleic Acids Mediated by Thiyl RadicalsTetrahedron vol. 48, No. 26, pp. 5543-5556, 1992.

Joon Seok Park, Noble 2-[3-(Cyclope.ntyloxy)-44 ethoxyphenyl]-1-indolinone Derivatives. Part 1 . . . , Arch Pharm Res vol. 24, No. 5, 367-370, 2001.

K. Kormendy, Uber Reaktionen in Polyaminsynthesen, Mit, Phthaliminoalkylhaloiden, 1. Acta Ch mica, Apr. 1958.

Makoto Inaba, Reversal of Resistance to Vincristine in P388 Leukemia by Various Polycyollic Clinical Drugs, with a Special Emphasis on Quinacrine, cancerres.aacrjournals.org, 1998.

Martin Groisy-Delcey, Diphenyl Quinolines and Isoquinolines: Synthesis and Primary Biological Evaluation, Bioorganic & Medicinal Chemistry 8 (2000) 2629-2641.

Martin S. Kitching, Synthesis of 3-Alkoxy- and 3-Alkylarnino-2-alkyl-3-arylisoindolinones, Synlett, 997-999, 1999.

Mun Ir Ahmed, et al, Preparation of Some Isoindolo [2,1-f] phenanthridine Derivatives, J.Amer. Chem. Soc., 1936, 58, 1325.

Nikitin, et al., Synthesis of 5-alkyl- and 5-aryl-1,5-dihydro-2H-pyrrol-2-ones via coupling of 5-chloro-1,5-dihydro-2H-pyrrol-2-ones with organometallic compounds, Can. J. Chem. 78: 1285-1288 (2000).

Price Truit, 3-Phenylphthalirnidines, New Cornpounds,J. Med Chem Sep. 1965.

Rainer Liebl, Notiz zur Synthese von 3-[Alkyl(aryl)thiio]isoindolinonen aus 2-Forrnylbenzoesaure-methylester, Liebigs Ann. Chem. 1093-1094-1985.

V.A. Usov, et al., Formation of Isoquinolones and Isoindolones in the Oxidation of 2-Aryl-1-phenylamino-3-phenyliminoindenes, Kimiya Geterotsiklichestkiky Soedinelii, vol. 5, No. 4, pp. 640-644, 1969.

Ahmed, Munir, et al., "Preparation of Some Isoindolo[2,1-f]phenanthridine Derivatives," J. Chem. Soc., Perkin Trans. 1, pp. 601-605, 1977.

Bartfeld, H.D., et al., "3-Oxo-Isoindole," Tetrahedron Letters, 10, pp. 757-760, 1970.

Beanlands, D.S., et al., "Therapeutic trial of a new oral diuretic," Document No. 55:60933, retrieved from CAPLUS on Jan. 29, 2010.

Chàne, Patrick, et al., "A Small Synthetic Peptide, which Inhibits the p53-hdm2 Interaction, Stimulates the p53 Pathway in Tumour Cell Lines," JMB, J. Mol. Biol., 299, pp. 245-253, 2000.

Donehower, Lawrence A., et al., "Mice deficient for p53 are developmentally normal but susceptible to spontaneous tumours," Nature, 356, pp. 215-221, Mar. 19, 1992.

Epsztajn, Jan, "Application of Organolithium and Related Reagents in Synthesis. Part 23: Synthetic Strategies Based on ortho-Aromatic Metallation. Synthesis of 4b-Arylisoindolo[2,1-a]quinolone derivatives," Tetrahedron, 56, pp. 4837-4844, 2000.

Ghosh, Mithua, et al., "Overexpression of Mdm2 and MdmX Fusion Proteins Alters p53 Mediated Transactivation, Ubiquitination, and Degradation," American Chemical Society, Biochemistry, 42, pp. 2291-2299, 2003.

Griffiths, Jonathan, et al., "Model Studies for Damage to Nucleic Acids Mediated by Thiyl Radicals," Tetrahedron, 48 (26), pp. 5543-5556, 1992.

Inaba, Makoto, et al., "Reversal of Resistance to Vincristine in P388 Leukemia by Various Polycyclic Clinical Drugs, with a Special Emphasis on Quinacrine", Cancer Research, 48, pp. 2064-2067, Apr. 15, 1988.

Lane, D.P., "p53, guardian of the genome," Nature, 358, pp. 15-16, Jul. 2, 1992.

Levine, Arnold J., "p53, the Cellular Gatekeeper for Growth and Division," Cell, 88, pp. 323-331, Feb. 7, 1997.

Liebl, Rainer, et al., "Notiz zur Synthese von 3-[Alkyl(aryl)thio]isoindolinonen aus 2-Formylbenzoisäure-methylester," Liebigs Ann. Chem, pp. 1093-1094, 1985.

Oliner, J.D., et al., "Amplification of a gene encoding a p53-associated protein in human sarcomas," Nature, 358, pp. 80-83, Jul. 2, 1992.

Park, Joon Seok, et al., "Noble 2[3-(Cyclopentyloxy)-4-Methoxyphenyl]-1-Isoindolinone Derivatives. Part 1: Synthesis and SAR Studies for the Inhibition of TNF-α Production," Arch Pharm Res, 24 (5), pp. 367-370, 2001.

Schon, Oliver, et al., "Molecular Mechanism of the Interaction between MDM2 and p53," JMB, J. Mol. Biol., 323, pp. 491-501, 2002.

Toledo, Franck, et al., "Regulating the p53 pathway: in vitro hypotheses, in vivo veritas," Nature Reviews Cancer, 6, pp. 909-923, Dec. 2006.

Vassilev, Lyubomir T., "In Vivo Activation of the p53 Pathway by Small-Molecule Antagonists of MDM2," Science, 303, pp. 844-848, Feb. 6, 2004.

Charlesworth, E. H., et al., "Fluoranthene studies. III. A synthesis of 3-bromo-6-nitrofluorenone," Canadian Journal of Chemistry, 46(3), pp. 463-465, 1968.

Croisy-Delcey, Martine, et al., "Diphenyl Quinolines and Isoquinolines: Synthesis and Primary Biological Evaluation," Bioorganic & Medicinal Chemistry, 8(11), pp. 2629-2641, 2000.

Golik, Uri, "The synthesis of some 2,4-benzodiazepin-1-ones, potent C.N.S. agents," Journal of Heterocyclic Chemistry, 12(5), pp. 903-908, 1975.

Ito, Yoshikatsu, et al., "Solid-State and Solution Photolyses of Tetracyanobenzene with Benzyl Cyanides or Benzyl Alcohols," Tetrahedron, 56 (37), pp. 7139-7152, 2000.

Kitching, Martin S., et al., "Synthesis of 3-Alkoxy- and 3-Alkylamino-2-alkyl-3-arylisoindolinones," Synlett, S1, pp. 997-999, 1999.

Körmendy, K, "Über Reaktionen in Polyaminsynthesen Mit Phthaliminoalkylhaloiden, I," Acta Chimica Academiae Scientiarum hungaricae, 17, pp. 255-261, 1958.

Lencbergs, I., et al., "3-Hydroxy-3-(α-aminobenzyl)-2-substituted 1-isoindolinones," Document 95:150329 retrieved from CAPLUS on May 21, 2010.

Liebl, Rainer, et al., "Notiz zur Synthese von 3-[Alkyl(aryl)thio]isoindolinonen aus 2-Formylbenzoesäure-methylester," Liebigs Annalen der Chemie, 5, pp. 1093-1094, 1985.

Truit, Price, et al., "3-Phenylphthalimidines1," J. Med Chem, 8(5), pp. 731-732, 1965.

* cited by examiner

HCT+/+    13.1 ± 3.1 µM

HCT-/-    33.9 ± 4.1 µM

HCT+/+    15.1 ± 0.3 µM

HCT-/-    19.8 ± 1.0 µM

THERAPEUTIC AGENTS

REFERENCE TO RELATED APPLICATION

This Application is a 371 of PCT/GB2009/001599, filed Jun. 25, 2009 and claims the priority of GB 0811643.6, filed Jun. 25, 2008.

The entire contents of each recited priority document is hereby specifically incorporated, in each of their respective entireties, for all purposes.

The invention relates to a series of isoindolin-1-one derivatives which find particular utility as pharmaceuticals, in particular in the treatment of cancer.

Under conditions of stress such as hypoxia and DNA damage it is known that the cellular level of the protein p53 increases. P53 is known to initiate transcription of a number of genes which govern progression through the cell cycle, the initiation of DNA repair and programmed cell death[1,2]. Thus, p53 is a tumour suppressor.

The activity of p53 is tightly regulated by the MDM2 protein, the transcription of which is itself regulated by p53. p53 is inactivated when it becomes bound to the p53 transactivation domain of the MDM2 protein. Once inactivated the functions of p53 are repressed and the p53-MDM2 complex becomes a target for ubiquitinylation.

In normal cells the balance between active p53 and inactive MDM2-bound p53 is maintained in an autoregulatory negative feed back loop[3,4]. That is to say that p53 can activate MDM2 expression, which in turn leads to the repression of p53.

It has been found that inactivation of p53 by mutation is common in around half of all tumours. Furthermore, in around 7% of tumours, over expression of MDM2 results in the loss of functional p53, thereby allowing malignant transformation and uncontrolled tumour growth[5].

X-ray crystal studies of the MDM2-p53 complex have been conducted and have revealed a hydrophobic pocket on the surface of MDM2 into which the side chains of Phe 19, Trp 23 and Leu 26 on p53 bind[6]. Therefore, inhibition of the MDM2-p53 binding interaction is an attractive target for researchers developing treatments for cancer as a means of restoring normal p53 activity in cells overexpressing MDM2 and thereby exerting an anti-tumour effect.

A number of inhibitors of the MDM2-p53 interaction have been discovered including peptide inhibitors, the natural product chlorofusin, and small molecules such as the imidazolines described in WO 03/051359[8-11].

The invention describes a novel series of compounds which inhibit the MDM2-p53 interaction and which have exciting in vitro activity.

According to a first aspect of the invention there is provided a compound of formula I:

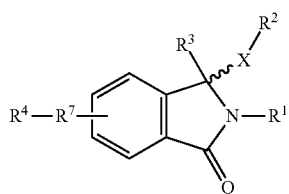

or a compound of formula II:

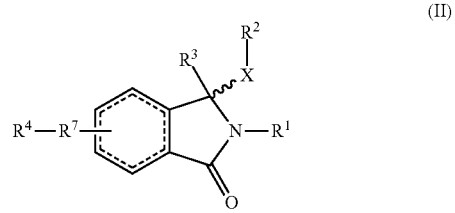

or a pharmaceutically acceptable salt thereof, wherein in both formulae I and II:

X is selected from O, N or S;

$R^1$ is selected from hydrogen, substituted or unsubstituted alkyl, substituted or unsubstituted hydroxyalkyl, substituted or unsubstituted alkylamine, substituted or unsubstituted aryl, substituted or unsubstituted heteroaryl, substituted or unsubstituted aralkyl, and substituted or unsubstituted heteroaralkyl;

$R^2$ is selected from hydrogen, substituted or unsubstituted alkenyl or alkynyl, substituted or unsubstituted branched hydroxyalkyl, substituted or unsubstituted cycloalkyl having 6 ring carbon atoms or greater, substituted or unsubstituted cycloalkenyl, hydroxyalkylaralkyl, hydroxyalkylheteroaralkyl, and a carboxylic acid-containing group;

$R^3$ is selected from hydrogen, substituted or unsubstituted alkyl, substituted or unsubstituted hydroxyalkyl, substituted or unsubstituted alkylamine, substituted or unsubstituted alkoxy, substituted or unsubstituted aryl, substituted or unsubstituted heteroaryl, substituted or unsubstituted aralkyl, and substituted or unsubstituted heteroaralkyl; and $R^4$-$R^7$ represents groups $R^4$, $R^5$, $R^6$ and $R^7$ which are independently selected from hydrogen, halo, hydroxy, substituted or unsubstituted alkyl, substituted or unsubstituted hydroxyalkyl, substituted or unsubstituted alkenyl, substituted or unsubstituted alkynyl, substituted or unsubstituted heteroaryl, substituted or unsubstituted heteroaralkyl, substituted or unsubstituted alkylamine, substituted or unsubstituted alkoxy, trifluoromethyl, amino, nitro, carboxyl, carbonyl, methylsulfone, trifluoromethylsulfone, cyano and substituted or unsubstituted sulfonamide;

wherein, where $R^2$ is substituted or unsubstituted branched hydroxyalkyl, X is O or S;

and wherein, where $R^2$ is hydrogen, at least one of $R^4$-$R^7$ is not hydrogen and $R^3$ is not a benzimidazole derivative;

and wherein, in the formula II, the 6-membered ring may have 0, 1, or 2 C=C double bonds.

According to a second aspect of the invention there is provided a compound of formula I or formula II, or a pharmaceutically acceptable salt thereof, wherein X is selected from O, N or S;

$R^1$ is selected from substituted aryl, substituted heteroaryl, substituted aralkyl, and substituted heteroaralkyl;

$R^2$ is selected from halo, acetyl, substituted or unsubstituted acyclic alkyl, substituted or unsubstituted hydroxyalkyl, substituted or unsubstituted alkylamine, substituted or unsubstituted alkoxyalkyl, substituted or unsubstituted aryl, substituted or unsubstituted heteroaryl, substituted or unsubstituted aralkyl, and substituted or unsubstituted heteroalkyl;

$R^3$ is selected from hydrogen, hydroxy, substituted or unsubstituted alkyl, substituted or unsubstituted hydroxyalkyl, substituted or unsubstituted alkylamine, substituted or unsubstituted alkoxy, substituted or unsubstituted aryl or heteroaryl, and substituted or unsubstituted aralkyl or heteroalkyl; and $R^4$-$R^7$ represents groups $R^4$, $R^5$, $R^6$ and $R^7$ which are independently selected from hydrogen, halo, hydroxy, substituted or unsubstituted alkyl, substituted or unsubstituted hydroxyalkyl, substituted or unsubstituted alkenyl, substituted or unsubstituted alkynyl, substituted or unsubstituted heteroaryl, substituted or unsubstituted heteroaralkyl, substituted or unsubstituted alkylamine, substituted or unsubstituted alkoxy, trifluoromethyl, amino, nitro, carboxyl, carbonyl, methylsulfone, trifluoromethylsulfone, cyano and substituted or unsubstituted sulfonamide;

wherein when $R^2$ is a straight chain hydroxyalkyl, $R^1$ is not selected from 4-nitrobenzyl or 4-chlorobenzyl;

and wherein, where $R^2$ is hydrogen, at least one of $R^4$-$R^7$ is not hydrogen and $R^3$ is not a benzimidazole derivative or a benzimidazoline derivative;

and wherein when $R^3$ is a phenyl group, $R^1$ cannot be 4-methoxybenzyl or 4-hydroxybenzyl group;

and wherein, in the formula II, the 6-membered ring may have 0, 1, or 2 C=C double bonds.

In the compounds of formula II, the 6-membered aromatic ring may be completely saturated, or it may have one carbon-carbon double bond, or alternatively it may have two carbon-carbon double bonds. All of these variations are individually envisaged within the scope of the invention.

According to a third aspect of the invention there is provided a compound as defined in the first or second aspects for use in therapy. Further, in a fourth aspect of the invention there is provided a compound as defined in the first or second aspects for use in treating cancer.

In a fifth aspect of the invention there is provided a compound as defined in the first or second aspects, wherein said compound inhibits the interaction of MDM2 protein with p53.

In an sixth aspect of the invention there is provided a compound as defined in the first or second aspects, for use as an active pharmaceutical substance for the treatment of cancer.

In an seventh aspect of the invention a compound of the first or second aspects may be used in the manufacture of a medicament; and in an eighth aspect a compound of the first or second aspects may be used in the manufacture of a medicament for the treatment of cancer.

Also disclosed as a ninth aspect of the invention is a pharmaceutical composition comprising an effective amount of at least one compound as defined in the first or second aspects of the invention and a pharmaceutically acceptable carrier.

In a tenth aspect of the invention there is provided a method of treating a mammal comprising the steps of administering a medicament comprising at least one compound as defined in the first or second aspects of the invention.

In an eleventh aspect of the invention there is provided a kit comprising at least one compound as defined in the first or second aspects of the invention; and instructions for use. The kit may additionally comprise a second compound as defined in the first or second aspects of the invention or an alternative cancer treatment compound known in the art.

Advantageously, the compounds of the present invention have been shown to be good inhibitors of the formation of the MDM2-p53 complex.

The term "halo" is used herein to denote a halogen atom which is typically selected from fluorine, chlorine, bromine or iodine.

The term "alkyl" is used herein to denote, in particular, a lower alkyl group, i.e. a cyclic, branched (including ring structures formed via the linking of two branches at the same carbon atom) or straight chain hydrocarbon having one to eight carbon atoms, for example propyl. Cyclic alkyls, or cycloalkyls are defined herein as non-aromatic saturated hydrocarbons having at least one carbon-atom ring (typically having from 6 to 10 ring carbon atoms), for example cyclohexyl or cyclooctyl.

The term "alkenyl" is used herein to denote an alkyl group including one or more carbon-carbon double bonds, for example butenyl or cyclopentenyl.

The term "alkynyl" is used herein to denote an alkyl group including one or more carbon-carbon triple bonds, for example butynyl.

The term "aryl" is used herein to denote a carbocyclic group or structure having at least one aromatic ring. The said ring may form part of a multiple condensed ring structure, for example phenyl, naphthalene or anthracene.

The term "aralkyl" is used herein to denote an alkyl chain, as hereinbefore defined, in which there is an aryl group attached thereto, as hereinbefore defined, for example benzyl.

The term "heteroaryl" is used herein the denote an aryl group, as hereinbefore defined in which said group comprises at least one hetero atom, selected from, for example N, O or S, in said at least one aromatic ring. Examples of heteroaryl groups which may be used in accordance with the invention include, but are not limited to, pyridine, pyrrole, furan, thiophene and imidazole.

The term "heteroaralkyl" is used herein to denote an aralkyl substituent, as hereinbefore defined, in which said at least one aromatic ring comprises at least one heteroatom selected from, for example N, O or S. Examples of heteroaralkyl groups which may be used in accordance with the invention include, but are not limited to, methylpyridine and methylfuran.

The term "substituted alkyl" is used herein to denote an alkyl substituent, as hereinbefore defined, which is substituted with one or more functional groups.

The term "substituted alkenyl" is used herein to denote an alkenyl substituent, as herein before defined, which is substituted with one or more functional groups.

The term "substituted alkynyl" is used herein to denote an alkynyl substituent, as hereinbefore defined, which is substituted with one or more functional groups.

The term "substituted aryl" is used herein to denote an aryl substituent, as hereinbefore defined, which is substituted with one or more functional groups. Examples of substituted aryl groups which may be used in accordance with the invention include, but are not limited to, halophenyl, methylphenyl, nitrophenyl or cyanophenyl.

The term "substituted heteroaryl" is used herein to denote a heteroaryl substituent, as hereinbefore defined, which is substituted with one or more functional groups.

The term "substituted aralkyl" is used herein to denote an aralkyl substituent, as hereinbefore defined, which is substituted with one or more functional groups. Examples of substituted aralkyl groups which may be used in accordance with the invention include, but are not limited to, halobenzyl, benzonitrile, acetylbenzyl, benzoylbenzyl, nitrobenzyl, cyanobenzyl, methoxybenzyl, carboxamidobenzyl, or methylbenzyl.

The term "substituted heteroaralkyl" is used herein to denote a heteroaralkyl substituent, as hereinbefore defined, which is substituted with one or more functional groups.

The term "alkoxy" is used herein to denote an alkyl group, as hereinbefore defined, which is linked to a second chemical structure, which may be any of the foregoing, by way of an oxygen atom. The carbon chain of the alkyl group may be substituted with one or more functional groups to provide a "substituted alkoxy". Examples of alkoxy groups which may be used in accordance with the invention include, but are not limited to, ethoxy, methoxy and propoxy.

The term "alkylamine" is used herein to denote an alkyl group, as hereinbefore defined, comprising at least one amine function. The carbon chain of the alkyl group may be substituted with one or more functional groups. The amine function may be primary, secondary or tertiary. Examples of alkylamine groups which may be used in accordance with the invention include, but are not limited to, ethylamine and diethylamine. The amine function may form part of a cyclic or heteroaromatic structure or another functionality, for example amide.

As referred to herein suitable functional groups for substitution as described above include, but are not limited to, any of the following which may be used alone or in combination: halo, hydroxyl, hydroxyalkyl, acyl, acetamide, carboxyl, cyano, carboxamide (carbamoyl), sulfonamide, sulfone, sulfoxide, amino, alkoxy or silico ligand.

Compounds of interest include those of formula I or formula II as defined in the first aspect of the invention wherein $R^1$ is selected from substituted or unsubstituted aryl, and substituted or unsubstituted aralkyl; $R^2$ is selected from hydroxyalkenyl, hydroxyalkynyl, branched 5-carbon hydroxyalkyl, hydroxycycloalkyl, hydroxycycloalkenyl, hydroxymethylcycloalkyl, hydroxymethylcycloalkylmethylene, and hydroxylalkylbenzyl; and $R^3$ is selected from substituted or unsubstituted aryl, and substituted or unsubstituted aralkyl.

Where $R^1$ is selected from substituted or unsubstituted aryl, and substituted or unsubstituted aralkyl it is typically a substituted aralkyl, particularly a substituted benzyl. The substituted benzyl may be, for instance, benzonitrile, chlorobenzyl, bromobenzyl, iodobenzyl, methylbenzyl, acetylbenzyl, benzoylbenzyl, cyanobenzyl, methoxybenzyl, carboxamidobenzyl, or nitrobenzyl. Typically, the substituted benzyl is nitrobenzyl, however isosteres of this functional group may also be advantageously used such as benzoyl, benzylcarboxylate, benzylcarboxylate alkyl ester, benzylsulfoxide or benzylsulfone. Other substituted benzyl groups may also be used, such as bromobenzyl, iodobenzyl, azobenzyl, aminobenzyl, or thioetherbenzyls.

The substituted benzyl may be substituted with one or more functional groups at any of positions 2- to 6-, however it is typical that a single substituent is present at the 3-, 4- or 5-position, typically the 4-position. Alternatively, $R^1$ may be a propyl group or unsubstituted benzyl.

Where $R^1$ is selected from substituted or unsubstituted heteroaryl, nitrogen is typically the heteroatom in the ring, and the heteroaryl is typically an unsubstituted pyridyl. Alternatively, the heteroaryl could be an N-pyridine oxide. In both embodiments, the nitrogen atom may be in the 2-, 3-, or 4-position.

In a further embodiment of $R^1$, there may be a further alkylene group between the benzyl moiety and the nitrogen atom of the isoindolinone. Alternatively, the alkyl carbon atom of the benzyl may be further substituted with an alkyl group, such as a methyl group.

Typically, when $R^2$ is an alkenyl substituent, it will be selected from hydroxybutenyl, hydroxycyclohexenyl or hydroxycyclopentenyl, most often 4-hydroxybut-2-enyl, 4-hydroxycyclohex-2-enyl or 4-hydroxycyclopent-2-enyl. However, when $R^2$ is a hydroxyalkynyl, it is typically a hydroxybutynyl, typically 4-hydroxybut-2-ynyl.

When $R^2$ is a branched 5-carbon hydroxyalkyl, it is typically a branched propyl chain such as hydroxy-2,2-dimethylpropyl or hydroxy-2,2-cyclopropylpropyl. The hydroxyl group will typically be a terminal hydroxy as would be found in 3-hydroxy-2,2-dimethylpropyl or 1-hydroxy-2,2-cyclopropylpropyl.

In embodiments where $R^2$ is a substituted or unsubstituted cycloalkyl having 6 ring carbon atoms or greater it will typically be selected from hydroxycyclooctyl, hydroxymethylcyclohexylmethylene, and hydroxycyclohexyl. Typically the selection will be from 5-hydroxycyclooctyl, 2-hydroxymethylcyclohexylmethylene, 4-hydroxycyclohexyl, and 4-hydroxymethylcyclohexylmethylene.

In alternative embodiments $R^2$ may be a hydroxyalkylbenzyl, it is typical in these embodiments that $R^2$ is a hydroxymethylbenzyl such as 4-hydroxymethylbenzyl or 3-hydroxymethylbenzyl. Alternatively, $R^2$ may comprise a linear alkoxy or amino group, such as an alkylamine where alkyl has the same meaning as given hereinabove. Typical amines include n-propylamine.

According to a further embodiment of the invention, when $R^2$ is a carboxylic acid-containing group, it may be a succinic acid-containing group, such as a succinic acid methyl cyclopropylmethyl group.

According to a further embodiment of the invention, $R^2$ may be a 2-hydroxymethyl allyl group.

According to a further embodiment of the invention, $R^2$ may be hydrogen where at least one of $R^4$-$R^7$ is not hydrogen and $R^3$ is not a benzimidazole derivative.

Typically, $R^3$ be selected from a singly substituted phenyl, typically a halophenyl, often chlorophenyl or bromophenyl, most often 4-chlorophenyl, although the substituent (regardless of identity) may be at any of the 2- to 6-positions.

Additional compounds of interest include those of formula I or formula II as defined in the second aspect of the invention wherein $R^1$ is substituted aralkyl, $R^2$ is acyclic hydroxyalkyl, and $R^3$ is substituted aryl. In these embodiments $R^1$, may be any of the substituents described above with regard to the first aspect of the invention, however it is typical that $R^1$ is a substituted 1-ethylphenyl or a substituted benzyl. Although there may be more than one substituent which may be substituted at any of the 2- to 6-positions on the encompassed phenyl group, it is typical that only a single substituent be present, often a halo group, typically present at the 4-position. Often the halophenyl will be a chlorophenyl and it is currently typical that when $R^1$ is a substituted 1-ethylphenyl, $R^1$ is 1-(4-chlorophenyl)-ethyl. Either the R- or the S-enantiomer of this substituted 1-ethylphenyl substituent may be used, however the S-enantiomer is typical.

When $R^1$ is a substituted benzyl, it is typically nitrobenzyl, more typically 4-nitrobenzyl, 4-cyanobenzyl, 4-chlorobenzyl, 4-bromobenzyl, or 4-iodobenzyl. Most typically, $R^1$ is 4-nitrobenzyl.

Where $R^2$ is acyclic hydroxyalkyl it is typical that the alkyl is an n-alkyl chain. Typically, the chain length is 2 to 6 carbons, typically 4 carbons. The most typical acyclic hydroxyalkyl is 4-hydroxy-n-butyl or hydroxypropyl.

As with the first aspect of the invention it is typical that $R^3$ is selected from a singly substituted phenyl, typically a halophenyl, often chlorophenyl or bromophenyl, most often 4-chlorophenyl, although the substituent (regardless of identity) may be at any of the 2- to 6-positions.

In typical embodiments of the compounds of the first and second aspects of the invention, $R^4$, $R^5$, $R^6$ and $R^7$ are each hydrogen atoms and X is independently O. However, in some compounds, one or more of $R^4$ to $R^7$ is H with two of the remaining R groups linked so as to form a 5- to 7-membered ring structure. The ring structure is typically saturated and may comprise at least one heteroatom selected from N, O or S. Alternatively, $R^4$ to $R^7$ may each be independently selected from methyl, t-butyl, chlorine, bromine and fluorine. In some aspects of the invention, one (or more) of $R^4$-$R^7$ may independently be chlorine, or one of $R^4$-$R^7$ may be chlorine and another may be fluorine.

It will be understood that where reference is made in this specification to compounds of formulae I or II such reference should be construed as extending also to their pharmaceutically acceptable salts and to other pharmaceutically acceptable bio precursors (for instance, prodrug, chemically protected or solvated forms) where relevant.

Salts

The term "salt" is used in the specification to denote the combination of a charged form of a compound with an oppositely charged ion to produce a neutral product. Examples of pharmaceutically acceptable salts are discussed in Berge et al., 1977, "Pharmaceutically Acceptable Salts." J. Pharm. ScL. Vol. 66, pp. 1-19.

Unless otherwise specified, a reference to a particular compound also includes salt foams thereof.

For example, if the compound is anionic, or has a functional group which may be anionic (such as, —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (for example, $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group that may be cationic (such as, —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Prodrugs

The term "prodrug" is used in the specification to denote modified forms or derivatives of a pharmacologically active compound which biodegrade or are modified in vivo so as to become converted into said active compound after administration, especially intravenous administration, in the course of therapeutic treatment of a mammal. Typically, the prodrug is inactive, or less active than the active compound, but may provide advantageous handling, administration, or metabolic properties. Such prodrugs are commonly chosen because of an enhanced solubility of aqueous media which helps to overcome formulation problems, and also in some cases to give a relatively slow or controlled release of the active agent.

Unless otherwise specified, a reference to a particular compound also includes prodrugs thereof.

For example, some prodrugs are esters of the active compound (for instance, a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT or LIDEPT). For example, the prodrug may be a sugar derivative or other glycoside conjugate, or may be an amino acid ester derivative.

Solvates

The term "solvate" is used in the specification to denote a complex of solute (for instance the active compound or salt of active compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

Chemically Protected Forms

The term "chemically protected form" is used in the specification to denote a compound in which one or more reactive functional groups are protected from undesirable chemical reactions under specified conditions (for instance, pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule.

Unless otherwise specified, a reference to a particular compound also includes chemically protected forms thereof.

A wide variety of such "protecting," "blocking," or "masking" methods are used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)$CH_3$, —OAc).

It should be understood that all plausible and compatible combinations of the embodiments described above are explicitly disclosed herein. Each of these combinations is disclosed herein to the same extent as if each individual combination was specifically and individually recited. It should also be understood that where any of the compounds referred to can exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) fauns; keto-, enol-, and enolate-forms; syn- and anti-forms; synclinal- and anticlinal-forms; α- and)-β-forms; axial and equatorial forms; boat-, chair-, twist-, envelope-, and half chair-fauns; and combinations thereof, hereinafter collectively referred to as "isomers" (or "isomeric forms") all such forms, mixtures thereof, and their preparation and uses are within the scope of the invention.

It should be noted, however, that stereo chemical considerations are likely to be important and there may be considerable selectivity such that different enantiomers or diastereoisomers have significantly different inhibitory activity.

Examples of isoindolin-1-one compounds which are at present of particular interest or typically of use in carrying out the invention comprise the following:

TABLE 1

| Number | Compound Name | Structure | ELISA IC$_{50}$ (μM)* |
|---|---|---|---|
| NU8292 | 3-(4-Chlorophenyl)-3-(4-hydroxycyclopent-2-enyloxy)-2-(4-(aminomethyl)benzonitrile)isoindolin-1-one | 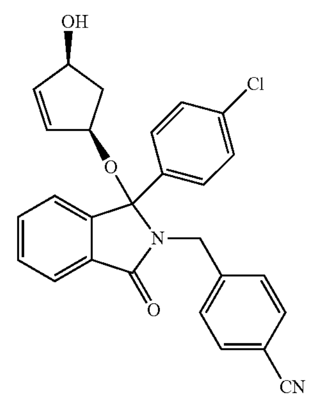 [SMILES: N#Cc1ccc(CN2C(=O)c3ccccc3C2(O[C@H]2C=C[C@@H](O)C2)c2ccc(Cl)cc2)cc1] | 2.3 ± 0.3 |
| NU8293 | 3-(4-Chlorophenyl)-3-(4-hydroxycyclopent-2-enyloxy)-2-(4-chlorophenyl)isoindolin-1-one | 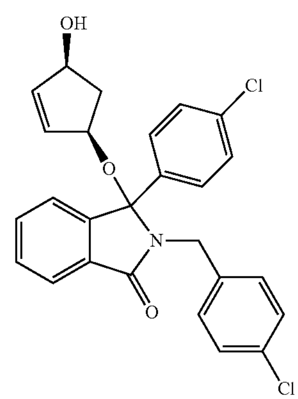 [SMILES: O=C1c2ccccc2C(O[C@H]2C=C[C@@H](O)C2)(c2ccc(Cl)cc2)N1Cc1ccc(Cl)cc1] | 1.5 ± 0.3 |
| NU8294 | 3-(4-chlorophenyl)-3-(4-hydroxycyclopentenyloxy)-2-propylisoindolin-1-one 389.13 C$_{22}$H$_{22}$ClNO$_3$? | 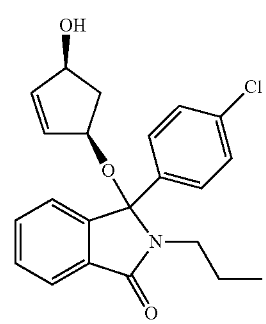 [SMILES: CCCN1C(=O)c2ccccc2C1(O[C@H]1C=C[C@@H](O)C1)c1ccc(Cl)cc1] | 15.1 ± 2.1 |

TABLE 1-continued

| Number | Compound Name | Structure | ELISA IC$_{50}$ (μM)* |
|---|---|---|---|
| NU8295 | 3-(4-Chlorophenyl)-3-(4-hydroxycyclopent-2-enyloxy)-2-(4-methylbenzyl)isoindolin-1-one | 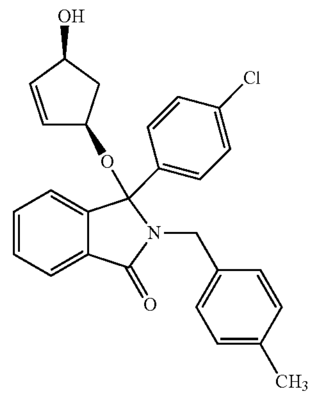 | 1.4 ± 0.4 |
| NU8298 | 2-benzyl-3-(4-chlorophenyl)-3-((1R,4S)-4-hydroxycyclopent-2-enyloxy)isoindolin-1-one | 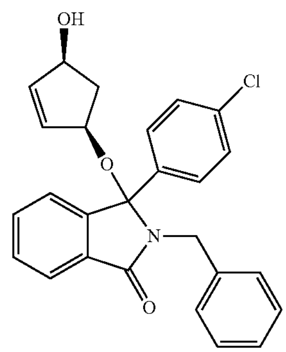 [SMILES: O=C1c2ccccc2C(O[C@H]2C=C[C@@H](O)C2)(c2ccc(Cl)cc2)N1Cc1ccccc1] | 2.3 ± 0.3 |
| NU8362 | 3-(4-Chlorophenyl)-3-(4-hydroxybutoxy)-2-[2-(4-nitrophenyl)-ethyl]-2,3-dihydroisoindol-1-one | 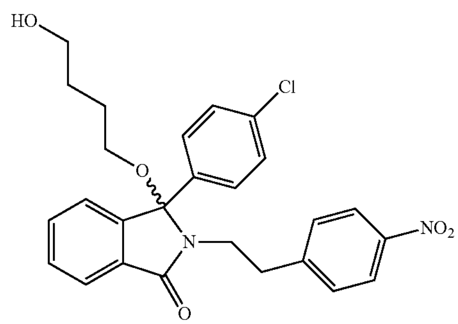 [SMILES: O=C1c2ccccc2C(OCCCCO)(c2ccc(Cl)cc2)N1CCc1ccc([N+](=O)[O-])cc1] | 3.2 ± 1.0 |
| NU8368 | 3-(4-Chlorophenyl)-2-[1-(4-chlorophenyl)-ethyl]-3-(4-hydroxybutoxy)-2,3-dihydro-isoindol-1-one | 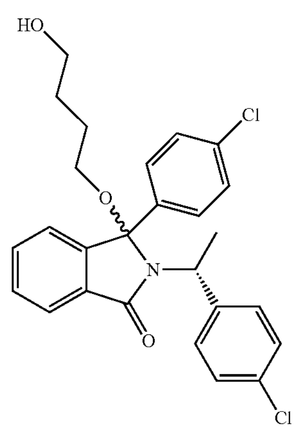 [SMILES: C[C@H](c1ccc(Cl)cc1)N1C(=O)c2ccccc2C1(OCCCCO)c1ccc(Cl)cc1] | 2.5 ± 0.8 |

TABLE 1-continued

| Number | Compound Name | Structure | ELISA IC$_{50}$ (μM)* |
|---|---|---|---|
| NU8370 | 4-[1-(4-Chlorophenyl)-1-(4-hydroxybutoxy)-3-oxo-1,3-dihydro-isoindol-2-ylmethyl]-benzonitrile | 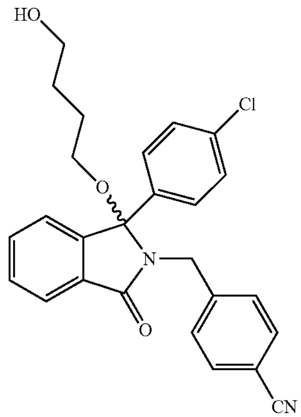 [SMILES: N#Cc1ccc(CN2C(=O)c3ccccc3C2(OCCCCO)c2ccc(Cl)cc2)cc1] | 3.5 ± 1.5 |

*Mean ± SE of n = 3 repeat experiments unless otherwise indicated

Particularly useful examples of isoindolin-1-ones for use in carrying out the invention and which have been found to have particularly potent activity comprise the following:

TABLE 2

| Number | Compound Name | Structure | ELISA IC$_{50}$ (nM)* |
|---|---|---|---|
| NU8297 | 3-(4-Chlorophenyl)-3-(4-hydroxycyclopent-2-enyloxy)-2-(4-nitrobenzyl)isoindolin-1-one | 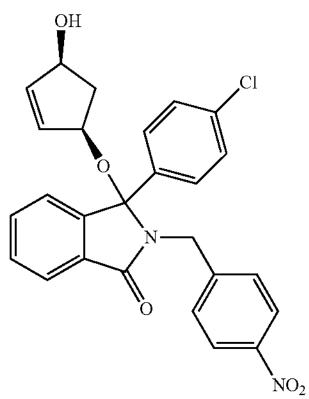 [SMILES: O=C1c2ccccc2C(O[C@H]2C=C[C@@H](O)C2)(c2ccc(Cl)cc2)N1Cc1ccc([N+](=O)[O-])cc1] | 1.4 ± 0.3 μM (n = 3) |
| NU8350 | 3-(4-Chlorophenyl)-3-(4-hydroxybut-2-enyloxy)-2-(4-nitrobenzyl)-2,3-dihydroisoindol-1-one | 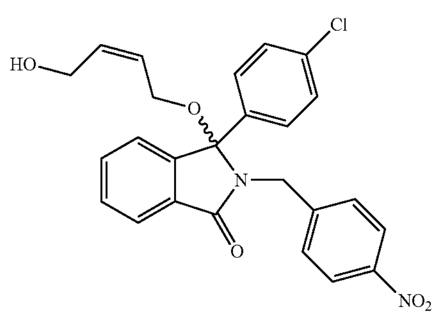 [SMILES: O=C1c2ccccc2C(OC/C=C\CO)(c2ccc(Cl)cc2)N1Cc1ccc([N+](=O)[O-])cc1] | 402 ± 9 |

TABLE 2-continued

| Number | Compound Name | Structure | ELISA IC$_{50}$ (nM)* |
|---|---|---|---|
| NU8351 | 3-(4-Chlorophenyl)-3-(4-hydroxybut-2-enyloxy)-2-(4-nitrobenzyl)-2,3-dihydroisoindol-1-one | 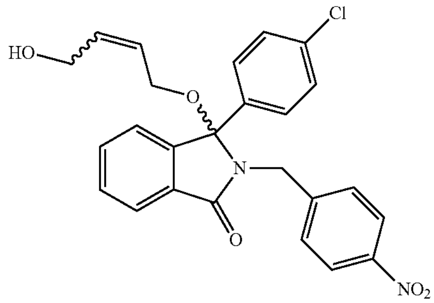 [SMILES: O=C1c2ccccc2C(OCC=CCO)(c2ccc(Cl)cc2)N1Cc1ccc([N+](=O)[O-])cc1] | 405 ± 10 |
| NU8352 | 3-(4-Chlorophenyl)-3-(5-hydroxycyclooctyloxy)-2-(4-nitrobenzyl)-2,3-dihydroisoindol-1-one | 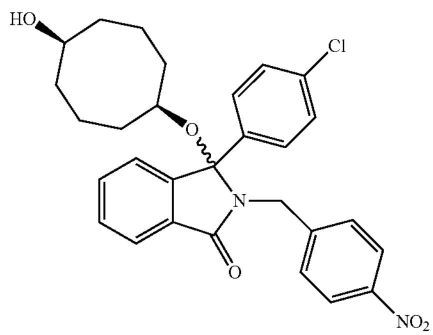 [SMILES: O=C1c2ccccc2C(O[C@H]2CCC[C@@H](O)CCC2)(c2ccc(Cl)cc2)N1Cc1ccc([N+](=O)[O-])cc1] | 375 ± 36 (n = 5) |
| NU8353 | 3-(4-Chlorophenyl)-3-(3-hydroxy-2,2-dimethylpropoxy)-2-(4-nitrobenzyl)-2,3-dihydro-isoindol-1-one | 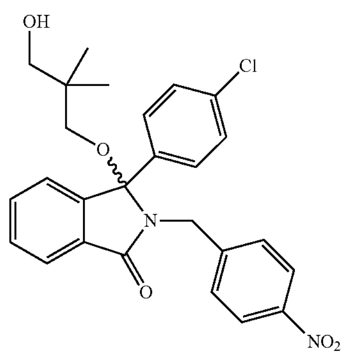 [SMILES: CC(C)(CO)COC1(c2ccc(Cl)cc2)c2ccccc2C(=O)N1Cc1ccc([N+](=O)[O-])cc1] | 395 ± 75 |
| NU8354 | 3-(4-Chlorophenyl)-3-(1-hydroxymethylcyclopropyl methoxy)-2-(4-nitrobenzyl)-2,3-dihydroisoindol-1-one | 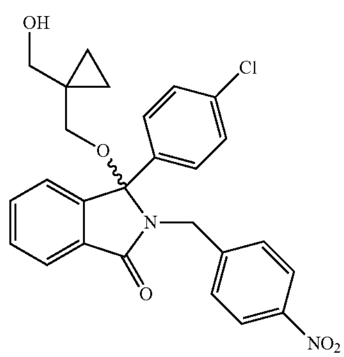 | 298 ± 22 (n = 8) |
| NU8354A | (+)-3-(4-Chlorophenyl)-3-(1-hydroxymethylcyclopropyl methoxy)-2-(4-nitro-benzyl)-2,3-dihydroisoindol-1-one | | 164 ± 18 (n = 7) |
| NU8354B | (−)-3-(4-Chlorophenyl)-3-(1-hydroxymethylcyclopropyl methoxy)-2-(4-nitrobenzyl)-2,3-dihydroisoindol-1-one | | 1333 ± 120 (n = 7) |

TABLE 2-continued

| Number | Compound Name | Structure | ELISA IC$_{50}$ (nM)* |
|---|---|---|---|
| NU8357 | 3-(4-Chlorophenyl)-3-(4-hydroxybut-2-ynyloxy)-2-(4-nitrobenzyl)-2,3-dihydroisoindol-1-one | 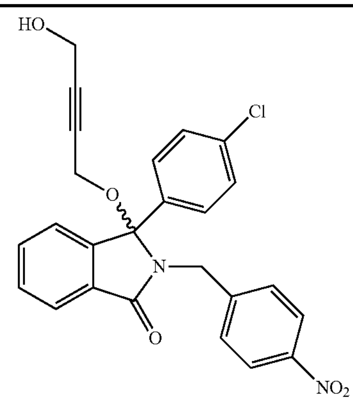 | 656 ± 113 (n = 5) |
| NU8358 | 3-(4-Chlorophenyl)-3-(4-hydroxymethylcyclohexyl methoxy)-2-(4-nitrobenzyl)-2,3-dihydroisoindol-1-one | 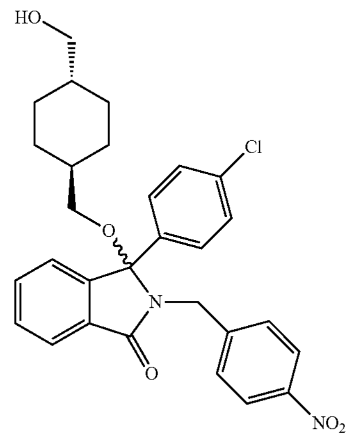 [SMILES: O=C1c2ccccc2C(OC[C@H]2CC[C@H](CO)CC2)(c2ccc(Cl)cc2)N1Cc1ccc([N+](=O)[O-])cc1] | 582 ± 75 (n = 5) |
| NU8359 | 3-(4-Chlorophenyl)-3-(2-hydroxymethylcyclohexyl methoxy)-2-(4-nitrobenzyl)-2,3-dihydroisoindol-1-one | 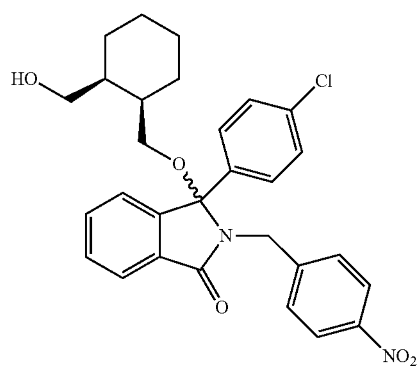 [SMILES: O=C1c2ccccc2C(OC[C@@H]2CCCC[C@@H]2CO)(c2ccc(Cl)cc2)N1Cc1ccc([N+](=O)[O-])cc1] | 569 ± 74 (n = 5) |
| NU8360 | 3-(4-Chlorophenyl)-3-(4-hydroxycyclohexyloxy)-2-(4-nitrobenzyl)-2,3-dihydroisoindol-1-one | 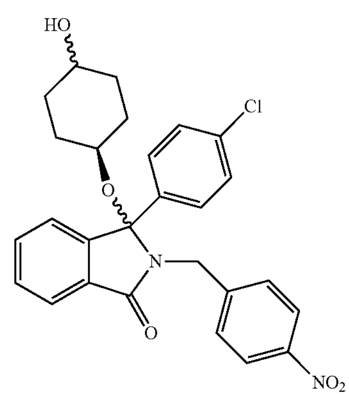 | 388 ± 107 (n = 5) |

TABLE 2-continued

| Number | Compound Name | Structure | ELISA IC$_{50}$ (nM)* |
|---|---|---|---|
| NU8361 | 3-(4-Chlorophenyl)-3-(4-hydroxy-cyclohex-2-enyloxy)-2-(4-nitrobenzyl)-2,3-dihydroisoindol-1-one | 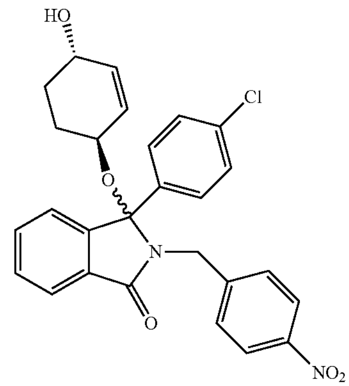 [SMILES: O=C1c2ccccc2C(O[C@@H]2C=C[C@@H](O)CC2)(c2ccc(Cl)cc2)N1Cc1ccc([N+](=O)[O-])cc1] | 306 ± 92 (n = 5) |
| NU8365 | 3-(4-Chlorophenyl)-2-[1-(4-chlorophenyl)-ethyl]-3-(4-hydroxybutoxy)-2,3-dihydroisoindol-1-one | 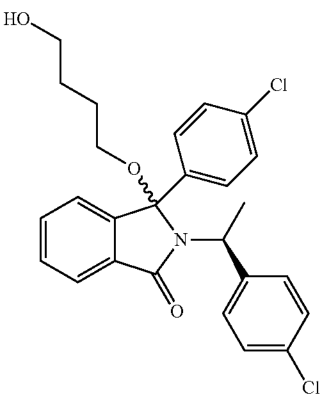 [SMILES: C[C@@H](c1ccc(Cl)cc1)N1C(=O)c2ccccc2C1(OCCCCO)c1ccc(Cl)cc1] | 869 ± 64 |
| NU8366 | 3-(4-Chlorophenyl)-3-(4-hydroxymethylbenzyloxy)-2-(4-nitro-benzyl)-2,3-dihydroisoindol-1-one | 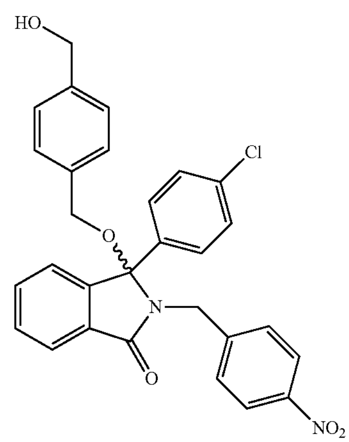 [SMILES: O=C1c2ccccc2C(OCc2ccc(CO)cc2)(c2ccc(Cl)cc2)N1Cc1ccc([N+](=O)[O-])cc1] | 983 ± 170 |

TABLE 2-continued

| Number | Compound Name | Structure | ELISA IC$_{50}$ (nM)* |
|---|---|---|---|
| NU8367 | 3-(4-Chlorophenyl)-3-(3-hydroxymethylbenzyloxy)-2-(4-nitrobenzyl)-2,3-dihydroisoindol-1-one | 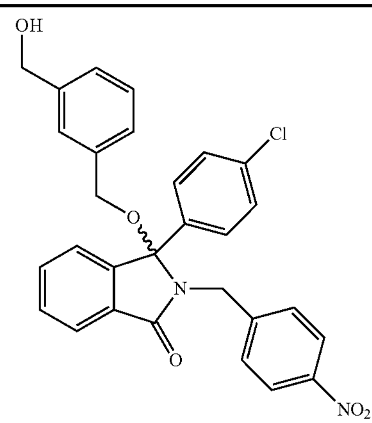 | 732 ± 126 |

*Mean ± SE of n = 3 repeat experiments unless otherwise indicated

Further typical examples of isoindolin-1-ones for use in carrying out the invention and which have been found to have particularly potent activity comprise the following:

TABLE 3

| Number | Compound Descriptions | Structure | MDM2 IC$_{50}$ (μm) |
|---|---|---|---|
| NU8380 | 3-(3-aminopropoxy)-3-(4-chlorophenyl)-2-(4-nitrobenzyl) isoindolin-1-one | 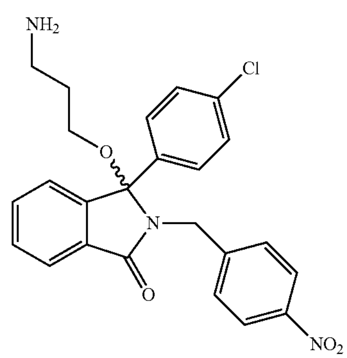 [SMILES: NCCCOC1(c2ccc(Cl)cc2)c2ccccc2C(=O)N1Cc1ccc([N+](=O)[O-])cc1] | 2.46 ± 0.39 μM (n = 5) |
| NU8390 | 3-(4-bromophenyl)-3-(4-hydroxybutoxy)-2-(4-nitrobenzyl) isoindolin-1-one | 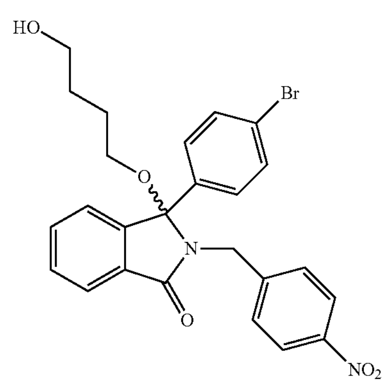 [SMILES: O=C1c2ccccc2C(OCCCCO)(c2ccc(Br)cc2)N1Cc1ccc([N+](=O)[O-])cc1] | 570 ± 59 nM |

TABLE 3-continued

| Number | Compound Descriptions | Structure | MDM2 IC$_{50}$ (μm) |
|---|---|---|---|
| NU8391 | 3-(4-bromophenyl)-3-((1-(hydroxymethyl)cyclopropyl)methoxy)-2-(4-nitrobenzyl)isoindolin-1-one | 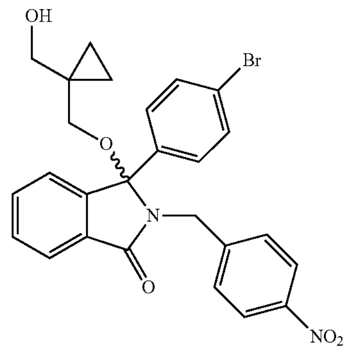 | 368 ± 45 nM |
| NU8392 | 3-(4-bromophenyl)-3-(3-hydroxypropoxy)-2-(4-nitrobenzyl)isoindolin-1-one | 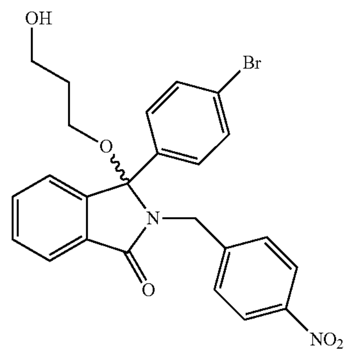 [SMILES: O=C1c2ccccc2C(OCCCO)(c2ccc(Br)cc2)N1Cc1ccc([N+](=O)[O-])cc1] | 1.4 ± 0.16 μM |
| NU8393 | 3-(4-chlorophenyl)-3-hydroxy-4-methyl-2-(4-nitrobenzyl)isoindolin-1-one | 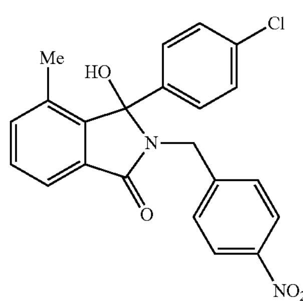 | 2.2 ± 0.34 μM |
| NU8394 | 3-(4-chlorophenyl)-3-hydroxy-7-methyl-2-(4-nitrobenzyl)isoindolin-1-one | 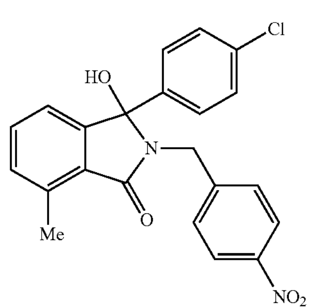 [SMILES: Cc1cccc2c1C(=O)N(Cc1ccc([N+](=O)[O-])cc1)C2(O)c1ccc(Cl)cc1] | 6.9 ± 2.7 μM |

TABLE 3-continued

| Number | Compound Descriptions | Structure | MDM2 IC$_{50}$ (μm) |
|---|---|---|---|
| NU8395 | 3-(4-chlorophenyl)-3-hydroxy-5-methyl-2-(4-nitrobenzyl) isoindolin-1-one | 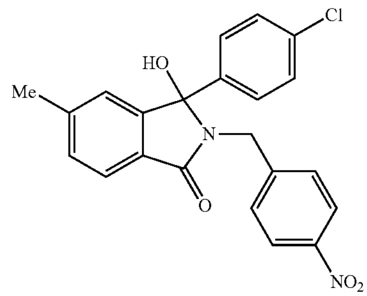 [SMILES: Cc1ccc2c(c1)C(O)(c1ccc(Cl)cc1)N(Cc1ccc([N+](=O)[O-])cc1)C2=O] | 5.08 ± 0.65 μM |
| NU8396 | 5-tert-butyl-3-(4-chlorophenyl)-3-hydroxy-2-(4-nitrobenzyl) isoindolin-1-one | 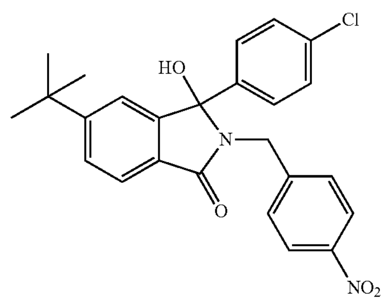 [SMILES: CC(C)(C)c1ccc2c(c1)C(O)(c1ccc(Cl)cc1)N(Cc1ccc([N+](=O)[O-])cc1)C2=O] | 12.7 ± 1.4 μM |
| NU8397 | 6-tert-butyl-3-(4-chlorophenyl)-3-hydroxy-2-(4-nitrobenzyl) isoindolin-1-one | 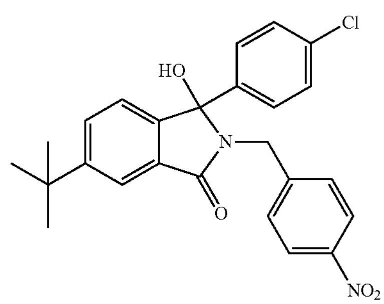 [SMILES: CC(C)(C)c1ccc2c(c1)C(=O)N(Cc1ccc([N+](=O)[O-])cc1)C2(O)c1ccc(Cl)cc1] | 837 ± 49 nM |
| NU8398 | 4-chloro-3-(4-chlorophenyl)-3-hydroxy-2-(4-nitrobenzyl) isoindolin-1-one | 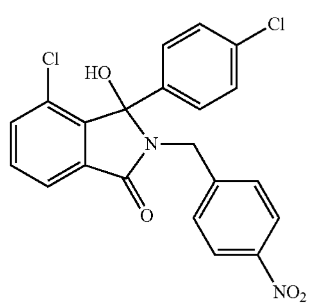 [SMILES: O=C1c2cccc(Cl)c2C(O)(c2ccc(Cl)cc2)N1Cc1ccc([N+](=O)[O-])cc1] | 510 ± 32 nM |

TABLE 3-continued

| Number | Compound Descriptions | Structure | MDM2 IC$_{50}$ (μm) |
|---|---|---|---|
| NU8399 | 6-tert-butyl-3-(4-chlorophenyl)-3-((1-(hydroxymethyl)cyclopropyl)methoxy)-2-(4-nitrobenzyl)isoindolin-1-one | 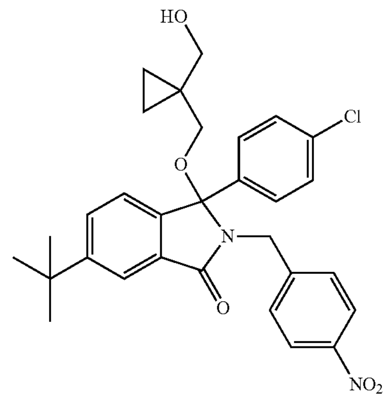 [SMILES: CC(C)(C)c1ccc2c(c1)C(=O)N(Cc1ccc([N+](=O)[O-])cc1)C2(OCC1(CO)CC1)c1ccc(Cl)cc1] | 152 ± 27 nM |
| NCL-00010485 | 3-(4-chlorophenyl)-5-fluoro-3-hydroxy-2-(4-nitrobenzyl)isoindolin-1-one | 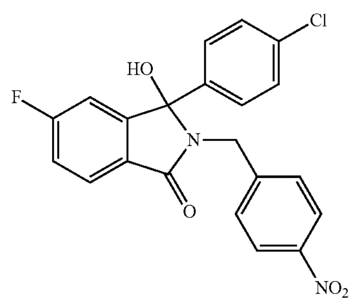 [SMILES: O=C1c2ccc(F)cc2C(O)(c2ccc(Cl)cc2)N1Cc1ccc([N+](=O)[O-])cc1] | 3.76 ± 0.54 |
| NCL-00010486 | 3-(4-chlorophenyl)-6-fluoro-3-hydroxy-2-(4-nitrobenzyl)isoindolin-1-one | 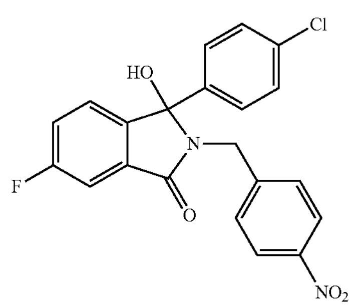 [SMILES: O=C1c2cc(F)ccc2C(O)(c2ccc(Cl)cc2)N1Cc1ccc([N+](=O)[O-])cc1] | 5.19 ± 1.51 |
| NCL-00010487 | 5,6-dichloro-3-(4-chlorophenyl)-3-((1-(hydroxymethyl)cyclopropyl)methoxy)-2-(4-nitrobenzyl)isoindolin-1-one | 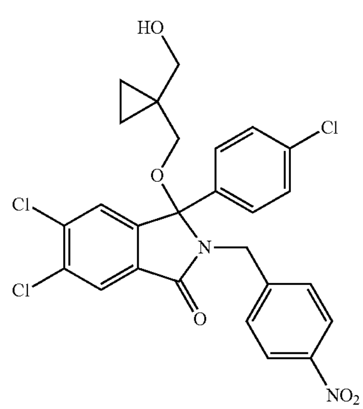 [SMILES: O=C1c2cc(Cl)c(Cl)cc2C(OCC2(CO)CC2)(c2ccc(Cl)cc2)N1Cc1ccc([N+](=O)[O-])cc1] | 3.67 ± 1.15 |

TABLE 3-continued

| Number | Compound Descriptions | Structure | MDM2 IC$_{50}$ (μm) |
|---|---|---|---|
| NCL-00010488 | 4-((7-chloro-1-(4-chlorophenyl)-1-hydroxy-3-oxoisoindolin-2-yl)methyl)benzonitrile | 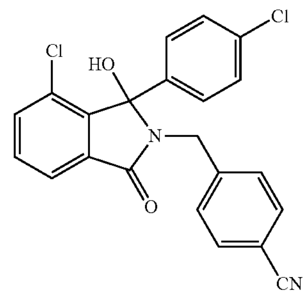 [SMILES: N#Cc1ccc(CN2C(=O)c3cccc(Cl)c3C2(O)c2ccc(Cl)cc2)cc1] | 1.62 ± 0.97 |
| NCL-00010489 | 4-((4-chloro-1-(4-chlorophenyl)-1-hydroxy-3-oxoisoindolin-2-yl)methyl)benzonitrile | 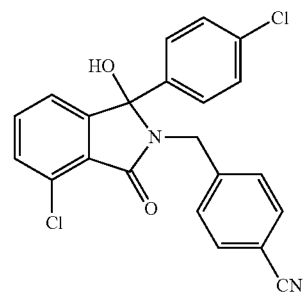 [SMILES: N#Cc1ccc(CN2C(=O)c3c(Cl)cccc3C2(O)c2ccc(Cl)cc2)cc1] | 8.95 ± 2.16 |
| NCL-00010490 | 2-(4-bromobenzyl)-4-chloro-3-(4-chlorophenyl)-3-hydroxy-isoindolin-1-one | 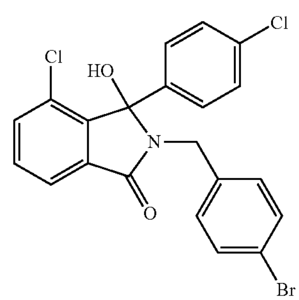 [SMILES: O=C1c2cccc(Cl)c2C(O)(c2ccc(Cl)cc2)N1Cc1ccc(Br)cc1] | 0.847 ± 0.082 |
| NCL-00010492 | 4-((7-chloro-1-(4-chlorophenyl)-1-((1-(hydroxymethyl)cyclopropyl)methoxy)-3-oxoisoindolin-2-yl)methyl)benzonitrile | 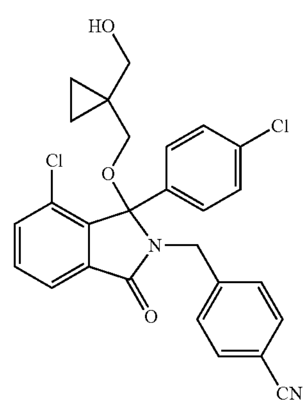 [SMILES: N#Cc1ccc(CN2C(=O)c3cccc(Cl)c3C2(OCC2(CO)CC2)c2ccc(Cl)cc2)cc1] | 0.185 ± 0.017 |

TABLE 3-continued

| Number | Compound Descriptions | Structure | MDM2 IC$_{50}$ (μm) |
|---|---|---|---|
| NCL-00010493 | 2-(4-bromobenzyl)-4-chloro-3-(4-chlorophenyl)-3-((1-(hydroxymethyl)cyclopropyl)methoxy)isoindolin-1-one | 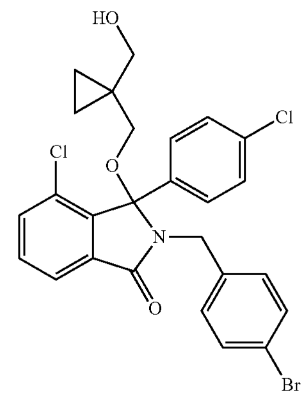 [SMILES: O=C1c2cccc(Cl)c2C(OCC2(CO)CC2)(c2ccc(Cl)cc2)N1Cc1ccc(Br)cc1] | 0.169 ± 0.003 |
| NCL-00010494 | 3-(4-chlorophenyl)-3-hydroxy-2-(4-nitrobenzyl)-2,3,4,5,6,7-hexahydro-1H-isoindol-1-one | 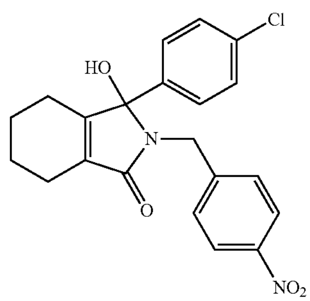 [SMILES: O=C1C2=C(CCCC2)C(O)(c2ccc(Cl)cc2)N1Cc1ccc([N+](=O)[O-])cc1] | 2.81 ± 0.07 |
| NCL-00010495 | 3-(4-chlorophenyl)-5-fluoro-3-((1-(hydroxymethyl)cyclopropyl)methoxy)-2-(4-nitrobenzyl)isoindolin-1-one | 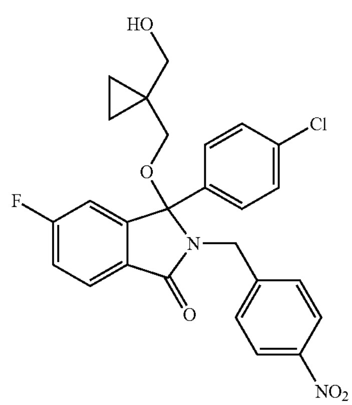 [SMILES: O=C1c2ccc(F)cc2C(OCC2(CO)CC2)(c2ccc(Cl)cc2)N1Cc1ccc([N+](=O)[O-])cc1] | 0.295 ± 0.065 |
| NCL-00010496 | 3-(4-chlorophenyl)-6-fluoro-3-((1-(hydroxymethyl)cyclopropyl)methoxy)-2-(4-nitrobenzyl)isoindolin-1-one | 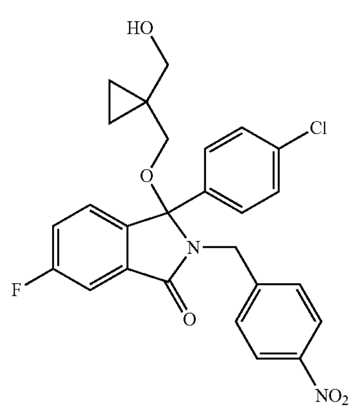 [SMILES: O=C1c2cc(F)ccc2C(OCC2(CO)CC2)(c2ccc(Cl)cc2)N1Cc1ccc([N+](=O)[O-])cc1] | 0.852 ± 0.09 |

TABLE 4
| Number | Compound Description | Structure | MDM2 IC$_{50}$ (μm) |
|---|---|---|---|
| NU8400 | 5-tert-butyl-3-(4-chlorophenyl)-3-((1-(hydroxymethyl)cyclopropyl)methoxy)-2-(4-nitrobenzyl)isoindolin-1-one | 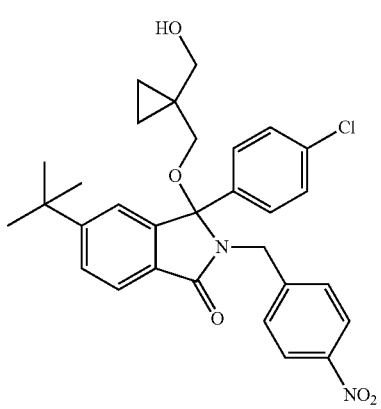 [SMILES: CC(C)(C)c1ccc2c(c1)C(OCC1(CO)CC1)(c1ccc(Cl)cc1)N(Cc1ccc([N+](=O)[O-])cc1)C2=O] | 733 ± 29 nM |
| NU8401 | 3-(4-chlorophenyl)-3-((1-(hydroxymethyl)cyclopropyl)methoxy)-5-methyl-2-(4-nitrobenzyl)isoindolin-1-one | 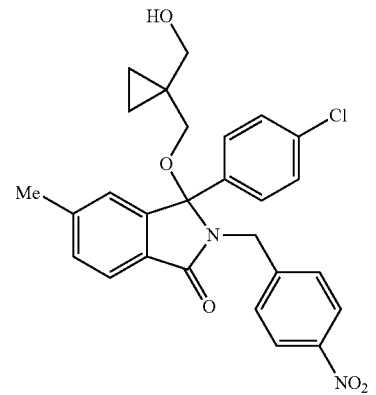 [SMILES: Cc1ccc2c(c1)C(OCC1(CO)CC1)(c1ccc(Cl)cc1)N(Cc1ccc([N+](=O)[O-])cc1)C2=O] | 492 ± 35 nM |
| NU8405 | 3-(4-chlorophenyl)-3-((1-(hydroxymethyl)cyclopropyl)methoxy)-4-methyl-2-(4-nitrobenzyl)isoindolin-1-one | 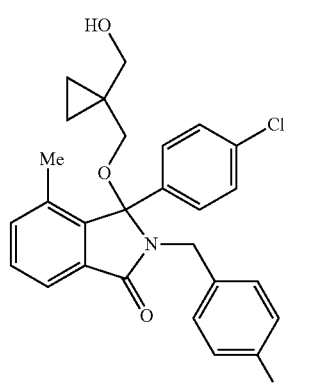 | 274 ± 35 nM |

TABLE 4-continued

| Number | Compound Description | Structure | MDM2 IC$_{50}$ (μm) |
|---|---|---|---|
| NU8406 | 4-chloro-3-(4-chlorophenyl)-3-((1-(hydroxymethyl)cyclopropyl)methoxy)-2-(4-nitrobenzyl)isoindolin-1-one | 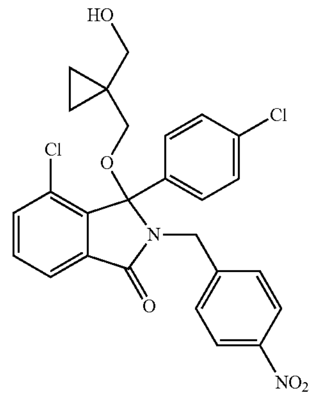 [SMILES: O=C1c2cccc(Cl)c2C(OCC2(CO)CC2)(c2ccc(Cl)cc2)N1Cc1ccc([N+](=O)[O-])cc1] | 143 ± 26 nM |
| NU8412 | 3-(4-chlorophenyl)-3-hydroxy-6-methyl-2-(4-nitrobenzyl)isoindolin-1-one | 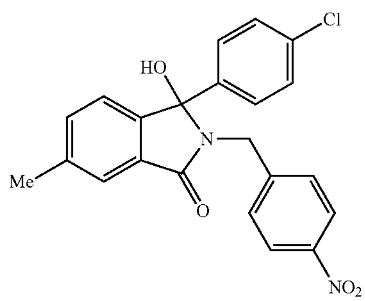 [SMILES: Cc1ccc2c(c1)C(=O)N(Cc1ccc([N+](=O)[O-])cc1)C2(O)c1ccc(Cl)cc1] | 1.46 ± 0.36 |
| NU8413 | 6-bromo-3-(4-chlorophenyl)-3-hydroxy-2-(4-nitrobenzyl)isoindolin-1-one | 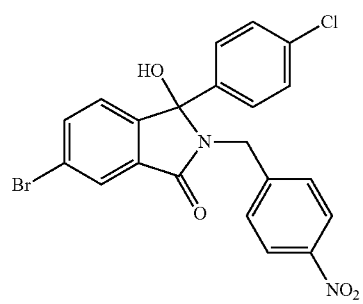 [SMILES: O=C1c2cc(Br)ccc2C(O)(c2ccc(Cl)cc2)N1Cc1ccc([N+](=O)[O-])cc1] | 5.37 ± 0.51 |
| NU8414 | 5-bromo-3-(4-chlorophenyl)-3-hydroxy-2-(4-nitrobenzyl)isoindolin-1-one | 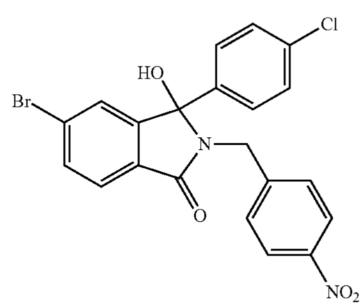 [SMILES: O=C1c2ccc(Br)cc2C(O)(c2ccc(Cl)cc2)N1Cc1ccc([N+](=O)[O-])cc1] | 5.68 ± 0.16 |

TABLE 4-continued

| Number | Compound Description | Structure | MDM2 IC$_{50}$ (μm) |
|---|---|---|---|
| NU8415 | 4-((1-(4-chlorophenyl)-1-((1-(hydroxymethyl)cyclopropyl)methoxy)-3-oxoisoindolin-2-yl)methyl)benzonitrile | 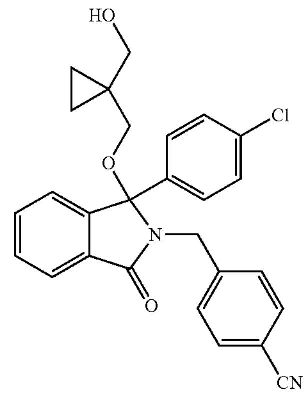 [SMILES: N#Cc1ccc(CN2C(=O)c3ccccc3C2(OCC2(CO)CC2)c2ccc(Cl)cc2)cc1] | 1.79 ± 0.67 |
| NU8416 | 2-(4-chlorobenzyl)-3-(4-chlorophenyl)-3-((1-(hydroxymethyl)cyclopropyl)methoxy)isoindolin-1-one | 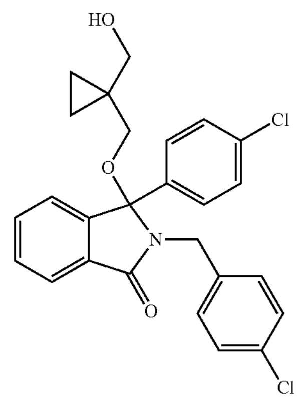 [SMILES: O=C1c2ccccc2C(OCC2(CO)CC2)(c2ccc(Cl)cc2)N1Cc1ccc(Cl)cc1] | 2.31 ± 0.56 |
| NU8417 | 2-(4-bromobenzyl)-3-(4-chlorophenyl)-3-((1-(hydroxymethyl)cyclopropyl)methoxy)isoindolin-1-one | 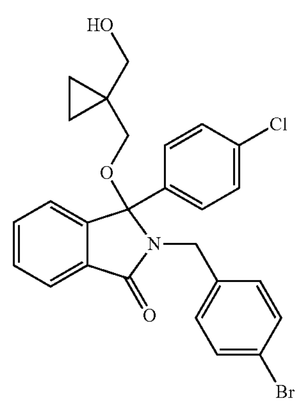 [SMILES: O=C1c2ccccc2C(OCC2(CO)CC2)(c2ccc(Cl)cc2)N1Cc1ccc(Br)cc1] | 1.20 ± 0.61 |
| NU8418 | 3-(4-chlorophenyl)-2-((R)-1-(4-chlorophenyl)ethyl)-3-((1-(hydroxymethyl)cyclopropyl)methoxy)isoindolin-1-one | 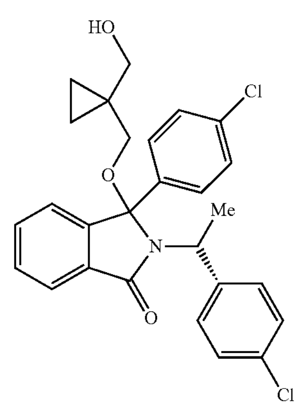 | 8.8 ± 2.1 |

TABLE 4-continued

| Number | Compound Description | Structure | MDM2 IC$_{50}$ (μm) |
|---|---|---|---|
| NU8419 | 3-(4-chlorophenyl)-2-((S)-1-(4-chlorophenyl)ethyl)-3-((1-(hydroxymethyl)cyclopropyl)methoxy)isoindolin-1-one | 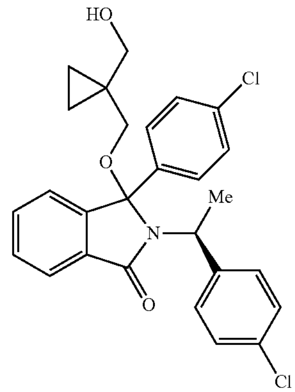 [SMILES: C[C@@H](c1ccc(Cl)cc1)N1C(=O)c2ccccc2C1(OCC1(CO)CC1)c1ccc(Cl)cc1] | 8.9 ± 1.9 |
| NU8424 | 5-bromo-3-(4-chlorophenyl)-3-((1-(hydroxymethyl)cyclopropyl)methoxy)-2-(4-nitrobenzyl)isoindolin-1-one | 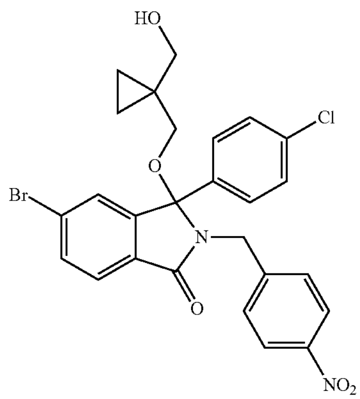 [SMILES: O=C1c2ccc(Br)cc2C(OCC2(CO)CC2)(c2ccc(Cl)cc2)N1Cc1ccc([N+](=O)[O-])cc1] | 902 ± 71 nM |
| NU8425 | 6-bromo-3-(4-chlorophenyl)-3-((1-(hydroxymethyl)cyclopropyl)methoxy)-2-(4-nitrobenzyl)isoindolin-1-one | 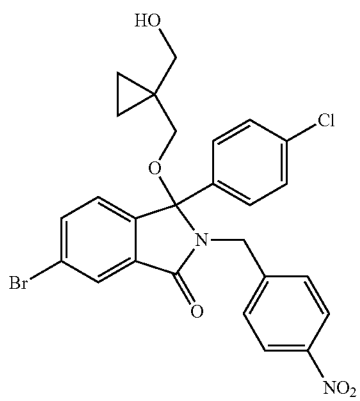 [SMILES: O=C1c2cc(Br)ccc2C(OCC2(CO)CC2)(c2ccc(Cl)cc2)N1Cc1ccc([N+](=O)[O-])cc1] | 1.03 ± 0.04 |
| NU8429 | 3-(4-chlorophenyl)-3-((1-(hydroxymethyl)cyclopropyl)methoxy)-2-(pyridin-2-ylmethyl)isoindolin-1-one | 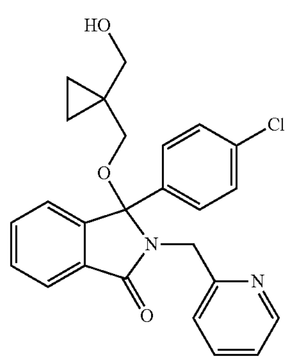 [SMILES: O=C1c2ccccc2C(OCC2(CO)CC2)(c2ccc(Cl)cc2)N1Cc1ccccn1] | 10.6 ± 0.8 |

TABLE 5

| Name | | Structure | MDM2-p53 ELISA IC$_{50}$ (uM) |
|---|---|---|---|
| NU8398 | 4-chloro-3-(4-chlorophenyl)-3-hydroxy-2-(4-nitrobenzyl)isoindolin-1-one | 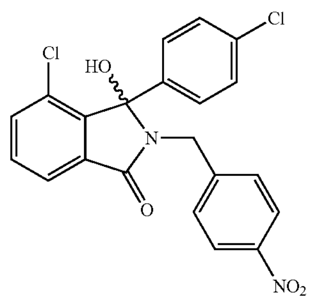 [SMILES: O=C1c2cccc(Cl)c2C(O)(c2ccc(Cl)cc2)N1Cc1ccc([N+](=O)[O-])cc1] | 0.51 ± 0.03 |
| NCL-00013774 | (?)-4-chloro-3-(4-chlorophenyl)-3-((1-(hydroxymethyl)cyclopropyl)methoxy)-2-(4-nitrobenzyl)isoindolin-1-one | 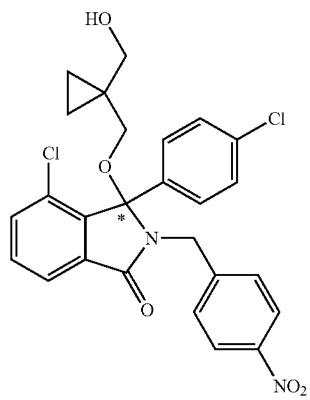 [SMILES: O=C1c2cccc(Cl)c2C(OCC2(CO)CC2)(c2ccc(Cl)cc2)N1Cc1ccc([N+](=O)[O-])cc1] | 0.04 ± 0.004 |
| NCL-00013775 | (?)-4-chloro-3-(4-chlorophenyl)-3-((1-(hydroxymethyl)cyclopropyl)methoxy)-2-(4-nitrobenzyl)isoindolin-1-one | 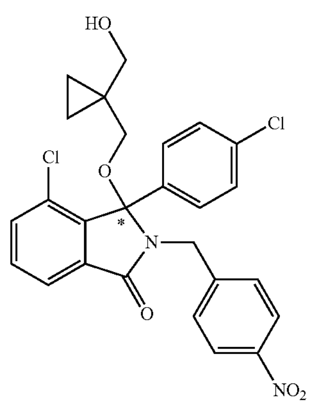 [SMILES: O=C1c2cccc(Cl)c2C(OCC2(CO)CC2)(c2ccc(Cl)cc2)N1Cc1ccc([N+](=O)[O-])cc1] | 1.26 ± 0.008 |
| NCL-00016654 | 7-chloro-3-(4-chloro-phenyl)-3-hydroxy-2-(4-nitro-benzyl)-2,3-dihydro-isoindol-1-one | 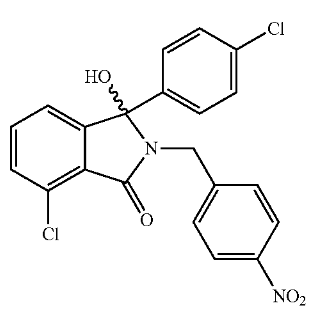 [SMILES: O=C1c2c(Cl)cccc2C(O)(c2ccc(Cl)cc2)N1Cc1ccc([N+](=O)[O-])cc1] | 4.54 |

TABLE 5-continued

| Name | | Structure | MDM2-p53 ELISA IC$_{50}$ (uM) |
|---|---|---|---|
| NCL-00016045 | 2-(4-acetylbenzyl)-3-(4-chlorophenyl)-3-hydroxy-2,3-dihydroisoindol-1-one | 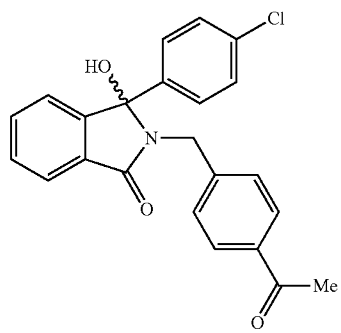 [SMILES: CC(=O)c1ccc(CN2C(=O)c3ccccc3C2(O)c2ccc(Cl)cc2)cc1] | 89 |
| NCL-00014529 | 3-(4-chlorophenyl)-3-(1-hydroxymethyl-cyclopropylmethoxy)-2-(4-iodobenzyl)-2,3-dihydroisoindol-1-one | 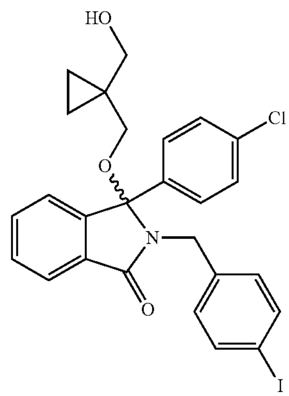 [SMILES: O=C1c2ccccc2C(OCC2(CO)CC2)(c2ccc(Cl)cc2)N1Cc1ccc(I)cc1] | 1.5 |
| NCL-00014531 | 2-(4-acetylbenzyl)-3-(4-chlorophenyl)-3-(1-hydroxymethylcyclopropyl-methoxy)-2,3-dihydroisoindol-1-one | 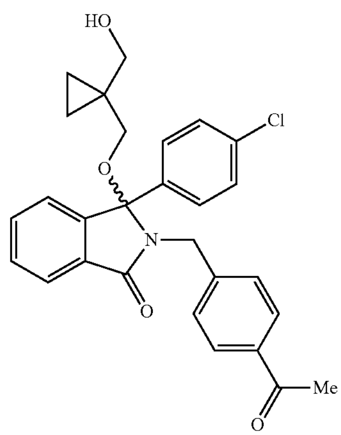 [SMILES: CC(=O)c1ccc(CN2C(=O)c3ccccc3C2(OCC2(CO)CC2)c2ccc(Cl)cc2)cc1] | 17 |
| NCL-00016046 | 3-(4-chlorophenyl)-3-hydroxy-2-naphthalen-1-ylmethyl-2,3-dihydroisoindol-1-one | 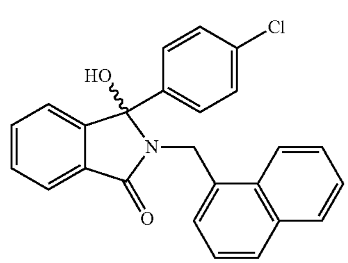 [SMILES: O=C1c2ccccc2C(O)(c2ccc(Cl)cc2)N1Cc1cccc2ccccc12] | 96 |

TABLE 5-continued

| Name | Structure | MDM2-p53 ELISA IC$_{50}$ (uM) |
|---|---|---|
| NCL-00016047 2-(3-bromobenzyl)-3-(4-chlorophenyl)-3-hydroxy-2,3-dihydroisoindol-1-one | | |
| NCL-00016106 3-(4-chlorophenyl)-3-(1-hydroxymethylcyclopropyl-methoxy)-2-naphthalen-1-ylmethyl-2,3-dihydroisoindol-1-one | | 49 |
| NCL-00016107 2-(3-bromobenzyl)-3-(4-chlorophenyl)-3-(1-hydroxymethyl-cyclopropyl-methoxy)-2,3-dihydroisoindol-1-one | | 47 |
| NCL-00016655 3-hydroxy-2-(4-nitrobenzyl)-3-phenyl-2,3-dihydroisoindol-1-one | | 87 |

TABLE 5-continued

| Name | Structure | MDM2-p53 ELISA IC$_{50}$ (uM) |
|---|---|---|
| NCL-00016656 3-(1-hydroxymethylcyclo-propylmethoxy)-2-(4-nitrobenzyl)-3-phenyl-2,3-dihydroisoindol-1-one | | 8.3 |
| NCL-00016657 3-hydroxy-2-(4-nitrobenzyl)-3-(4-fluorophenyl)-2,3-dihydroisoindol-1-one | | 9.46 |
| NCL-00016149 succinic acid mono-{1-[7-chloro-1-(4-chlorophenyl)2-(4-nitrobenzyl)-3-oxo-2,3-dihydro-1H-isoindol-1-yloxymethyl]cyclopropylmethyl}ester | | 0.019 ± 0.009 |
| NCL-00016659 succinic acid mono-{1-[7-chloro-1-(4-chlorophenyl)-2-(4-cyanobenzyl)-3-oxo-2,3-dihydro-1H-isoindol-1-yloxymethyl]cyclopropyl-methyl}ester | | 0.102 (n = 2) |

TABLE 5-continued

| Name | Structure | MDM2-p53 ELISA IC$_{50}$ (uM) |
|---|---|---|
| NCL-00016653 succinic acid mono-{1-[2-(4-bromobenzyl)-7-chloro-1-(4-chlorophenyl)-3-oxo-2,3-dihydro-1H-isoindol-1-yloxymethyl]cyclopropyl-methyl}ester | | 0.102 (n = 2) |
| NCL-00016865 3-(4-chlorophenyl)-3-((1-(hydroxymethyl)cyclopropyl)methoxy)-2-(4-methylbenzyl)isoindolin-1-one | | 2.3 |
| NCL-00016866 3-(4-chlorophenyl)-3-((1-(hydroxymethyl)cyclopropyl)methoxy)-2-(4-methoxybenzyl)isoindolin-1-one | | 2.8 |

TABLE 5-continued

| Name | Structure | MDM2-p53 ELISA IC$_{50}$ (uM) |
|---|---|---|
| NCL-00016895 3-(4-chlorophenyl)-3-(2-(hydroxymethyl)allyloxy)-2-(4-nitrobenzyl)isoindolin-1-one | | 0.68 |
| NCL-00016896 3-(4-fluorophenyl)-3-((1-(hydroxymethyl)cyclopropyl)methoxy)-2-(4-nitrobenzyl)isoindolin-1-one | | 2.7 |
| NCL-00016897 4-chloro-3-(4-chlorophenyl)-5-fluoro-3-hydroxy-2-(4-nitrobenzyl)isoindolin-1-one | | 34 |

Of the compounds in Table 5 above, those wherein $R^2$ is hydrogen and all of $R^4$-$R^7$ are H are used as intermediate compounds in the preparation of the compounds of the invention.

Studies of the p53 binding pocket on the MDM2 protein guided the nature of the molecules synthesised. Thus the present invention provides small molecule inhibitors of MDM2-p53 interaction based on an isoindolinone scaffold. Preliminary screening studies, using an in vitro MDM2-p53 binding assay identified the particularly useful isoindolin-1-one compounds (Tables 2-4) as inhibitors of MDM2-p53 interaction having an IC$_{50}$ in the range 100-1000 nM (IC$_{50}$ is the concentration of a particular compound required to inhibit 50% of a specific measured activity, in this case inhibition of the MDM2-p53 interaction). The isoindolin-1-ones were found to be active in the inhibition of the MDM2-p53 interaction.

The inhibitory efficacies of the compounds of the present invention have been determined using the ELISA assay which for the avoidance of doubt is described below.

As referred to herein "cancer" or "tumour" includes, but is not limited to, lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, skin cancer, squamous cancer, Kaposi's sarcoma, melanoma, malignant melanoma, lymphoma, or leukemia. Compounds of the present invention have been shown to inhibit the interaction of p53 with MDM2. Such inhibition leads to cell arrest and apoptosis.

Accordingly, the compounds of the present invention are of particular interest for the treatment of a range of selected cancer tumours, and the invention further provides a method for the treatment of a patient suffering from cancer. Thus, a therapeutically effective non-toxic amount of a compound of the first and second aspects of the invention, may be suitably administered orally, parenterally (including subcutaneously, intramuscularly, and intravenously or topically). The administration will generally be carried out repetitively at intervals, for example once or several times a day.

The amount of the compound, which is required in order to be effective as an anti tumour agent for treating mammals will of course vary and is ultimately at the discretion of the medical or veterinary practitioner treating the mammal in each particular case. The factors to be considered by such a practitioner include the route of administration and pharmaceutical formulation; the mammal's body weight, surface area, age and general condition; and the chemical form of the compound to be administered. However, a suitable effective anti tumour dose may be in the range of about 1.0 to about 75 mg/kg bodyweight, typically in the range of about 5 to 40 mg/kg with most suitable doses being for example in the range of 10 to 30 mg/kg. In daily treatment for example, the total daily dose may be given as a single dose, multiple doses, such as two to six times per day, or by intravenous infusion for any selected duration. For example, in the case of a 75 kg mammal, the dose range could be about 75 to 500 mg per day and it is expected that a typical dose would commonly be about 100 mg per day. If discrete multiple doses are indicated, treatment might typically be 50 mg of the compound of formula given 4 times per day in the form of a tablet capsule, liquid (for example, syrup) or injection.

The dosing will depend upon the subject or patient which may be a chordate, a vertebrate, a mammal, a placental mammal, a marsupial, a monotreme (for instance, duckbilled platypus), a rodent, murine (for instance, a mouse), a lagomorph (for instance, a rabbit), avian, canine, feline, equine, porcine, ovine (for instance, a sheep), bovine, a primate, simian (for instance, a monkey or ape), a monkey (for instance, marmoset, baboon), an ape (for instance, gorilla, chimpanzee, orangutang, gibbon), or a human. Furthermore, the subject/patient may be any of its forms of development, for example, a foetus. Typically, the subject is a human.

While it may be possible for the compounds of the first or second aspects of the invention to be administered alone as the raw chemical, it is preferable to present the compound in a pharmaceutical composition. Thus, the invention also provides pharmaceutical compositions comprising an effective amount of a compound as hereinbefore defined which forms the active therapeutic ingredient. Such pharmaceutical compositions for medical use will be formulated in accordance with any of the methods well known in the art of pharmacy for administration in any convenient manner. The compounds will usually be admixed with at least one other ingredient providing a compatible pharmaceutically acceptable additive carrier, diluent or excipient, and may be presented in unit dosage faun.

The carrier(s) must be pharmaceutically acceptable in the sense of being compatible with the other ingredients of the formulation and not deleterious to the recipient thereof.

The possible formulations include those suitable for oral, rectal, topical and parenteral (including subcutaneous intramuscular and intravenous) administration or for administration to the lung or other absorptive site such as the nasal passages.

All methods of formulation in making up such pharmaceutical compositions will generally include the step of bringing a compound as defined in the first to third aspects of the invention into association with a carrier which constitutes one or more accessory ingredients. Usually, the formulations are prepared by uniformly and intimately bringing the compound into association with a liquid carrier or with a finely divided solid carrier or with both and then, if necessary, shaping the product into desired formulations.

Formulations of the present invention suitable for oral administration may be presented as discrete units such as capsules, cachets, tables or lozenges, each containing a predetermined amount of the compound; as a powder or granules; or a suspension in an aqueous liquid or non-aqueous liquid such as a syrup, an elixir, an emulsion or a draught. The compound may also be presented as bolus, electuary or paste.

A tablet may be made by compression or moulding, optionally with one or more accessory ingredients. Compressed tablets may be prepared by compressing, in a suitable machine, the compound in a free-flowing form such as a powder or granules, optionally mixed with a binder, lubricant, inert diluent, surface active or dispersing agent. Moulded tablets may be made by moulding in a suitable machine, a mixture of the powdered compound with any suitable carrier.

A syrup may be made by adding the compound to a concentrated, aqueous solution of a sugar, for example sucrose, to which may be added any desired accessory ingredients. Such accessory ingredient(s) may include flavourings, one or more agents to retard crystallisation of the sugar or one or more agents to increase the solubility of any other ingredient, such as a polyhydric alcohol, for example glycerol or sorbitol.

Formulations for rectal administration may be presented as a suppository with a carrier, for instance cocoa butter.

Formulations suitable for parental administration conveniently comprise a sterile aqueous preparation of a compound of the first or second aspects of the invention, which is typically isotonic with the blood of the recipient.

In addition to the aforementioned ingredients, formulations of this invention, for example ointments, creams and such like, may include one or more accessory ingredients, for example a diluent, buffer, flavouring agent, binder, surface active agent, thickener, lubricant and/or a preservative (including an antioxidant) or other pharmaceutically inert excipient.

The compounds of the present invention may also be made up for administration in liposomal formulations, which can be prepared by methods well-known in the art.

Where the compound is provided as part of a kit, it is typical that the kit contains a compound as defined in the first or second aspect of the invention, or a composition comprising a compound as described herein (typically provided in a suitable container and/or with suitable packaging); and instructions for use (for example, written instructions on how to administer the active compound or composition). The instructions may also include a list of indications for which the active ingredient is a suitable treatment.

The isoindolinone compounds of the present invention may be administered alone or as a combination therapy. For instance, the compounds described herein may also be used in combination with one another or in conjunction with other agents, for example, cytotoxic agents or anticancer agents. Examples of treatments and therapies include, but are not limited to, chemotherapy (the administration of active agents, including, for instance, drugs, antibodies (as in immunotherapy), prodrugs (as in photodynamic therapy, GDEPT, ADEPT, etc.)); surgery; radiation therapy; photodynamic therapy; gene therapy; and controlled diets. The particular combination would be at the discretion of the physician who would select dosages using his common general knowledge and dosing regimens known to a skilled practitioner.

Analytical Techniques
ELISA Assay

Streptavidin-coated 96-well plates are used to immobilise a biotin-tagged IP3 p53-derived peptide (MPRFMDY-WEGLN). This is a peptide analogue derived from the p53 binding site for MDM2 (QETFSDLWKLLP). IP3 has a higher affinity for MDM2 than the native peptide and has been used elsewhere to identify antagonists of the binding between MDM2 and p53 (Stoll et al 2001). Aliquots of MDM2 generated by in vitro translation are pre-incubated for 20 minutes at room temperature (i.e. 20-25° C.) with test compounds and controls, before transfer into the IP3-coated 96-well plates. Following a further incubation period of 90 minutes at 4° C., the plates are washed to remove unbound MDM2 and the residual bound MDM2 is detected using a primary monoclonal antibody (MDM2 Ab-1, clone IF2, Oncogene Research Products) and HRP-conjugated secondary antibody (Goat anti-mouse, Dako PO447). The HRP (horseradish peroxidase) is measured by a chemiluminescence reaction using standard reagents (Amersham Pharmacia™ RPN 2106) and an automatic injection 96-well plate illuminometer (EG & G Berthold Microplate LB 96V).

For validation and subsequently as positive controls, IP3 & AP peptides are used, together with the isoindolin-1-one lead compound that at the time shows the highest degree of antagonistic activity. 3-(4-Chloro-phenyl)-3-(4-hydroxy-3, 5-dimethoxy-benzyloxy)-2-propyl-2,3-dihydro-isoindolin-1-one (NU8231) is currently included as a standard "lead compound" positive control. AP is an octomer synthetic peptide that inhibits the p53-MDM2 interaction with high potency ($IC_{50}$=5.0 nM) and has been reported to stimulate p53 and downstream apoptotic pathways in intact tumour cell lines (Chene et al 2000). The AP peptide is included as a positive control for biological evaluation of the isoindolinones in the cell free binding assays.

All compounds are dissolved in DMSO and tested at a range of concentrations in the presence of a fixed final concentration of 5% DMSO. The percentage inhibition of complex formation is expressed relative to a DMSO only control and an $IC_{50}$, defined as the concentration required for 50% inhibition of MDM2-p53 complex formation, determined by interpolation.

The ELISA assay showed a standard error for n=3 independent $IC_{50}$ determinations of 10-15% of the mean value. Thus, the variation in the $IC_{50}$ determination for an individual compound was much smaller than the range of values for the compounds evaluated thus far is (26.7>500 μM).

Western Blot Method

Osteosarcoma cell line SJSA-1 was plated out in 55 mm dishes at a density of $2.5 \times 10^5$ cells in 3 mL of RPMI 1640 medium (Sigma) supplemented with 10% foetal bovine serum (FBS, Gibco), 1% (v/v) HEPES (Gibco), 1% (v/v) sodium pyruvate (Gibco) and 1.25 g/500 ml glucose (Sigma) for 48 hours in a 37° C. humidified incubator (Sanyo, MCO 20AIC) at a $CO_2$ concentration of 5%.

The dishes were treated with 3-(4-Chloro-phenyl)-3-(4-hydroxy-3,5-dimethoxy-benzyloxy)-2-propyl-2,3-dihydro-isoindolin-1-one (NU8231) at a final concentration of 5, 10, and 20 μM (at 1% DMSO) together with a 1% DMSO and an untreated control sample for 6 hours. The medium was then aspirated and the dishes were washed with 3 mL of cold PBS. The cells were then lysed in 40 μL of Sodium Dodecyl Sulphate (SDS, Sigma) lysis buffer, boiled at 100° C. for 10 minutes before sonication for 3×5 seconds at 20 microns (Soniprep 150, MSE).

The protein concentration for each of the samples was then determined using BCA Protein Assay Kit (Pierce), and 1:1 loading buffer consisting of (3-mercaptoethanol (Sigma) and 0.5% bromophonol-blue (Sigma) were added to 40 μg of protein and made up to a final volume of 30 μL and boiled for 5 minutes at 100° C.

The samples were then loaded onto a precast 4-20% gradient polyacrylamide Tris-Glycine gels (15 wells, 1.5 mm thickness, Invitrogen Life Technologies), along with a pre-stained marker protein (SeeBlue, Invitrogen). The Gels were processed in Novex XCell (Invitrogen) at 180V and blotted onto a High Bond C membrane (Amersham Life Science) overnight at 30V.

The membrane was then blocked for one hour at room temperature in TBS-Tween containing 5% non-fat milk (TBST-M) followed by incubation with primary antibodies for MDM2 (MDM2-Ab 1, 1:500, Oncogene), p53 (p53-D07, 1:1000, Novacastra), p21 (p21 Ab1, 1:100, Oncogene) and Actin (Actin AC40, 1:1000, Sigma) in PBST-M for 1 hour.

The membrane was then washed three times in TBST (15 minutes per wash) and then incubated for an additional 1 hour with a anti mouse or a rabbit horseradish peroxidase (HRP) secondary antibody (Dako, 1:1000) in PBST-M followed by a final wash consisting of six washes with TBST at 5 minutes per wash. Enhanced chemiluminescence (ECL, Amersham) detection reagents were then added onto the membrane which was exposed to a blue light sensitive X-ray film (Fuji Photo Film Co Ltd) and developed in an automated X-ray film processor, (Mediphot 937).

Results

The invention will now be described, by way of example only, by reference to the accompanying figures, of which:

NU8296 corresponds to 3-(4-chlorophenyl)-3-((1S,3R)-3-hydroxy cyclopentyloxy)-2-(4-nitrobenzyl)isoindolin-1-one, a further compound in the isoindolin-1-one series, the structure of which is given below.

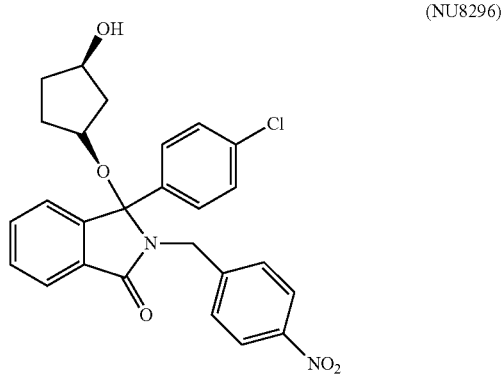

(NU8296)

Nutlin-3 is the proprietary name for (±)-4-[4,5-bis-(4-Chlorophenyl)-2-(2-isopropoxy-4-methoxyphenyl)-4,5-dihydroimidazole-1-carbonyl]-piperazin-2-one, the structure of which is given below. Nutlin-3 has been found to have an $IC_{50}$ of 45±4 nM and is included in the tests to provide a comparison of the efficacy of the inventive compounds with a known inhibitor of the MDM2-p53 interaction.

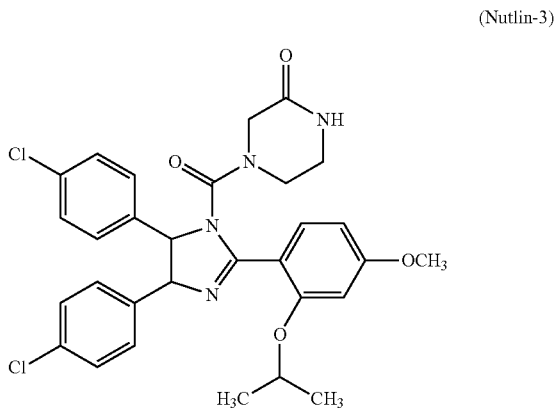 [SMILES: COc1ccc(C2=NC(c3ccc(Cl)cc3)C(c3ccc(Cl)cc3)N2C(=O)N2CCNC(=O)C2)c(OC(C)C)c1]

(Nutlin-3)

Figure 1:
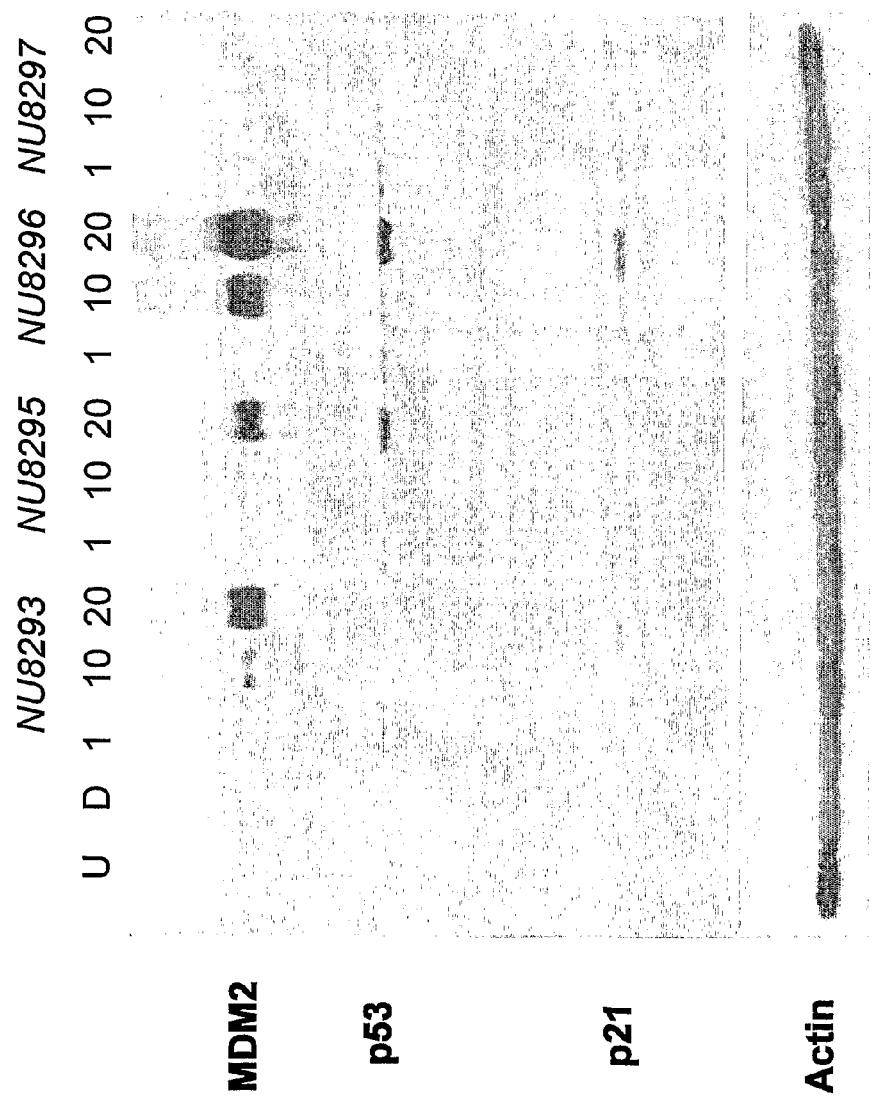
FIG. 1 is a Western Blot assay illustrating the effects of NU8293, NU8295, NU8296 and NU8297 in the SJSA-1 cell line.

FIG. 1 shows the induction of increased levels of p53, p21 and MDM2 protein by treatment of MDM2 amplified SJSA-1 cells with NU8293, NU8295 and NU8291 in the 1-20 µM concentration range. This is consistent with the inhibition of MDM2-p53 binding and release of p53 activity from negative regulation by MDM2 in these cells, resulting in the increased expression and accumulation of MDM2 and p21 proteins. NU8297 did not show any evidence of activity in this experiment.

Figure 2:
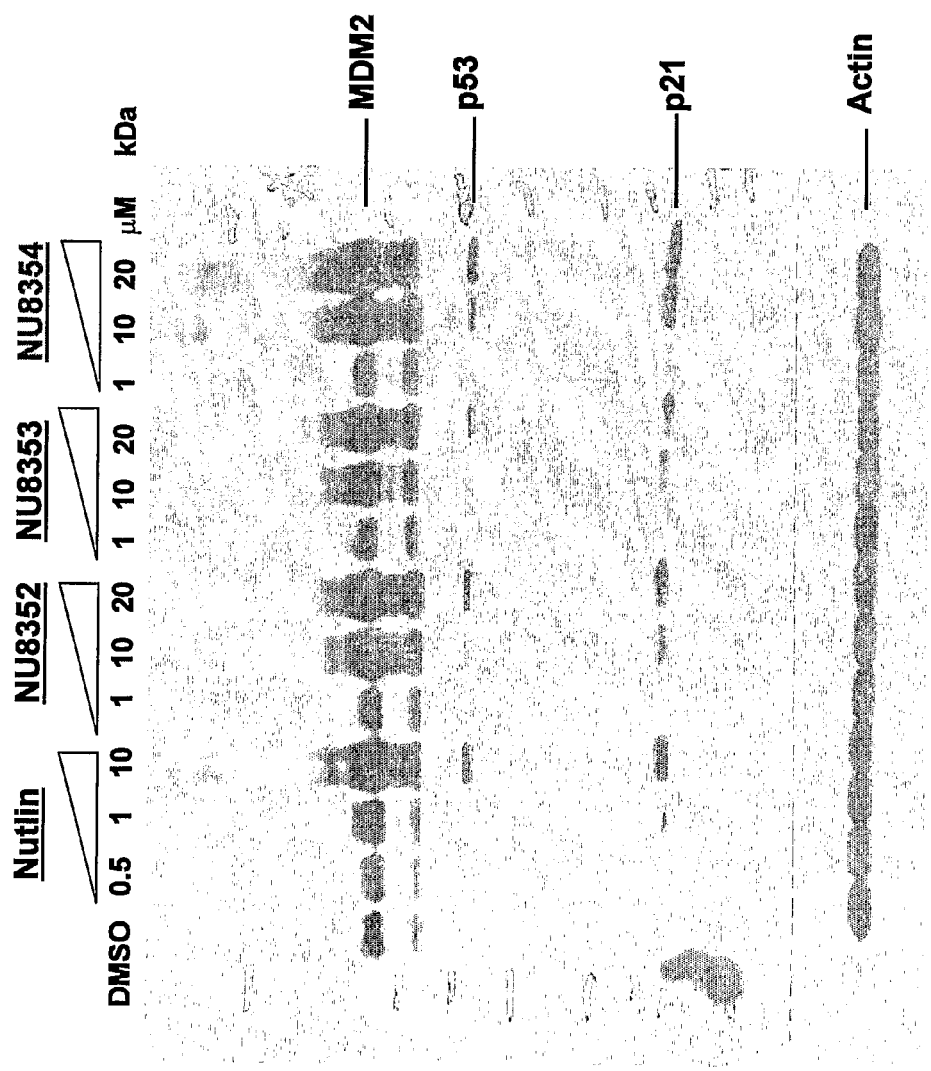
FIG. 2 is a Western Blot assay illustrating the effects of NU8352, NU8353 and NU8354 compared with the effects with Nutlin-3 in the SJSA-1 cell line.

FIG. 2 shows that NU8534 treatment results in strong induction of MDM2, p53, and p21, when compared with the positive control Nutlin-3; this is clear, for instance, from a comparison of the effects at a concentration of 10 µM. These results are consistent with the transcriptional activation of p53 resulting from its release from MDM2 inhibition.

Figure 3:
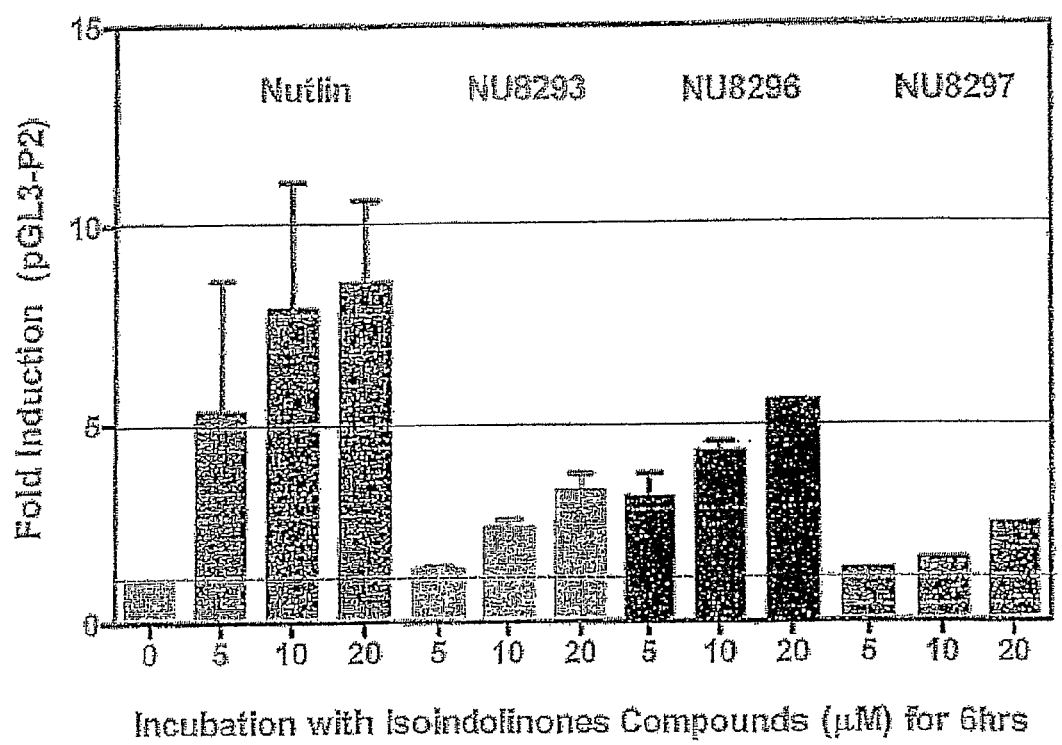
FIG. 3 is a graph illustrating the effect of the NU8293, NU8296 and NU8297 isoindolinones on p53-dependent transcriptional activity measured by a Luciferase based reporter genes assay.

FIG. 3 shows examples of activation of p53 dependent transcriptional activity by NU8293, NU8296 and NU8297 measured by a luciferase based p53-dependent reporter gene assay. This provides further evidence that this series of compounds specifically induces p53-dependent transcriptional activity, consistent with the release of active p53 by inhibition of MDM2-p53 binding in intact cells. The time course of activation is similar to that seen with nutlin-3 and concentration ranges required are comparable.

Figure 4:
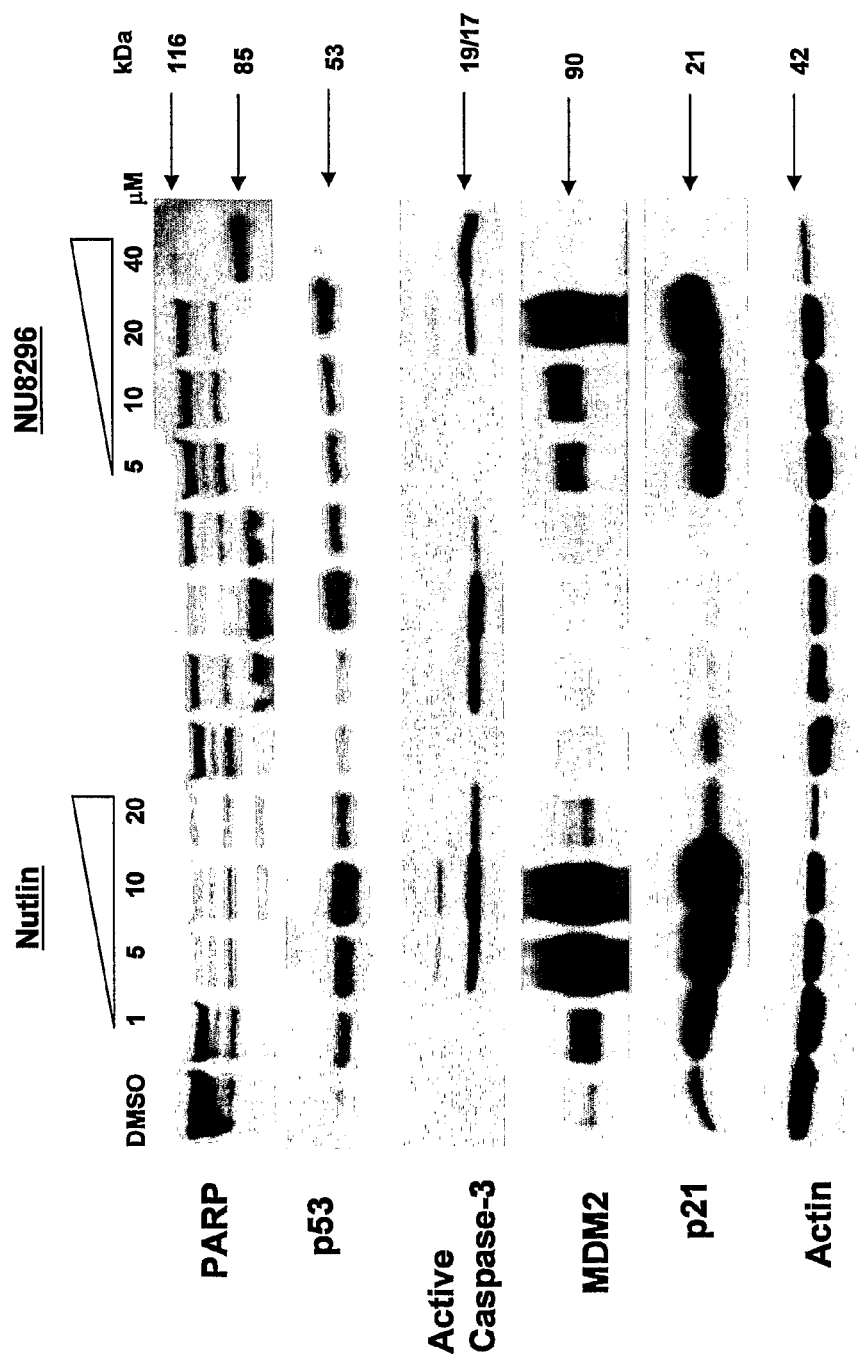
FIG. 4 is a western blot illustrating the dose response effects of NU8296 and Nutlin-3 (and NU8291, which is not part of this invention) on PARP and Caspase 3 cleavage in the SJSA-1 cell line.

FIG. 4 shows the dose dependence of PARP and caspase-3 cleavage in SJSA-1 cells detected after 48 hours of treatment with NU8296 in comparison to nutlin-3. The levels of PARP and caspase-3 cleavage are comparable to those observed with nutlin-3 in the same dose range.

Figure 5:
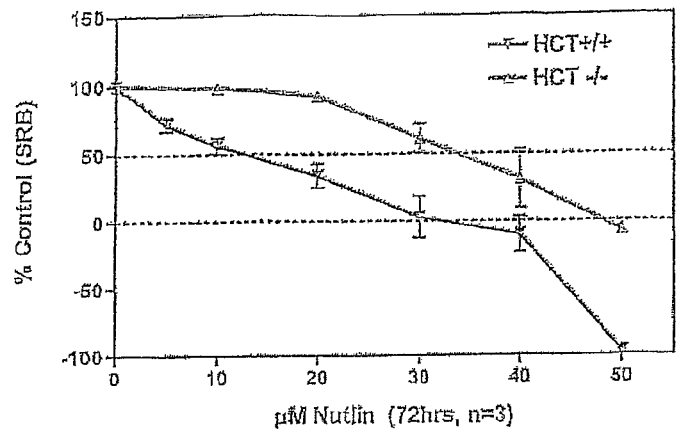
FIG. 5 is a graph illustrating the growth inhibitory effects of Nutlin-3 in p53 wild-type and p53 deleted versions of the HCT116 cell line with concentrations for 50% growth inhibition shown.
Figure 6:
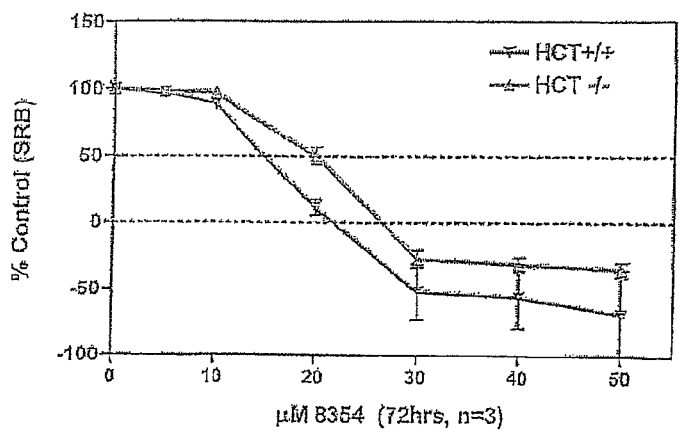
FIG. 6 is a graph illustrating the effect of NU8354 as a growth inhibitor in wild-type and p53 mutant versions of the HCT116 cell line with concentrations for 50% growth inhibition shown.

FIGS. 5 and 6 show that NU8534 is growth inhibitory in wild-type p53 HCT116 cells, as is Nutlin-3. These effects are consistent with the transcriptional activation of p53 and consequent induction of the $p21^{WAF1}$ cyclin dependent kinase inhibitor and hence growth arrest. Furthermore, NU8354 displays greater growth inhibition in the p53 wt HCT116 cell line than the p53−/− HCT116 cells, as does Nutlin-3. These effects demonstrate a predominantly p53-dependent mechanism of growth inhibitory activity. In addition, NU8354 shows greatest growth inhibitory activity in MDM2 amplified and p53 wt cell lines.

Figure 7:
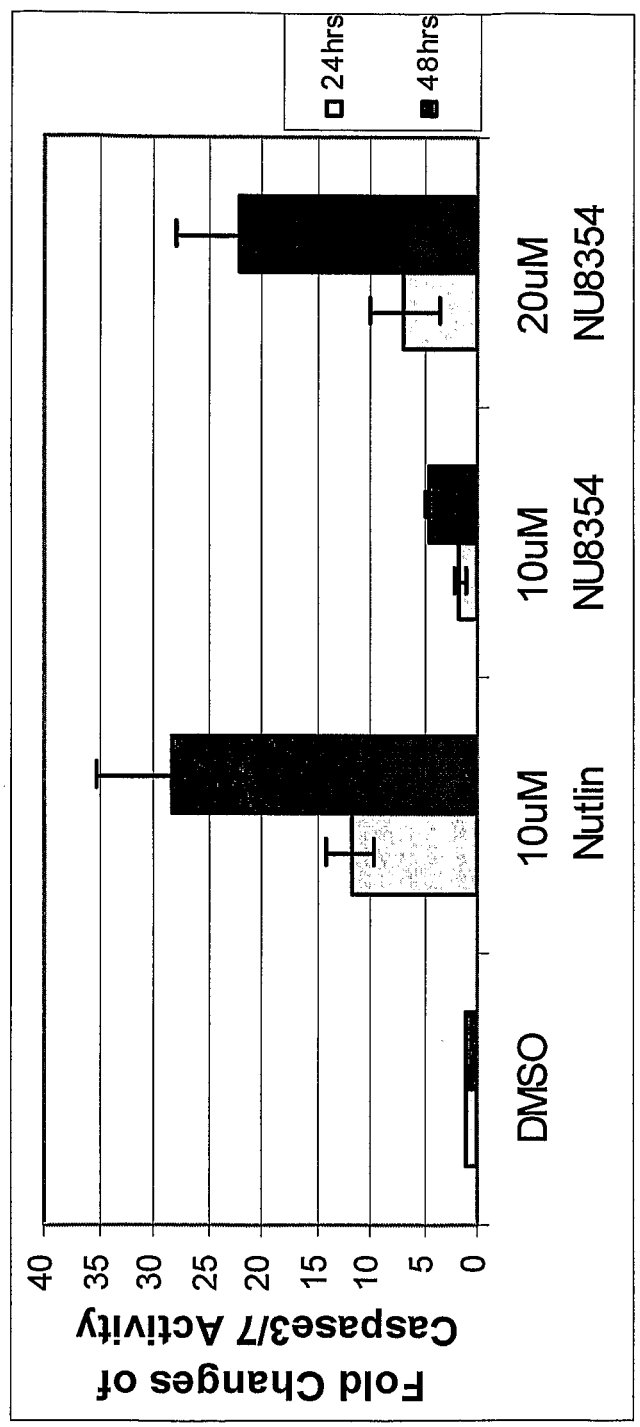
FIG. 7 is a graph illustrating the induction of Caspase 3 and 7 enzymatic activity by NU8354 in the SJSA-1 cell line.

FIG. 7 shows that NU8354 induces Caspase 3 and 7 enzymatic activity over a 24 and 48 hr exposure in SJSA cells; this is an indication of the induction of apoptosis and is consistent with the western blot evidence of PARD and caspase-3 cleavage.

Figure 8:
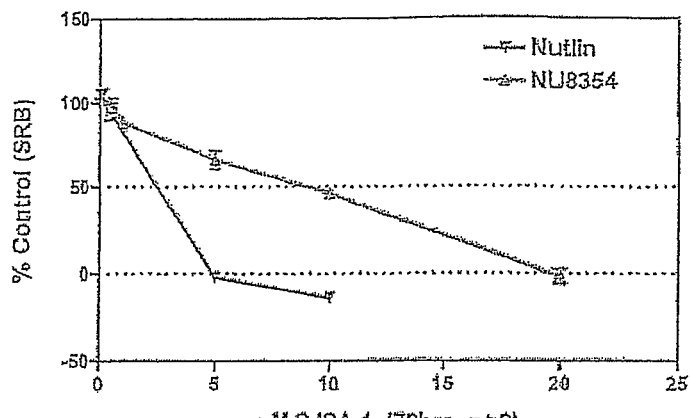
FIG. 8 is a graph illustrating the growth inhibition dose response to exposure of Nutlin-3 and NU8354 in the SJSA-1 cell line.
Figure 9:
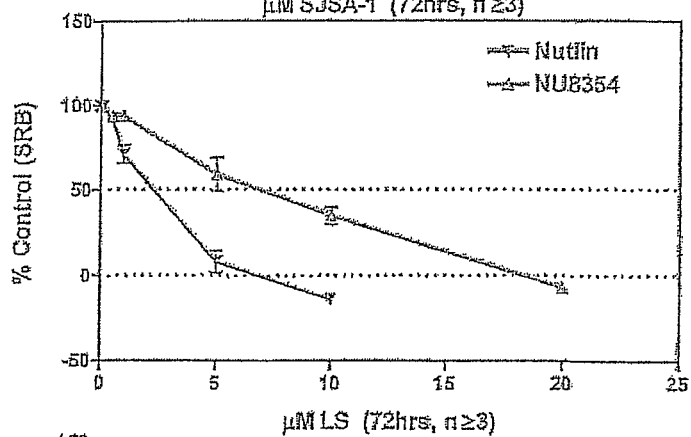
FIG. 9 is a graph illustrating the growth inhibition dose response to exposure of Nutlin-3 and NU8354 in the LS cell line.
Figure 10:
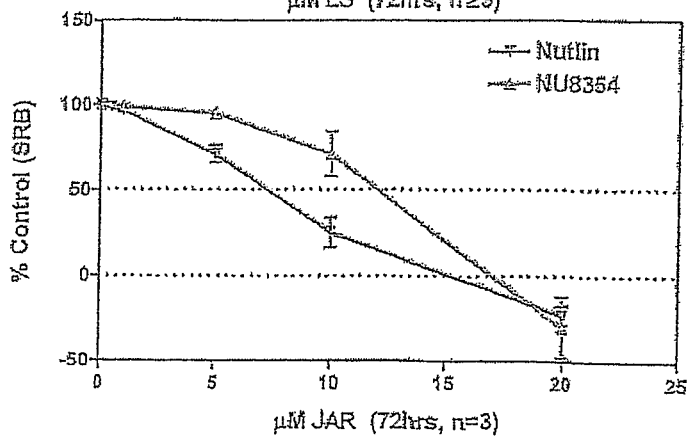
FIG. 10 is a graph illustrating the growth inhibition dose response to drug exposure of Nutlin-3 and NU8354 in the TAR cell line.

FIGS. 8 to 10 show growth inhibition by NU8354 in the 5-20 µM concentration range for a panel of MDM2 amplified cell lines, which are generally found to be more sensitive than cell lines not amplified for MDM2.

Figure 11:
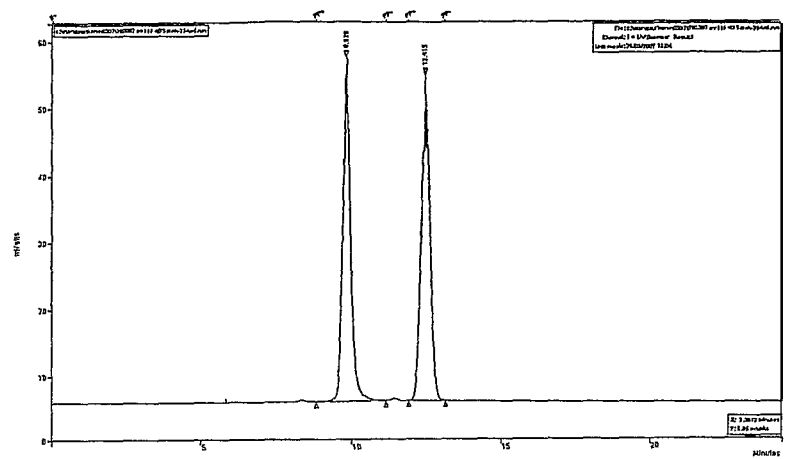
FIG. 11 is an analytical chromatogram of NU8354 on a Chiracel AD column (4.6 mm×25 cm) with 40% EtOH, pentane as eluant in isocratic mode.

FIG. 11 shows the analytical chromatogram of NU8354 on a Chiracel AD column (4.6 mm×25 cm) with 40% EtOH, pentane as eluant in isocratic mode. The (+)-enantiomer NU8354A has a retention time of 9.8 minutes, whereas the (−)-enantiomer NU8354B elutes at 12.4 minutes. The absolute configuration of the enantiomers has not been determined.

Figure 12:
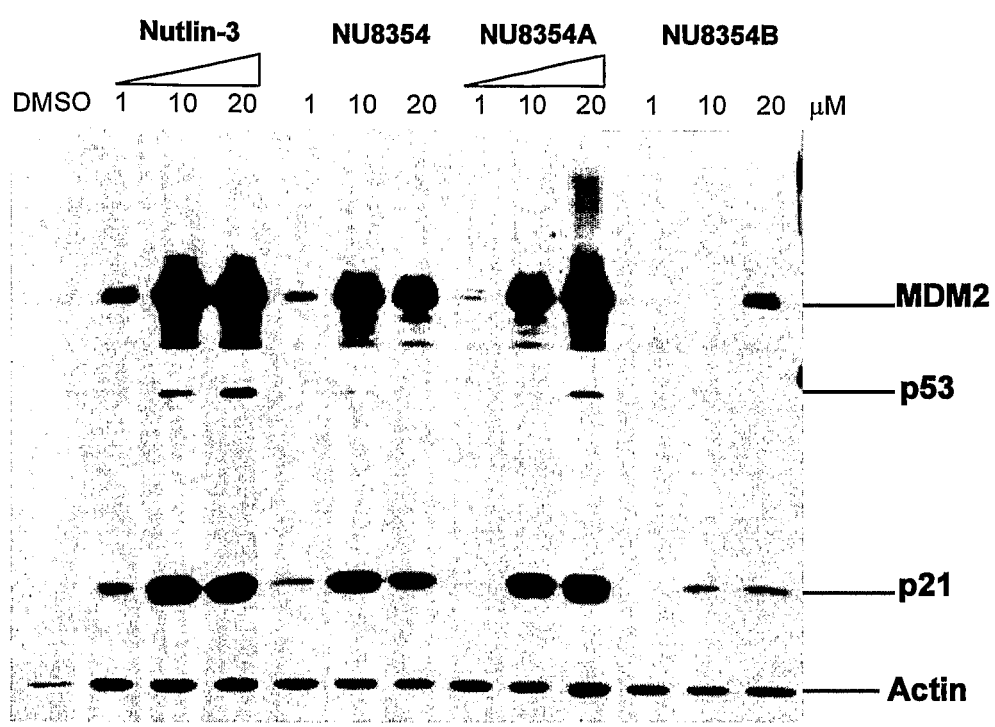
FIG. 12 shows the cellular activity of Nutlin-3, NU8354 and enantiomers NU8354A and NU8354B in SJSA-1 cells by Western blotting.

FIG. 12 shows the cellular activity of Nutlin-3, NU8354 and enantiomers NU8354A and NU8354B in SJSA-1 cells by Western blotting. Nutlin-3 shows a strong dose dependent increase in MDM2, p53 and p21 levels from 1 to 20 µM. A similar but weaker effect is observed for NU8354 with a maximal effect observed at 10 µM. The activity of NU8354A is slightly weaker than Nutlin at the 20 µM dose and significantly weaker at the lower doses. The NU8354B enantiomer displays little cellular activity with weak induction of p21 and MDM2 at the 20 µM dose. These results are consistent with NU8354A being the enantiomer which confers the majority of the biological activity of the racemate and the observed $IC_{50}$s in the in vitro ELISA assay.

In summary, NU8534 shows a range of cellular effects consistent with the disruption of MDM2-p53 binding, the proposed mechanism of action. In comparison with the positive control Nutlin-3, the effects are similar across a panel of cell lines with differing p53 and MDM2 status, in terms of p53 activation, growth inhibition and apoptosis.

Synthetic Data

The present invention will now be described further by way of example only. The following examples and description of stages in synthetic routes of preparation of various compounds of interest serve further to illustrate the present invention.

3-(4-Fluorophenyl)-3-hydroxy-2-propyl-2,3-dihydroisoindol-1-one

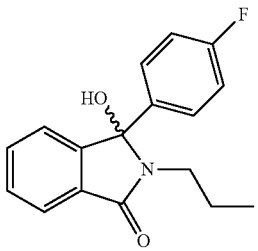 [SMILES: CCCN1C(=O)c2ccccc2C1(O)c1ccc(F)cc1]

THF (25 mL) was added to 2-(4-fluorobenzoyl)benzoic acid (5 g, 20.4 mmol) followed by thionyl chloride (2.97 mL, 40.9 mmol) and a catalytic amount of DMF (3 drops). The system was stirred under nitrogen for 4 h at room temperature. Removal of the solvent gave 3-chloro-3-(4-fluorophenyl)-3H-isobenzofuran-1-one as a colourless oil (5.35 g, 20.4 mmol, 100%).

Distilled THF (25 mL) was added to 3-chloro-3-(4-chlorophenyl)-3H-isobenzofuran-1-one (5.35 g, 20.4 mmol) followed by n-propylamine (1.85 mL, 22.5 mmol), triethylamine (2.85 mL, 26.5 mmol) resulting in the formation a creamy white/yellow precipitate. The mixture was stirred at room temperature under nitrogen for 4 h then the solvent was removed under vacuum. The residue was taken up in ethyl acetate (30 mL), washed with water (3×20 mL), brine (10 mL), dried (MgSO$_4$) and evaporated. Recrystallisation (ethyl acetate) gave the title compound as a white solid (4.35 g, 15.2 mmol, 75%); $R_f$=0.48 (40:60: EtOAc: petrol). mp 172.3-174.6° C. $\lambda_{max}$ (CH$_3$OH)/nm 210. IR: 3231, 2965, 1673, 1602, 1504, 1407, 1223 cm$^{-1}$. $^1$H NMR: (300 MHz, d$_6$-DMSO) δ 0.75 (t, 3H, J=7.4 Hz, CH$_2$—CH$_2$—CH$_3$), 1.42 (m, 2H, N—CH$_2$—CH$_2$), 2.87 (m, 1H, N—CH$_2$), 3.14 (m, 1H, N—CH$_2$), 7.15 (m, 2H, Ar—H), 7.25 (m, 1H, Ar—H), 7.35 (m, 2H, Ar—H), 7.53 (dquin, 2H, J=7.4, 1.4 Hz, Ar—H), 7.71 (m, 1H, Ar—H). $^{13}$C NMR: (75 MHz, d$_6$-DMSO) δ 11.8, 22, 90.4, 115.4, 115.7, 122.7, 123, 128.3, 128.4, 129.5, 130.8, 132.7, 136.8, 136.9, 149.7, 160.5, 162.2, 163.7, 166.8. LCMS (ESI+) m/z=161.1, 227.1, 268.1, 286.1 [M+H]$^+$. Anal. Calcd. for C$_{17}$H$_{16}$FNO$_2$: C, 71.56; H, 5.65; N, 4.91%. Found C, 71.61; H, 5.70; N, 4.99%. HRMS (EI) m/z Calcd. for C$_{17}$H$_{16}$FNO$_2$: 285.1165. Found 285.1166.

3-(4-Fluorophenyl)-3-(3-hydroxycyclopentyloxy)-2-propyl-2,3-dihydroisoindol-1-one

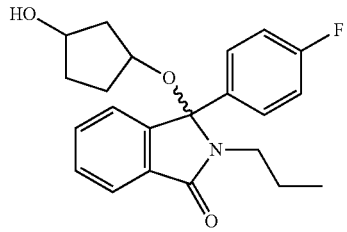 [SMILES: CCCN1C(=O)c2ccccc2C1(OC1CCC(O)C1)c1ccc(F)cc1]

Distilled THF (20 mL) was added to 3-(4-fluorophenyl)-3-hydroxy-2-propyl-2,3-dihydroisoindol-1-one (200 mg, 0.7 mmol) followed by thionyl chloride (0.06 mL, 0.84 mmol) and a catalytic amount of DMF (3 drops). The mixture was stirred at room temperature under nitrogen for 4 h and monitored by TLC. Removal of the solvent under vacuum gave 3-chloro-3-(4-fluorophenyl)-2-propyl-2,3-dihydroisoindol-1-one as a colourless oil (212 mg, 0.69 mmol, 100%) which was used immediately without further purification.

Distilled THF was added to 3-chloro-3-(4-fluorophenyl)-2-propyl-2,3-dihydroisoindol-1-one (212 mg, 0.69 mmol) followed by 1,3-cyclopentanediol (0.65 mL, 6.9 mmol). The mixture was stirred at room temperature under nitrogen for 4 h and monitored by TLC. On completion the solvent was removed under vacuum, the residue was taken up in ethyl acetate (30 mL), washed with water (3×20 mL), brine (10 mL) and dried (MgSO$_4$). The solvent was removed to give the crude product. HPLC (H$_2$O:MeOH, 270 nm) gave NU8279 as a clear glass (126 mg, 0.34 mmol, 49%); $R_f$=0.21 (40:60: EtOAc:petrol). $\lambda_{max}$ (CH$_3$OH)/nm 220.5. IR: 3387, 2936, 1683, 1604, 1505, 1366 cm$^{-1}$. $^1$H NMR: (300 MHz, d$_4$-MeOH) δ 0.77 (t, 3H, J=7.4 Hz, CH$_2$—CH$_2$—CH$_3$), 1.15 (m, 1H, N—CH$_2$—CH$_2$), 1.32 (m, 1H, N—CH$_2$—CH$_2$), 1.40-2.05 (m, 6H, cyclopentane), 3.12 (m, 1H, N—CH$_2$), 3.29 (m, 1H, N—CH$_2$), 3.90 (m, 1H, cyclopentane), 4.31 (m, 1H, cyclopentane), 7.07 (t, 2H, J=9 Hz, Ar—H), 7.23 (m, 1H, Ar—H), 7.39 (m, 2H, Ar—H), 7.60 (m, 2H, Ar—H), 7.87 (m, 1H, Ar—H). $^{13}$C NMR: (125 MHz, d$_4$-MeOH) δ 12.2, 22.9, 32.7, 33.1, 34.2, 43.1, 44.3, 44.8, 72.8, 73, 75.7, 96.5, 116.3, 116.6, 124.3, 125.7, 130, 130.1, 131.6, 133.6, 134.1, 137.1, 148.1, 166.2, 170.7. LCMS (ESI+) m/z=227.1, 268.1, 370.3 [M+H]$^+$, 392.3 [M+Na]$^+$. HRMS (EI) m/z Calcd. for C$_{22}$H$_{24}$FNO$_3$: 369.1740. Found 369.1737.

3-(4-Chlorophenyl)-3-hydroxy-2-(4-nitrobenzyl)-2,3-dihydroisoindol-1-one

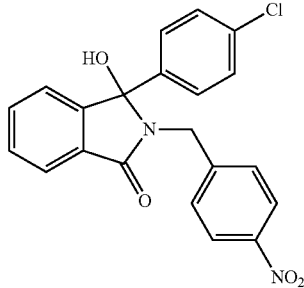

THF (25 mL) was added to 2-(4-chlorobenzoyl)benzoic acid (1 g, 3.8 mmol) followed by thionyl chloride (0.55 mL, 7.6 mmol) and a catalytic amount of DMF (3 drops). The system was stirred under nitrogen for 4 h at room temperature and monitored by TLC. Removal of the solvent gave 3-chloro-3-(4-chlorophenyl)-3H-isobenzofuran-1-one as a colourless oil (1.06 g, 3.8 mmol, 100%).

Distilled THF (25 mL) was added to 3-chloro-3-(4-chlorophenyl)-3H-isobenzofuran-1-one (3.2 g, 11.5 mmol), 4-nitrobenzylamine hydrochloride (2.3 g, 12.6 mmol), and triethylamine (4.8 mL, 34.5 mmol). The mixture was stirred at room temperature under nitrogen for 4 h and monitored by TLC. On completion the solvent was removed under vacuum, the residue was taken up in ethyl acetate (30 mL), washed with water (3×20 mL), brine (10 mL) and dried (MgSO$_4$). The solvent was removed under vacuum. Recrystallisation (ethyl acetate) gave 3-(4-Chlorophenyl)-3-hydroxy-2-(4-nitrobenzyl)-2,3-dihydroisoindol-1-one as a light yellow solid (2.95 g, 7.47 mmol, 65%); $R_f$=0.4 (40:60: EtOAc:petrol). mp 197.1-199.7° C. $\lambda_{max}$ (CH$_3$OH)/nm 225. IR: 3215, 1676, 1517, 1395, 1341 cm$^1$. $^1$H NMR: (300 MHz, d$_6$-DMSO) δ 4.35 (d, 1H, J=16.3 Hz, N—CH$_2$), 4.61 (d, 1H, J=16.3 Hz, N—CH$_2$), 7.28 (m, 4H, Ar—H), 7.45 (m, 3H, Ar—H), 7.58 (m, 2H, Ar—H), 7.79 (m, 1H, Ar—H), 8.05 (m, 2H, Ar—H). $^{13}$C NMR: (75 MHz, d$_6$-DMSO) δ 42.1, 90.5, 123.1, 123.3, 128.4, 128.7, 129.1, 129.9, 130.3, 133.2, 133.3, 138.9, 146.4, 146.5, 149.4, 167.1. LCMS (ESI+) m/z=307.2, 368.2, 377.1. Anal. Calcd. for C$_{21}$H$_{15}$ClN$_2$O$_4$: C, 63.89; H, 3.83; N, 7.10%. Found C, 63.78; H, 3.92; N, 7.12%. HRMS (EI) m/z Calcd. for C$_{21}$H$_{15}$ClN$_2$O$_4$: 394.0720. Found 394.0714.

3-(4-Chlorophenyl)-2-[1-(4-chlorophenyl)-ethyl]-3-hydroxy-2,3-dihydroisoindol-1-one

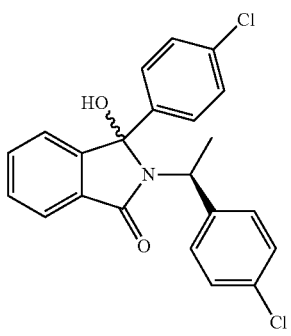 [SMILES: C[C@@H](c1ccc(Cl)cc1)N1C(=O)c2ccccc2C1(O)c1ccc(Cl)cc1]

To a solution of 2-(4-chlorobenzoyl)benzoic acid (5 g, 19.2 mmol, 1 equiv.) in dry THF (20 mL) was added under nitrogen atmosphere thionylchloride (3.0 mL, 38.3 mmol, 2 equiv.) and 3 drops of anhydrous DMF. The reaction mixture was stirred for 4 h at room temperature and concentrated in vacuo. The resulting pale yellow oil was taken up in dry THF (20 mL), and (S)-4-chloro-α-methylbenzylamine (2.43 g, 15.6 mmol, 1.1 equiv.) and DIPEA (3.49 mL, 21.1 mmol, 1.1 equiv.) were added under nitrogen atmosphere. The reaction mixture was stirred overnight at room temperature and the solvents were removed in vacuo. The residue was taken up in EtOAc (100 mL), filtered, and the filtrate washed with water (3×50 mL) and brine (1×50 mL). The organic layer was dried over MgSO$_4$, filtered and concentrated in vacuo to afford a solid, which was recrystallised (EtOAc/Petrol) as a white crystalline powder (3.10 g, 55%). $^1$H NMR (300 MHz, CDCl$_3$): Mixture of two diastereoisomers: 7.74-7.09 (m, 13H, Ar—H and OH), 4.52 and 4.45 (q, J=6.9 Hz, 1H, CH*), 1.75 and 1.48 (d, J=7.2 Hz, 3H, CH$_3$). $^{13}$C NMR (75 MHz, CDCl$_3$): Mixture of two diastereoisomers: 166.94, 166.43, 149.17, 149.11, 142.01, 141.51, 139.65, 139.33, 133.24, 133.14, 132.90, 131.76, 131.60, 131.54, 131.47, 129.79, 129.71, 129.52, 128.67, 128.62, 128.26, 127.88, 127.84, 123.13, 122.74, 122.70, 91.19, 90.94, 51.22, 50.46, 20.21, 18.24. FTIR: 3103 (OH), 1665 (C=O) cm$^{-1}$. m/z (ES): 398 [M+H]$^+$. Anal.: calc. for C$_{22}$H$_{17}$Cl$_2$NO$_2$+0.3 H$_2$O: C, 65.45; H, 4.40; N, 3.47. Found: C, 65.00; H, 4.30; N, 3.60.

General Procedure A

To a solution of the corresponding isoindolone (1.37 mmol, 1 equiv.) in dry THF (10 mL) was added under nitrogen atmosphere, thionylchloride (214 μL, 2.75 mmol, 2 equiv.) and 3 drops of DMF. The reaction mixture was stirred for 4 h at room temperature and concentrated in vacuo. The resulting pale yellow oil was taken up in dry THF (10 mL), and the alcohol (2.75 mmol, 2 equiv) and potassium carbonate (380 mg, 2.75 mmol, 2 equiv.) were added. The reaction mixture was stirred overnight at room temperature and the solvents were removed in vacuo. The residue was taken up in EtOAc (50 mL) and washed with water (3×25 mL) and brine (1×25 mL). The organic layer was dried over MgSO$_4$, filtered and concentrated in vacuo to afford an oil which was purified by flash chromatography (silica; EtOAc/petrol).

General Procedure B: Synthesis of 3-Alkoxy-3-(4-chlorophenyl)isoindolin-1-ones

To a solution of the appropriate 3-chloro-3-(4-chlorophenyl)isoindolin-1-one, THF was added the appropriate alcohol (5.0 mol equiv unless stated otherwise) and K$_2$CO$_3$ (5.0 mol equiv unless stated otherwise). The mixture was allowed to stir at room temperature for 4 hours under nitrogen and monitored by TLC. Upon completion the mixture was extracted with EtOAc (15 mL), washed with saturated brine (3×10 mL), water (3×10 mL) and dried (MgSO$_4$). Removal of the solvent under reduced pressure yielded the crude 3-alkoxy-2,3-dihydroisoindolin-1-one.

General Procedure B1: Synthesis of 3-alkoxy-2,3-dihydroisoindolin-1-ones

To a solution of cis-cyclopentane or cis-cyclopentene diol (2.5 equiv) and K$_2$CO$_3$ (2.5 equiv) in THF (3 mL) was added the appropriate 3-chloro-3-(4-chlorophenyl)isoindolin-1-one (1 equiv) in THF (3 mL) dropwise over 3 hours with stirring under nitrogen at room temperature. The solution was stirred for a further hour and monitored by TLC. Upon completion the mixture was extracted with EtOAc (15 mL), washed with saturated brine (3×10 mL), water (3×10 mL) and dried (MgSO$_4$). The solvent was removed under reduced pressure to yield the crude 3-alkoxy-2,3-dihydroisoindolin-1-one.

3-(4-Chlorophenyl)-3-hydroxy-2-(4-chlorobenzyl)-isoindolin-1-one

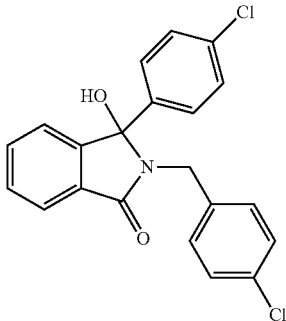 [SMILES: O=C1c2ccccc2C(O)(c2ccc(Cl)cc2)N1Cc1ccc(Cl)cc1]

Distilled THF (25 mL) was added to 3-chloro-3-(4-chlorophenyl)-3H-isobenzofuran-1-one (1.071 g, 3.84 mmol) followed by triethylamine (855.1.1 mg, 8.45 mmol, 1.178 mL) and para-chlorobenzylamine (543.36 mg, 3.84 mmol, 0.467 mL) resulting in the formation of a white precipitate. The mixture was stirred at room temperature under nitrogen for 4 hours and monitored by TLC. Upon completion the mixture was then extracted with EtOAc (15 mL) and washed with saturated sodium bicarbonate (3×10 mL), water (3×10 mL) and dried (Na$_2$SO$_4$). The solvent was removed under reduced pressure and the resultant precipitate recrystallised (EtOAc, petrol) to give the title product as a fine white crystalline solid (1.191 g, 3.20 mmol, 83%). $^1$H NMR: (300 MHz, DMSO) δ ppm 4.23 (d, 1H, J=15.59, H$_9$) 4.45 (d, 1H, J=15.62 H$_{9'}$) 7.25 (m, 9H, H$_1$-H$_5$, H$_{10}$-H$_{13}$) 7.56 (m, 2H, H$_6$-H$_7$) 7.76 (d, 1H, H$_8$). $^{13}$C NMR: (75 Hz, DMSO); δ 42.09 (N—CH$_2$), 90.55 (O—C—N), 122.98, 123.19, 128.02, 128.39, 128.57, 129.76, 130.21, 130.66, 131.60, 133.07, 133.15, 137.44, 139.33, 149.52 (Ar), 167.16 (C=O). Mp: 156.2-156.9° C. IR: 1467, 1661, 3184 cm$^{-1}$.

3-(4-Chlorophenyl)-3-hydroxy-2-propylisoindolin-1-one

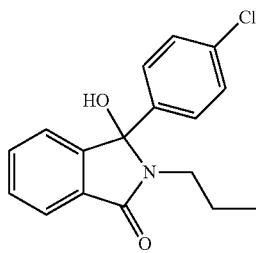

Distilled THF (20 mL) was added to 3-chloro-3-(4-chlorophenyl)-3H-isobenzofuran-1-one (535.4 mg, 1.91 mmol) followed by triethylamine (398.9 mg, 0.549 mL, 3.94 mmol) and n-propylamine (159.8 mg, 0.22 mL, 1.792 mmol). The mixture was stirred at room temperature under nitrogen for 4 hours and monitored by TLC. Upon completion the mixture was then extracted with EtOAc (15 mL) and washed with saturated sodium bicarbonate (3×10 mL), water (3×10 mL) and dried (Na$_2$SO$_4$). Recrysallisation from a minimum amount of boiling ethyl acetate and an excess of petrol yielded the title product as a white crystalline solid (425 mg, 1.409 mmol, 77%). $^1$H NMR: (300 Hz, CDCl$_3$) δ ppm 0.76 (t, 3H, H$_{11}$), 1.45 (m, 2H, H$_{10}$), 2.86 (m, 1H, H$_9$), 3.36 (m, 1H, H$_{9'}$), 7.16 (d, 1H, H$_5$), 7.38 (dd, 4H, H$_1$-H$_4$), 7.45 (m, 2H, H$_6$-H$_7$), 7.70 (d, 1H, H$_8$). $^{13}$C NMR: (75 Hz, DMSO); δ 11.87 (N—CH$_2$—CH$_2$—CH$_3$), 21.96 (N—CH$_2$—CH$_2$), 40.69 (N—CH$_2$), 90.50 (O—C—N), 122.75, 122.99, 128.24, 128.76, 129.58, 131.04, 131.24, 132.73, 133.13, 139.94, 149.59 (Ar), 166.96 (C=O). Mp: 201.5-201.7° C. IR: 1466, 1608, 1664, 2968, 3157 cm$^{-1}$.

2-Benzyl-3-(4-chlorophenyl)-3-hydroxy-2,3-dihydroisoindolin-1-one

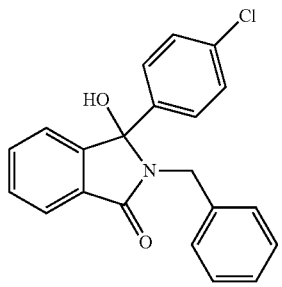 [SMILES: O=C1c2ccccc2C(O)(c2ccc(Cl)cc2)N1Cc1ccccc1]

Distilled THF (25 mL) was added to 3-chloro-3-(4-chlorophenyl)-3H-isobenzofuran-1-one (1.042 g, 3.84 mmol) followed by triethylamine (777.1 mg, 7.68 mmol, 1.06 mL)) and benzylamine (616 mg, 5.76 mmol, 0.79 mL) resulting in the formation of a yellow/cream precipitate. The mixture was stirred at room temperature under nitrogen for 4 hours and monitored by TLC. Upon completion the mixture was then extracted with EtOAc (15 mL) and washed with saturated sodium bicarbonate (3×10 mL), water (3×10 mL) and dried (Na$_2$SO$_4$). Recrystallisation of the cream precipitate from a minimum amount of boiling ethyl acetate and excess petrol to yielded the title product as a white crystalline solid (1.0378 g, 2.96 mmol, 77% yield). $^1$H NMR: (300 Hz, CDCl$_3$) δ ppm 4.24 (d, 1H, J=15.48 Hz, H$_9$), 4.42 (d, 1H, J=15.48 Hz, H$_{9'}$), 7.16 (m, 5H, H$_{10}$-H$_{14}$), 7.25 (m, 5H, H$_1$-H$_5$), 7.56 (m, 2H, H$_6$-H$_7$), 7.75 (d, 1H, H$_8$). $^{13}$C NMR: (75 Hz, DMSO); δ 42.80 (N—CH$_2$), 90.60 (O—C—N), 122.95, 123.18, 126.78, 128.07, 128.35, 128.41, 128.51, 129.70, 130.81, 132.97, 133.07, 138.42, 139.46, 149.59 (Ar), 167.20 (C=O). IR: 1463, 1664, 2936, 3285 cm$^{-1}$.

3-(4-Chlorophenyl)-3-hydroxy-2-(4-methylbenzyl)-isoindolin-1-one

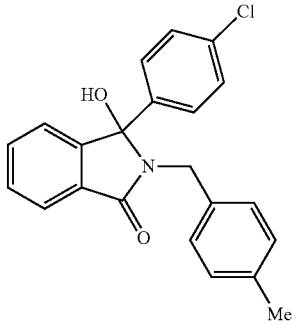 [SMILES: Cc1ccc(CN2C(=O)c3ccccc3C2(O)c2ccc(Cl)cc2)cc1]

Distilled THF (25 mL) was added to 3-chloro-3-(4-chlorophenyl)-3H-isobenzofuran-1-one (1.071 g, 3.84 mmol) followed by triethylamine (855.1.1 mg, 8.45 mmol, 1.178 mL) and para-methylbenzylamine (465.3 mg, 3.84 mmol, 0.489 mL) resulting in the formation of a bright yellow precipitate. The mixture was stirred at room temperature under nitrogen for 4 hours and monitored by TLC. Upon completion the mixture was then extracted with EtOAc (15 mL) and washed with saturated sodium bicarbonate (3×10 mL), water (3×10 mL) and dried (Na$_2$SO$_4$). Recrystallisation of the cream/yellow residue from a minimum amount of boiling ethyl acetate and excess petrol yielded the title product as a fine pale yellow crystalline solid (1.090 g, 3.10 mmol, 81%). $^1$H NMR: (300 MHz, DMSO) δ ppm 2.21 (s, 3H, H$_{12}$), 4.20 (d, 1H, J=15.62 Hz, H$_9$), 4.40 (d, 1H, J=15.36 Hz, H$_{9'}$), 6.95 (d, 2H J=7.97 Hz, H$_{11}$, H$_{13}$), 7.04 (d, 2H J=8.00 Hz, H$_{10}$-H$_{14}$) 7.27 (m, 5H, H$_1$-H$_5$), 7.55 (m, 2H, H$_6$-H$_7$) 7.74 (d, 1H, H$_8$). $^{13}$C NMR: (75 Hz, DMSO) δ 20.90 (CH$_3$), 42.53 (N—CH$_2$), 90.57 (O—C—N), 122.89, 123.15, 128.36, 128.38, 128.61, 129.66, 130.85, 132.91, 133.03, 135.37, 135.84, 139.51 (Ar), 167.10 (C=O). IR: 1398, 1468, 1660, 2921, 3138 cm$^{-1}$.

2-(4-(Aminomethyl)benzonitrile)-3-(4-chlorophenyl)-3-hydroxyisoindolin-1-one

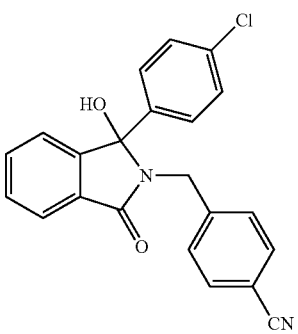 [SMILES: N#Cc1ccc(CN2C(=O)c3ccccc3C2(O)c2ccc(Cl)cc2)cc1]

Distilled THF (25 mL) was added to 3-chloro-3-(4-chlorophenyl)-3H-isobenzofuran-1-one (1.071 g, 3.84 mmol) followed by triethylamine (777.14 mg, 7.68 mmol, 1.07 mL) and 4-(aminomethyl)benzonitrile (507.6 mg, 3.84 mmol). The mixture was stirred at room temperature under nitrogen for 4 hours and monitored by TLC. Upon completion the mixture was then extracted with EtOAc (15 mL) and washed with saturated sodium bicarbonate (3×10 mL), water (3×10 mL) and dried (Na$_2$SO$_4$). Removal of solvent after washing produced a viscous orange oil. Trituration under petrol yielded a yellow/orange solid which was recrystallised from a minimum amount of boiling ethyl acetate and excess petrol to produce the title product as a fine pale yellow crystalline solid (665 mg, 1.83 mmol, 50%). $^1$H NMR: (300 MHz, DMSO) δ ppm 4.31 (d, 2H, J=16.12 Hz, H$_9$), 4.55 (d, 2H J=16.15 Hz, H$_{9'}$), 7.26 (m, 5H, H$_1$-H$_5$), 7.37 (d, 2H J=8.29 Hz, H$_{10}$, H$_{13}$), 7.58 (m, 2H, H$_6$-H$_7$), 7.64 (d, 2H J=8.26 Hz, H$_{11}$-H$_{12}$), 7.77 (d, 1H, H$_8$). $^{13}$C NMR: (75 Hz, DMSO); δ 42.51 (N—CH$_2$), 60.02 (CN) 90.57 (O—C—N), 109.82, 119.08, 123.06, 123.25, 128.40, 128.62, 129.16, 129.83, 130.54, 132.03, 133.19, 133.26, 133.52, 139.19, 144.24, 149.48 (Ar), 167.23 (C=O). IR: 1397, 1655, 2227 cm$^{-1}$.

4-((1-(4-chlorophenyl)-1-(4-hydroxycyclopent-2-enyloxy)-3-oxoisoindolin-2-yl)methyl)benzonitrile (NU8292)

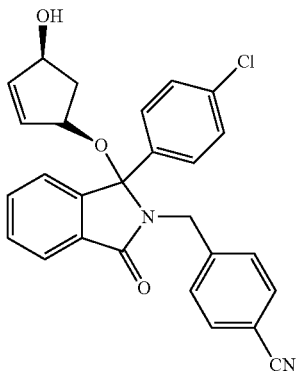

Distilled THF (10 mL) was added to 2-(4-(aminomethyl)benzonitrile)-3-(4-chlorophenyl)-3-hydroxyisoindolin-1-one (400 mg, 1.10 mmol), thionyl chloride (288.9 mg, 2.42 mmol, 0.18 mL) and catalytic DMF (3 drops) as for general procedure B1. 3-Chloro-3 chlorophenyl)-2-(4-(aminomethyl)benzonitrile) isoindolin-1-one was produced as a viscous clear oil (419 mg, 1.10 mmol) which was used immediately without further purification. Distilled THF (3 mL) was added to 3-chloro-3-(4-chlorophenyl)-2-(4-(aminomethyl)benzonitrile)isoindolin-1-one (419 mg, 1.10 mmol) and the resultant solution added dropwise to cis-cyclopentene diol (275 mg, 2.75 mmol) and dried K$_2$CO$_3$ (380.05 mg, 2.75 mmol) in distilled THF (3 mL) as for general procedure B1. Removal of the solvent yielded the crude product as a yellow oil (364 mg). Purification by flash column chromatography yielded the title product as a yellow oily solid (105.4 mg, 0.23 mmol, 21%). $^1$H NMR: (300 MHz, DMSO) δ ppm 1.31 (m, 1H, H$_{15/15'}$), 1.73, 2.11 (m, 1H, H$_{15/15'}$), 3.89 (br s, 1H, OH), 4.22 (m, 1H, H$_{16}$), 4.42 (d, 1H, J=7.10 Hz, H$_{9/9'}$), 4.52 (d, 1H J=7.03 Hz, H$_{9/9'}$), 4.98, 5.04 (dd, 1H, H$_{17/18}$), 5.01, 5.27 (dd, 1H, H$_{17/18}$), 5.75 (m, 1H, H$_{14}$), 7.24 (m, 7H, H$_1$-H$_5$, H$_{10}$, H$_{13}$) 7.62 (m, 4H, H$_{6/7}$, H$_{11/12}$), 7.87 (d, 1H, Mp: 126.4-127.8° C.

IR: 1382, 1609, 2229, 3061 cm$^{-1}$. HR-MS (EI): Calculated mass: [M+Na]$^+$479.1133, Found: 479.1134.

3-(4-Chlorophenyl)-3-(4-hydroxycyclopent-2-enyloxy)-2-(4-chlorobenzyl) isoindolin-1-one (NU8293)

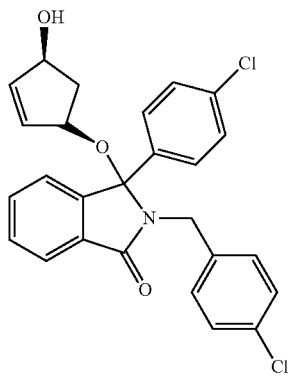

Distilled THF (10 mL) was added to 3-(4-Chlorophenyl)-3-hydroxy-2-(4-chlorobenzyl)-isoindolin-1-one (200 mg, 0.54 mmol), thionyl chloride (141.37 mg, 1.18 mmol, 0.09 mL) and catalytic DMF (3 drops) as for general procedure B1. 3-Chloro-3-(4-chlorophenyl)-2-(4-chlorobenzyl)isoindolin-1-one was produced as a viscous colourless oil (210 mg, 0.54 mmol) which was used immediately without further purification. Distilled THF (3 mL) was added to 3-chloro-3-(4-chlorophenyl)-2-(4-chlorobenzyl)isoindolin-1-one (210.8 mg, 0.54 mmol) and the resultant solution added dropwise to cis-cyclopentene diol (135 mg, 1.35 mmol) and dried potassium carbonate (186.6 mg, 1.35 mmol) in distilled THF (3 mL) as for general procedure B1. Removal of the solvent yielded the crude product as a yellow oil (224 mg). The sample was purified by flash column chromatography (EtOAc:Petrol, 40:60) to yield the title product as a yellow viscous oil. (103.9 mg, 0.23 mmol, 43%). $^1$H NMR: (300 MHz, DMSO) δ ppm 1.27 (m, 1H, H$_{15/15'}$), 1.41, 1.68 (m, 1H, H$_{15/15'}$) 3.86 (m, 1H, H$_{16}$), 4.16 (m, 1H, H$_{14}$) 4.31 (d, 1H, J=15.49, H$_{9/9'}$) 4.50 (d, 1H, J=15.48 H$_{9/9'}$) 4.93, 5.75 (dd, 1H, H$_{17/18}$) 5.25, 5.70 (dd, 1H, H$_{17/18}$), 7.21 (m, 9H, H$_1$-H$_5$, H$_{10}$-H$_{13}$) 7.63 (m, 2H, H$_6$-H$_7$) 7.85 (d, 1H, H$_8$). IR: 1467, 1683, 2926, 3397 cm$^{-1}$.

3-(4-Chlorophenyl)-3-(4-hydroxycyclopent-2-enyloxy)-2-propylisoindolin-1-one (NU8294)

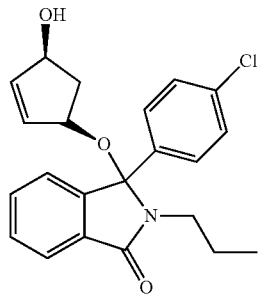

Distilled THF (5 mL) was added to 3-(4-chlorophenyl)-3-hydroxy-2-propylisoindolin-1-one (104 mg, 0.33 mmol), thionyl chloride (86.83 mg, 0.73 mmol, 0.05 mL) and catalytic DMF (3 drops) as for general procedure B1. 3-Chloro-3-(4-chlorophenyl)-2-propylisoindolin-1-one was produced as an orange oil (105 mg, 0.33 mmol) which was used immediately without further purification. Distilled THF (6 mL) was added to 3-chloro-3-(4-chlorophenyl)-2-propylisoindolin-1-one (211.2, 0.66 mmol), cis-cyclopentene diol (330 mg, 3.3 mmol) and potassium carbonate (456 mg, 3.3 mmol) as for general procedure B. Removal of the solvent yielded the crude product as a colourless oil (160.2 mg). The sample was purified by flash column chromatography (EtOAc:Petrol, 40:60) to yield the title product as an colourless viscous oil. (129 mg, 0.43 mmol, 51% yield). $^1$H NMR: (300 Hz, DMSO) δ ppm 0.76 (t, 3H, $H_{11}$), 1.36 (m, 1H, $H_{13}/H_{13'}$), 1.49, 1.76 (m, 1H, $H_{13}/H_{3'}$), 3.12 (m, 2H $H_{10}$) 3.96 (m, 1H, $H_9/H_{9'}$), 4.26 (m, 1H, $H_9/H_{9'}$), 5.29, 5.87, (dd, 1H, $H_{15}/H_{16}$) 5.74, 5.79 (dd, 1H, $H_{15}/H_{16}$) 7.23 (d, 1H), 7.38 (m, 4H, $H_1$-$H_5$), 7.61 (m, 2H, $H_6$-$H_7$), 7.76 (d, 1H, $H_8$). IR: 1365, 1682, 2969, 3363 cm$^{-1}$.

3-(4-Chlorophenyl)-3-(4-hydroxycyclopent-2-enyloxy)-2-(4-methylbenzyl) isoindolin-1-one (NU8295)

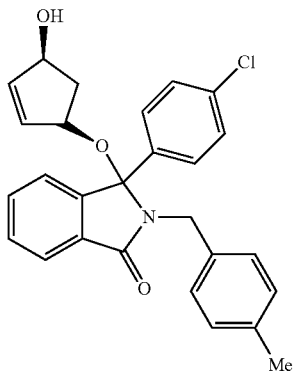

Distilled THF (10 mL) was added to 3-(4-chlorophenyl)-3-hydroxy-2-(4-methylbenzyl)-isoindolin-1-one (400 mg, 1.13 mmol), thionyl chloride (295.8 mg, 2.48 mmol, 0.18 mL) and catalytic DMF (3 drops) as for general procedure B1. 3-Chloro-3-(4-chlorophenyl)-2-(4-methylbenzyl)isoindolin-1-one was produced as a viscous yellow oil (418 mg, 1.13 mmol) which was used immediately without further purification. Distilled THF (3 mL) was added to 3-chloro-3-(4-chlorophenyl)-2-(4-methylbenzyl)isoindolin-1-one (418.1 mg, 1.13 mmol) and the resultant solution added dropwise to cis-cyclopentene diol (285 mg, 2.85 mmol) and dried $K_2CO_3$ (390.41 mg, 2.85 mmol) in distilled THF (3 mL) as for general procedure B1. Removal of the solvent yielded the crude product as a green oil (359 g). Purification by flash column chromatography yielded the title product as a colourless viscous oil (242.1 mg, 0.55 mmol, 50%) $^1$H NMR: (300 MHz, DMSO) δ ppm 1.19 (m, 1H, $H_{16/16'}$), 1.67, 2.05 (m, 1H, $H_{16/16'}$) 2.21 (s, 3H, $H_{12}$), 3.85 (m, 1H, $H_{17}$), 4.06 (d, 1H, J=15.21 Hz, $H_{9/9'}$), 4.32 (m, 1H, $H_{15}$) 4.53 (d, 1H, J=15.21 Hz, $H_{9/9'}$), 4.81, 5.74, (dd, 1H, $H_{18/19}$) 5.20, 5.66 (dd, 1H, $H_{18/19}$), 6.95 (m, 4H, $H_{10}$, $H_{11}$, $H_{13}$, $H_{14}$), 7.25 (m, 5H, $H_1$-$H_5$), 7.65 (m, 2H, $H_6$-$H_7$) 7.74 (d, 1H, $H_8$). IR: 1380, 1467, 1699, 2922 cm$^{-1}$. HR-MS (EI): Calculated mass: [M+H]$^+$ 446.1517. Found: 446.1517.

3-(4-Chlorophenyl)-3-(4-hydroxycyclopent-2-enyloxy)-2-(4-nitrobenzyl) isoindolin-1-one (NU8297)

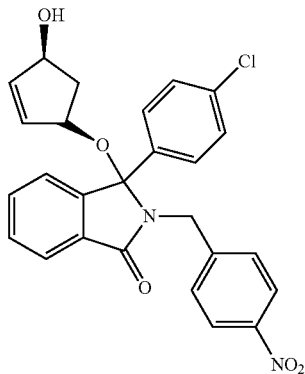

Distilled THF (10 mL) was added to 3-(4-chlorophenyl)-3-hydroxy-2-(4-nitrobenzyl)isoindolin-1-one (200 mg, 0.52 mmol), thionyl chloride (136.8 mg, 1.15 mmol, 0.08 mL) and catalytic DMF (3 drops) as for general procedure B1. 3-Chloro-3-(4-chlorophenyl)-2-(4-nitrobenzyl)isoindolin-1-one was produced as a viscous yellow oil (208.5 mg, 0.52 mmol) which was used immediately without further purification. Distilled THF (3 mL) was added to 3-chloro-3-(4-chlorophenyl)-2-(4-nitrobenzyl)isoindolin-1-one (208.5 mg, 0.52 mmol) and the resultant solution added dropwise to cis-cyclopentene diol (260 mg, 2.6 mmol) and dried potassium carbonate (359 mg, 2.6 mmol) in distilled THF (3 mL) as for general procedure B1. Removal of the solvent yielded the crude product as a yellow oil (262 mg). The sample was purified by flash column chromatography (EtOAc:Petrol, 40:60) to yield the title product as a yellow viscous oil. (211 mg, 44.4 mmol, 85%). $^1$H NMR: (300 MHz, DMSO) δ ppm 1.34, (m, 1H, $H_{15}/H_{16}$) 1.74, 2.2 (m, 1H, $H_{15}/H_{16}$) 4.22 (dt, 1H, $H_{16}$) 4.40 (d, 1H, J=15.99 Hz, $H_9/H_{9'}$), 4.63 (d, 1H, J=16.02 Hz, $H_9/H_{9'}$), 4.93, 4.98, (dd, 1H, $H_{17}/H_{18}$), 5.15, 5.29 (dd, 1H, $H_{17}/H_{18}$), 5.76 (m, 1H, $H_{14}$) 7.26 (m, 7H, $H_1$-$H_5$, $H_{10}$, $H_{13}$), 7.66 (m, 2H, $H_6$-$H_7$), 7.88 (d, 1H, $H_8$), 8.00 (m, 2H, $H_{11}$, $H_{12}$).

2-Benzyl-3-(4-chlorophenyl)-3-(4-hydroxycyclopent-2-enyloxy) isoindolin-1-one (NU8298)

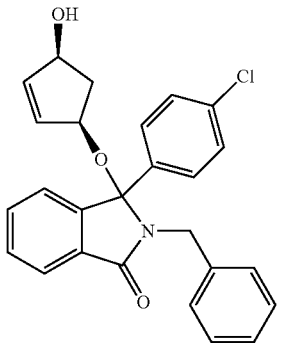 [SMILES: O=C1c2ccccc2C(O[C@H]2C=C[C@@H](O)C2)(c2ccc(Cl)cc2)N1Cc1ccccc1]

Distilled THF (25 mL) was added to 2-benzyl-3-(4-chlorophenyl)-3-hydroxy-2,3-dihydroisoindolin-1-one (400 mg, 1.145 mmol), thionyl chloride (299.6 mg, 2.51 mmol, 0.18 mL) and catalytic DMF (3 drops) as for general procedure B1. 3-Chloro-3-(4-chlorophenyl)-2-benzylisoindolin-1-one was produced as a colourless oil (421 mg, 1.145 mmol) which was used immediately without further purification. Distilled THF (25 mL) was added to 3-chloro-3-(4-chlorophenyl)-2-benzylisoindolin-1-one (421 mg, 1.145 mmol), cis-cyclopentene diol (572 mg, 5.725 mmol) and potassium carbonate (792.9 mg, 5.725 mmol) as for general procedure B. Removal of the solvent yielded the crude product as a pink oil (354 mg). The sample was purified by flash column chromatography (EtOAc:Petrol, 40:60) to yield the title product as a cream oily solid (277.5 mg, 0.643 mmol, 56% yield). $^1$H NMR: (300 Hz, CDCl$_3$) δ ppm 0.84, 1.66 (m, 1H, H$_{16}$/H$_{16'}$) 1.26 (m, 1H, H$_{16}$/H$_{16'}$) 3.85 (m, 1H, H$_{17}$) 3.36 (m, 1H, H$_{15}$) 4.15 (d, 1H, J=15.27 Hz, H$_9$/H$_{9'}$), 4.62 (d, 1H, J=15.31 Hz, H$_9$/H$_{9'}$), 4.68, 5.73 (dd, 1H, H$_{18}$/H$_{19}$), 5.21, 5.64 (dd, 1H, H$_{18}$/H$_{19}$), 7.18 (m, 10H, H$_1$-H$_5$, H$_{10}$-H$_{14}$), 7.62 (m, 2H, H$_6$-H$_7$), 7.83 (d, 1H, H$_8$). Mp: 63.4-63.9° C. IR: 1489, 1683, 3061, 3379 cm$^{-1}$.

3-(4-Chlorophenyl)-3-(4-hydroxybut-2-enyloxy)-2-(4-nitrobenzyl)-2,3-dihydroisoindol-1-one (NU8350)

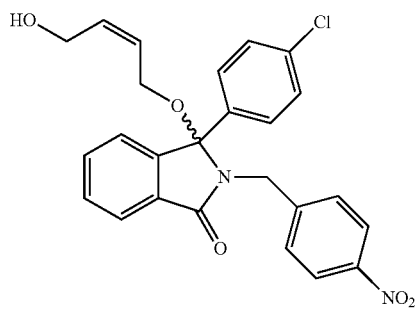

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and cis-butenediol (445 mg, 5.05 mmol, 5 equiv.) using General Procedure A and obtained as a yellow oil (272 mg, 58%). $^1$H NMR (300 MHz, CDCl$_3$): 8.04-8.00 (m, 2H, O$_2$N—C—CH), 7.93-7.91 (m, 1H, C(O)=C=CH), 7.57-7.51 (m, 2H, Ar—H), 7.39-7.36 (m, 2H, Ar—H), 7.23-7.12 (m, 5H, Ar—H), 5.62-5.53 (m, 1H, OCH$_2$Cl), 5.35-5.26 (m, 1H, OCH$_2$CH), 4.64 and 4.26 (dd: AB, J=15.0 Hz, 2H, N—CH$_2$), 3.79 (d, J=6.6 Hz, HO—CH$_2$), 3.48-3.29 (m, 2H, O—CH$_2$). $^{13}$C NMR (75 MHz, CDCl$_3$): 168.17, 147.45, 145.07, 144.60, 136.86, 134.98, 133.07, 132.00, 131.44, 130.24, 130.02, 128.71, 127.99, 126.79, 123.89, 123.35, 95.00, 59.20, 58.48, 42.57. m/z (ES): 465 [M+H]$^+$. Anal.: calc. for C$_{25}$H$_{21}$ClN$_2$O$_5$: C, 64.59; H, 4.55; N, 6.02. Found: C, 64.39; H, 4.67; N, 5.67.

3-(4-Chlorophenyl)-3-(4-hydroxybut-2-enyloxy)-2-(4-nitrobenzyl)-2,3-dihydroisoindol-1-one (NU8351)

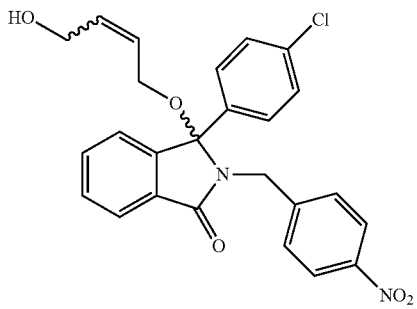 [SMILES: O=C1c2ccccc2C(OC/C=C\CO)(c2ccc(Cl)cc2)N1Cc1ccc([N+](=O)[O-])cc1]

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and cis/trans-butenediol (445 mg, 5.05 mmol, 5 equiv.) using General Procedure A and obtained as a yellow oil (291 mg, 62%). $^1$H NMR (300 MHz, CDCl$_3$): 8.04-8.01 (m, 2H, O$_2$N—C—CH), 7.94-7.91 (m, 1H, C(O)=C=CH), 7.57-7.51 (m, 2H, Ar—H), 7.40-7.36 (m, 2H, Ar—H), 7.23-7.13 (m, 5H, Ar—H), 5.62-5.53 (m, 1H, OCH$_2$CH), 5.35-5.27 (m, 1H, OCH$_2$CB), 4.64 and 4.26 (dd: AB, J=15.0 Hz, 2H, N—CH$_2$), 3.79 (d, J=6.6 Hz, HO—CH$_2$), 3.48-3.29 (m, 2H, O—CH$_2$). $^{13}$C NMR (75 MHz, CDCl$_3$): 168.17, 147.50, 145.10, 144.60, 136.91, 135.01, 133.07, 132.01, 131.49, 130.25, 130.04, 128.73, 128.00, 126.83, 123.90, 123.35, 95.03, 59.23, 58.51, 42.60. m/z (ES): 465 [M+H]$^+$. HPLC: R$_f$=3.51 min. Anal.: calc. for C$_{25}$H$_{21}$ClN$_2$O$_5$: C, 64.59; H, 4.55; N, 6.02. Found: C, 64.23; H, 4.63; N, 5.73.

3-(4-Chlorophenyl)-3-(5-hydroxycyclooctyloxy)-2-(4-nitrobenzyl)-2,3-dihydroisoindol-1-one (NU8352)

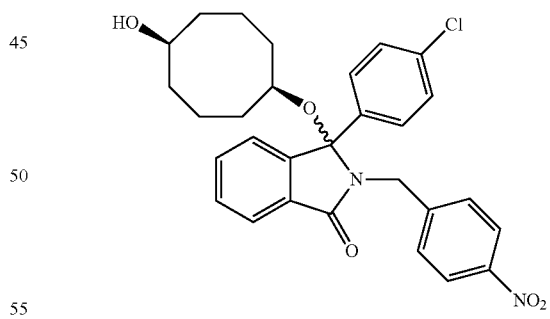

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and cis-1,5-cyclooctanediol (728 mg, 5.05 mmol, 5 equiv.) using General Procedure A and obtained as a yellow solid (342 mg, 65%). $^1$H NMR (300 MHz, CDCl$_3$): 7.95-7.91 (m, 3H, O$_2$N—C—CH and C(O)=C=CH), 7.60-7.52 (m, 2H, Ar—H), 7.18-7.03 (m, 7H, Ar—H), 4.86 and 4.20 (dd: AB, J=15.3 Hz, 2H, N—CH$_2$), 3.59-3.52 (m, 1H, HO—CH), 3.24-3.18 (m, 1H, O—CH), 1.83-1.29 (m, 12H, CH$_2$). $^{13}$C NMR (75 MHz, CDCl$_3$): 168.29, 147.21, 145.92, 144.85, 137.61, 134.77, 132.60, 131.79, 130.16, 129.68, 128.34, 128.27, 124.02, 123.62, 123.08, 94.52, 73.62, 71.25, 42.75, 36.51, 35.92, 34.32, 33.94, 20.30, 20.12 Anal.: calc. for C$_{39}$H$_{32}$ClN$_3$O$_6$+ 0.5 EtOAc: C, 66.34; H, 5.77; N, 5.16. Found: C, 66.25; H, 5.91; N, 5.00. Mp: 69-72° C. (EtOAc).

3-(4-Chloro-phenyl)-3-(3-hydroxy-2,2-dimethyl-propoxy)-2-(4-nitro-benzyl)-2,3-dihydro-isoindol-1-one (NU8353)

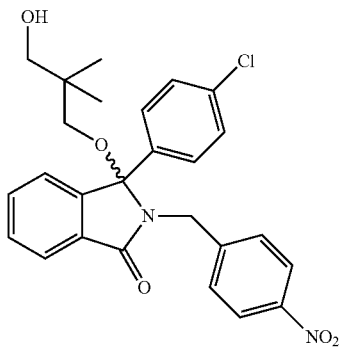 [SMILES: CC(C)(CO)COC1(c2ccc(Cl)cc2)c2ccccc2C(=O)N1Cc1ccc([N+](=O)[O-])cc1]

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and neopentyl glycol (526 mg, 5.05 mmol, 5 equiv.) using General Procedure A and obtained as an off-white solid (267 mg, 55%). $^1$H NMR (300 MHz, CDCl$_3$): 8.02-7.98 (m, 2H, O$_2$N—C—CH), 7.96-7.93 (m, 1H, C(O)=C=CH), 7.58-7.55 (m, 2H, Ar—H), 7.32-7.28 (m, 2H, Ar—H), 7.15-7.12 (m, 5H, Ar—H), 4.58 and 4.44 (dd: AB, J=15.3 Hz, 2H, N—CH$_2$), 3.39 (s, 2H, HO—CH$_2$), 2.78 and 2.63 (dd: AB, J=8.7 Hz, 2H, N—CH$_2$), 0.83 (d, J=3.9 Hz, CH$_3$). $^{13}$C NMR (75 MHz, CDCl$_3$): 168.30, 147.33, 145.19, 144.60, 137.31, 134.90, 133.08, 131.64, 130.17, 129.85, 128.61, 127.95, 123.81, 123.23, 123.16, 94.54, 69.57, 69.02, 42.42, 36.41, 21.75. m/z (ES): 481 [M+H]$^+$. Anal.: calc. for C$_{26}$H$_{25}$ClN$_2$O$_5$+0.25 H$_2$O: C, 64.32; H, 5.31; N, 5.77. Found: C, 64.32; H, 5.34; N, 5.57.

3-(4-Chlorophenyl)-3-(1-hydroxymethylcyclopropyl-methoxy)-2-(4-nitrobenzyl)-2,3-dihydroisoindol-1-one (NU8354)

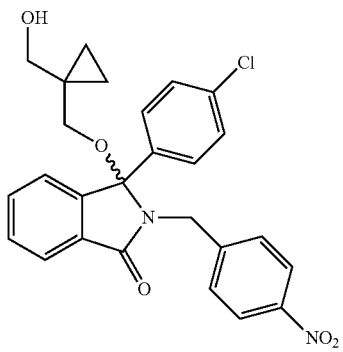

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and cyclopropane dimethanol (516 mg, 5.05 mmol, 5 equiv.) using General Procedure A and obtained as an off-white solid (305 mg, 63%). $^1$H NMR (300 MHz, CDCl$_3$): 8.01-7.98 (m, 2H, O$_2$N—C—CH), 7.92-7.89 (m, 1H, C(O)=C=CH), 7.55-7.52 (m, 2H, Ar—H), 7.32-7.29 (m, 2H, Ar—H), 7.19-7.12 (m, 5H, Ar—H), 4.49 (s, 2H, N—CH$_2$), 3.51-3.43 (m, 2H, HOCH$_2$), 2.81 (s, 2H, OCH$_2$), 0.43-0.40 (m, 2H, CH$_2$), 0.22-0.12 (m, 2H, CH$_2$). $^{13}$C NMR (75 MHz, CDCl$_3$): 168.54, 145.52, 144.95, 137.47, 135.29, 133.45, 131.87, 130.50, 130.21, 128.98, 128.30, 124.16, 123.60, 123.48, 94.96, 67.84, 42.75, 22.68, 8.94, 8.90 Anal.: calc. for C$_{26}$H$_{23}$ClN$_2$O$_5$: C, 65.20; H, 4.84; N, 5.85, Found: C, 64.83; H, 4.92; N, 5.63.

Racemic NU8354 was separated into its two enantiomers by chiral HPLC (Chiracel AD column; 1 cm×25 cm; 40% EtOH, pentane):

NU8354A, RT=9.8 min; α=+22.66°, 0.406 g/100 ml;

and NU8354B, RT=12.4 min; α=−20.10°, 0.398 g/100 ml.

3-(4-Chlorophenyl)-3-(4-hydroxybut-2-ynyloxy)-2-(4-nitrobenzyl)-2,3 dihydroisoindol-1-one (NU8357)

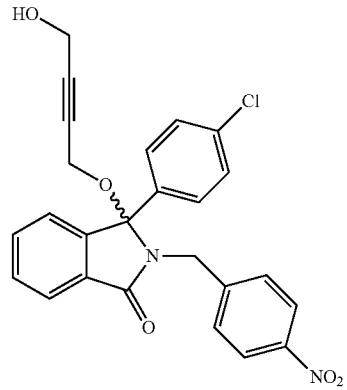 [SMILES: O=C1c2ccccc2C(OCC#CCO)(c2ccc(Cl)cc2)N1Cc1ccc([N+](=O)[O-])cc1]

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and butynediol (435 mg, 5.05 mmol, 5 equiv.) using General Procedure A and obtained as a yellow solid (271 mg, 58%). $^1$H NMR (300 MHz, CDCl$_3$): 8.05-7.93 (m, 3H, O$_2$N—C—CH and C(O)=C=CH), 7.61-7.54 (m, 2H, Ar—H), 7.36-7.33 (m, 2H, Ar—H), 7.24-7.16 (m, 5H, Ar—H), 4.60 and 4.52 (d: AB, J=15.0 Hz, 2H, N—CH$_2$), 4.20-4.18 (m, 2H, HO—CH$_2$), 3.83 and 3.52 (dt: AB, J=1.8, 15.3 Hz, 2H, O—CH$_2$), 2.42 (t, J=6.0 Hz, 1H, OH). $^{13}$C NMR (75 MHz, CDCl$_3$): 169.24, 148.20, 145.18, 137.24, 135.88, 133.78, 132.49, 131.29, 130.78, 129.43, 128.79, 124.81, 124.43, 124.14, 95.88, 86.01, 81.28, 54.04, 52.97, 51.55, 43.60. m/z (ES): 463

[M+H]+. calc. for $C_{25}H_{19}ClN_2O_5$+0.2 $H_2O$: C, 64.36; H, 4.20; N, 6.01. Found: C, 64.11; H, 3.72; N, 5.53.

3-(4-Chlorophenyl)-3-(4-hydroxymethylcyclohexyl-methoxy)-2-(4-nitrobenzyl)-2,3-dihydroisoindol-1-one (NU8358)

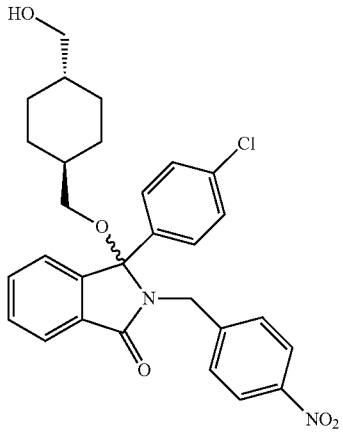 [SMILES: O=C1c2ccccc2C(OC[C@H]2CC[C@H](CO)CC2)(c2ccc(Cl)cc2)N1Cc1ccc([N+](=O)[O-])cc1]

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and trans-cyclohexane-1,4-dimethanol (728 mg, 5.05 mmol, 5 equiv.) using General Procedure A and obtained as a yellow solid (374 mg, 71%). $^1$H NMR (300 MHz, $CDCl_3$): 8.05-7.92 (m, 3H, $O_2N$—C=CH and C(O)=C=CH), 7.56-7.53 (m, 2H, Ar—H), 7.38-7.10 (m, 7H, Ar—H), 4.59 and 4.35 (d: AB, J=15.0 Hz, 2H, N—$CH_2$), 3.44 (d, J=6.3 Hz, 2H, HO—$CH_2$), 2.65-2.53 (m, 2H, $OCH_2$), 1.81-1.74 (m, 3H, OH and CH), 1.44-1.32 (m, 2H), 0.93-0.79 (m, 5H). $^{13}$C NMR (75 MHz, $CDCl_3$): 168.26, 145.41, 144.82, 137.42, 134.84, 132.93, 130.01, 128.63, 128.01, 123.80, 123.24, 123.18, 94.67, 68.41, 68.26, 42.41, 40.59, 38.04, 29.68, 29.31, 28.90. m/z (ES): 521 [M+H]+. Anal.: calc. for $C_{29}H_{29}ClN_2O_5$+0.2 $H_2O$: C, 66.38; H, 5.66; N, 5.34. Found: C, 66.23; H, 5.79; N, 4.99.

3-(4-Chlorophenyl)-3-(2-hydroxymethylcyclohexyl-methoxy)-2-(4-nitrobenzyl)-2,3-dihydroisoindol-1-one (NU8359)

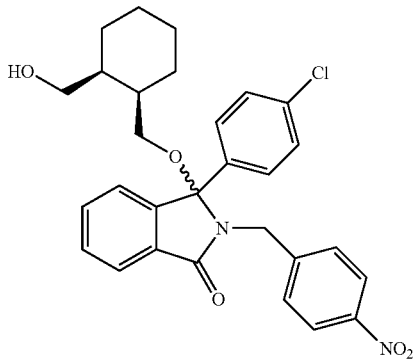 [SMILES: O=C1c2ccccc2C(OC[C@@H]2CCCC[C@@H]2CO)(c2ccc(Cl)cc2)N1Cc1ccc([N+](=O)[O-])cc1]

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and cis-1,2-cyclohexane-dimethanol (728 mg, 5.05 mmol, 5 equiv.) using General Procedure A and obtained as a yellow solid (337 mg, 64%). $^1$H NMR (300 MHz, $CDCl_3$): mixture of diastereoisomers: 8.08-7.93 (m, 3H, $O_2N$—C—CH and C(O)=C=CH), 7.58-7.54 (m, 2H, Ar—H), 7.43-7.36 (m, 2H, Ar—H), 7.23-7.11 (m, 5H, Ar—H), 4.61 and 4.25 (d: AB, J=15.0 Hz, 2H, N—$CH_2$); and 4.59 and 4.36 (d: AB, J=15.0 Hz, 2H, N—$CH_2$), 3.53-3.24 (m, 2H, HO—$CH_2$), 2.87-2.61 (m, 2H, $OCH_2$), 1.87-1.09 (m, 10H, CH). $^{13}$C NMR (75 MHz, $CDCl_3$): mixture of diastereoisomers: 168.25, 147.42, 145.37, 145.20, 144.84, 144.76, 137.28, 137.12, 134.97, 134.88, 133.03, 131.55, 131.41, 130.15, 130.10, 129.98, 129.94, 128.81, 128.69, 127.98, 127.92, 123.91, 123.81, 123.33, 123.30, 123.10, 123.06, 95.07, 94.97, 63.91, 63.57, 63.44, 63.31, 42.50, 42.43, 40.77, 39.99, 37.18, 27.40, 27.09, 26.21, 26.16, 23.77, 23.44, 23.29. Anal.: calc. for $C_{29}H_{29}ClN_2O_5$+0.3 $CH_2Cl_2$+0.1 $H_2O$: C, 64.18; H, 5.49; N, 5.11. Found: C, 64.34; H, 5.49; N, 4.95.

3-(4-Chlorophenyl)-3-(4-hydroxycyclohexyloxy)-2-(4-nitrobenzyl)-2,3-dihydroisoindol-1-one (NU8360)

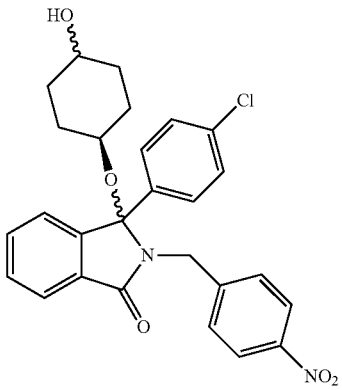

The named compound was synthesised from 3-(4-Chlorophenyl)-3-hydroxy-2-(4-nitrobenzyl)-2,3-dihydroisoindol-1-one (400 mg, 1.01 mmol, 1 equiv.) and cis/trans-1,4-cyclohexanediol (586 mg, 5.05 mmol, 5 equiv.) using General Procedure A and obtained as a white solid (338 mg, 68%). $^1$H NMR (300 MHz, $CDCl_3$): mixture of diastereoisomers: 7.93-7.90 (m, 3H, $O_2N$—C=CH and C(O)=C=CH), 7.56-7.51 (m, 2H, Ar—H), 7.18-7.02 (m, 7H, Ar—H), 4.78 and 4.24 (d: AB, J=15.0 Hz, 2H, N—$CH_2$); 3.70-3.62 (m, 1H, HOCH—), 3.26-3.09 (m, 1H, OCH), 1.86-1.26 (m, 10H, $CH_2$). $^{13}$C NMR (75 MHz, $CDCl_3$): mixture of diastereoisomers: 168.33, 147.16, 146.01, 144.80, 137.66, 134.74, 132.72, 131.58, 130.21, 130.16, 129.68, 128.31, 128.28, 128.23, 128.19, 123.81, 123.09, 94.30, 94.28, 71.41, 69.22, 68.61, 67.66, 42.65, 32.51, 32.32, 30.95, 30.65, 30.33, 29.19, 29.03. m/z (ES): 493 [M+H]+. HPLC: $R_t$=3.43 min. Anal.: calc. for $C_{27}H_{25}ClN_2O_5$+0.1 $H_2O$: C, 65.54; H, 5.14; N, 5.66. Found: C, 65.09; H, 5.20; N, 5.24.

3-(4-Chlorophenyl)-3-(4-hydroxycyclohex-2-enyloxy)-2-(4-nitrobenzyl)-2,3-dihydroisoindol-1-one (NU8361)

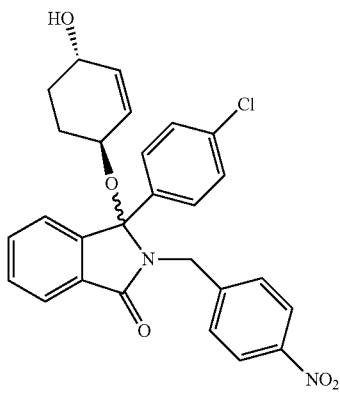 [SMILES: O=C1c2ccccc2C(O[C@@H]2C=C[C@@H](O)CC2)(c2ccc(Cl)cc2)N1Cc1ccc([N+](=O)[O-])cc1]

The named compound was synthesised from 3-(4-chlorophenyl)-3-hydroxy-2-(4-nitrobenzyl)-2,3-dihydroisoindol-1-one (400 mg, 1.01 mmol, 1 equiv.) and trans-1,4-cyclohex-2-enediol (576 mg, 5.05 mmol, 5 equiv.) using General Procedure A and obtained as a white solid (263 mg, 53%). $^1$H NMR (300 MHz, CDCl$_3$): mixture of diastereoisomers: 7.96-7.92 (m, 3H, O$_2$N—C—CH and C(O)=C=CH), 7.61-7.55 (m, 2H, Ar—H), 7.22-7.03 (m, 71-1, Ar—H), 5.75 and 5.34 (m, 2H, CH=CH), 4.83 and 4.28 (m, 2H, N—CH$_2$), 4.27 (m, 1H, HO—CR), 3.74-3.71 (m, 1H, OCH), 3.70-3.62 (m, 1H, HOCH—), 3.26-3.09 (m, 1H, OCH), 2.12-1.14 (m, 4H, CH$_2$). $^{13}$C NMR (75 MHz, CDCl$_3$): mixture of diastereoisomers: 168.57, 147.55, 146.08, 145.06, 144.99, 137.66, 137.57, 135.16, 134.64, 134.10, 133.20, 131.90, 130.68, 130.61, 130.09, 130.04, 129.96, 128.67, 128.65, 128.59, 128.55, 124.28, 124.15, 123.48, 123.46, 94.90, 94.82, 68.43, 68.30, 65.91, 65.76, 43.06, 30.85, 30.52, 28.58. m/z (ES): 491 [M+H]$^+$. HPLC: R$_f$=3.39 min. Anal.: calc. for C$_{27}$H$_{23}$ClN$_2$O$_5$+0.2 H$_2$O: C, 65.57; H, 4.78; N, 5.67. Found: C, 65.32; H, 5.00; N, 5.18.

3-(4-Chlorophenyl)-3-hydroxy-2-[2-(4-nitrophenyl)ethyl]-2,3-dihydroisoindol-1-one

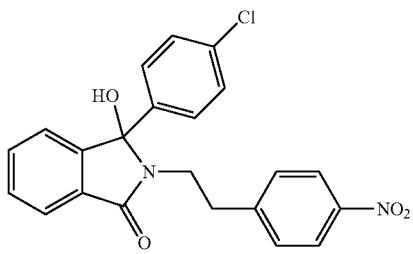 [SMILES: O=C1c2ccccc2C(O)(c2ccc(Cl)cc2)N1CCc1ccc([N+](=O)[O-])cc1]

To a solution of 2-(4-chlorobenzoyl)benzoic acid (5 g, 19.2 mmol, 1 equiv.) in dry THF (20 mL) was added under nitrogen atmosphere thionylchloride (3.0 mL, 38.3 mmol, 2 equiv.) and 3 drops of anhydrous DMF. The reaction mixture was stirred for 4 h at room temperature and concentrated in vacuo. The resulting pale yellow oil was taken up in dry THF (20 mL), and the amine 2-(4-nitrophenyl)ethylamine hydrochloride (4.30 g, 21.1 mmol, 1.1 equiv.) and DIPEA (3.49 mL, 21.1 mmol, 1.1 equiv.) were added under nitrogen atmosphere. The reaction mixture was stirred overnight at room temperature and the solvents were removed in vacuo. The residue was taken up in EtOAc (100 mL), filtered, and the filtrate washed with water (3×50 mL) and brine (1×50 mL). The organic layer was dried over MgSO$_4$, filtered and concentrated in vacuo to afford a buff-coloured solid, which was recrystallised from EtOAc/Petrol ether (4.47 g, 57%). $^1$H NMR (300 MHz, d$^6$-DMSO): 8.09 (d, J=8.4 Hz, 2H, O$_2$N—C—CH), 7.74 (d, J=6.6 Hz, 1H, C(O)=C=CH), 7.60-7.51 (m, 2H, Ar—H), 7.40-7.26 (m, 8H, Ar—H and OH), 3.69-3.57 (m, 1H, N—CH), 3.28-3.19 (m, 1H, N—CH), 2.96-2.89 (m, 2H, N—CH$_2$—CH$_2$). $^{13}$C NMR (75 MHz, d$^6$-DMSO): 166.38, 148.77, 147.11, 145.85, 138.81, 132.57, 132.21, 130.08, 129.34, 128.97, 128.05, 127.51, 122.95, 122.36, 122.13. FTIR: 3240, 1166, 1520, 1338 cm$^{-1}$. m/z (ES): 409 [M+H]$^+$. HPLC: R$_f$=3.36 min. Anal.: calc. for C$_{22}$H$_{17}$ClN$_2$O$_4$: C, 64.63, H, 4.19, N, 6.85. Found: C, 65.02; H, 4.27; N, 6.74. Mp: 206-208° C. (EtOAc). UV: λ$_{max}$=268 nm (EtOH).

3-(4-Chlorophenyl)-3-(4-hydroxybutoxy)-2-[2-(4-nitrophenyl)ethyl]-2,3-dihydroisoindol-1-one (NU8362)

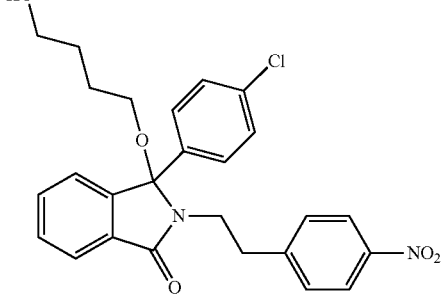

The named compound was synthesised from 3-(4-chlorophenyl)-3-hydroxy-2-[2-(4-nitrophenyl)ethyl]-2,3-dihydroisoindol-1-one (562 mg, 1.37 mmol, 1 equiv.) and 1,4-butanediol (616 mg, 6.85 mmol, 5 equiv.) using General Procedure A and obtained as a white solid (306 mg, 63%). $^1$H NMR (300 MHz, CDCl$_3$): 8.11-8.08 (m, 2H, O$_2$N—C—CH), 7.91-7.88 (m, 1H, C(O)=C=CH), 7.55-7.53 (m, 2H, Ar—H), 7.30-7.14 (m, 7H, Ar—H), 3.66 (m, 2H, N—CH$_2$), 3.45 (t, J=8.1 Hz, 2H, HO—CH$_2$), 3.16-3.11 and 3.03-2.99 (m, 2H, OCH$_2$), 3.00-2.89 and 2.73-2.66 (m, 2H, NCH$_2$CH$_2$), 1.75-1.63 (m, 5H, CH$_2$ and OH). $^{13}$C NMR (75 MHz, CDCl$_3$): 168.23, 147.02, 146.62, 145.32, 137.69, 134.84, 132.74, 131.98, 129.99, 129.48, 128.74, 127.87, 123.65, 123.51, 123.10, 94.54, 62.79, 62.43, 40.51, 34.21, 29.60, 26.07. HPLC: R$_f$=3.45 min. calc. for C$_{26}$H$_{25}$ClN$_2$O$_5$: C, 64.93; H, 5.24; N, 5.82. Found: C, 64.82; H, 5.18; N, 5.68.

3-(4-Chlorophenyl)-2-[1-(4-chlorophenyl)-ethyl]-3-(4-hydroxybutoxy)-2,3-dihydroisoindol-1-one (NU8365)

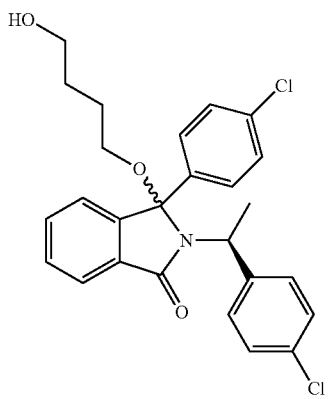 [SMILES: C[C@@H](c1ccc(Cl)cc1)N1C(=O)c2ccccc2C1(OCCCCO)c1ccc(Cl)cc1]

The named compound was synthesised from 3-(4-chlorophenyl)-2-[1-(4-chlorophenyl)-ethyl]-3-hydroxy-2,3-dihydroisoindol-1-one (498 mg, 1.37 mmol, 1 equiv.) and 1,4-butanediol (616 mg, 6.85 mmol, 5 equiv.) using General Procedure A and obtained as a pale yellow oil (242 mg, 51%). $^1$H NMR (300 MHz, CDCl$_3$): 7.87-7.83 (m, 1H, C(O)=C=CH), 7.53-7.46 (m, 2H, Ar—H), 7.07-7.03 (m, 9H, Ar—H), 4.41 (q, J=7.2 Hz, 1H, N—CH), 3.70 (m, 2H, HO—CH$_2$), 3.29-3.25 and 3.01-2.95 (m, 2H, OCH$_2$), 1.86 (d, J=7.2 Hz, 3H, CH$_3$), 1.77-1.68 (m, 4H, CH$_2$). $^{13}$C NMR (75 MHz, CDCl$_3$): 168.31, 145.26, 141.47, 137.76, 134.79, 133.15, 133.06, 132.84, 130.20, 129.67, 128.75, 128.41, 128.27, 123.71, 123.27, 95.44, 63.35, 62.89, 52.49, 29.96, 26.48, 20.08. m/z (ES): 470 [M+H]$^+$. HPLC: R$_f$=3.76 min. Anal.: calc. for C$_{26}$H$_{25}$Cl$_2$NO$_3$: C, 66.39; H, 5.36; N, 2.98. Found: C, 66.33; H, 5.25; N, 2.46.

3-(4-Chlorophenyl)-3-(4-hydroxymethylbenzyloxy)-2-(4-nitrobenzyl)-2,3-dihydroisoindol-1-one (NU8366)

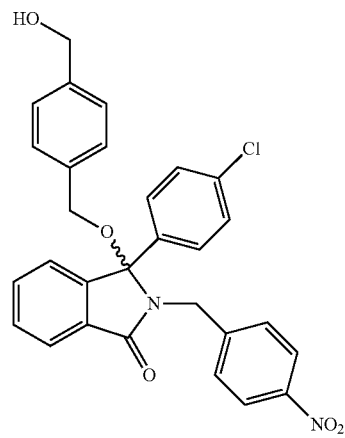 [SMILES: O=C1c2ccccc2C(OCc2ccc(CO)cc2)(c2ccc(Cl)cc2)N1Cc1ccc([N+](=O)[O-])cc1]

The named compound was synthesised from 3-(4-chlorophenyl)-3-hydroxy-2-(4-nitrobenzyl)-2,3-dihydroisoindol-1-one (541 mg, 1.37 mmol, 1 equiv.) and 1,4-benzenedimethanol (946 mg, 6.85 mmol, 5 equiv.) using General Procedure A and obtained as a white solid (405 mg, 78%). $^1$H NMR (300 MHz, CDCl$_3$): 8.01-7.85 (m, 3H, O$_2$N—C—CH and C(O)=C=CH), 7.61-7.53 (m, 2H, Ar—H), 7.37-7.18 (m, 9H, Ar—H), 6.93 (d, J=7.8 Hz, 2H, Ar—H), 4.85 and 4.67 (d: AB, J=15.0 Hz, 2H, N—CH$_2$), 4.66 (d, J=5.7 Hz, CH$_2$—OH), 3.90 and 3.68 (d: AB, J=11.7 Hz, 2H, OCH$_2$), 2.12 (t, J=6.0 Hz, 1H, OH). $^{13}$C NMR (75 MHz, CDCl$_3$): 168.52, 147.63, 145.39, 144.90, 141.16, 137.34, 136.39, 135.37, 133.42, 131.73, 130.57, 130.32, 129.19, 128.38, 127.30, 127.11, 124.34, 123.69, 95.52, 65.26, 65.12, 42.89. m/z (ES): 515 [M+H]$^+$. HPLC: R$_f$=3.56 min. Anal.: calc. for C$_{29}$H$_{23}$ClN$_2$O$_5$: C, 67.64; H, 4.50; N, 5.44, Found: C, 67.38; H, 4.43; N, 5.26.

3-(4-Chlorophenyl)-3-(3-hydroxymethylbenzyloxy)-2-(4-nitrobenzyl)-2,3-dihydroisoindol-1-one (NU8367)

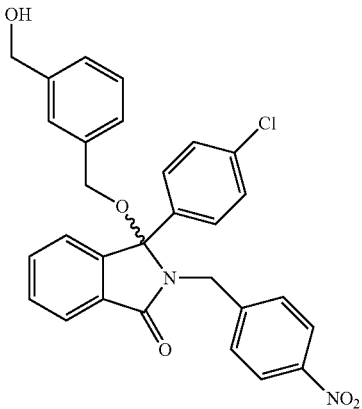 [SMILES: O=C1c2ccccc2C(OCc2cccc(CO)c2)(c2ccc(Cl)cc2)N1Cc1ccc([N+](=O)[O-])cc1]

The named compound was synthesised from 3-(4-chlorophenyl)-3-hydroxy-2-(4-nitrobenzyl)-2,3-dihydroisoindol-1-one (541 mg, 1.37 mmol, 1 equiv.) and 1,3-benzenedimethanol (946 mg, 6.85 mmol, 5 equiv.) using General Procedure A and obtained as a white solid (390 mg, 75%). $^1$H NMR (300 MHz, CDCl$_3$): 8.01-7.90 (m, 3H, O$_2$N—C—CH and C(O)=C=CH), 7.62-7.53 (m, 2H, Ar—H), 7.39-7.17 (m, 9H, Ar—H), 6.95-6.91 (m, 2H, Ar—H), 4.80 and 4.13 (d: AB, J=15.0 Hz, 2H, N—CH$_2$), 4.64 (d, J=5.1 Hz, CH$_2$—OH), 3.93 and 3.73 (d: AB, J=11.4 Hz, 2H, OCH$_2$), 1.95 (t, J=5.4 Hz, 1H, OH). $^{13}$C NMR (75 MHz, CDCl$_3$): 168.51, 145.42, 144.88, 141.59, 137.45, 135.37, 133.39, 131.79, 130.56, 130.34, 129.17, 128.81, 128.38, 126.61, 126.51, 125.82, 124.32, 123.69, 95.55, 65.42, 65.35, 42.91. m/z (ES): 515 [M+H]$^+$. HPLC: R$_f$=3.58 min. Anal.: calc. for C$_{29}$H$_{23}$ClN$_2$O$_5$+0.15 CH$_2$Cl$_2$: C, 66.34; H, 4.46; N, 5.31. Found: C, 66.12; H, 4.44; N, 5.03.

3-(4-Chloro-phenyl)-2-[1-(4-chloro-phenyl)-ethyl]-3-hydroxy-2,3-dihydro-isoindol-1-one

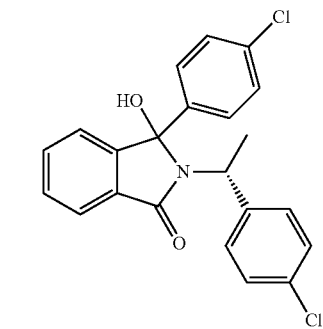 [SMILES: C[C@H](c1ccc(Cl)cc1)N1C(=O)c2ccccc2C1(O)c1ccc(Cl)cc1]

To a solution of (R)-4-chloro-α-methylbenzylamine hydrochloride (2.95 mL, 21.1 mmol, 1.1 equiv.) in dry THF (20 mL) was added under nitrogen atmosphere thionylchloride (3.0 mL, 38.3 mmol, 2 equiv.) and 3 drops of anhydrous DMF. The reaction mixture was stirred for 4 h at room temperature and concentrated in vacuo. The resulting pale yellow oil was taken up in dry THF (20 mL), and the amine 2-(4-nitrophenyl)ethylamine hydrochloride (4.30 g, 21.1 mmol, 1.1 equiv.) and DIPEA (3.49 mL, 21.1 mmol, 1.1 equiv.) were added under nitrogen atmosphere. The reaction mixture was stirred overnight at room temperature and the solvents were removed in vacuo. The residue was taken up in EtOAc (100 mL), filtered, and the filtrate washed with water (3×50 mL) and brine (1×50 mL). The organic layer was dried over MgSO$_4$, filtered and concentrated in vacuo to afford a white crystalline powder, which was recrystallised from EtOAc/Petrol ether (4.98 g, 65%). $^1$H NMR (300 MHz, d$^6$-DMSO): Mixture of two diastereoisomers: 7.64-7.61 (m, 1H and 1H, Ar—H), 7.46-7.30 (m, 5H and 5H, Ar—H), 7.26-7.02 (m, 5H and 5H, Ar—H), 6.90 (d, J=8.7 Hz, 1H and 1H, Ar—H), 4.58 and 4.43 (q, J=6.9 Hz, 1H, CH*), 4.18 and 4.11 (br s, 1H, OH), 1.69 and 1.56 (d, J=7.2 Hz, 3H, CH$_3$). $^{13}$C NMR (75 MHz, d$^6$-DMSO): 167.33, 167.26, 148.29, 148.25, 141.08, 140.53, 137.44, 137.32, 134.74, 134.67, 132.96, 132.91, 132.75, 132.72, 131.30, 131.21, 129.82, 129.45, 129.40, 128.81, 128.70, 128.43, 128.36, 128.25, 128.00, 123.44, 123.41, 122.47, 91.93, 91.50, 52.07, 52.01, 19.84, 18.43. FTIR: 3119, 1667 cm$^{-1}$. m/z (ES): 398 [M+H]$^+$. HPLC: R$_t$=3.57 min. Anal.: calc. for C$_{22}$H$_{17}$Cl$_2$NO$_2$: C, 66.34; H, 4.30; N, 3.52. Found: C, 66.24; H, 4.28; N, 3.50.

3-(4-Chloro-phenyl)-2-[1-(4-chloro-phenyl)-ethyl]-3-(4-hydroxy-butoxy)-2,3-dihydro-isoindol-1-one (NU8368)

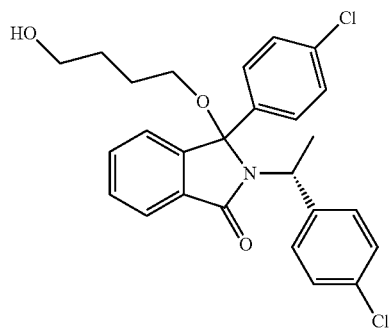 [SMILES: C[C@H](c1ccc(Cl)cc1)N1C(=O)c2ccccc2C1(OCCCCO)c1ccc(Cl)cc1]

The named compound was synthesised from 3-(4-chloro-phenyl)-2-[1-(4-chloro-phenyl)-ethyl]-3-hydroxy-2,3-dihydro-isoindol-1-one (498 mg, 1.37 mmol, 1 equiv.) and 1,4-butanediol (616 mg, 6.85 mmol, 5 equiv.) using General Procedure B and obtained as a clear oil (304 mg, 64%). $^1$H NMR (300 MHz, CDCl$_3$): 7.87-7.84 (m, 1H, C(O)=C=CH), 7.53-7.46 (m, 2H, Ar—H), 7.07-7.00 (m, 9H, Ar—H), 4.41 (q, J=7.2 Hz, 1H, N—CH), 3.70 (m, 2H, HO—CH$_2$), 3.31-3.24 and 3.02-2.95 (m, 2H, OCH$_2$), 1.86 (d, J=7.2 Hz, 3H, CH$_3$), 1.76-1.66 (m, 4H, CH$_2$). $^{13}$C NMR (75 MHz, CDCl$_3$): 168.32, 145.27, 141.48, 137.77, 134.80, 133.15, 133.06, 132.84, 130.20, 129.67, 128.74, 128.41, 123.72, 123.27, 95.45, 63.36, 62.88, 52.49, 29.96, 26.48, 20.08. m/z (ES): 470 [M+H]$^+$. Anal.: calc. for C$_{26}$H$_{25}$Cl$_2$NO$_3$+0.3 H$_2$O: C, 65.62; H, 5.43; N, 2.94. Found: C, 65.58; H, 5.77; N, 2.45.

4-[1-(4-Chloro-phenyl)-1-(4-hydroxy-butoxy)-3-oxo-1,3-dihydro-isoindol-2-ylmethyl]-benzonitrile (NU8370)

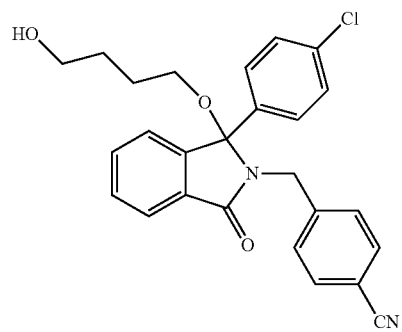 [SMILES: N#Cc1ccc(CN2C(=O)c3ccccc3C2(OCCCCO)c2ccc(Cl)cc2)cc1]

The named compound was synthesised from 2-(4-(aminomethyl)benzonitrile)-3-(4-chlorophenyl)-3-hydroxyisoindolin-1-one (513 mg, 1.37 mmol, 1 equiv.) and 1,4-butanediol (616 mg, 6.85 mmol, 5 equiv.) using General Procedure B and obtained as a white solid (302 mg, 67%). $^1$H NMR (300 MHz, CDCl$_3$): 7.94-7.91 (m, 1H, C(O)=C=CH), 7.55-7.52 (m, 2H, Ar—H), 7.47 and 7.33 (d: A$_2$B$_2$, J=8.4 Hz, 4H, Ar—H), 7.20 (m, 4H, Ar—H), 7.13-7.10 (m, 1H, Ar—H), 4.60 and 4.24 (d: AB, J=15.0 Hz, 2H, NCH$_2$), 3.56 (t, J=5.4 Hz, 2H, HOCH$_2$), 2.80-2.74 (m, 2H, OCH$_2$), 1.53-1.16 (m, 4H, CH$_2$). $^{13}$C NMR (75 MHz, CDCl$_3$): 168.18, 145.32, 142.86, 137.20, 134.77, 132.90, 131.86, 131.46, 129.99, 129.85, 128.61, 127.95, 123.77, 123.08, 118.41, 111.33, 94.78, 62.82, 62.34, 42.68, 29.41, 25.67. Anal.: calc. for C$_{29}$H$_{23}$ClN$_2$O$_3$+0.2 H$_2$O: C, 69.37; H, 5.16; N, 6.22. Found: C, 69.29; H, 5.20, N: 6.04.

All references to General Procedures A-F made hereinbelow are references to the General Procedures A-F outlined immediately below and do not refer to General Procedures A-C hereinabove.

General Procedure A

To a suspension of the corresponding phthalic anhydride (1 equiv.) in chlorobenzene (8 equiv.) was added aluminium chloride (2.4 equiv.) The mixture was heated to 90° C. for 2 h and then cooled to room temperature. Ice was added followed by conc. HCl (5 mL) and the mixture was extracted into dichloromethane (DCM) (3×50 mL) and then washed with 10% Na$_2$CO$_3$ solution (2×50 mL). The Na$_2$CO$_3$ washings were combined and acidified to pH3 with conc. HCl. The resulting precipitate was collected by filtration and dried in a vacuum oven.

General Procedure B

To a solution of the corresponding benzoic acid (1 equiv.) in dry THF (10 mL) was added under a nitrogen atmosphere thionyl chloride (2 equiv.) and 3 drops of anhydrous DMF. The reaction mixture was stirred for 4 h at room temperature and concentrated in vacuo. The resulting pale yellow oil was taken up in dry THF (10 mL) and the amine (1.1 equiv.) and DIPEA (1.1 equiv.) were added under nitrogen atmosphere. The reaction mixture was stirred overnight at room temperature and the solvents were removed in vacuo. The residue was taken up in EtOAc (50 mL), filtered and the filtrate washed with water (3×25 mL) and brine (1×25 mL). The organic layer was dried over MgSO$_4$, filtered and concentrated in vacuo to afford a solid which was recrystallised from EtOAc/petrol ether or purified by flash chromatography (Biotage SP4).

General Procedure C

To solution of the corresponding isoindolinone (1 equiv.) in dry THF (10 mL) was added under a nitrogen atmosphere thionyl chloride (2 equiv.) and 3 drops of anhydrous DMF. The reaction mixture was stirred for 4 h at room temperature and concentrated in vacuo. The resulting pale yellow oil was taken up in dry THF (10 mL) and the alcohol (2 equiv.) and potassium carbonate (2 equiv.) were added. The reaction mixture was stirred overnight at room temperature and the solvents were removed in vacuo. The residue was taken up in EtOAc (50 mL) and washed with water (3×25 mL) and brine (1×25 mL). The organic layer was dried over $MgSO_4$, filtered and concentrated in vacuo to afford an oil which was purified by flash chromatography (Biotage SP4).

General Procedure D

To a solution of the corresponding isoindolinone (1 equiv.) in anhydrous DCM (5 mL) was added mCPBA (1.1 equiv.). The reaction mixture was stirred at 30° C. for 4 h and then diluted with DCM (30 mL), washed with saturated $NaHCO_3$ solution (30 mL), water (30 mL) and brine (30 mL). The organic layer was dried over $MgSO_4$, filtered and concentrated in vacuo to afford an oil which was purified by flash chromatography (Biotage SP4).

General Procedure E

To a solution of the corresponding ester (1 equiv.) in dry THF was added under a nitrogen atmosphere potassium trimethylsilanolate (1.1 equiv.). The reaction mixture was stirred at room temperature overnight. Further potassium trimethylsilanolate (1.1 equiv.) was added and the mixture was again stirred at room temperature overnight. The solvent was concentrated in vacuo to afford a solid which was purified by flash chromatography (Biotage SP4).

General Procedure F

To a solution of the corresponding isoindolinone (1 equiv.) in THF (10 mL) was added pyridine (2 equiv.), 4-dimethylamino pyridine (catalytic) and succinic anhydride (2 equiv.). The reaction mixture was heated under reflux for 48 h, cooled to RT and the solvent concentrated in vacuo. The residue was dissolved in EtOAc (50 mL), washed with water (2×20 mL), brine (20 mL), dried over $Na_2SO_4$ and concentrated in vacuo. The product was purified by flash chromatography.

Intermediates

Synthesis of 2-(4-bromobenzoyl)benzoic acid

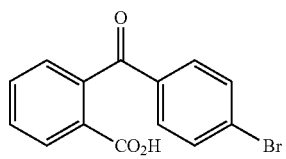

To a suspension of the phthalic anhydride (2 g, 13.50 mmol) in bromobenzene (11.38 mL, 108 mmol) was added aluminium chloride (3.60 g, 27.00 mmol). The mixture was heated to 90° C. for 2 h and then cooled to room temperature. Ice was added followed by conc. HCl (5 mL) and the mixture was extracted into DCM (3×50 mL) and then washed with 10% $Na_2CO_3$ solution (2×50 mL). The $Na_2CO_3$ washings were combined and acidified to pH3 with conc. HCl. The resulting precipitate was collected by filtration and dried in a vacuum oven. The named compound was obtained as a white solid (3.41 g, 83%).

$^1$H NMR (300 MHz, DMSO) δ 7.39-7.42 (m, 1H, —CH=CH—C($CO_2$H)), 7.51-7.53 (d AB, J=7.7 Hz, 2H, —CH—C(Br)), 7.73-7.66 (m, 4H, ArH), 7.97-8.00 (m, 1H, —CH=CH—CH—C($CO_2$H))

$^{13}$C NMR (DMSO, 75 MHz), δ 127.61, 128.89, 129.97, 130.09, 130.38, 130.71, 130.92, 132.07, 132.96, 136.46, 167.09, 194.21

IR: 665, 702, 736, 770, 812, 839, 924, 1009, 1065, 1148, 1252, 1279, 1422, 1485, 1570, 1670, 2546, 2657, 2832, 2988 $cm^{-1}$

LCMS (DMSO): Rt=3.01 min (on 5 min column)

UV (in EtOH): λ max=259 nm

Rf: 0.29 (50% EtOAc/petrol)

MP: 170-172° C.

Synthesis of a mixture of 2-(4-chlorobenzoyl)-3-methylbenzoic acid and 2-(4-chlorobenzoyl)-6-methylbenzoic acid

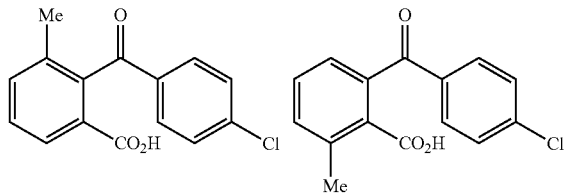

The named compounds were synthesised from 3-methylphthalic anhydride (3 g, 18.50 mmol) using General Procedure A and obtained as a white solid (2.98 g, 59%, ratio of 3- and 6-isomers is 20:1) which was used without further purification.

$^1$H NMR (300 MHz, DMSO)

Major isomer: δ 2.06 (s, 3H, $CH_3$), 7.45-7.61 (m, 6H, ArH), 7.86-7.88 (d, J=6.6 Hz, 1H, CH=C($CO_2$H)), 10.69 (br s, 1H, $CO_2$H)

$^{13}$C NMR (DMSO, 75 MHz), δ 18.63, 127.36, 128.94, 129.22, 129.53, 129.65, 130.06, 132.60, 134.94, 135.23, 137.74, 167.31, 193.10

IR: 675, 738, 754, 831, 919, 1009, 1088, 1144, 1264, 1288, 1400, 1580, 1678, 1749, 2556, 2643, 2817, 2961, 3406 $cm^{-1}$

LCMS (DMSO): Rt=3.49 min (on 5 min column)

UV (in EtOH): λ max=255 nm

Rf: 0.37 (50% EtOAc/petrol)

MP: 179-180° C.

Synthesis of a mixture of 2-(4-chlorobenzoyl)-4-methylbenzoic acid and 2-(4-chlorobenzoyl)-5-methylbenzoic acid

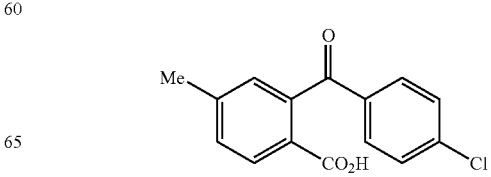

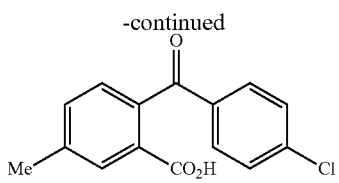

The named compounds were synthesised from 4-methylphthalic anhydride (3 g, 18.50 mmol) using General Procedure A and obtained as a white solid (4.60 g, 90%, ratio of 4- and 5-isomers is 2:1) which was used without further purification.

$^1$H NMR (300 MHz, DMSO) δ

Major isomer: 2.41 (s, 3H, CH$_3$), 7.23-7.25 (d, J=1.4 Hz, 1H, C(Me)-CH—C(COAr)), 7.43-7.48 (m, 1H, C(Me)-CH—CH—C(CO$_2$H)), 7.53-7.63 (m, 4H, ArH), 7.89-7.91 (d, J=8.0 Hz, 1H, —CH—CH—C(CO$_2$H)), 13.10 (br s, 1H, CO$_2$H)

Minor isomer: 2.44 (s, 3H, CH$_3$), 7.32-7.34 (d, J=7.7 Hz, 1H, C(Me)-CH—CH—C(COAr), 7.36-7.40 (m, 1H, C(Me)-CH—CH—C(COAr), 7.53-7.63 (m, 4H, ArH), 7.80-7.82 (d, J=1.1 Hz, 1H, C(Me)-CH—C(CO$_2$H)), 13.10 (br s, 1H, CO$_2$H)

$^{13}$C NMR (DMSO, 75 MHz), δ 21.28, 127.79, 127.95, 129.07, 130.12, 130.78, 133.17, 136.45, 137.22, 138.11, 140.24, 167.00, 190.90

IR: 683, 751, 780, 838, 934, 962, 1009, 1088, 1153, 1211, 1288, 1398, 1422, 1486, 1570, 1677, 2164, 2828, 3062 cm$^{-1}$

LCMS (DMSO): Rt=3.24 min (on 5 min column)

UV (in EtOH): λ max=253 nm

Rf: 0.42 (50% EtOAc/petrol)

MP: 163-164° C.

Synthesis of a mixture of 4-tert-butyl-2-(4-chlorobenzoyl)benzoic acid and 5-tert-butyl-2-(4-chlorobenzoyl)benzoic acid

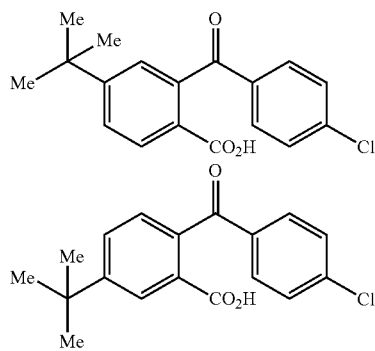

The named compounds were synthesised from 4-tertbutylphthalic anhydride (2.5 g, 12.24 mmol) using General Procedure A and obtained as a cream solid (3.56 g, 92%, ratio of 4- and 5-isomers is 1.3:1) which was used without further purification.

$^1$H NMR (300 MHz, DMSO) δ

Major isomer: 1.29 (s, 9H, (CH$_3$)$_3$), 7.35-7.38 (d, J=1.8 Hz, 1H, C($^t$Bu)-CH—CH—C(CO$_2$H)), 7.54-7.69 (m, 4H, ArH), 7.69-7.75 (m, 1H, C($^t$Bu)-CH—CH—C(COAr)), 7.94-7.97 (d, J=8.3 Hz, 1H, —CH—CH—C(CO$_2$H))

Minor isomer: 1.34 (s, 9H, (CH$_3$)$_3$), 7.40-7.41 (d, J=8.0 Hz, 1H, C($^t$Bu)-CH—CH—C(COAr), 7.54-7.69 (m, 4H, ArH), 7.74-7.77 (m, 1H, C($^t$Bu)-CH—CH—C(COAr), 7.99-8.00 (d, J=1.9 Hz, 1H, C($^t$Bu)-CH—C(CO$_2$H))

Both isomers:

$^{13}$C NMR (DMSO, 75 MHz), δ 31.07, 31.18, 34.96, 35.24, 124.45, 126.68, 126.99, 127.59, 127.85, 128.69, 129.06, 129.56, 130.22, 130.52, 130.87, 130.92, 136.41, 138.27, 138.61, 141.35, 153.12, 156.11, 166.93, 167.41, 195.70, 195.88

IR: 683, 712, 762, 808, 843, 907, 932, 1007, 1083, 1119, 1159, 1252, 1280, 1364, 1398, 1417, 1476, 1585, 2869, 2964 cm$^{-1}$

LCMS (DMSO): Rt=3.56 min (on 5 min column)

UV (in EtOH): λ max=255 nm

Rf=0.52 (50% EtOAc/petrol).

MP: 173-174° C.

Synthesis of 3-chloro-2-(4-chlorobenzoyl)benzoic acid and 6-chloro-2-(4-chlorobenzoyl)benzoic acid

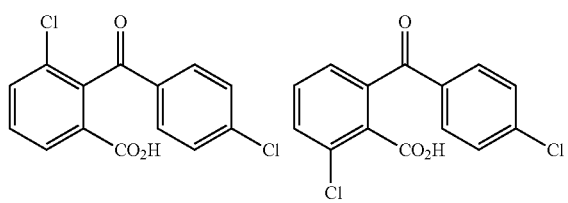

The named compounds were synthesised from 3-chlorophthalic anhydride (5 g, 27.39 mmol) using General Procedure A and obtained as a yellow solid (6.71 g, 83%, ratio of 3- and 6-isomers is 99:1) which was used without further purification.

$^1$H NMR (300 MHz, DMSO) δ

Major isomer (20): 7.56-7.59 (d AB, J=8.6 Hz, CH—C(Cl)—CH), 7.65-7.71 (m, 3H, ArH), 7.84-7.87 (dd, J=0.9, 8.0 Hz, 1H, CH—C(Cl)—C(COAr)), 8.03-8.06 (dd, J=0.9, 8.0 Hz, 1H, CH—C(CO$_2$H)), 13.65 (br s, 1H, CO$_2$H)

Minor isomer (21): too weak to analyse $^{13}$C NMR (DMSO, 75 MHz), δ 129.38, 130.51, 130.59, 130.64, 131.36, 131.82, 134.20, 135.73, 138.55, 139.88, 165.93, 195.17

IR: 672, 714, 743, 756, 824, 864, 920, 1009, 1090, 1154, 1206, 1255, 1298, 1400, 1461, 1582, 1676, 2656, 2825, 3067 cm$^{-1}$

LCMS (DMSO): Rt=3.34 min (on 5 min column)

UV (in EtOH): λ max=256 nm

Rf=0.29 (50% EtOAc/petrol)

MP: 184-185° C.

Synthesis of 4-bromo-2-(4-chlorobenzoyl)benzoic acid and 5-bromo-2-(4-chlorobenzoyl)benzoic acid

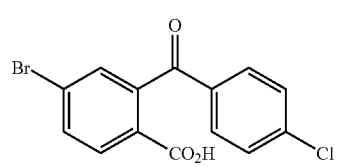 [SMILES: O=C(O)c1cc(Cl)c(Cl)cc1C(=O)c1ccc(Cl)cc1]

The named compounds were synthesised from 4-tertbutylphthalic anhydride (2.5 g, 12.24 mmol) using General Procedure A and obtained as a cream solid (3.47 g, 66%, ratio of 4- and 5-isomers is ~1:1) which was used without further purification.

$^1$H NMR (300 MHz, DMSO) δ

Compound 36: 7.54-7.66 (m, 4H, —C$_6$H$_4$Cl), 7.84-7.93 (m, 2H, ArH), 8.08-8.09 (d. J=1.7 Hz, 1H, C(Br)CHC(CO$_2$H)), 13.60 (br s, 1H, CO$_2$H)

Compound 35: 7.54-7.66 (m, 4H, —C$_6$H$_4$Cl), 7.70-7.72 (d, J=1.5 Hz, 1H, C(Br)CHC(COAr)), 7.84-7.93 (m, 2H, ArH), 13.60 (br s, 1H, CO$_2$H)

$^{13}$C NMR (DMSO, 75 MHz), δ 128.16, 129.15, 130.21, 130.90, 131.37, 132.12, 133.18, 135.21, 135.52, 138.35, 170.54, 193.35

IR: 756, 841, 883, 927, 1013, 1092, 1152, 1177, 1285, 1400, 1423, 1483, 1580, 1672, 2546 cm$^{-1}$

LCMS (DMSO): Rt=3.43 min (on 5 min column)

UV (in EtOH): λ max=255 nm

Rf=0.24 (50% EtOAc/petrol)

MP: 210-211° C.

Synthesis of
4,5-dichloro-2-(4-chlorobenzoyl)benzoic acid

The named compound was synthesised from 4,5-dichlorophthalic anhydride (2.5 g, 11.52 mmol) using General Procedure A and obtained as a yellow solid (1.98 g, 52%).

$^1$H NMR (300 1\4 Hz, DMSO) δ 7.56-7.59 (d AB, J=8.3 Hz, —CC$_2$H$_2$C$_2$H$_2$CCl), 7.67-7.70 (d AB, J=8.3 Hz, —CC$_2$H$_2$C$_2$H$_2$Cl), 7.87 (s, 1H, CH—C(COAr)), 8.14 (s, 1H, CH—C(CO$_2$H)), 13.85 (br s, 1H, CO$_2$H)

$^{13}$C NMR (DMSO, 75 MHz), δ 129.21, 130.76, 131.07, 131.11, 131.97, 134.15, 137.45, 138.23, 138.70, 139.76, 170.36, 198.58

IR: 768, 843, 868, 893, 964, 1009, 1090, 1126, 1167, 1257, 1343, 1422, 1478, 1545, 1582, 1678, 2228, 2563, 2834 cm$^{-1}$

UV (in EtOH): λ max=254 nm

Rf=0.18 (50% EtOAc/petrol)

MP: 195-197° C.

Synthesis of a mixture of 2-(4-chlorobenzoyl)-4-fluorobenzoic acid and 2-(4-chlorobenzoyl)-5-fluorobenzoic acid The named compounds were synthesised from 4-fluorophthalic anhydride (2.5 g, 15.05 mmol) using General Procedure A and obtained as a cream solid (3.51 g, 84%, ratio of 4- and 5-isomers is 3:2). The mixture was used without further purification.

$^1$H NMR (300 MHz, DMSO) δ

Major isomer: 7.24-7.27 (dd, J=2.0, 8.5 Hz, 1H, C(F)—CH—C(COAr)), 7.40-7.46 (m, 1H, C(F)—CH—CH—C(CO$_2$H)), 7.49-7.52 (m, 2H, ArH), 7.57-7.61 (m, 2H, ArH), 8.02-8.07 (dd, J=5.4, 8.5 Hz, 1H, CH—CH—(CO$_2$H))

Minor isomer: 7.40-7.46 (m, 1H, C(F)—CH—CH—C(COAr)), 7.49-7.52 (m, 3H, ArH), 7.57-7.61 (m, 2H, ArH), 7.66-7.70 (dd, J=1.9, 9.2 Hz, 1H, C(F)—CH—(CO$_2$H))

$^{13}$C NMR (DMSO, 75 MHz), δ 116.98, 119.25, 128.62, 129.15, 130.85, 130.92, 136.01, 138.40, 139.09, 166.10, 166.26, 196.59

IR: 681, 753, 784, 841, 860, 945, 974, 1011, 1086, 1140, 1174, 1211, 1278, 1401, 1427, 1486, 1580, 1672, 2822, 3070 cm$^{-1}$

LCMS (DMSO): Rt=3.76 min (on 5 min column)

UV (in EtOH): λ max=256 nm

Rf=0.33 (50% EtOAc/petrol)

MP: 153-155° C.

Synthesis of
2-(4-chlorobenzoyl)cyclohex-1-enecarboxylic acid

The named compound was synthesised from 3,4,5,6-tetrahydrophthalic anhydride (2.08 g, 13.69 mmol) using General Procedure A, purified by chromatography (Biotage SP4; 20%-40% EtOAc/petrol) and obtained as a yellow oil (2.69 g, 74%).

$^1$H NMR (300 MHz, DMSO) δ 1.50-1.70 (m, 4H, CH$_2$—C(COAr)—C(CO$_2$H)—CH$_2$), 2.15-2.17 (m, 4H, CH$_2$—CH$_2$—CH$_2$—C(CO$_2$H)), 7.93-7.48 (m, 4H, ArH), 8.16 (br s, 1H, CO$_2$H)

$^{13}$C NMR (DMSO, 75 MHz), δ 19.79, 21.01, 21.37, 21.45, 127.79, 128.84, 133.95, 137.48, 146.33, 149.31, 171.24, 192.87

IR: 687, 729, 757, 819, 907, 938, 966, 1038, 1072, 1169, 1206, 1246, 1375, 1422, 1489, 1597, 1736, 2865, 2937, 3318 cm$^{-1}$

LCMS (DMSO): Rt=3.72 min (on 5 min column)

UV (in EtOH): λmax=254 nm

Rf=0.48 (50% EtOAc/petrol)

Final Compounds

Synthesis of 3-(4-bromophenyl)-3-(4-hydroxybutoxy)-2-(4-nitrobenzyl)isoindolin-1-one (NU8390)

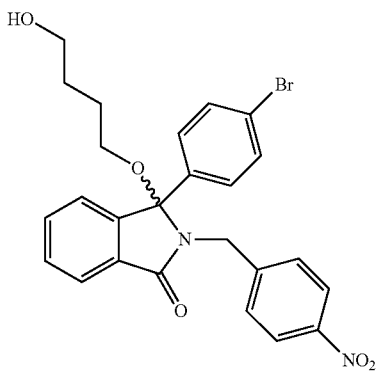 [SMILES: O=C1c2ccccc2C(OCCCCO)(c2ccc(Br)cc2)N1Cc1ccc([N+](=O)[O-])cc1]

The named compound was synthesised from NU8389 (0.50 g, 1.14 mmol) and 1,4-butanediol (0.20 mL, 2.28 mmol) using General Procedure C, purification by chromatography (Biotage SP4; 10%-50% EtOAc/petrol) and obtained as a pale yellow oil (0.50 g, 85%).

$^1$H NMR (300 MHz, CDCl$_3$) δ 1.36-1.45 (m, 4H, OCH$_2$—CH$_2$—CH$_2$), 2.76 (t, J=6.1 Hz, O—CH$_2$), 3.49 (t, J=6.2 Hz, HO—CH$_2$), 4.25 and 4.60 (dd: AB, J=15.0 Hz, 2H, N—CH$_2$), 7.08-7.13 (m, 3H, Ar—H), 7.29-7.36 (m, 4H, Ar—H), 7.48-7.51 (m, 2H, Ar—H), 7.87-7.89 (m, 1H, C(O)=C=CH), 7.97-8.00 (m, 2H, O$_2$N—C—CH)

$^{13}$C NMR (CDCl$_3$, 75 MHz), δ 26.01, 29.69, 42.69, 62.51, 63.19, 95.14, 123.21, 123.45, 123.55, 124.09, 128.61, 130.25, 130.34, 131.76, 131.92, 133.27, 138.13, 145.10, 145.58, 147.72, 168.49

IR: 696, 760, 804, 853, 928, 1005, 1063, 1099, 1177, 1276, 1341, 1381, 1425, 1467, 1519, 1605, 1687, 2872, 2925, 3397 cm$^{-1}$

LCMS (DMSO): Rt=3.72 min (on 5 min column)
UV (in EtOH): λ max=267 nm
Rf: 0.26 (50% EtOAc/petrol)
CHN: C$_{25}$H$_{23}$BrN$_2$O$_5$ requires C, 58.72; H, 4.53; N, 5.48. found C, 58.70; H, 4.24; N, 5.25

Synthesis of 3-(4-bromophenyl)-3-((1-(hydroxymethyl)cyclopropyl)methoxy)-2-(4-nitrobenzyl)isoindolin-1-one (NU8391)

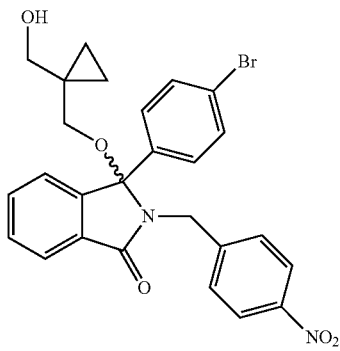

The named compound was synthesised from NU8389 (0.50 g, 1.14 mmol) and 1,1-bis(hydroxymethyl)cyclopropane (0.22 mL, 2.28 mmol) using General Procedure C, purification by chromatography (Biotage SP4; 10%-50% EtOAc/petrol) and obtained as white crystals (0.47 g, 78%).

$^1$H NMR (300 MHz, CDCl$_3$) δ 0.13-0.22 (m, 2H, CH$_2$), 0.42-0.43 (m, 2H, CH$_2$), 2.78-2.85 (m, 2H, OCH$_2$), 3.44-3.52 (m, 2H, HOCH$_2$), 4.50 (s, 2H, N—CH$_2$), 7.09-7.18 (m, 3H, Ar—H), 7.28-7.33 (m, 4H, Ar—H), 7.52-7.55 (m, 2H, Ar—H), 7.89-7.93 (m, 1H, C(O)=C=CH), 7.96-8.01 (m, 2H, O$_2$N—C—CH)

$^{13}$C NMR (CDCl$_3$, 75 MHz), δ 8.90, 22.64, 42.70, 67.72, 94.95, 123.33, 123.48, 123.59, 124.14, 128.59, 130.01, 130.20, 130.51, 131.94, 133.47, 138.00, 144.95, 145.42, 147.61, 168.54

IR: 697, 759, 805, 855, 928, 1007, 1065, 1097, 1177, 1275, 1341, 1383, 1426, 1466, 1519, 1605, 1685, 2873, 2917, 3078 cm$^{-1}$

LCMS (DMSO): Rt=3.88 min (on 5 min column)
UV (in EtOH): λ max=267 nm
Rf: 0.32 (50% EtOAc/petrol)
MP: 76-77° C.
CHN: C$_{26}$H$_{23}$BrN$_2$O$_5$ requires C, 59.67; H, 4.43; N, 5.35. found C, 59.71; H, 4.39; N, 5.17

Synthesis of 3-(4-bromophenyl)-3-(3-hydroxypropoxy)-2-(4-nitrobenzyl)isoindolin-1-one (NU8392)

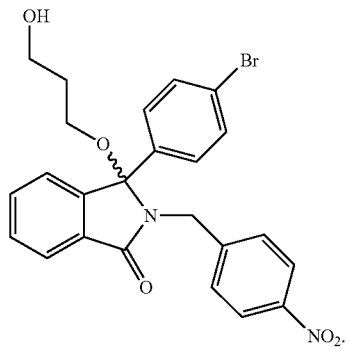 [SMILES: O=C1c2ccccc2C(OCCCO)(c2ccc(Br)cc2)N1Cc1ccc([N+](=O)[O-])cc1]

The named compound was synthesised from NU8389 (0.50 g, 1.14 mmol) and 1,3-propanediol (0.16 mL, 2.28 mmol) using General Procedure C, purification by chromatography (Biotage SP4; 10%-50% EtOAc/petrol) and obtained as a pale yellow oil (0.40 g, 70%).

$^1$H NMR (300 MHz, CDCl$_3$) δ 1.46-1.61 (m, 2H, OCH$_2$—CH$_2$), 2.92 (td, J=6.0, 1.9 Hz, O—CH$_2$), 3.60 (t, J=6.1 Hz, HO—CH$_2$), 4.34 and 4.60 (dd: AB, J=15.1 Hz, 2H, N—CH$_2$), 6.95-6.99 (m, 1H, Ar—H), 7.10-7.17 (m, 2H, Ar—H), 7.27-7.39 (m, 4H, Ar—H), 7.50-7.55 (m, 2H, Ar—H), 7.89-7.92 (m, 1H, C(O)=C=CH), 7.97-8.04 (m, 2H, O$_2$N—C—CH)

$^{13}$C NMR (CDCl$_3$, 75 MHz), δ 32.45, 42.71, 60.23, 60.80, 95.21, 123.31, 123.48, 123.61, 124.17, 128.57, 130.24, 130.47, 131.75, 131.99, 133.40, 137.99, 145.07, 145.43, 147.64, 168.58

IR: 697, 760, 805, 853, 927, 1010, 1063, 1098, 1177, 1278, 1339, 1381, 1423, 1467, 1518, 1603, 1688, 2879, 2925, 3409 cm$^{-1}$

LCMS (DMSO): Rt=3.73 min (on 5 min column)
UV (in EtOH): λ max=266 μm
Rf: 0.24 (50% EtOAc/petrol).
CHN: C$_{24}$H$_{21}$BrN$_2$O$_5$ requires C, 57.96; H, 4.26; N, 5.63. found C, 58.16; H, 4.28; N, 5.43

Synthesis of 3-(4-chlorophenyl)-3-hydroxy-4-methyl-2-(4-nitrobenzyl)isoindolin-1-one (NU8393) and 3-(4-chlorophenyl)-3-hydroxy-7-methyl-2-(4-nitrobenzyl)isoindolin-1-one (NU8394)

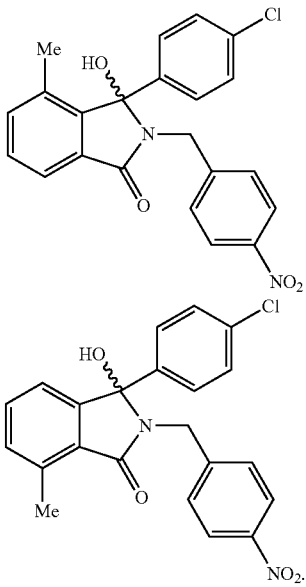

The named compounds were synthesised from a mixture of 2-(4-chlorobenzoyl)-3-methylbenzoic acid and 2-(4-chlorobenzoyl)-6-methylbenzoic acid (2 g, 7.28 mmol) and 4-nitrobenzylamine hydrochloride (1.51 g, 8.01 mmol) using General Procedure B, purified by chromatography (Biotage SP4; 10%-20% EtOAc/petrol) and obtained as a yellow solid (NU8393) and cream solid (NU8394) (1.45 g, 49%, ratio of 4- and 7-isomers is 20:1).

Analysis of major isomer (NU8393):
$^1$H NMR (300 MHz, CDCl$_3$) δ 2.07 (s, 3H, —CH$_3$), 4.02 (br s, 1H, OH), 4.16 and 4.46 (dd, J=15.3 Hz, 2H, N—CH$_2$—), 7.19-7.23 (m, 6H, Ar—H), 7.29-7.31 (dd, J=7.5, 1.5 Hz, 1H, —CH—CH—C(Me), 7.39-7.44 (t, J=7.6 Hz, 1H, —CH—CH—C(Me)-), 7.60-7.62 (dd, J=7.3, 1.1 Hz, 1H, C(O)—C=CH—), 7.93-7.97 (m, 2H, —CH—NO$_2$)
$^{13}$C NMR (CDCl$_3$, 75 MHz), δ 19.86, 42.76, 90.65, 121.58, 123.67, 125.66, 126.70, 128.39, 129.02, 129.69, 131.33, 132.01, 134.21, 136.85, 139.43, 145.52, 148.29, 166.89
IR: 695, 729, 760, 800, 851, 932, 982, 1014, 1075, 1193, 1271, 1341, 1397, 1487, 1517, 1609, 1680, 3238 cm$^{-1}$
LCMS (DMSO): Rt=3.75 min (on 5 min column)
HPLC purity (as area %): >95
UV (in EtOH): λ max=269 nm
EI-MS: calculated mass of ion 409.0950 [M+H]$^+$, measured mass of ion 409.0951 [M+H]$^+$
Rf: 0.47 (50% EtOAc/petrol)
MP: 175-176° C.
CHN: C$_{22}$H$_{17}$ClN$_2$O$_4$ requires C, 64.63; H, 4.19; N, 6.85. found C, 64.78; H, 4.40; N, 6.58

Analysis of minor isomer (NU8394):
$^1$H NMR (300 MHz, CDCl$_3$) δ 2.62 (s, 3H, —CH$_3$), 3.79 (br s, 1H, OH), 4.30 and 4.61 (dd, J=15.3 Hz, 2H, N—CH$_2$—), 7.07-7.19 (m, 1H, Ar—H), 7.21-7.26 (m, 5H, Ar—H), 7.31-7.41 (m, 3H, Ar—H), 7.97-8.00 (m, 2H, —CH—NO$_2$)
$^{13}$C NMR (CDCl$_3$, 75 MHz), δ 17.43, 42.78, 90.68, 120.41, 123.74, 126.76, 127.30, 128.18, 129.13, 129.79, 132.57, 133.06, 135.31, 137.40, 138.59, 145.87, 149.32, 168.65
IR: 696, 725, 779, 802, 854, 932, 966, 1011, 1088, 1171, 1199, 1279, 1337, 1378, 1423, 1481, 1516, 1602, 1678, 2852, 2923, 3338 cm$^{-1}$
LCMS (DMSO): Rt=3.70 min (on 5 min column)
HPLC purity (as area %): 90
UV (in EtOH): λ max=270 nm
EI-MS: calculated mass of ion 409.0950 [M+H]$^+$, measured mass of ion 409.0945 [M+H]$^+$
Rf: 0.58 (50% EtOAc/petrol)
MP: 158-159° C.

Synthesis of 3-(4-chloro-phenyl)-3-(1-hydroxymethyl-cyclopropylmethoxy)-2-(4-nitro-benzyl)-2,3-dihydro-isoindol-1-one (NU8354)

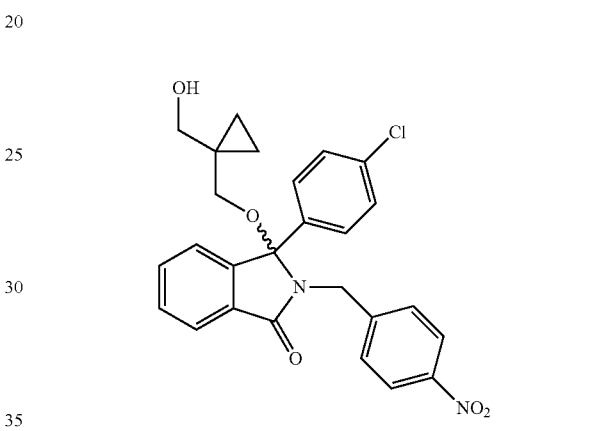

The named compound was synthesised from NU8260 (400 mg, 1.01 mmol) and 1,1-bis(hydroxymethyl)cyclopropane (0.19 mL, 2.03 mmol) using General Procedure C, purified by chromatography (Biotage SP4; 10%-50% EtOAc/petrol) and obtained as a cream solid (442 mg, 92%).
$^1$H NMR (300 MHz, CDCl$_3$) δ 0.12-0.22 (m, 2H, CH$_2$), 0.40-0.43 (m, 2H, CH$_2$), 2.81 (s, 2H, OCH$_2$), 3.43-3.51 (m, 2H, HOCH$_2$), 4.49 (s, 2H, N—CH$_2$), 7.12-7.19 (m, 5H, Ar—H), 7.29-7.32 (m, 2H, Ar—H), 7.52-7.55 (m, 2H, Ar—H), 7.89-7.92 (m, 1H, C(O)=C—CH), 7.98-8.01 (m, 2H, O$_2$N—C—CH)
$^{13}$C NMR (CDCl$_3$, 75 MHz), δ 8.90, 8.94, 22.68, 42.75, 67.84, 94.96, 123.48, 123.60, 124.16, 128.30, 128.98, 130.21, 130.50, 131.87, 133.45, 135.29, 137.47, 144.95, 145.52, 168.54
IR: 702, 769, 820, 858, 928, 955, 1009, 1036, 1065, 1090, 1176, 1231, 1277, 1341, 1383, 1427, 1470, 1514, 1599, 1705, 2878, 3076, 3471 cm$^{-1}$
LCMS (DMSO): Rt=3.78 min (on 5 min column)
UV (in EtOH): λ max=267 nm
EI-MS: calculated mass of ion 478.1290 [M+H]$^+$, measured mass of ion 478.1291 [M+H]$^+$
Rf: 0.32 (50% EtOAc/petrol)
MP: 148-149° C.
CHN: C$_{26}$H$_{23}$ClN$_2$O$_5$ requires C, 65.21; H, 4.84; N, 5.85. found C, 65.21; H, 4.99; N, 5.58
Separation of enantiomers achieved by chiral preparative HPLC (Daicel Chiralpak AD-H 250×10 mm; Hexane/Ethanol (4:1))
NU8354A (yellow solid)

Optical rotation: Specific rotation [α]=+22.66° (at 24.8° C., wavelength=589 nm, tube length=0.25 dm, concentration=0.406 g/100 ml)

NU8354B (off-white solid)

Optical Rotation Specific rotation [α]=−20.10° (at 24.8° C., wavelength=589 nm, tube length=0.25 dm, concentration=0.398 g/100 ml)

Synthesis of 3-(4-chlorophenyl)-3-hydroxy-5-methyl-2-(4-nitrobenzyl)isoindolin-1-one (NU8395) and 3-(4-chlorophenyl)-3-hydroxy-6-methyl-2-(4-nitrobenzyl)isoindolin-1-one (NU8412)

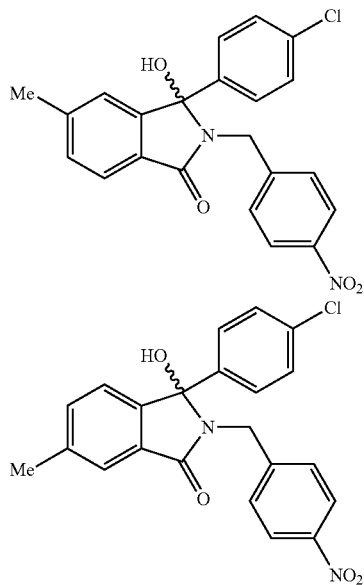

The named compounds were synthesised from a mixture of 2-(4-chlorobenzoyl)-4-methylbenzoic acid and 2-(4-chlorobenzoyl)-5-methylbenzoic acid (2 g, 7.28 mmol) and 4-nitrobenzylamine hydrochloride (1.51 g, 8.01 mmol) using General Procedure B, purified by chromatography (Biotage SP4; 10%-20% EtOAc/petrol) and obtained as a white solid (NU8395) and white solid (NU8412) (1.25 g, 42%, ratio of 5- and 6-isomers is 2:1).

Analysis of major isomer (NU8395):

$^1$H NMR (300 MHz, CDCl$_3$) δ 1.36 (s, 9H, —C(CH$_3$)), 3.64 (br s, 1H, OH), 4.21 and 4.64 (dd, J=15.3 Hz, 2H, N—CH$_2$—), 7.19-7.24 (dd, J=1.3 Hz 1H, —C—CH═C (Me)), 7.21-7.22 (m, 4H, Ar—H), 7.25-7.34 (m, 3H, Ar—H), 7.65-7.68 (dd, J=7.7 Hz, 1H, C(O)—C═CH—), 7.97-8.01 (m, 2H, —CH—NO$_2$)

$^{13}$C NMR (CDCl$_3$, 75 MHz), δ 22.12, 40.91, 94.13, 123.73, 124.04, 128.17, 129.16, 129.76, 130.42, 132.88, 134.89, 136.93, 139.91, 140.77, 141.02, 145.33, 148.58, 166.11

IR: 696, 729, 745, 770, 788, 800, 833, 853, 929, 961, 988, 1015, 1044, 1089, 1103, 1128, 1155, 1184, 1203, 1271, 1309, 1341, 1390, 1427, 1491, 1516, 1603, 1623, 1660, 1937, 2202, 2851, 2918, 3053, 3088, 3231 cm$^{-1}$

LCMS (DMSO): Rt=3.74 min (on 5 min column)

HPLC purity (as area %): >98

UV (in EtOH): λ max=268 nm

EI-MS: calculated mass of ion 426.1215 [M+NH$_4$]$^+$, measured mass of ion 426.1212 [M+NH$_4$]$^+$ Rf: 0.50 (50% EtOAc/petrol)

MP: 221-222° C.

CHN: C$_{22}$H$_{17}$ClN$_2$O$_4$ requires C, 64.63; H, 4.19; N, 6.85. found C, 64.76; H, 4.13, N: 6.58

Analysis of minor isomer (NU8412):

$^1$H NMR (300 MHz, CDCl$_3$) δ 2.40 (s, 3H, —CH$_3$), 4.27 (br s, 1H, OH), 4.26 and 4.56 (dd, J=15.3 Hz, 2H, N—CH$_2$—), 7.13-7.21 (m, 5H, Ar—H), 7.25-7.28 (m, 2H, Ar—H), 7.30-7.34 (m, 1H, —CH—CH—C(Me)-), 7.43-7.45 (dd, J=1.2 Hz, 1H, C(O)—C═CH—), 7.93-7.96 (m, 2H, —CH—NO$_2$)

$^{13}$C NMR (CDCl$_3$, 75 MHz), δ 21.64, 42.74, 91.34, 122.82, 123.65, 124.24, 128.18, 129.04, 129.77, 130.52, 134.42, 135.21, 137.27, 140.05, 140.80, 145.67, 146.24, 168.25

IR: 704, 731, 770, 787, 806, 831, 854, 932, 1013, 1061, 1090, 1132, 1174, 1199, 1256, 1310, 1343, 1383, 1433, 1491, 1518, 1607, 1660, 1678, 1983, 2018, 2224, 2255, 2853, 2922, 3320, 3342 cm$^{-1}$

LCMS (DMSO): Rt=4.09 min (on 5 min column)

UV (in EtOH): λ max=268 nm

ELMS: calculated mass of ion 407.0804 [M−H]$^-$, measured mass of ion 407.0800 [M−H]$^-$ Rf: 0.53 (50% EtOAc/petrol)

MP: 208-209° C.

CHN: C$_{22}$H$_{17}$ClN$_2$O$_4$ requires C, 64.63; H, 4.19; N, 6.85. found C, 64.95; H, 4.19; N, 6.83

Synthesis of 5-tert-butyl-3-(4-chlorophenyl)-3-hydroxy-2-(4-nitrobenzyl)isoindolin-1-one (NU8396) and 6-tert-butyl-3-(4-chlorophenyl)-3-hydroxy-2-(4-nitrobenzyl)isoindolin-1-one (NU8397)

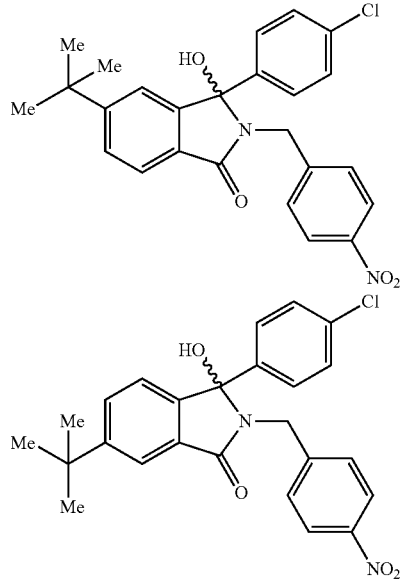

The named compounds were synthesised from a mixture of 4-tert-butyl-2-(4-chlorobenzoyl)benzoic acid and 5-tert-butyl-2-(4-chlorobenzoyl)benzoic acid (2.31 g, 7.28 mmol) and 4-nitrobenzylamine hydrochloride (1.51 g, 8.01 mmol) using General Procedure B, purified by chromatography (Biotage SP4; 10%-20% EtOAc/petrol) and obtained as a white solid (NU8396) and cream solid (NU8397) (2.43 g, 74%, ratio of 5- and 6-isomers is 1.3:1).

Analysis of major isomer (NU8396):

$^1$H NMR (300 MHz, CDCl$_3$) δ 4.25 and 4.68 (dd, J=15.4 Hz, 2H, N—CH$_2$—), 7.22-7.27 (m, 5H, Ar—H), 7.32-7.35 (m, 2H, Ar—H), 7.54-7.57 (dd, J=8.06, 1.62 Hz, 1H, —CH═CH—C($^t$Bu)-), 7.72-7.75 (dd, J=8.0 Hz, 1H, C(O)—C═CH—CH—C($^t$Bu)-), 8.00-8.03 (m, 2H, —CH—NO$_2$)

$^{13}$C NMR (CDCl$_3$, 75 MHz), δ 31.58, 41.48, 41.54, 91.51, 119.64, 123.70, 125.51, 126.81, 127.26, 128.20, 129.13, 129.71, 133.51, 134.89, 138.81, 141.91, 145.87, 149.50, 167.81

IR: 701, 802, 850, 932, 958, 1011, 1052, 1090, 1194, 1277, 1339, 1395, 1423, 1487, 1515, 1603, 1666, 2160, 2955, 3260, 3461 cm$^{-1}$

LCMS (DMSO): Rt=3.74 min (on 5 min column)

HPLC purity (as area %): >93

UV (in EtOH): λ max=268 nm

EI-MS: calculated mass of ion 451.1419 [M+H]$^+$, measured mass of ion 451.1413 [M+H]$^+$ Rf: 0.58 (50% EtOAc/petrol)

MP: 247-248° C.

CHN: C$_{25}$H$_{23}$ClN$_2$O$_4$ requires C, 66.59; H, 5.14; N, 6.21. found C, 66.64; H, 5.19; N, 5.89

Analysis of minor isomer (NU8397):

$^1$H NMR (300 MHz, CDCl$_3$) δ 1.36 (s, 9H, —C(CH$_3$)), 3.64 (br s, 1H, OH), 4.15 and 4.59 (dd, J=15.3 Hz, 2H, N—CH$_2$—), 7.19-7.24 (m, 5H, Ar—H), 7.27-7.30 (m, 2H, Ar—H), 7.57-7.61 (dd, J=8.04, 1.81 Hz, 1H, —CH═CH—C($^t$Bu)-), 7.90-7.91 (dd, J=1.5 Hz, 1H, C(O)—C═CH—C($^t$Bu)-), 7.97-8.00 (m, 2H, —CH—NO$_2$)

$^{13}$C NMR (CDCl$_3$, 75 MHz), δ 31.63, 35.54, 42.75, 91.31, 120.95, 122.56, 123.67, 128.18, 129.08, 129.75, 130.93, 145.75

IR: 706, 727, 808, 833, 849, 901, 924, 939, 1013, 1049, 1088, 1134, 1198, 1258, 1271, 1309, 1345, 1393, 1439, 1487, 1517, 1603, 1682, 1792, 1898, 1923, 1948, 1969, 2065, 2104, 2217, 2365, 2866, 2963, 3381 cm$^{-1}$

LCMS (DMSO): Rt=3.96 min (on 5 min column)

HPLC purity (as area %): >97

UV (in EtOH): λ max=268 nm

EI-MS: calculated mass of ion 451.1419 [M+H]$^+$, measured mass of ion 451.1420 [M+H]$^+$ Rf: 0.64 (50% EtOAc/petrol)

MP: 226-227° C.

CHN: C$_{25}$H$_{23}$ClN$_2$O$_4$+0.5EtOAc requires C, 65.52; H, 5.50; N, 5.66. found C, 65.44; H, 5.27; N, 5.47

Synthesis of 4-chloro-3-(4-chlorophenyl)-3-hydroxy-2-(4-nitrobenzyl)isoindolin-1-one (NU8398)

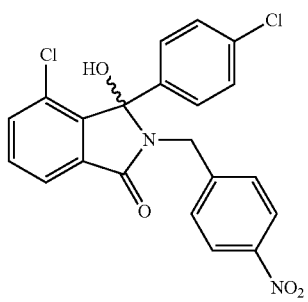 [SMILES: O=C1c2cccc(Cl)c2C(O)(c2ccc(Cl)cc2)N1Cc1ccc([N+](=O)[O-])cc1]

The named compound was synthesised from a mixture of 3-chloro-2-(4-chlorobenzoyl)benzoic acid and 6-chloro-2-(4-chlorobenzoyl)benzoic acid (2.15 g, 7.28 mmol) and 4-nitrobenzylamine hydrochloride (1.51 g, 8.01 mmol) using General Procedure B, purified by chromatography (Biotage SP4; 10%-20% EtOAc/petrol) and obtained as a white solid (1.96 g, 63%).

$^1$H NMR (300 MHz, CDCl$_3$) δ 4.28 (br s, 1H, OH), 4.28 and 4.63 (dd, AB, J=15.4 Hz, N—CH$_2$—), 7.19-7.22 (m, 4H, Ar—H), 7.31-7.33 (m, 2H, Ar—H), 7.44-7.49 (m, 2H, Ar—H), 7.72-7.75 (dd, J=3.2, 8.5 Hz, 1H, (C(O)—C═CH—), 7.98-8.00 (m, 2H, —CH—NO$_2$)

$^{13}$C NMR (CDCl$_3$, 75 MHz), δ 42.37, 90.90, 122.20, 123.22, 123.35, 128.21, 128.68, 129.44, 129.75, 131.69, 131.89, 134.14, 135.15, 147.37, 163.60, 163.86

IR: 696, 729, 759, 808, 856, 932, 996, 1070, 1092, 1144, 1174, 1271, 1342, 1397, 1462, 1518, 1592, 1682, 2026, 2171, 3220 cm$^{-1}$

LCMS (DMSO): 8.47 min (on 12 min column)

UV (in EtOH): λ max=268 nm

EI-MS: calculated mass of ion 429.0403 [M+H]$^+$, measured mass of ion 429.0401 [M+H]$^+$ Rf: 0.47 (50% EtOAc/petrol)

MP: 202-203° C.

CHN: C$_{21}$H$_{14}$Cl$_2$N$_2$O$_4$+0.2EtOAc requires C, 58.59; H, 3.52; N, 6.27. found C, 58.27; H, 3.21; N, 6.48

Synthesis of 6-tert-butyl-3-(4-chlorophenyl)-3-((1-(hydroxymethyl)cyclopropyl)methoxy)-2-(4-nitrobenzyl)isoindolin-1-one (NU8399)

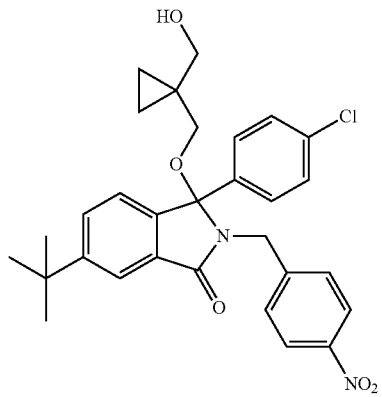 [SMILES: CC(C)(C)c1ccc2c(c1)C(=O)N(Cc1ccc([N+](=O)[O-])cc1)C2(OCC1(CO)CC1)c1ccc(Cl)cc1]

The named compound was synthesised from NU8397 (200 mg, 0.44 mmol) and 1,1-bis(hydroxymethyl)cyclopropane (0.09 mL, 0.89 mmol) using General Procedure C, purified by chromatography (Biotage SP4; 10%-50% EtOAc/petrol) and obtained as white crystals (182 mg, 75%).

$^1$H NMR (300 MHz, CDCl$_3$) δ 0.20-0.30 (m, 2H, cyclopropane CH$_2$), 0.47-0.50 (m, 2H, Cyclopropane CH$_2$), 1.42 (s, 9H, C(CH$_3$)), 2.12 (br s, 1H, OH), 2.86-2.90 (dd, AB, J=9.5 Hz, C—O—CH$_2$—), 3.51-3.60 (m, 2H, CH$_2$OH), 4.57 (s, 2H, N—CH$_2$—), 7.13-7.16 (dd, J=7.9 Hz, 1H, CH—CH—C($^t$Bu)), 7.21-7.26 (m, 4H, Ar—H), 7.37-7.40 (m, 2H, Ar—H), 7.62-7.65 (dd, J=8.0, 1.8 Hz, 1H, —CH—C($^t$Bu)), 7.99-8.00 (dd, J=1.3 Hz, 1H—C(O)—C—CH—), 8.04-8.06 (m, 2H, —CH—NO$_2$)

$^{13}$C NMR (CDCl$_3$, 75 MHz), δ 6.48, 20.00, 31.73, 41.69, 42.50, 68.00, 68.14, 94.86, 120.99, 122.07, 123.01, 123.62, 126.57, 126.82, 128.29, 128.95, 130.17, 135.15, 137.97, 139.28, 145.28, 147.59, 167.20

IR: 649, 704, 729, 754, 801, 813, 835, 853, 927, 949, 1012, 1031, 1059, 1091, 1135, 1177, 1200, 1259, 1280, 1313, 1342, 1377, 1398, 1434, 1463, 1489, 1520, 1600, 1686, 2013, 2093, 2139, 2165, 2189, 2208, 2870, 2922, 2960, 3001, 3075, 3428 cm$^{-1}$

LCMS (DMSO): Rt=3.72 min (on 5 min column)
HPLC purity (as area %): >98
UV (in EtOH): λ max=267 nm
EI-MS: calculated mass of ion 552.2260 [M+NH$_4$]$^+$, measured mass of ion 552.2253 [M+NH$_4$]$^+$
Rf: 0.53 (50% EtOAc/petrol)
MP: 104-105° C.
CHN: C$_{30}$H$_{31}$ClN$_2$O$_5$ requires C, 67.35; H, 5.84; N, 5.24. found C, 67.26; H, 5.89; N, 5.21

Synthesis of 5-tert-butyl-3-(4-chlorophenyl)-3-((1-(hydroxymethyl)cyclopropyl)methoxy)-2-(4-nitrobenzyl)isoindolin-1-one (NU8400)

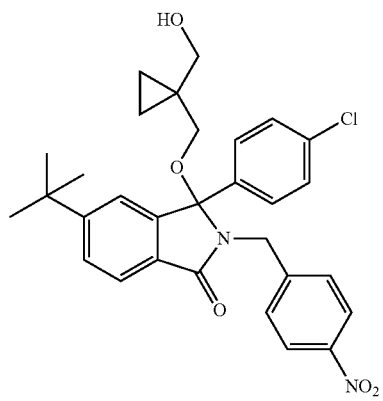 [SMILES: CC(C)(C)c1ccc2c(c1)C(OCC1(CO)CC1)(c1ccc(Cl)cc1)N(Cc1ccc([N+](=O)[O-])cc1)C2=O]

The named compound was synthesised from NU8396 (200 mg, 0.44 mmol) and 1,1-bis(hydroxymethyl)cyclopropane (0.09 mL, 0.89 mmol) using General Procedure C, purified by chromatography (Biotage SP4; 10%-50% EtOAc/petrol) and obtained as white crystals (43 mg, 18%).

$^1$H NMR (300 MHz, CDCl$_3$) δ 0.10-0.13 (m, 2H, cyclopropane CH$_2$), 0.41-0.44 (m, 2H, Cyclopropane CH$_2$), 1.26 (s, 9H, C(CH$_3$)), 1.69 (br s, 1H, OH), 2.71-2.78 (m, 2H, C—O—CH$_2$—), 3.41-3.52 (dd, AB, J=11.0 Hz, CH$_2$OH), 4.38-4.53 (dd, J=15.2 Hz, 2H, N—CH$_2$—), 7.13-7.15 (dd, J=1.1 Hz, 1H, C—CH—C($^t$Bu)), 7.16-7.21 (m, 4H, Ar—H), 7.29-7.32 (m, 2H, Ar—H), 7.55-7.58 (dd, J=8.1, 1.6 Hz, 1H, —CH—CH—C($^t$Bu)), 7.81-7.83 (dd, J=7.9 Hz, 1H—C(O)—C—CH—), 7.98-8.01 (m, 2H, —CH—NO$_2$)

$^{13}$C NMR (CDCl$_3$, 75 MHz), δ 8.95, 9.02, 22.69, 31.56, 42.72, 42.80, 67.94, 67.99, 93.23, 123.55, 123.70, 126.59, 127.79, 128.27, 128.91, 130.03, 130.11, 131.28, 133.01, 135.15, 138.50, 145.17, 147.27, 168.57

IR: 663, 691, 704, 730, 801, 843, 872, 893, 934, 951, 1013, 1059, 1091, 1132, 1189, 1240, 1260, 1281, 1342, 1382, 1398, 1425, 1465, 1490, 1520, 1605, 1686, 2010, 2872, 2926, 3073, 3413 cm$^{-1}$

LCMS: Rt=3.80 min (on 5 min column)
HPLC purity (as area %)=>97
UV (in EtOH): λ max=268 nm
EI-MS: calculated mass of ion 552.2260 [M+NH$_4$]$^+$, measured mass of ion 552.2260 [M+NH$_4$]$^+$
Rf: 0.50 (50% EtOAc/petrol)
MP: 89-90° C.
CHN: C$_{30}$H$_{31}$ClN$_2$O$_5$ requires C, 67.35; H, 5.84; N, 5.24. found C, 67.45; H, 6.01; N, 5.05

Synthesis of 3-(4-chlorophenyl)-3-((1-(hydroxymethyl)cyclopropyl)methoxy)-5-methyl-2-(4-nitrobenzyl)isoindolin-1-one (NU8401)

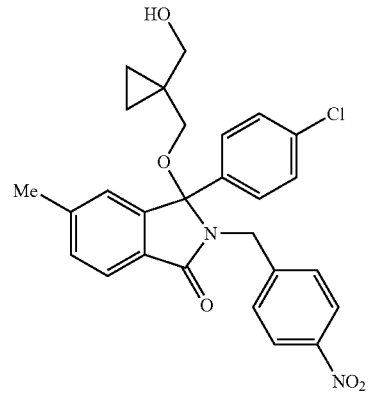 [SMILES: Cc1ccc2c(c1)C(OCC1(CO)CC1)(c1ccc(Cl)cc1)N(Cc1ccc([N+](=O)[O-])cc1)C2=O]

The named compound was synthesised from a mixture of NU8395 and NU8412 (200 mg, 0.49 mmol) and 1,1-bis(hydroxymethyl)cyclopropane (0.10 mL, 0.98 mmol) using General Procedure C, purified by chromatography (Biotage SP4; 10%-30% EtOAc/petrol) and obtained as a white solid (116 mg, 48%).

$^1$H NMR (300 MHz, CDCl$_3$) δ 0.07-0.28 (m, 2H, cyclopropane CH$_2$), 0.34-0.57 (m, 2H, cyclopropane CH$_2$), 2.33-2.40 (s, 3H, CH$_3$), 2.74-2.88 (m, 2H, C—O—CH$_2$—), 3.39-3.56 (m, 2H, CH$_2$OH)), 4.35-4.62 (s, 2H, N—CH$_2$—), 6.90-6.96 (m, 1H, Ar—H), 7.11-7.20 (m, 4H, Ar—H), 7.27-7.41 (m, 3H, Ar—H), 7.74-7.84 (dd, J=7.8 Hz, 1H, —C(O)—C=CH—), 7.92-8.08 (m, 2H, —CH—NO$_2$)

$^{13}$C NMR (CDCl$_3$, 75 MHz), δ 8.89, 8.98, 22.16, 22.70, 42.71, 67.87, 67.98, 94.77, 123.59, 123.87, 124.02, 128.22, 128.29, 128.96, 130.20, 131.51, 135.10, 135.26, 137.63, 140.40, 145.85, 147.74, 166.79

IR: 662, 683, 704, 734, 766, 781, 801, 829, 845, 860, 893, 916, 937, 961, 1011, 1032, 1077, 1094, 1134, 1156, 1175, 1211, 1273, 1342, 1391, 1420, 1463, 1487, 1518, 1609, 1682, 1925, 2162, 2853, 2882, 2925, 3009, 3086, 3406 cm$^{-1}$

LCMS (DMSO): Rt=3.73 min (on 5 min column)
HPLC purity (as area %): >96
UV (in EtOH): λ max=266 nm
EI-MS: calculated mass of ion 493.1525 [M+H]$^+$, measured mass of ion 493.1521 [M+H]$^+$
Rf=0.53 (50% EtOAc/petrol)
MP: 177-178° C.
CHN: C$_{27}$H$_{25}$ClN$_2$O$_5$ requires C, 65.79; H, 5.11; N, 5.68. found C, 65.57; H, 5.15, N: 5.45

Synthesis of 3-(4-chlorophenyl)-3-((1-(hydroxymethyl)cyclopropyl)methoxy)-4-methyl-2-(4-nitrobenzyl)isoindolin-1-one (NU8405)

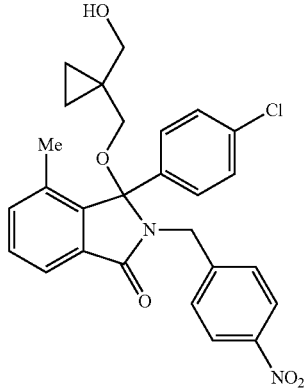

The named compound was synthesised from NU8393 (413 mg, 1.01 mmol) and 1,1-bis(hydroxymethyl)cyclopropane (0.19 mL, 2.03 mmol) using General Procedure C, purified by chromatography (Biotage SP4; 20%-40% EtOAc/petrol) and obtained as a yellow solid (252 mg, 50%).

$^1$H NMR (300 MHz, CDCl$_3$) δ −0.07-0.17 (m, 2H, cyclopropane CH$_2$), 0.25-0.34 (m, 2H, Cyclopropane CH$_2$), 1.81 (s, 3H, CH$_3$), 1.92 (br s, 1H, OH), 2.60-2.83 (dd, AB, J=9.4 Hz, C—O—CH$_2$—), 3.33-3.41 (m, 2H, CH$_2$OH), 4.19 and 4.42 (dd, AB, J=15.3 Hz, 2H, N—CH$_2$—), 6.88-6.97 (m, 2H, Ar—H)), 7.04-7.06 (m, 2H, Ar—H), 7.11-7.13 (dd, J=7.5 Hz, 1H, —CH—C(Me)), 7.26-7.30 (t, J=7.5 Hz, 1H, —CH—CH—C(Me)), 7.57-7.60 (dd, J=7.4 Hz, 1H—C(O)—C—CH—), 7.75-7.79 (m, 2H, —CH—NO$_2$)

$^{13}$C NMR (CDCl$_3$, 75 MHz), δ 8.82, 8.95, 17.30, 17.40, 22.68, 42.28, 67.60, 94.73, 121.62, 123.47, 128.45, 128.82, 129.94, 130.81, 132.18, 134.69, 135.24, 136.92, 142.26, 145.11, 147.50, 168.60

IR: 696, 762, 797, 930, 1013, 1067, 1186, 1229, 1286, 1340, 1393, 1427, 1487, 1520, 1605, 1677, 2864, 3455 cm$^{-1}$

LCMS (DMSO): Rt=3.68 min (on 5 min column)

HPLC purity (as area %): >96

UV (in EtOH): λ max=268 nm

EI-MS: calculated mass of ion 493.1525 [M+H]$^+$, measured mass of ion 493.1523 [M+H]$^+$ Rf: 0.36 (50% EtOAc/petrol); MP: 146-147° C.

CHN: C$_{27}$H$_{25}$ClN$_2$O$_5$ requires C, 65.79; H, 5.11; N, 5.68. found C, 65.78; H, 4.81; N, 5.65

Synthesis of 4-chloro-3-(4-chlorophenyl)-3-((1-(hydroxymethyl)cyclopropyl)methoxy)-2-(4-nitrobenzyl)isoindolin-1-one (NU8406)

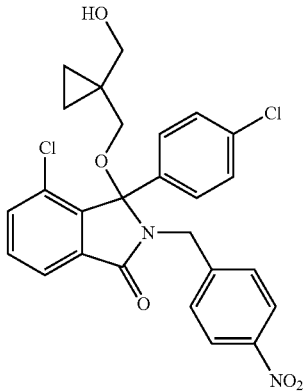

The named compound was synthesised from NU8398 (433 mg, 1.01 mmol) and 1,1-bis(hydroxymethyl)cyclopropane (0.19 mL, 2.03 mmol) using General Procedure C, purified by chromatography (Biotage SP4; 20%-50% EtOAc/petrol) and obtained as yellow crystals (321 mg, 62%).

$^1$H NMR (300 MHz, CDCl$_3$) δ 0.21-0.42 (m, 2H, cyclopropane CH$_2$), 0.47-0.54 (m, 2H, cyclopropane CH$_2$), 2.12 (br s, 1H, OH), 2.89-3.05 (m, 2H, C—O—CH$_2$—), 3.52-3.61 (m, 2H, CH$_2$OH), 4.30-4.59 (dd, AB, J=15.2 Hz, N—CH$_2$—), 7.15-7.18 (m, 4H, Ar—H), 7.28-7.33 (m, 2H, Ar—H), 7.48-7.58 (m, 2H, Ar—H), 7.87-7.89 (dd, J=7.1, 1.1 Hz, 1H, —C(O)—C=CH—), 7.98-8.01 (m, 2H, —CH—NO$_2$)

$^{13}$C NMR (CDCl$_3$, 75 MHz), δ 8.84, 8.90, 22.59, 42.54, 67.60, 68.10, 94.71, 122.63, 123.56, 128.65, 128.77, 130.09, 130.40, 132.28, 134.37, 135.27, 135.55, 135.57, 141.10, 144.62, 147.64, 167.04

IR: 696, 759, 816, 853, 930, 1011, 1074, 1144, 1171, 1234, 1341, 1384, 1428, 1462, 1489, 1519, 1699, 2872, 2923, 3422 cm$^{-1}$

HPLC purity (as area %): >92

UV (in EtOH): λ max=267 nm

EI-MS: calculated mass of ion 530.1244 [M+NH$_4$]$^+$, measured mass of ion 530.1242 [M+NH$_4$]$^+$ Rf: 0.30 (50% EtOAc/petrol); MP: 76-77° C.

CNN: C$_{26}$H$_{22}$Cl$_2$N$_2$O$_5$ requires C, 60.83; H, 4.32; N, 5.46. found C, 60.68; H, 4.30; N, 5.40

Synthesis of 5-bromo-3-(4-chlorophenyl)-3-hydroxy-2-(4-nitrobenzyl)isoindolin-1-one (NU8414) and 6-bromo-3-(4-chlorophenyl)-3-hydroxy-2-(4-nitrobenzyl)isoindolin-1-one (NU8413)

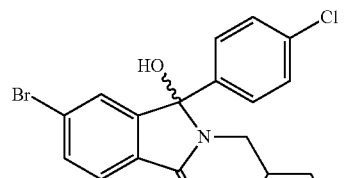

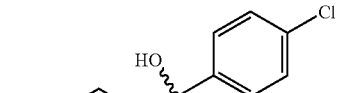

The named compounds were synthesised from a mixture of 4-bromo-2-(4-chlorobenzoyl)benzoic acid and 5-bromo-2-(4-chlorobenzoyl)benzoic acid (2.48 g, 7.28 mmol) and 4-nitrobenzylamine hydrochloride (1.51 g, 8.01 mmol) using General Procedure B, purified by chromatography (Biotage SP4; 20% EtOAc/petrol) and obtained as a cream solid (NU8414) and cream solid (NU8413) (1.83 g, 53%, ratio of 5- and 6-isomers is ~1:1).

Analysis of NU8414:

$^1$H NMR (300 MHz, MeOD) δ 4.50 and 4.68 (dd, J=15.7 Hz, 2H, N—CH$_2$—), 4.88 (br s, 1H, OH), 7.24-7.32 (m, 4H, Ar—H), 7.37-7.47 (m, 3H, Ar—H), 7.73-7.77 (dd, J=9.6 Hz, 1H, —CH—CH—C(Br)—), 7.99-8.01 (m, 1H, C(OH)—C=CH—CBr—), 8.04-8.09 (m, 2H, —CH—NO$_2$)

$^{13}$C NMR (MeOD, 75 MHz), δ 41.27, 93.73, 123.41, 124.51, 125.12, 127.77, 129.08, 129.64, 130.09, 130.90, 133.50, 134.67, 134.72, 140.45, 140.72, 142.17, 168.08

IR: 698, 781, 801, 827, 851, 895, 934, 1013, 1043, 1071, 1094, 1128, 1253, 1342, 1392, 1415, 1516, 1603, 1676, 2405, 2932, 3227 cm$^{-1}$

LCMS (DMSO): Rt=4.13 min (on 5 min column)

HPLC purity (as area %)=99

UV (in EtOH): λ max=267 nm

ELMS: calculated mass of ion 471.9820 [M−H], measured mass of ion 471.9818 [M−H]

Rf: 0.59 (50% EtOAc/petrol); MP: 221-222° C.

CHN: $C_{21}H_{14}BrClN_2O_4$ requires C, 53.25; H, 2.98; N, 5.91. found C, 53.48; H, 2.99; N, 5.79

Analysis of NU8413:

$^1$H NMR (300 MHz, CDCl$_3$) δ 3.94 (br s, 1H, OH), 4.22 and 4.53 (dd, J=15.3 Hz, 2H, N—CH$_2$—), 7.06-7.09 (d, J=8.0 Hz, 1H, CH—CH—C(Br)—), 7.11-7.14 (m, 4H, Ar—H), 7.17-7.22 (m, 2H, Ar—H), 7.56-7.60 (dd, J=8.0, 1.8 Hz, 1H, —CH—CH—C(Br)—), 7.71-7.72 (dd, J=1.6 Hz, 1H, C(O)—C=CH—), 7.88-7.91 (m, 2H, —CH—NO$_2$)

$^{13}$C NMR (CDCl$_3$, 75 MHz), δ 41.63, 94.94, 122.73, 123.76, 124.66, 127.26, 128.07, 129.28, 129.82, 132.04, 133.88, 135.53, 136.67, 143.14, 145.09, 145.38, 165.32

IR: 718, 754, 801, 827, 851, 930, 1011, 1063, 1090, 1183, 1273, 1311, 1342, 1389, 1437, 1487, 1516, 1599, 1672, 2853, 2923, 3163 cm$^{-1}$

LCMS (DMSO): Rt=4.21 min (on 5 min column)

HPLC purity (as area %)=98

UV (in EtOH): λ max=267 nm

EI-MS: calculated mass of ion 471.9820 [M−H], measured mass of ion 471.9814 [M−H]

Rf: 0.66 (50% EtOAc/petrol); MP: 218-219° C.

Synthesis of 4-((1-(4-chlorophenyl)-1-((1-(hydroxymethyl)cyclopropyl)methoxy)-3-oxoisoindolin-2-yl)methyl)benzonitrile (NU8415)

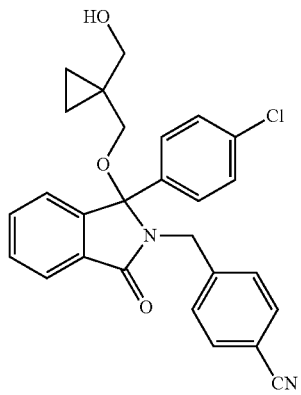 [SMILES: N#Cc1ccc(CN2C(=O)c3ccccc3C2(OCC2(CO)CC2)c2ccc(Cl)cc2)cc1]

The named compound was synthesised from NU8306 (379 mg, 1.01 mmol) and 1,1-bis(hydroxymethyl)cyclopropane (0.19 mL, 2.03 mmol) using General Procedure C, purified by chromatography (Biotage SP4; 20%-50% EtOAc/petrol) and obtained as white crystals (221 mg, 51%).

$^1$H NMR (300 MHz, CDCl$_3$) δ 0.01-0.19 (m, 2H, cyclopropane CH$_2$), 0.34-0.42 (m, 2H, cyclopropane CH$_2$), 1.96 (s, 1H, OH), 2.72-2.79 (m, 2H, C—O—CH$_2$), 3.39-3.49 (dd, J=11.3, 18.2 Hz, 2H, CH$_2$OH)), 4.40 (s, 2H, N—CH$_2$—), 7.05-7.12 (m, 5H, Ar—H), 7.18-7.21 (d, AB quartet, J=8.2 Hz, 2H, —CH—CH=C—CN), 7.35-7.37 (d, AB quartet, J=8.2 Hz, 2H, —CH=C—CN), 7.45-7.50 (m, 2H, Ar—H), 7.82-7.85 (m, 1H, —C(O)—C=CH—)

$^{13}$C NMR (CDCl$_3$, 75 MHz), δ 8.86, 22.61, 42.97, 67.43, 67.60, 94.88, 111.53, 118.74, 123.50, 124.06, 128.32, 128.88, 130.09, 130.45, 131.81, 132.17, 133.44, 135.07, 137.52, 143.10, 145.51, 168.57

IR: 700, 762, 810, 849, 926, 955, 1009, 1041, 1063, 1276, 1302, 1350, 1395, 1425, 1468, 1491, 1605, 1680, 2228, 2854, 2926, 3408 cm$^{-1}$

LCMS (DMSO): Rt=3.90 min (on 5 min column)

HPLC purity (as area %): >98

UV (in EtOH): λ max=225 nm

EI-MS: calculated mass of ion 459.1470 [M+H]$^+$, measured mass of ion 459.1471 [M+H]$^+$ Rf: 0.32 (50% EtOAc/petrol); MP: 136-137° C.

CHN: $C_{27}H_{23}ClN_2O_3$ requires C, 70.66; H, 5.05; N, 6.10. found C, 70.39; H, 5.05; N, 6.09

Synthesis of 2-(4-chlorobenzyl)-3-(4-chlorophenyl)-3-((1-(hydroxymethyl)cyclopropyl)methoxy)isoindolin-1-one (NU8416)

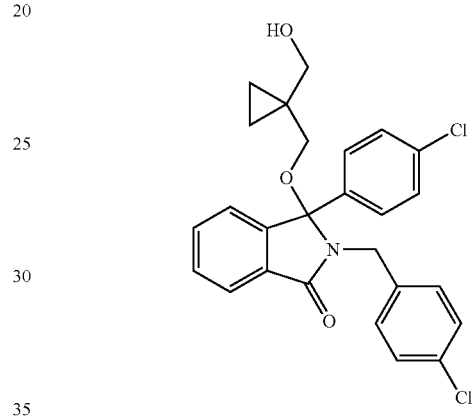

The named compound was synthesised from NU8314 (200 mg, 0.52 mmol) and 1,1-bis(hydroxymethyl)cyclopropane (0.10 mL, 1.04 mmol) using General Procedure C, purified by chromatography (Biotage SP4; 20%-40% EtOAc/petrol) and obtained as white crystals (192 mg, 79%).

$^1$H NMR (300 MHz, CDCl$_3$) δ 0.05-0.12 (m, 2H, cyclopropane CH$_2$), 0.34-0.39 (m, 2H, cyclopropane CH$_2$), 1.97 (s, 1H, OH), 2.63-2.79 (dd, AB, J=9.4 Hz, 2H, —C—O—CH$_2$), 3.34-3.50 (dd, AB, J=11.3 Hz, 2H, CH$_2$OH)), 4.16-4.49 (dd, AB, J=14.9 Hz, 2H, N—CH$_2$—), 7.07-7.09 (m, 4H, Ar—H), 7.10-7.14 (m, 5H, Ar—H), 7.44-7.47 (m, 2H, Ar—H), 7.83-7.86 (m, 1H, —C(O)—C=CH—)

$^{13}$C NMR (CDCl$_3$, 75 MHz), δ 8.82, 22.55, 42.76, 60.56, 67.70, 95.09, 123.33, 124.00, 128.30, 128.57, 128.90, 130.28, 130.94, 132.00, 133.22, 133.58, 134.94, 136.32, 137.66, 145.68, 168.48

IR: 700, 728, 761, 803, 812, 847, 924, 953, 1009, 1037, 1067, 1092, 1176, 1232, 1285, 1318, 1355, 1383, 1425, 1470, 1487, 1609, 1098, 2882, 2927, 3489 cm$^{-1}$

LCMS (DMSO): Rt=3.91 min (on 5 min column)

HPLC purity (as area %): >99

UV (in EtOH): λ max=222 nm

EI-MS: calculated mass of ion 468.1128 [M+H]$^+$, measured mass of ion 468.1128 [M+H]$^+$ Rf=0.41 (50% EtOAc/petrol); MP: 118-119° C.

Synthesis of 2-(4-bromobenzyl)-3-(4-chlorophenyl)-3-((1-(hydroxymethyl)cyclopropyl)methoxy)isoindolin-1-one (NU8417)

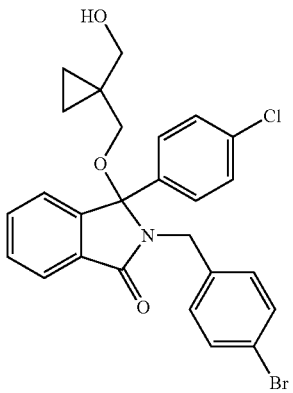 [SMILES: O=C1c2ccccc2C(OCC2(CO)CC2)(c2ccc(Cl)cc2)N1Cc1ccc(Br)cc1]

The named compound was synthesised from NU8315 (433 mg, 1.01 mmol) and 1,1-bis(hydroxymethyl)cyclopropane (0.19 mL, 2.03 mmol) using General Procedure C, purified by chromatography (Biotage SP4; 20%-40% EtOAc/petrol) and obtained as white crystals (333 mg, 64%).

$^1$H NMR (300 MHz, DMSO) δ −0.02-0.08 (m, 2H, cyclopropane CH$_2$), 0.26-0.33 (m, 2H, cyclopropane CH$_2$), 2.59-2.80 (dd, AB, J=9.0 Hz, 2H, —C—O—CH$_2$), 3.16-3.45 (m, 2H, CH$_2$OH)), 4.21-4.42 (dd, AB, J=15.4 Hz, 2H, N—CH$_2$—), 4.45 (s, 1H, OH), 7.03-7.06 (d, J=8.4 Hz, 2H, Ar—H), 7.19-7.22 (m, 3H, Ar—H), 7.29-7.40 (m, 4H, Ar—H), 7.56-7.65 (m, 2H, Ar—H), 7.83-7.85 (m, 1H, —C(O)—C=CH—)

$^{13}$C NMR (DMSO, 75 MHz), δ 7.94, 22.19, 40.98, 65.96, 73.03, 94.24, 120.42, 123.40, 123.59, 123.83, 128.45, 128.66, 130.99, 131.16, 131.40, 131.76, 133.49, 137.13, 138.13, 143.48, 167.64

IR: 679, 721, 760, 795, 814, 849, 922, 953, 1008, 1036, 1066, 1092, 1177, 1232, 1285, 1317, 1356, 1385, 1420, 1471, 1612, 1692, 2586, 2884, 2944, 3499 cm$^{-1}$

LCMS (DMSO): Rt=4.06 min (on 5 min column)
HPLC purity (as area %): >99
UV (in EtOH): λ max=223 nm
EI-MS: calculated mass of ion 512.0623 [M+H]$^+$, measured mass of ion 512.0627 [M+H]$^+$
Rf=0.41 (50% EtOAc/petrol); MP: 161-162° C.
CHN: C$_{26}$H$_{23}$BrClNO$_3$ requires C, 60.89; H, 4.52; N, 2.73. found C, 60.95; H, 4.61; N, 2.74

Synthesis of 3-(4-chlorophenyl)-2-(R)-1-(4-chlorophenyl)ethyl)-3-((1-(hydroxymethyl)cyclopropyl)methoxy)isoindolin-1-one (NU8418)

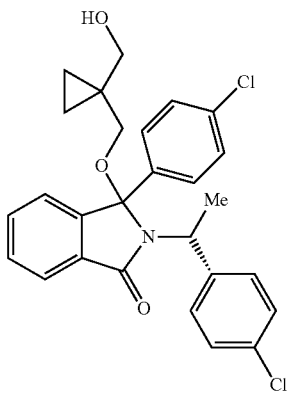

The named compound was synthesised from NU8301 (401 mg, 1.01 mmol) and 1,1-bis(hydroxymethyl)cyclopropane (0.19 mL, 2.03 mmol) using General Procedure C, purified by chromatography (Biotage SP4; 20%-40% EtOAc/petrol) and obtained as a pale yellow oil (146 mg, 30%).

$^1$H NMR (300 MHz, CDCl$_3$) δ 0.36-0.44 (m, 2H, cyclopropane CH$_2$), 0.48-0.59 (m, 2H, cyclopropane CH$_2$), 1.88 (d, J=7.3 Hz, 3H, CH$_3$), 2.30 (br s, 1H, OH), 2.88-3.30 (dd, AB, J=9.5 Hz, 2H, —C—O—CH$_2$), 3.58-3.67 (m, 2H, CH$_2$OH)), 4.30-4.38 (q, J=7.2, 14.4 Hz, 1H, N—CH—), 6.96-7.01 (m, 7H, Ar—H), 7.04-7.07 (m, 1H, Ar—H), 7.43-7.47 (m, 2H, Ar—H), 7.80-7.83 (m, 1H, —C(O)—C=CH—)

$^{13}$C NMR (CDCl$_3$, 75 MHz), δ 8.96, 9.03, 20.41, 22.93, 52.80, 60.59, 67.83, 95.25, 123.28, 123.75, 128.27, 128.43, 128.68, 129.57, 130.31, 133.09, 133.08, 134.82, 137.55, 141.72, 144.99, 168.30

IR: 699, 727, 762, 815, 868, 938, 1011, 1032, 1070, 1088, 1176, 1321, 1398, 1467, 1489, 1597, 1682, 2876, 2930, 3389 cm$^{-1}$

LCMS (DMSO): Rt=4.15 min (on 5 min column)
HPLC purity (as area %): >97
UV (in EtOH): λ max=221 nm
EI-MS: calculated mass of ion 482.1284 [M+H]$^+$, measured mass of ion 482.1279 [M+H]$^+$
Rf=0.42 (50% EtOAc/petrol)

Synthesis of 3-(4-chlorophenyl)-2-((S)-1-(4-chlorophenyl)ethyl)-3-((1-(hydroxymethyl)cyclopropyl)methoxy)isoindolin-1-one (NU8419)

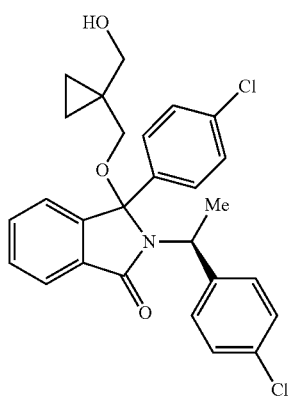 [SMILES: C[C@@H](c1ccc(Cl)cc1)N1C(=O)c2ccccc2C1(OCC1(CO)CC1)c1ccc(Cl)cc1]

The named compound was synthesised from NU8347 (401 mg, 1.01 mmol) and 1,1-bis(hydroxymethyl)cyclopropane (0.19 mL, 2.03 mmol) using General Procedure C, purified by chromatography (Biotage SP4; 10%-30% EtOAc/petrol) and obtained as a pale yellow oil (60 mg, 12%).

$^1$H NMR (300 MHz, CDCl$_3$) δ 0.36-0.44 (m, 2H, cyclopropane CH$_2$), 0.48-0.59 (m, 2H, cyclopropane CH$_2$), 1.88 (d, J=7.3 Hz, 3H, CH$_3$), 2.30 (br s, 1H, OH), 2.88-3.30 (dd, AB, J=9.5 Hz, 2H, —C—O—CH$_2$), 3.58-3.67 (m, 2H, CH$_2$OH)), 4.30-4.38 (q, J=7.2, 14.4 Hz, 1H, N—CH—), 6.96-7.01 (m, 7H, Ar—H), 7.04-7.07 (m, 1H, Ar—H), 7.43-7.47 (m, 2H, Ar—H), 7.80-7.83 (m, 1H, —C(O)—C=CH—)

$^{13}$C NMR (CDCl$_3$, 75 MHz), δ 8.96, 9.03, 20.41, 22.93, 52.80, 60.59, 67.83, 95.25, 123.28, 123.75, 128.27, 128.43, 128.68, 129.57, 130.31, 133.09, 133.08, 134.82, 137.55, 141.72, 144.99, 168.30

IR: 698, 727, 761, 815, 866, 1011, 1031, 1068, 1090, 1176, 1331, 1396, 1487, 1583, 1695, 2876, 2923, 3415 cm$^{-1}$

LCMS (DMSO): Rt=4.19 min (on 5 min column)

HPLC purity (as area %): >98

UV (in EtOH): λ max=221 nm

EI-MS: calculated mass of ion 482.1284 [M+H]$^+$, measured mass of ion 482.1285 [M+H]$^+$ Rf=0.42 (50% EtOAc/petrol)

Synthesis of 5-bromo-3-(4-chlorophenyl)-3-((1-(hydroxymethyl)cyclopropyl)methoxy)-2-(4-nitrobenzyl)isoindolin-1-one (NU8424)

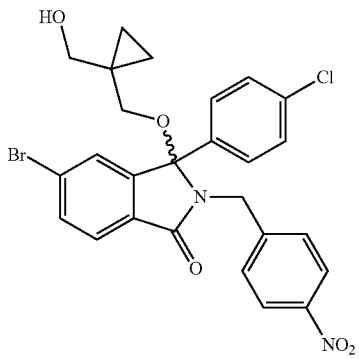 [SMILES: O=C1c2ccc(Br)cc2C(OCC2(CO)CC2)(c2ccc(Cl)cc2)N1Cc1ccc([N+](=O)[O-])cc1]

The named compound was synthesised from NU8414 (200 mg, 0.42 mmol) and 1,1-bis(hydroxymethyl)cyclopropane (0.08 mL, 0.84 mmol) using General Procedure C, purified by chromatography (Biotage SP4; 20%-40% EtOAc/petrol) and obtained as a yellow oil (204 mg, 87%).

$^1$H NMR (300 MHz, CDCl$_3$) δ 0.17-0.27 (m, 2H, cyclopropane CH$_2$), 0.44-0.51 (m, 2H, cyclopropane CH$_2$), 2.05 (s, 1H, OH), 2.83-2.90 (dd, AB, J=9.5 Hz, 2H, C—O—CH$_2$), 3.49-3.58 (dd, AB, J=11.5 Hz, 2H, CH$_2$OH), 4.45-4.56 (dd, AB, J=15.4 Hz, 2H, N—CH$_2$—), 7.16-7.19 (m, 4H, Ar—H), 7.29-7.33 (m, 3H, Ar—H), 7.66-7.70 (dd, J=1.6, 8.0 Hz, 1H, —CH—CH—Br), 7.78-7.80 (dd, J=8.0 Hz, 1H, —C(O)—C=CH—), 7.99-8.02 (d, AB, J=8.7 Hz, 2H, CH—C—NO$_2$)

$^{13}$C NMR (CDCl$_3$, 75 MHz), δ 8.90, 22.62, 42.79, 67.47, 67.72, 94.47, 123.62, 125.52, 126.92, 128.25, 128.41, 129.12, 130.24, 130.60, 134.00, 135.54, 136.72, 144.61, 147.35, 147.71, 167.66

IR: 702, 726, 799, 818, 855, 883, 934, 1011, 1032, 1078, 1128, 1176, 1277, 1343, 1387, 1420, 1488, 1521, 1601, 1684, 2854, 2922, 3420 cm$^{-1}$

HPLC purity (as area %): >86

UV (in EtOH): λ max=267 nm

EI-MS: calculated mass of ion 574.0739 [M+NH$_4$]$^+$, measured mass of ion 574.0735 [M+NH$_4$]$^+$ Rf=0.37 (50% EtOAc/petrol); MP: 156-158° C.

Synthesis of 6-bromo-3-(4-chlorophenyl)-3-((1-(hydroxymethyl)cyclopropyl)methoxy)-2-(4-nitrobenzyl)isoindolin-1-one (NU8425)

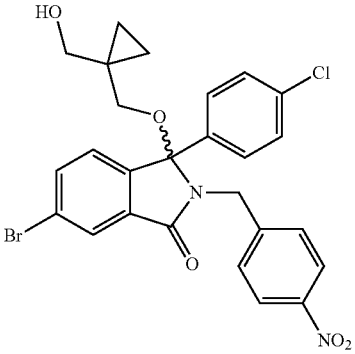 [SMILES: O=C1c2cc(Br)ccc2C(OCC2(CO)CC2)(c2ccc(Cl)cc2)N1Cc1ccc([N+](=O)[O-])cc1]

The named compound was synthesised from NU8413 (200 mg, 0.42 mmol) and 1,1-bis(hydroxymethyl)cyclopropane (0.08 mL, 0.84 mmol) using General Procedure C, purified by chromatography (Biotage SP4; 20%-40% EtOAc/petrol) and obtained as an orange solid (154 mg, 66%).

$^1$H NMR (300 MHz, CDCl$_3$) δ 0.21-0.31 (m, 2H, cyclopropane CH$_2$), 0.49-0.56 (m, 2H, cyclopropane CH$_2$), 2.13 (br s, 1H, OH), 2.88-2.92 (m, 2H, C—O—CH$_2$), 3.53-3.62 (dd, AB, J=11.4 Hz, 2H, CH$_2$OH), 4.52-4.62 (dd, AB, J=15.9 Hz, 2H, N—CH$_2$—), 7.12-7.14 (d, J=8.0 Hz, 1H, CH—CH—CBr), 7.20-7.26 (m, 4H, Ar—H), 7.34-7.38 (m, 2H, Ar—H), 7.72-7.75 (dd, J=1.8, 8.0 Hz, 1H, —CH—CH—CBr—), 8.04-8.07 (m, 2H, CH—C—NO$_2$), 8.09-8.10 (d, J=1.6 Hz, 1H, C(=O)—C=CH—C—Br)

$^{13}$C NMR (CDCl$_3$, 75 MHz), δ 8.88, 8.93, 22.65, 42.84, 67.50, 67.72, 94.75, 123.62, 124.81, 125.13, 127.39, 128.24, 129.07, 130.21, 133.68, 133.71, 135.46, 136.52, 136.83, 144.17, 144.60, 147.70, 167.09,

IR: 696, 725, 820, 854, 926, 1011, 1176, 1277, 1341, 1376, 1425, 1489, 1519, 1602, 1699, 2924, 3077, 3422 cm$^{-1}$

HPLC purity (as area %): >98

UV (in EtOH): λ max=267 nm

EI-MS: calculated mass of ion 556.0395 [M]$^+$, measured mass of ion 556.0389 [M]$^+$ Rf=0.41 (50% EtOAc/petrol); MP: 66-68° C.

Synthesis of 3-(4-chlorophenyl)-3-((1-(hydroxymethyl)cyclopropyl)methoxy)-2-(pyridin-2-ylmethyl)isoindolin-1-one (NU8429)

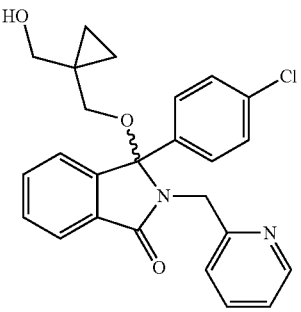 [SMILES: O=C1c2ccccc2C(OCC2(CO)CC2)(c2ccc(Cl)cc2)N1Cc1ccccn1]

The named compound was synthesised from NU8423 (354 mg, 1.01 mmol) and 1,1-bis(hydroxymethyl)cyclopropane (0.19 mL, 2.03 mmol) using General Procedure C, purified by chromatography (Biotage SP4; 50% EtOAc/petrol-EtOAc) and obtained as yellow crystals (383 mg, 87%).

$^1$H NMR (300 MHz, CDCl$_3$) δ 0.04-0.17 (m, 2H, cyclopropane CH$_2$), 0.30-0.37 (m, 2H, cyclopropane CH$_2$), 2.57-3.18 (dd, J=9.3 Hz, 2H, C—O—CH$_2$), 3.25-3.63 (dd, J=11.3 Hz, 2H, CH$_2$OH), 4.10 (br s, 1H, OH), 4.36-4.48 (dd, AB, J=15.2 Hz, 2H, N—CH$_2$—), 6.94-7.02 (m, 3H, ArH), 7.04-7.07 (m, 1H, Ar—H), 7.10-7.15 (m, 2H, Ar—H), 7.19-7.22 (m, H, Ar—H), 7.35-7.42 (m, 3H, Ar—H), 7.76-7.79 (m, 1H, —C(O)—C=CH—), 8.22-8.23 (m, 1H, —C=N—CH=)

$^{13}$C NMR (CDCl$_3$, 75 MHz), δ 8.79, 8.86, 22.64, 45.64, 67.13, 67.55, 94.79, 122.33, 123.40, 123.93, 124.07, 128.30, 128.69, 130.18, 132.12, 133.09, 134.57, 136.53, 137.86, 145.68, 148.96, 157.14, 168.40

IR: 700, 760, 813, 846, 928, 969, 1009, 1038, 1069, 1088, 1113, 1179, 1229, 1279, 1315, 1352, 1377, 1421, 1469, 1595, 1695, 2854, 2909, 3277 cm$^{-1}$

HPLC purity (as area %): >97

UV (in EtOH): λ max=261 mu

EI-MS: calculated mass of ion 435.1470 [M+H]$^+$, measured mass of ion 435.1471 [M+H]$^+$ Rf=0.01 (50% EtOAc/petrol); MP: 123-125° C.

Synthesis of 3-(4-chlorophenyl)-5-fluoro-3-hydroxy-2-(4-nitrobenzyl)isoindolin-1-one (NCL-00010485) and 3-(4-chlorophenyl)-6-fluoro-3-hydroxy-2-(4-nitrobenzyl)isoindolin-1-one (NCL-00010486)

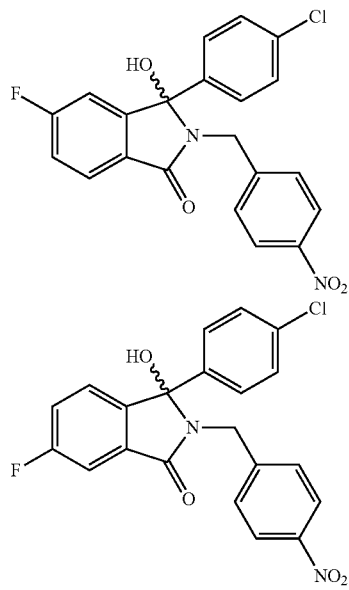

The named compounds were synthesised from a mixture of 2-(4-chlorobenzoyl)-4-fluorobenzoic acid and 2-(4-chlorobenzoyl)-5-fluorobenzoic acid (2.39 g, 8.58 mmol) and 4-nitrobenzylamine hydrochloride (1.78 g, 9.44 mmol) using General Procedure B, purified by chromatography (Biotage SP4; 25% EtOAc/petrol) and obtained as a cream solid (NCL-00010485) and a yellow solid (NCL-00010486) (2.56 g, 72%, ratio of 5- and 6-isomers is 3:2).

Analysis of major isomer (NCL-00010485):

$^1$H NMR (300 MHz, CDCl$_3$) δ 4.22-4.66 (dd AB, J=15.4 Hz, 2H, N—CH$_2$), 5.28 (s, 1H, OH), 6.85-6.89 (dd, J=7.7, 2.2 Hz, 1H, C(OH)CCH—C(F)), 7.06-7.13 (m, 1H, C(=O)—C=CH—CH=), 7.15-7.22 (m, 4H, —C$_6$H$_4$Cl), 7.30-7.36 (d AB, J=8.7 Hz, 2H, —C$_2$H$_2$C$_2$H$_2$C(NO$_2$)), 7.72-7.76 (dd, J=8.3, 4.8 Hz, 1H, C(=O)C=CH—), 7.93-7.96 (d AB, J=8.7 Hz, 2H, —C$_2$H$_2$C(NO$_2$))

$^{13}$C NMR (DMSO, 75 MHz), δ 42.35, 86.69, 113.40, 117.58, 123.23, 125.67, 126.79, 128.46, 128.74, 129.39, 133.52, 138.52, 140.85, 146.22, 147.54, 158.81, 166.24

IR: 710, 775, 804, 832, 933, 970, 1015, 1054, 1092, 1155, 1201, 1263, 1342, 1394, 1484, 1519, 1607, 1676, 3235 cm$^{-1}$

LCMS (DMSO): Rt=4.03 min (on 5 min column)

HPLC purity (as area %): >98

UV (in EtOH): λ max=272 nm

EI-MS: calculated mass of ion 430.0964 [M+NH$_4$]$^+$, measured mass of ion 430.0958 [M+NH$_4$]$^+$ Rf=0.50 (50% EtOAc/petrol); MP: 222-224° C.

Analysis of minor isomer (NCL-00010486):

$^1$H NMR (300 MHz, CDCl$_3$) δ 4.25-4.65 (dd AB, J=15.4 Hz, 2H, N—CH$_2$), 4.73 (s, 1H, OH), 7.13-7.24 (m, 6H, ArH), 7.30-7.33 (d AB, J=8.7 Hz, 2H, —C$_2$H$_2$C$_2$H$_2$C(NO$_2$)), 7.35-7.39 (dd, J=7.2, 2.1 Hz, 1H, C(=O)C=CH—), 7.94-7.98 (d AB, J=8.7 Hz, 2H, —C$_2$H$_2$C(NO$_2$))

$^{13}$C NMR (DMSO, 75 MHz), δ 42.43, 90.42, 113.29, 116.37, 123.23, 125.58, 128.45, 128.70, 129.42, 133.48, 134.84, 138.76, 139.16, 142.38, 146.18, 160.19, 166.08

IR: 776, 806, 831, 851, 891, 932, 1013, 1059, 1092, 1173, 1197, 1267, 1310, 1342, 1390, 1449, 1484, 1518, 1607, 1680, 2160, 2852, 2925, 3267 cm$^{-1}$

LCMS (DMSO): Rt=4.03 min (on 5 min column)

HPLC purity (as area %): >97

UV (in EtOH): λ max=267 nm

EI-MS: calculated mass of ion 412.0621 [M+H]$^+$, measured mass of ion 412.0619 [M+H]$^+$ Rf=0.58 (50% EtOAc/petrol); MP: 188-190° C.

Synthesis of 5,6-dichloro-3-(4-chlorophenyl)-3-((1-(hydroxymethyl)cyclopropyl)methoxy)-2-(4-nitrobenzyl)isoindolin-1-one (NCL-00010487)

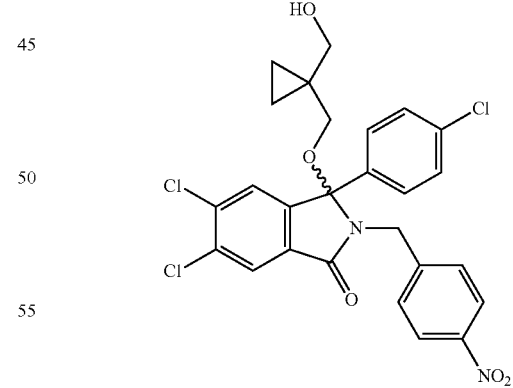

The named compound was synthesised from NU8432 (350 mg, 0.75 mmol) and 1,1-bis(hydroxymethyl)cyclopropane (0.16 mL, 1.67 mmol) using General Procedure C, purified by chromatography (Biotage SP4; 20%-40% EtOAc/petrol) and obtained as a yellow oil (302 mg, 73%).

$^1$H NMR (300 MHz, CDCl$_3$) δ 0.20-0.30 (m, 2H, CH$_2$), 0.46-0.50 (m, 2H, CH$_2$), 2.25 (s, 1H, OH), 2.90 (s, 2H, OCH$_2$), 3.50-3.60 (dd AB, J=11.2, 8.8 Hz, 2H, HOCH$_2$), 4.46-

4.58 (dd AB, J=15.2, 5.6 Hz, 2H, N—CH$_2$), 7.19-7.20 (m, 4H, —C$_6$H$_4$Cl), 7.29-7.32 (m, 3H, N$_2$O=C=CH—CH= and C(O=)C=CH—), 7.98-8.01 (m, 3H, O$_2$N—C=CH and C(O)=C=CH)

$^{13}$C NMR (CDCl$_3$, 75 MHz), δ 8.87, 8.90, 22.60, 42.93, 67.27, 67.68, 94.36, 123.63, 125.76, 126.01, 128.22, 129.17, 130.23, 131.44, 135.56, 135.66, 136.41, 138.31, 144.38, 144.77, 147.72, 166.46

IR: 754, 804, 837, 889, 934, 1011, 1070, 1095, 1166, 1201, 1235, 1339, 1402, 1489, 1514, 1601, 1688, 2857, 2923, 3482 cm$^{-1}$

LCMS (DMSO): Rt=4.65 min (on 5 min column)

HPLC purity (as area %): >99

UV (in EtOH): λ max=266 nm

EI-MS: calculated mass of ion 569.0408 [M+Na]$^+$, measured mass of ion 569.0408 [M+Na]$^+$ Rf=0.45 (50% EtOAc/petrol)

Synthesis of 4-((7-chloro-1-(4-chlorophenyl)-1-hydroxy-3-oxoisoindolin-2-yl)methyl)benzonitrile (NCL-00010488) and 4-((4-chloro-1-(4-chlorophenyl)-1-hydroxy-3-oxoisoindolin-2-yl)methyl)benzonitrile (73/NCL-00010489)

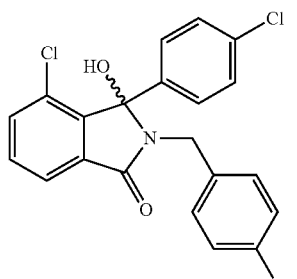

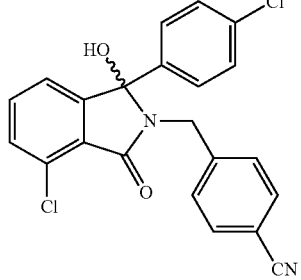

The named compounds were synthesised from a mixture of 3-chloro-2-(4-chlorobenzoyl)benzoic acid and 6-chloro-2-(4-chlorobenzoyl)benzoic acid (2.15 g, 7.28 mmol) and 4-cyanobenzylamine hydrochloride (1.35 g, 8.01 mmol) using General Procedure B, purified by chromatography (Biotage SP4; 20% EtOAc/petrol) and obtained as a white solid (NCL-00010488) and brown crystals (NCL-00010489) (1.98 g, 66%, ratio of 7- and 4-isomers is 99:1)

Analysis of major isomer (NCL-00010488):

$^1$H NMR (300 MHz, CDCl$_3$) δ 3.50 (br s, 1H, OH), 4.22-4.61 (dd AB, J=15.3 Hz, 2H, N—CH$_2$—), 7.22-7.30 (m, 6H, ArH), 7.40-7.51 (m, 4H, ArH), 7.75-7.78 (dd, J=5.8, 2.6 Hz, 1H, C(O)—C=CH)

$^{13}$C NMR (CDCl$_3$, 75 MHz), δ 42.97, 91.15, 107.13, 109.45, 122.61, 128.49, 129.02, 129.65, 130.01, 130.54, 132.09, 132.13, 132.34, 132.40, 135.02, 143.99, 145.12, 165.73

IR: 669, 710, 766, 812, 853, 930, 1002, 1069, 1088, 1146, 1175, 1277, 1352, 1404, 1462, 1490, 1582, 1661, 2228, 2919, 3205 cm$^{-1}$

LCMS (DMSO): Rt=3.99 min (on 5 min column)

HPLC purity (as area %): >97

UV (in EtOH): λ max=227 nm

EI-MS: calculated mass of ion 407.0360 [M−H]$^-$, measured mass of ion 407.0363 [M−H]$^-$ Rf=0.42 (50% EtOAc/petrol); MP: 210-211° C.

Analysis of minor isomer (NCL-00010489):

$^1$H NMR (300 MHz, CDCl$_3$) δ 4.02 (br s, 1H, OH), 4.29-4.60 (dd AB, J=15.1 Hz, 2H, N—CH$_2$—), 7.16-7.19 (dd, J=7.2, 1.2 Hz, 1H, C(OH)—C=CH—), 7.20-7.22 (m, 4H, —C$_6$H$_4$Cl), 7.26-7.29 (m, 2H, ArH), 7.37-7.47 (m, 4H, ArH)

$^{13}$C NMR (CDCl$_3$, 75 MHz), δ 43.17, 94.29, 100.01, 115.88, 128.17, 128.53, 129.18, 129.92, 131.95, 132.32, 132.77, 134.26, 134.36, 135.53, 136.47, 143.28, 144.23, 167.99

IR: 672, 698, 736, 789, 801, 845, 928, 956, 1013, 1088, 1169, 1205, 1269, 1350, 1382, 1460, 1489, 1597, 1686, 1790, 2226, 1851, 2922, 3076, 3358 cm$^{-1}$

LCMS (DMSO): Rt=3.95 min (on 5 min column)

HPLC purity (as area %): >88

UV (in EtOH): λ max=227 nm

EI-MS: calculated mass of ion 426.0771 [M+NH$_4$]$^+$, measured mass of ion 426.0777 [M+NH$_4$]$^+$ Rf=0.57 (50% EtOAc/petrol); MP: 191-193° C.

Synthesis of 2-(4-bromobenzyl)-4-chloro-3-(4-chlorophenyl)-3-hydroxyisoindolin-1-one (NCL-00010490)

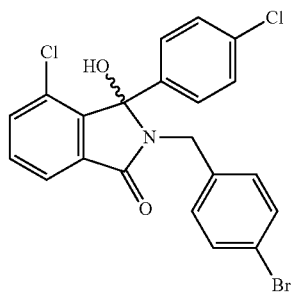 [SMILES: O=C1c2cccc(Cl)c2C(O)(c2ccc(Cl)cc2)N1Cc1ccc(Br)cc1]

The named compound was synthesised from a mixture of 3-chloro-2-(4-chlorobenzoyl)benzoic acid and 6-chloro-2-(4-chlorobenzoyl)benzoic acid (2.15 g, 7.28 mmol) and 4-bromobenzylamine (1.49 g, 8.01 mmol) using General Procedure B, purified by chromatography (Biotage SP4; 20% EtOAc/petrol) and obtained as a white solid (1.57 g, 47%).

$^1$H NMR (300 MHz, DMSO) δ 3.40 (br s, 1H, OH), 4.06-4.55 (dd AB, J=15.0 Hz, 2H, N—CH$_2$—), 7.01-7.07 (m, 2H, C—C$_2$H$_2$C$_2$H$_2$Br), 7.23-7.32 (m, 6H, ArH), 7.44-7.50 (m, 2H, ArH), 7.72-7.75 (dd, J=5.7, 2.8 Hz, 1H, C(=O)—C=CH)

$^{13}$C NMR (DMSO, 75 MHz), δ 44.30, 91.18, 121.62, 122.51, 126.33, 127.34, 128.29, 128.58, 128.94, 130.81, 131.73, 134.30, 137.00, 139.90, 141.07, 145.12, 167.02

IR: 671, 711, 766, 814, 847, 928, 1009, 1072, 1150, 1198, 1285, 1356, 1399, 1464, 1489, 1585, 1656, 3193 cm⁻¹

LCMS (DMSO): Rt=4.72 min (on 5 min column)

HPLC purity (as area %): >97

UV (in EtOH): λ max=222 nm

EI-MS: calculated mass of ion 459.9512 [M−H]⁻, measured mass of ion 459.9515 [MNH]⁻

Rf=0.57 (50% EtOAc/petrol); MP: 211-212° C.

Synthesis of 4-((7-chloro-1-(4-chlorophenyl)-1-((1-(hydroxymethyl)cyclopropyl)methoxy)-3-oxoisoindolin-2-yl)methyl)benzonitrile (NCL-00010492)

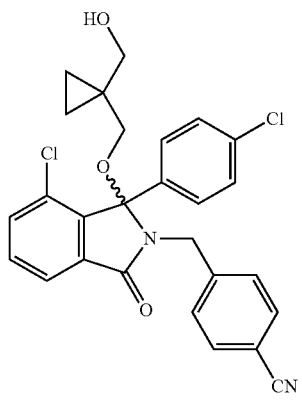 [SMILES: N#Cc1ccc(CN2C(=O)c3cccc(Cl)c3C2(OCC2(CO)CC2)c2ccc(Cl)cc2)cc1]

The named compound was synthesised from NCL-00010488 (413 mg, 1.01 mmol) and 1,1-bis(hydroxymethyl)cyclopropane (0.19 mL, 2.03 mmol) using General Procedure C, purified by chromatography (Biotage SP4; 20%-60% EtOAc/petrol) and obtained as white crystals (305 mg, 61%).

¹H NMR (300 MHz, CDCl₃) δ 0.23-0.34 (m, 2H, cyclopropane CH₂), 0.38-0.46 (m, 2H, cyclopropane CH₂), 2.28 (s, 3H, OH), 2.78-2.92 (dd AB, J=9.1 Hz, 2H, —O—CH₂), 3.43-3.53 (dd AB, J=11.4 Hz, 2H, CH₂OH), 4.30-4.45 (dd AB, J=15.2 Hz, 2H, N—CH₂—), 7.02-7.10 (m, 2H, ArH), 7.12-7.16 (m, 4H, ArH), 7.33-7.37 (m, 2H, C₂H₂—C(CN)), 7.38-7.42 (m, 1H, —CH═CH—C(Cl)—C═C(OCH₂—), 7.43-7.49 (m, 1H, —CH═C(Cl)—C—C(OCH₂—)), 7.78-7.80 (dd, J=7.2, 1.2 Hz, 1H, C(═O)—C═CH)

¹³C NMR (CDCl₃, 75 MHz), δ 8.80, 8.86, 22.54, 42.80, 67.46, 68.04, 94.69, 111.59, 118.67, 122.60, 128.66, 128.72, 129.98, 130.36, 132.17, 132.25, 134.33, 134.41, 135.17, 135.56, 141.10, 142.72, 167.04

IR: 761, 814, 854, 928, 1012, 1144, 1172, 1233, 1275, 1651, 1384, 1423, 1462, 1588, 1697, 2229, 2874, 2920, 3423 cm⁻¹

LCMS (DMSO): Rt=4.02 min (on 5 min column)

HPLC purity (as area %): >96

UV (in EtOH): λ max=226 nm

EI-MS: calculated mass of ion 426.0255 [M+H]⁺, measured mass of ion 426.0257 [M+H]⁺

Rf=0.26 (50% EtOAc/petrol); MP: 70-72° C.

Synthesis of 2-(4-bromobenzyl)-4-chloro-3-(4-chlorophenyl)-3-((1-(hydroxymethyl)cyclopropyl)methoxy)isoindolin-1-one (NCL-00010493)

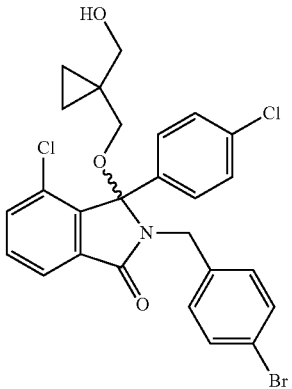 [SMILES: O=C1c2cccc(Cl)c2C(OCC2(CO)CC2)(c2ccc(Cl)cc2)N1Cc1ccc(Br)cc1]

The named compound was synthesised from NCL-00010490 (468 mg, 1.01 mmol) and 1,1-bis(hydroxymethyl)cyclopropane (0.19 mL, 2.03 mmol) using General Procedure C, purified by chromatography (Biotage SP4; 20%-40% EtOAc/petrol) and obtained as white crystals (304 mg, 55%).

¹H NMR (300 MHz, DMSO) δ 0.06-0.27 (m, 2H, cyclopropane CH₂), 0.35-0.40 (m, 2H, cyclopropane CH₂), 2.23 (s, 3H, OH), 2.82 (s, 2H, —O—CH₂), 3.41-3.50 (dd AB, J=11.8 Hz, 2H, CH₂OH), 4.15-4.38 (dd AB, J=14.9 Hz, 2H, N—CH₂—), 6.93-6.96 (d, AB, J=8.4 Hz, 2H, —C₂H₂C₂H₂Br), 7.10-7.15 (m, 4H, ArH), 7.19-7.23 (d AB, J=8.4 Hz, 2H, C₂H₂—C(Br)), 7.37-7.47 (m, 2H, ArH), 7.77-7.81 (dd, J=7.1, 1.2 Hz, 1H, C(═O)—C═CH), ¹³C NMR (DMSO, 75 MHz), δ 8.83, 8.97, 22.50, 42.70, 67.65, 68.08, 94.91, 121.69, 122.54, 128.72, 130.23, 131.15, 131.59, 132.10, 134.17, 134.63, 135.06, 135.63, 136.46, 141.22, 166.96

IR: 713, 759, 818, 924, 951, 1009, 1071, 1144, 1172, 1233, 1349, 1383, 1461, 1487, 1587, 1690, 2873, 2923, 3404 cm⁻¹

LCMS (DMSO): Rt=4.27 min (on 5 min column)

HPLC purity (as area %): >94

UV (in EtOH): λ max=222 nm

EI-MS: calculated mass of ion 563.0498 [M+NH₄]⁺, measured mass of ion 563.0491 [M+NH₄]⁺

Rf=0.39 (50% EtOAc/petrol); MP: 59-61° C.

Synthesis of 3-(4-chlorophenyl)-3-hydroxy-2-(4-nitrobenzyl)-2,3,4,5,6,7-hexahydroisoindol-1-one (NCL-00010494)

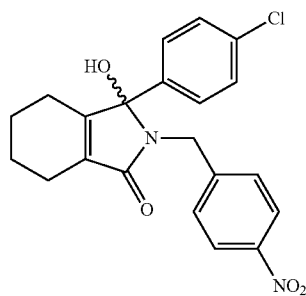 [SMILES: O=C1C2=C(CCCC2)C(O)(c2ccc(Cl)cc2)N1Cc1ccc([N+](=O)[O-])cc1]

The named compound was synthesised from, 2-(4-chlorobenzoyl)cyclohex-1-enecarboxylic acid (1.00 g, 3.78 mmol) and 4-nitrobenzylamine hydrochloride (0.78 g, 4.16 mmol) using General Procedure B, purified by chromatography (Biotage SP4; 30% EtOAc/petrol) and obtained as a yellow solid (0.67 g, 44%).

$^1$H NMR (300 MHz, CDCl$_3$) δ 1.60-1.80 (m, 4H, —C(=O)—C—CH$_2$CH$_2$CH$_2$CH$_2$C—C(OH), 2.20-2.33 (m, 4H, —C(=O)—C=CH$_2$CH$_2$CH$_2$CH$_2$C—C(OH)), 4.19-4.61 (dd AB, J=15.6 Hz, 2H, N—CH$_2$—), 4.73 (s, 1H, OH), 7.24-7.30 (m, 4H, —C$_6$H$_4$Cl), 7.33-7.36 (d AB, J=8.6 Hz, 2H, —C$_2$H$_2$C$_2$H$_2$C(NO$_2$)), 7.97-8.00 (d AB, J=8.6 Hz, 2H, —C$_2$H$_2$C(NO$_2$))

$^{13}$C NMR (CDCl$_3$, 75 MHz), δ 20.31, 21.02, 22.11, 22.26, 42.59, 92.16, 123.50, 127.94, 129.09, 129.66, 131.47, 134.97, 136.12, 146.31, 147.42, 157.64, 171.18

IR: 697, 727, 797, 824, 853, 914, 968, 1013, 1045, 1092, 1136, 1202, 1283, 1339, 1435, 1489, 1520, 1603, 1661, 2853, 2932, 3159 cm$^{-1}$

LCMS (DMSO): Rt=4.02 min (on 5 min column)
HPLC purity (as area %): >98
UV (in EtOH): λ max=272 nm
EI-MS: calculated mass of ion 399.1106 [M+H]$^+$, measured mass of ion 399.1112 [M+H]$^+$
Rf=0.39 (50% EtOAc/petrol); MP: 144-146° C.

Synthesis of 3-(4-chlorophenyl)-5-fluoro-3-((1-(hydroxymethyl)cyclopropyl)methoxy)-2-(4-nitrobenzyl)isoindolin-1-one (NCL-00010495)

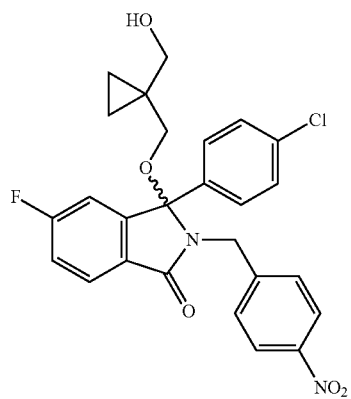 [SMILES: O=C1c2ccc(F)cc2C(OCC2(CO)CC2)(c2ccc(Cl)cc2)N1Cc1ccc([N+](=O)[O-])cc1]

The named compound was synthesised from NCL-00010485 (150 mg, 0.36 mmol) and 1,1-bis(hydroxymethyl)cyclopropane (0.07 mL, 0.72 mmol) using General Procedure C, purified by chromatography (Biotage SP4; 20%-40% EtOAc/petrol) and obtained as white crystals (85 mg, 47%).

$^1$H NMR (300 MHz, CDCl$_3$) δ 0.10-0.25 (m, 2H, cyclopropane CH$_2$), 0.40-0.49 (m, 2H, cyclopropane CH$_2$), 1.69 (s, 3H, OH), 2.84 (s, 2H, —O—CH$_2$), 3.43-3.54 (dd AB, J=11.3 Hz, 2H, CH$_2$OH), 4.48 (s, 2H, N—CH$_2$—), 6.82-6.85 (dd, J=7.5, 2.0 Hz, 1H, ArH), 7.15-7.17 (m, 4H, —C$_6$H$_4$Cl), 7.18-7.25 (dt, J=8.7, 2.2 Hz, 1H, ArH)), 7.28-7.31 (d AB, J=8.6 Hz, 2H, —C$_2$H$_2$C$_2$H$_2$C(NO$_2$)), 7.87-7.92 (dd, J=8.3, 4.8 Hz, 1H, C(=O)—C=CH), 7.98-8.01 (d AB, J=8.7 Hz, 2H, —C$_2$H$_2$C(NO$_2$))

$^{13}$C NMR (CDCl$_3$, 75 MHz), δ 8.91, 22.64, 42.86, 67.62, 67.77, 94.30, 110.87, 111.19, 118.11, 118.39, 123.63, 126.40, 128.22, 129.12, 130.22, 135.56, 136.88, 144.75, 148.23, 167.48, 168.20

IR: 683, 772, 802, 836, 936, 1013, 1059, 1093, 1150, 1178, 1220, 1264, 1342, 1383, 1427, 1487, 1520, 1605, 1697, 2876, 2927, 3082, 3407 cm$^{-1}$

LCMS (DMSO): Rt=4.12 min (on 5 min column)
HPLC purity (as area %): >98
UV (in EtOH): λ max=267 nm
EI-MS: calculated mass of ion 514.1540 [M+NH$_4$]$^+$, measured mass of ion 514.1540 [M+NH$_4$]$^+$
Rf=0.35 (50% EtOAc/petrol); MP: 61-63° C.

Synthesis of 3-(4-chlorophenyl)-6-fluoro-3-((1-(hydroxymethyl)cyclopropyl)methoxy)-2-(4-nitrobenzyl)isoindolin-1-one (NCL-00010496)

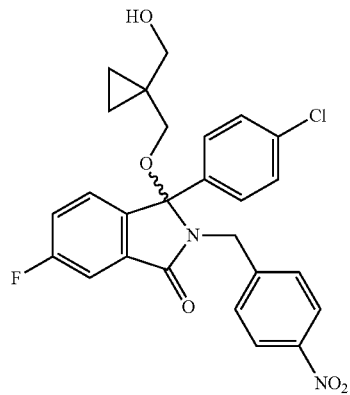 [SMILES: O=C1c2cc(F)ccc2C(OCC2(CO)CC2)(c2ccc(Cl)cc2)N1Cc1ccc([N+](=O)[O-])cc1]

The named compound was synthesised from NCL-00010486 (150 mg, 0.36 mmol) and 1,1-bis(hydroxymethyl)cyclopropane (0.07 mL, 0.72 mmol) using General Procedure C, purified by chromatography (Biotage SP4; 20%-40% EtOAc/petrol) and obtained as white crystals (115 mg, 64%).

$^1$H NMR (300 MHz, CDCl$_3$) δ 0.22-0.31 (m, 2H, cyclopropane CH$_2$), 0.48-0.55 (m, 2H, cyclopropane CH$_2$), 2.10 (s, 3H, OH), 2.90 (s, 2H, —O—CH$_2$), 3.52-3.62 (dd AB, J=11.4 Hz, 2H, CH$_2$OH), 4.51-4.62 (dd AB, J=15.5 Hz, 2H, N—CH$_2$—), 7.19-7.25 (m, 5H, —C$_6$H$_4$Cl and C(F)=CH—CH=), 7.27-7.30 (dd, J=8.6, 2.2 Hz, 1H, —C(F)=CH—CH=)), 7.34-7.37 (d AB, J=8.6 Hz, 2H, —C$_2$H$_2$C$_2$H$_2$C(NO$_2$)), 7.62-7.65 (dd, J=7.2, 2.1 Hz, 1H, C(=O)—C=CH), 8.04-8.06 (d AB, J=8.6 Hz, 2H, —C$_2$H$_2$C(NO$_2$))

$^{13}$C NMR (CDCl$_3$, 75 MHz), δ 8.87, 8.92, 22.64, 42.90, 67.55, 67.64, 94.64, 110.93, 111.25, 121.03, 123.61, 125.35, 125.46, 128.25, 129.03, 130.20, 135.38, 137.11, 141.00, 144.64, 162.64, 167.32

IR: 701, 777, 802, 830, 928, 1011, 1065, 1092, 1177, 1227, 1264, 1342, 1379, 1447, 1484, 1520, 1605, 1694, 2874, 2928, 3408 cm$^{-1}$

LCMS (DMSO): Rt=4.05 min (on 5 min column)
HPLC purity (as area %): >98
UV (in EtOH): λ max=267 nm
EI-MS: calculated mass of ion 514.1540 [M+NH$_4$]$^+$, measured mass of ion 514.1537 [M+NH$_4$]$^+$
Rf=0.45 (50% EtOAc/petrol); MP: 64-66° C.

Synthesis of 4-chloro-3-(4-chlorophenyl)-3-hydroxy-2-(4-nitrobenzyl)isoindolin-1-one (NU8398) and 7-chloro-3-(4-chlorophenyl)-3-hydroxy-2-(4-nitrobenzyl)-2,3-dihydroisoindol-1-one (AW379B, NCL-00016654)

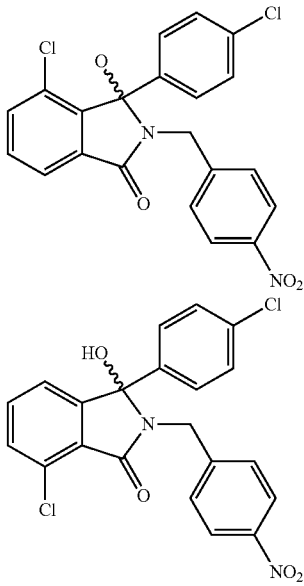

The named compounds were synthesised from a mixture of 3-chloro-2-(4-chlorobenzoyl)benzoic acid and 6-chloro-2-(4-chlorobenzoyl)benzoic acid (2.15 g, 7.28 mmol) and 4-nitrobenzylamine hydrochloride (1.51 g, 8.01 mmol) using General Procedure B, purified by chromatography (Silica; 10%-20% EtOAc/petrol) and obtained as a white solid (NU8398) and a white solid (NCL-00016654) (1.96 g, 63%, ratio of isomers NU8398:NCL-00016654 is 99:1).

Analysis of Major Isomer (NU8398):

$^1$H NMR (300 MHz, CDCl$_3$) δ 4.28 (br s, 1H, OH), 4.28 and 4.63 (dd, AB, J=15.4 Hz, 2H, N—CH$_2$—), 7.19-7.22 (m, 4H, Ar—H), 7.31-7.33 (m, 2H, Ar—H), 7.44-7.49 (m, Ar—H), 7.72-7.75 (dd, J=3.2, 8.5 Hz, 1H, (C(O)—C=CH—), 7.98-8.00 (m, 2H, —CH—NO$_2$). $^{13}$C NMR (CDCl$_3$, 75 MHz), δ 42.37, 90.90, 122.20, 123.22, 123.35, 128.21, 128.68, 129.44, 129.75, 131.69, 131.89, 134.14, 135.15, 147.37, 163.60, 163.86. IR: 696, 729, 759, 808, 856, 932, 996, 1070, 1092, 1144, 1174, 1271, 1342, 1397, 1462, 1518, 1592, 1682, 2026, 2171, 3220 cm$^{-1}$. LCMS (DMSO): 8.47 min (on 12 min column). UV (in EtOH): λ max=268 nm. EI-MS: calculated mass of ion 429.0403 [M+H]$^+$, measured mass of ion 429.0401 [M+H]$^+$. Rf: 0.47 (50% EtOAc/petrol). MP: 202-203° C. CHN: C$_{21}$H$_{14}$Cl$_2$N$_2$O$_4$+0.2EtOAc requires C, 58.59; H, 3.52; N, 6.27. found C, 58.27; H, 3.21; N, 6.48.

Analysis of Minor Isomer (NCL-00016654)

$^1$H NMR (300 MHz, CDCl$_3$) δ 3.90 (s, 1H, OH), 4.30-4.66 (dd, AB, J=15.2 Hz, 2H, N—CH$_2$—), 7.17-7.20 (dd, J=1.2, 7.2 Hz, 1H, CH—C(COH)—), 7.21-7.24 (m, 4H, —C$_6$H$_4$Cl), 7.29-7.35 (dd AB, J=8.8 Hz, 2H, —CC$_2$H$_2$C$_2$H$_2$CNO$_2$), 7.37-7.48 (m, 2H, ArH), 7.94-8.00 (dd AB, J=8.8 Hz, 2H, —CC$_2$H$_2$C$_2$H$_2$CNO$_2$). $^{13}$C NMR (CDCl$_3$, 75 MHz), δ 42.88, 90.25, 121.72, 123.70, 126.42, 128.16, 129.23, 130.01, 132.04, 132.10, 135.64, 136.58, 145.18, 147.78, 151.26, 165.68. IR: 612, 852, 934, 1093, 1343, 1387, 1515, 1604, 1686, 2850, 2932, 3078, 3332 cm$^{-1}$. LCMS (DMSO): RT=3.47 min (on 5 min column), m/z=427 ES$^-$. HPLC purity (as area %): >98. UV (in EtOH): λ max=270 nm. EI-MS: calculated mass of ion 429.0403 [M+H]$^+$, measured mass of ion 429.0403 [M+H]$^+$. Rf=0.55 (50% EtOAc/petrol). MP: 172-174° C.

Synthesis of 2-(4-acetylbenzyl)-3-(4-chlorophenyl)-3-hydroxy-2,3-dihydroisoindol-1-one (NCL-00016045/AW344)

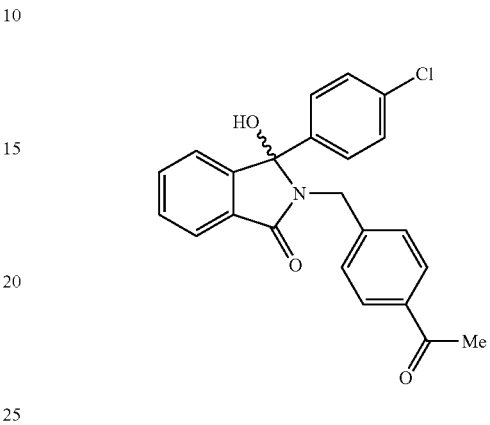

The named compound was synthesised from 2-(4-chlorobenzoyl)-benzoic acid (687 mg, 2.63 mmol) and 4-acetylbenzylammonium trifluoroacetate (630 mg, 2.40 mmol) using General Procedure B, purified by chromatography (Silica; 10%-50% EtOAc/petrol) and obtained as white crystals (552 mg, 54%).

$^1$H NMR (300 MHz, CDCl$_3$) δ 2.44 (s, 3H, CH$_3$), 4.10-4.60 (dd AB, J=15.1 Hz, 2H, N—CH$_2$), 5.03 (s, 1H, OH), 7.15-7.21 (m, 4H, ArH), 7.24-7.28 (m, 3H, ArH), 7.40-7.52 (m, 2H, ArH), 7.57-7.60 (d AB, J=8.2 Hz, 2H, ArH), 7.65-7.69 (m, 1H, —CH—C(C=O)). $^{13}$C NMR (CDCl$_3$, 75 MHz), δ 26.39, 42.98, 91.38, 123.01, 123.59, 128.23, 128.32, 128.76, 129.14, 129.75, 130.64, 133.01, 134.69, 136.17, 137.96, 143.66, 149.26, 168.06, 198.01. IR: 696, 725, 770, 804, 849, 905, 956, 1013, 1061, 1089, 1200, 1263, 1352, 1398, 1427, 1468, 1603, 1666, 2055, 2846, 2934, 3007, 3140 cm$^{-1}$. LCMS (DMSO): RT=3.78 min (on 5 min column), m/z=392 ES$^+$. HPLC purity (as area %): >98. UV (in EtOH): λ max=254 nm. EI-MS: calculated mass of ion 392.1048 [M+H]$^+$, measured mass of ion 392.1051 [M+H]$^+$. Rf=0.19 (25% EtOAc/petrol). MP: 147-150° C.

Synthesis of 2-(4-benzoylbenzyl)-3-(4-chlorophenyl)-3-hydroxy-2,3-dihydroisoindol-1-one (AW357, NCL-00014532)

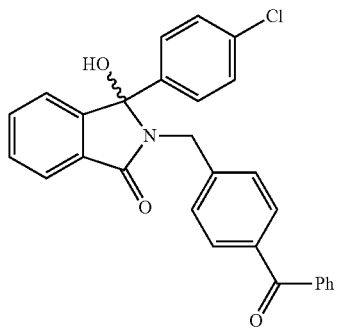 [SMILES: O=C(c1ccccc1)c1ccc(CN2C(=O)c3ccccc3C2(O)c2ccc(Cl)cc2)cc1]

The named compound was synthesised from 2-(4-chlorobenzoyl)-benzoic acid (791 mg, 3.03 mmol) and 4-acetylbenzylammonium trifluoroacetate (640 mg, 1.97 mmol) using General Procedure B, purified by chromatography (Silica; 10%-30% EtOAc/petrol) and obtained as white crystals (414 mg, 46%).

$^1$H NMR (300 MHz, CDCl$_3$) δ 4.20-4.56 (dd AB, J=15.1 Hz, 2H, N—CH$_2$), 6.01 (s, 1H, OH), 7.14-7.20 (m, 4H, ArH), 7.21-7.28 (m, 3H, ArH), 7.31-7.43 (m, 6H, ArH), 7.50-7.53 (m, 1H, —CH—C(C=O)), 7.56-7.62 (m, 3H, ArH). $^{13}$C NMR (CDCl$_3$, 75 MHz), δ 43.02, 91.46, 123.09, 123.74, 128.37, 128.55, 128.83, 128.99, 129.87, 130.15, 130.26, 130.57, 132.65, 133.16, 134.78, 136.45, 137.86, 137.97, 143.06, 149.28, 168.18, 196.74. IR: 698, 735, 763, 810, 864, 927, 1015, 1063, 1090, 1198, 1275, 1313, 1350, 1400, 1468, 1597, 1655, 2023, 2157, 2931, 3065, 3179 cm$^{-1}$.

LCMS (DMSO): 3.88 min (on 5 min column), m/z=454 ES$^+$

HPLC purity (as area %): >97. UV (in EtOH): λ max=259 nm. EI-MS: calculated mass of ion 454.1204 [M+H]$^+$, measured mass of ion 454.1206 [M+H]$^+$. Rf=0.45 (25% EtOAc/petrol). MP: 163-164° C.

Synthesis of 3-(4-chlorophenyl)-3-hydroxy-2-(4-iodobenzyl)-2,3-dihydroisoindol-1-one (AW345, NCL-00014527)

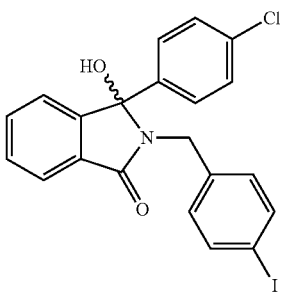 [SMILES: O=C1c2ccccc2C(O)(c2ccc(Cl)cc2)N1Cc1ccc(I)cc1]

The named compound was synthesised from 2-(4-chlorobenzoyl)-benzoic acid (1.76 g, 6.75 mmol) and 4-iodobenzylamine hydrochloride (2 g, 7.42 mmol) using General Procedure B, recrystallised from EtOAc/petrol, purified by chromatography (Silica; 6%-50% EtOAc/petrol) and obtained as a white solid (1.72 g, 52%).

$^1$H NMR (300 MHz, CDCl$_3$) δ 337 (s, 1H, OH), 4.17-4.46 (dd AB, J=15.6 Hz, 2H, N—CH$_2$), 6.98-7.01 (d AB, J=7.8 Hz, 2H, CC$_2$H$_2$C$_2$H$_2$C(I)), 7.23-7.32 (m, 5H, ArH), 7.50-7.62 (m, 4H, ArH), 7.75-7.78 (m, 1H, —CH—C(C=O)). $^{13}$C NMR (CDCl$_3$, 75 MHz), δ 167.15, 149.54, 139.34, 138.32, 136.90, 133.21, 133.03, 130.80, 130.70, 129.73, 128.57, 128.38, 123.18, 122.98, 92.38, 90.59, 42.32. IR: 694, 719, 762, 790, 845, 926, 1007, 1063, 1093, 1119, 1198, 1288, 1352, 1391, 1412, 1467, 1659, 2912, 3175, 3178 cm$^{-1}$. LCMS (DMSO): RT=4.89 min (on 5 min column), m/z=476 ES$^+$. HPLC purity (as area %): >99. UV (in EtOH): λ max=231 nm. EI-MS: calculated mass of ion 475.9909 [M+H]$^+$, measured mass of ion 475.9905 [M+H]$^+$. Rf=0.29 (25% EtOAc/petrol). MP: 184-185° C.

Synthesis of 3-(4-chlorophenyl)-3-(1-hydroxymethylcyclopropylmethoxy)-2-(4-iodobenzyl)-2,3-dihydroisoindol-1-one (AW350, NCL-00014529)

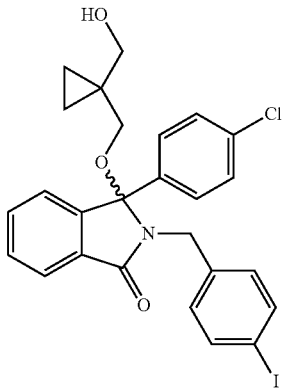 [SMILES: O=C1c2ccccc2C(OCC2(CO)CC2)(c2ccc(Cl)cc2)N1Cc1ccc(I)cc1]

The named compound was synthesised from NCL-00014527 (499 mg, 1.01 mmol) and 1,1-bis(hydroxymethyl)cyclopropane (0.19 mL, 2.03 mmol) using General Procedure C, purified by chromatography (Silica; 10%-40% EtOAc/petrol) and obtained as white crystals (487 mg, 83%).

$^1$H NMR (300 MHz, CDCl$_3$) δ 0.10-0.15 (m, 2H, cyclopropane CH$_2$), 0.35-0.42 (m, 2H, cyclopropane CH$_2$), 1.85 (s, 1H, OH), 2.62-2.80 (dd AB, J=9.4 Hz, 2H, iso-O—CH$_2$—), 3.32-3.48 (m, 2H, —CH$_2$OH) 4.12-4.50 (dd AB, J=14.8 Hz, 2H, N—CH$_2$), 6.85-6.93 (d AB, J=8.3 Hz, 2H, CC$_2$H$_2$C$_2$H$_2$C(I)), 7.09-7.13 (m, 1H, —CH—CH=C(C=O)), 7.13-7.18 (m, 4H, ArH), 7.44-7.51 (m, 4H, ArH), 7.85-7.89 (m, 1H, —CH—C(C=O)).

$^{13}$C NMR (CDCl$_3$, 75 MHz), δ 8.85, 22.56, 42.94, 67.81, 67.93, 94.68, 95.11, 123.30, 124.00, 128.27, 128.93, 130.28, 131.54, 133.20, 135.03, 137.45, 137.48, 137.63, 144.90, 145.62, 168.40. IR: 679, 758, 792, 812, 847, 877, 922, 953, 1035, 1065, 1091, 1177, 1229, 1277, 1318, 1356, 1386, 1418, 1471, 1611, 1684, 1769, 2817, 2880, 2943, 3005, 3063, 3508 cm$^{-1}$. LCMS (DMSO): RT=4.03 min (on 5 min column), m/z=560 ES$^+$. HPLC purity (as area %): >98. UV (in EtOH): λ max=229 nm. EI-MS: calculated mass of ion 560.0484 [M+H]$^+$, measured mass of ion 560.0472 [M+H]$^+$. Rf=0.36 (50% EtOAc/petrol). MP: 164-165° C.

Synthesis of 3-(4-chlorophenyl)-2-(4-fluorobenzyl)-3-(1-hydroxymethylcyclopropylmethoxy)-2,3-dihydro-isoindol-1-one (AW351, NCL-00014530)

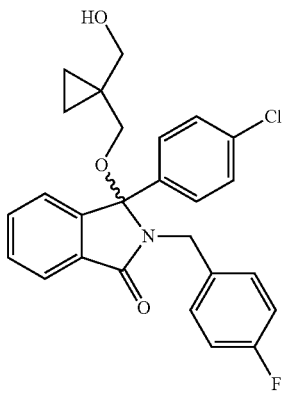 [SMILES: O=C1c2ccccc2C(OCC2(CO)CC2)(c2ccc(Cl)cc2)N1Cc1ccc(F)cc1]

The named compound was synthesised from 3-(4-chlorophenyl)-2-(4-fluoro-benzyl)-3-hydroxy-2,3-dihydroisoindol-1-one (372 mg, 1.01 mmol) and 1,1-bis(hydroxymethyl)cyclopropane (0.19 mL, 2.03 mmol) using General Procedure C, purified by chromatography (Silica; 10%-40% EtOAc/petrol) and obtained as yellow crystals (238 mg, 52%).

$^1$H NMR (300 MHz, CDCl$_3$) δ 0.01-0.04 (m, 2H, cyclopropane CH$_2$), 0.29-0.34 (m, 2H, cyclopropane CH$_2$), 2.05 (s, 1H, OH), 2.57-2.75 (dd AB, J=9.4 Hz, 2H, iso-O—CH$_2$—), 3.28-3.46 (dd AB, J=11.3 Hz, 2H, —CH$_2$OH) 4.11-4.$\overline{45}$ (dd AB, J=14.8 Hz, 2H, N—CH$_2$), 6.71-6.$\overline{77}$ (m, 2H, ArH), 7.03-7.08 (m, 3H, —ArH), 7.08-7.13 (m, 4H, ArH), 7.39-7.42 (m, 2H, ArH), 7.78-7.82 (m, 1H, —CH—C(C=O)). $^{13}$C NMR (CDCl$_3$, 75 MHz), δ 8.80, 21.08, 4$\overline{2.70}$, 67.75, 95.11, 115.06, 123.31, 123.96, 128.30, 128.87, 130.25, 131.20, 131.30, 133.16, 133.70, 134.89, 137.76, 145.75, 164.12, 168.47. IR: 760, 808, 844, 918, 951, 1008, 1042, 1063, 1086, 1110, 1158, 1222, 1309, 1346, 1393, 1429, 1468, 1508, 1602, 1674, 2848, 2929, 3005, 3080, 3396 cm$^{-1}$. LCMS (DMSO): RT=3.78 min (on 5 min column), m/z=452 ES$^+$. HPLC purity (as area %): >96. UV (in EtOH): λ max=254 nm. EI-MS: calculated mass of ion 452.1423 [M+H]$^+$, measured mass of ion 452.1419 [M+H]$^+$. Rf=0.49 (50% EtOAc/petrol). MP: 130-132° C.

Synthesis of 2-(4-acetylbenzyl)-3-(4-chlorophenyl)-3-(1-hydroxymethylcyclopropylmethoxy)-2,3-dihydroisoindol-1-one (AW354, NCL-00014531)

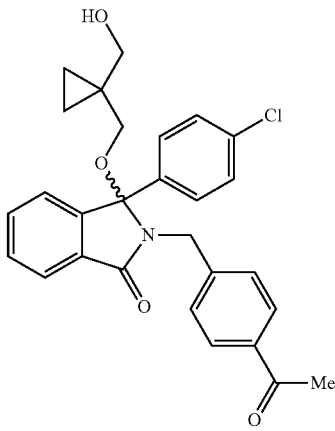 [SMILES: CC(=O)c1ccc(CN2C(=O)c3ccccc3C2(OCC2(CO)CC2)c2ccc(Cl)cc2)cc1]

The named compound was synthesised from NCL-00016045 (270 mg, 0.69 mmol) and 1,1-bis(hydroxymethyl)cyclopropane (0.13 mL, 1.38 mmol) using General Procedure C, purified by chromatography (Silica; 20%-70% EtOAc/petrol) and obtained as a yellow oil (108 mg, 33%).

$^1$H NMR (300 MHz, CDCl$_3$) δ −0.05-0.03 (m, 2H, cyclopropane CH$_2$), 0.20-0.31 (m, 2H, cyclopropane CH$_2$), 1.76 (br s, 1H, OH), 2.42 (s, 3H, CH$_3$) 2.58-2.70 (dd AB, J=9.4 Hz, 2H, iso-O—CH$_2$—), 3.23-3.$\overline{37}$ (dd AB, J=11.3 Hz, 2H, —CH$_2$OH) 4.20-4.$\overline{44}$ (dd AB, J=15.0 Hz, 2H, N—CH$_2$), 6.95-$\overline{7.10}$ (m, 5H, —ArH), 7.11-7.16 (m, 2H, ArH), 7.38-7.41 (m, 2H, ArH), 7.59-7.64 (m, 2H, ArH), 7.76-7.80 (m, 1H, —CH—C(C=O))

$^{13}$C NMR (CDCl$_3$, 75 MHz), δ 8.84, 21.10, 26.63, 43.12, 67.85, 69.40, 95.09, 123.37, 124.07, 128.31, 128.48, 128.89, 129.61, 130.35, 132.04, 133.26, 135.03, 136.75, 137.61, 142.97, 145.65, 168.47, 197.58

IR: 698, 763, 811, 849, 926, 957, 1012, 1061, 1092, 1177, 1267, 1353, 1383, 1417, 1466, 1607, 1680, 2875, 2922, 3001, 3368, 3402 cm$^{-1}$. LCMS (DMSO): 4.14 min (on 5 min column). HPLC purity (as area %): >97. LTV (in EtOH): λ max=251 nm. EI-MS: calculated mass of ion 476.1623 [M+H]$^+$, measured mass of ion 476.618 [M+H]$^+$. Rf=0.21 (50% EtOAc/petrol).

Synthesis of 2-(4-benzoylbenzyl)-3-(4-chlorophenyl)-3-(1-hydroxymethylcyclopropylmethoxy)-2,3-dihydroisoindol-1-one (AW360, NCL-00014533)

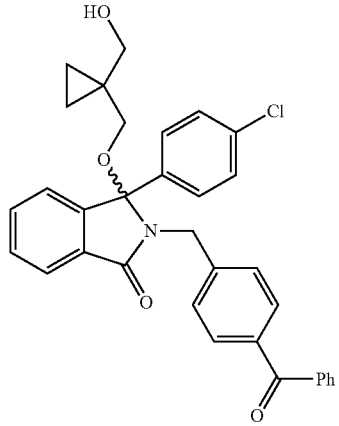 [SMILES: O=C(c1ccccc1)c1ccc(CN2C(=O)c3ccccc3C2(OCC2(CO)CC2)c2ccc(Cl)cc2)cc1]

The named compound was synthesised from NCL-00014532 (142 mg, 0.31 mmol) and 1,1-bis(hydroxymethyl)cyclopropane (0.06 mL, 0.63 mmol) using General Procedure C, purified by chromatography (Silica; 10%-50% EtOAc/petrol) and obtained as yellow crystals (124 mg, 74%).

$^1$H NMR (300 MHz, CDCl$_3$) δ −0.08-0.03 (m, 2H, cyclopropane CH$_2$), 0.25-0.30 (m, 2H, cyclopropane CH$_2$), 1.94 (br s, 1H, OH), 2.60-2.69 (dd AB, J=9.4 Hz, 2H, iso-O—CH$_2$—), 3.23-3.37 (dd AB, J=11.3 Hz, 2H, —C$_1$H$_2$OH) 4.22-$\overline{4.42}$ (dd AB, J=15.0 Hz, 2H, N—CH$_2$), 6.96-$\overline{7.05}$ (m, 5H, —C$_6$H$_4$Cl & —CHCHC(C=O—N—), 7.09-7.12 (d AB, J=8.1$\overline{7}$Hz, 2H, —N—CH2-CC$_2$H$_2$C$_2$H$_2$C(C(=O)Ph), 7.25-7.42 (m, 7H, ArH), 7.53-7.$\overline{56}$ (d AB, J=8.1 Hz, 2H, —N—CH2-CC$_2$H$_2$C$_2$H$_2$C(C(=O)Ph), 7.73-7.76 (m, 1H, —CH—C(C=$\overline{O}$)). $^{13}$C NMR (CDCl$_3$, 75 MHz), δ 8.86, 22.6$\overline{5}$, 43.11, 67.74, 69.30, 95.07, 123.41, 124.08, 128.40, 128.56, 128.87, 129.07, 129.26, 130.18, 130.36, 132.04, 132.55, 133.28, 134.97, 137.09, 137.72, 138.15, 142.32, 145.69, 168.52, 196.28. IR: 699, 727, 764, 813, 858, 922, 1013, 1063, 1092, 1177, 1276, 1314, 1383, 1466, 1605, 1656, 1690, 2877, 2921, 3063, 3411 cm$^{-1}$. LCMS (DMSO): 4.88 min (on 5 min column). HPLC purity (as area %): >94. UV (in EtOH): λ max=261 nm. EI-MS: calculated mass of ion 560.1599 [M+Na]$^+$, measured mass of ion 560.1601 [M+Na]$^+$. Rf=0.40 (50% EtOAc/petrol). MP: 69-71° C.

Synthesis of 3-(4-chlorophenyl)-3-hydroxy-2-naphthalen-1-ylmethyl-2,3-dihydroisoindol-1-one (AW364, NCL-00016046)

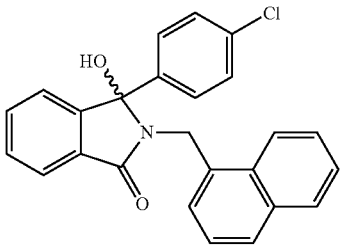 [SMILES: O=C1c2ccccc2C(O)(c2ccc(Cl)cc2)N1Cc1cccc2ccccc12]

The named compound was synthesised from 2-(4-chlorobenzoyl)-benzoic acid (2.24 g, 8.59 mmol) and 1-naphthylmethylamine (1.36 mL, 9.44 mmol) using General Procedure B, purified by chromatography (Silica; 6%-50% EtOAc/petrol) and obtained as yellow crystals (0.35 g, 10%).

¹H NMR (300 MHz, MeOD) S 4.90 (s, 1H, OH), 4.90-5.27 (dd AB, J=15.2 Hz, 2H, N—CH₂), 6.75-6.79 (m, 2H, ArH), 6.95-6.98 (d AB, J=8.5 Hz, 2H, ArH), 7.13-7.27 (m, 3H, ArH), 7.35-7.61 (m, 5H, ArH), 7.72-7.75 (m, 1H, —CH—C(C=O)), 7.86-7.89 (m, 1H, ArH), 8.17-8.19 (m, 1H, N—CH₂—C—C(C)=CH)). ¹³C NMR (MeOD, 75 MHz), δ 41.89, 92.80, 124.27, 124.59, 125.20, 126.37, 126.89, 127.38, 129.00, 129.05, 129.32, 129.40, 129.96, 131.05, 132.00, 133.36, 134.02, 134.55, 135.03, 135.47, 139.68, 151.56, 170.26. IR: 694, 762, 833, 929, 973, 1011, 1060, 1091, 1112, 1195, 1268, 1360, 1396, 1468, 1599, 1674, 2070, 2873, 2967, 3053, 3270, 3331 cm⁻¹. LCMS (DMSO): RT=4.19 min (on 5 min column), m/z=398 ES⁻. HPLC purity (as area %): >92. UV (in EtOH): λ max=223 nm. EI-MS: calculated mass of ion 400.1099 [M+H]⁺, measured mass of ion 400.1099 [M+H]⁺. Rf=0.15 (25% EtOAc/petrol). MP: 75-76° C.

Synthesis of 2-(3-bromobenzyl)-3-(4-chlorophenyl)-3-hydroxy-2,3-dihydroisoindol-1-one (AW365, NCL-00016047)

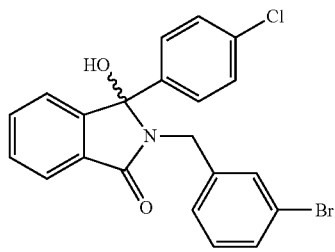 [SMILES: O=C1c2ccccc2C(O)(c2ccc(Cl)cc2)N1Cc1cccc(Br)c1]

The named compound was synthesised from 2-(4-chlorobenzoyl)-benzoic acid (2.24 g, 8.59 mmol) and 3-bromobenzylamine hydrochloride (2.10 g, 9.44 mmol) using General Procedure B, recrystallised from EtOAc/petrol and obtained as orange crystals (2.12 g, 58%).

¹H NMR (300 MHz, CDCl₃) δ 4.12-4.33 (dd AB, J=15.0 Hz, 2H, N—CH₂), 4.54 (br s, 1H, OH), 6.93-7.04 (m, 2H, —CH—CH=CH—CBr), 7.08-7.10 (m, 1H, ArH), 7.12-7.19 (m, 4H, —C₆H₄Cl), 7.20-7.29 (m, 2H, ArH), 7.41-7.53 (m, 2H, ArH), 7.64-7.69 (m, 1H, =CH—C—C(=O)). ¹³C NMR (CDCl₃, 75 MHz), δ 42.70, 91.40, 122.52, 122.56, 123.06, 123.95, 127.78, 128.27, 128.89, 130.01, 130.15, 130.54, 132.20, 133.36, 135.09, 137.20, 140.35, 149.08, 168.05. IR: 664, 696, 721, 764, 802, 837, 879, 926, 976, 1011, 1059, 1088, 1191, 1306, 1348, 1399, 1427, 1468, 1572, 1600, 1668, 2875, 2932, 3016, 3246 cm⁻¹. LCMS (DMSO): RT=4.32 min (on 5 min column), m/z=428 ES⁻. HPLC purity (as area %): >98. UV (in EtOH): λ max=254 nm. EI-MS: calculated mass of ion 428.0047 [M+H]⁺, measured mass of ion 428.0041 [M+H]⁺. Rf=0.42 (50% EtOAc/petrol). MP: 167-170° C.

Synthesis of 3-(4-chlorophenyl)-3-(1-hydroxymethylcyclopropylmethoxy)-2-naphthalen-1-ylmethyl-2, 3-dihydroisoindol-1-one (AW366, NCL-00016106)

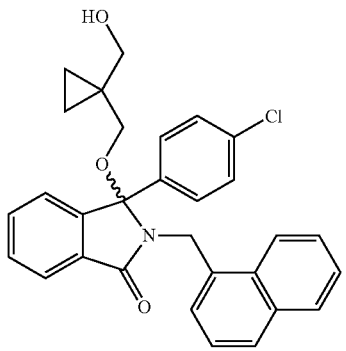 [SMILES: O=C1c2ccccc2C(OCC2(CO)CC2)(c2ccc(Cl)cc2)N1Cc1cccc2ccccc12]

The named compound was synthesised from NCL-00016046 (270 mg, 0.69 mmol) and 1,1-bis(hydroxymethyl)cyclopropane (0.13 mL, 1.38 mmol) using General Procedure C, purified by chromatography (Biotage SP4; 6%-25% EtOAc/petrol) and obtained as cream crystals (153 mg, 47%).

¹H NMR (300 MHz, CDCl₃) δ −0.35-0.15 (m, 2H, cyclopropane CH), 0.12-0.25 (m, 2H, cyclopropane CH), 1.80 (br s, 1H, OH), 2.38-2.70 (dd AB, J=9.4 Hz, 2H, CH₂O—C), 3.18-3.31 (dd AB, J=11.1 Hz, 2H, C₁H₂OH), 4.63-5.27 (dd AB, J=14.9 Hz, 2H, N—CH₂), 7.02-7.07 (m, 5H, C₆H₄Cl & ArH)), 7.15-7.30 (m, 2H, ArH), 7.43-7.48 (m, 4H, ArH), 7.68-7.71 (m, 1H, NCH₂C—CHCHCH—C), 7.76-7.79 (m, 1H, —CH—C(C=O)), 7.93-7.97 (m, 1H, N—CH₂—CC(C)=CHCHCHC—C), 8.29-8.32 (m, 1H, N—CH₂—C—C(C)=CH)).

¹³C NMR (CDCl₃, 75 MHz), δ 8.58, 8.61, 22.36, 41.25, 67.68, 67.78, 95.41, 123.17, 124.09, 124.54, 125.35, 126.02, 126.70, 128.05, 128.50, 128.68, 128.85, 129.09, 130.15, 131.92, 132.40, 132.91, 133.19, 134.03, 134.49, 137.55, 146.16, 168.32. IR: 696, 767, 810, 839, 923, 945, 1012, 1065, 1110, 1271, 1356, 1389, 1467, 1487, 1598, 1685, 2874, 2923, 3004, 3051, 3395 cm⁻¹. LCMS (DMSO): RT=3.99 min (on 5 min column), m/z=484 ES⁺. HPLC purity (as area %): >95. UV (in EtOH): λ max=223 nm. EI-MS: calculated mass of ion 484.1674 [M+H]⁺, measured mass of ion 484.1673 [M+H]⁺. Rf=0.10 (25% EtOAc/petrol). MP: 82-84° C.

Synthesis of 2-(3-bromobenzyl)-3-(4-chlorophenyl)-3-(1-hydroxymethylcyclopropylmethoxy)-2,3-dihydro-isoindol-1-one (AW367, NCL-00016107)

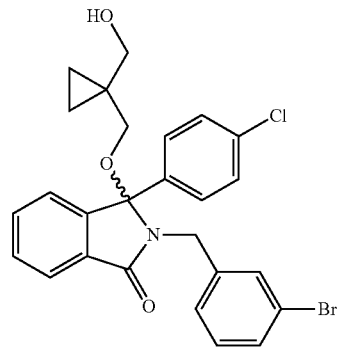 [SMILES: O=C1c2ccccc2C(OCC2(CO)CC2)(c2ccc(Cl)cc2)N1Cc1cccc(Br)c1]

The named compound was synthesised from NCL-00016047 (292 mg, 0.68 mmol) and 1,1-bis(hydroxymethyl)cyclopropane (0.13 mL, 1.35 mmol) using General Procedure C, purified by chromatography (Biotage SP4; 6%-50% EtOAc/petrol) and obtained as a pale yellow oil (253 mg, 73%).

$^1$H NMR (300 MHz, CDCl$_3$) δ −0.05-0.05 (m, 2H, cyclopropane CH), 0.22-0.31 (m, 2H, cyclopropane CH), 2.33 (br s, 1H, OH), 2.54-2.73 (dd AB, J=9.3 Hz, 2H, CH$_2$O—C), 3.26-3.32 (dd AB, J=11.0 Hz, 2H, CH$_2$OH), 4.10-4.31 (dd AB, J=14.9 Hz, 2H, N—CH$_2$), 6.81-6.87 (m, 1H, —CH—CH=CH—CBr), 6.95-7.05 (m, 7H, ArH), 7.09-7.11 (m, 1H, —CH=CH—C—C(=O)), 7.33-7.35 (m, 2H, —CH=CH—C—C(O—CH$_2$—)), 7.71-7.74 (m, 1H, =CH—C—C(=O)). $^{13}$C NMR (CDCl$_3$, 75 MHz), δ 8.76, 8.82, 22.58, 42.81, 67.52, 67.60, 94.99, 122.50, 123.40, 124.03, 128.19, 128.32, 128.86, 130.02, 130.30, 130.60, 132.00, 132.55, 133.25, 134.98, 137.61, 140.02, 145.69, 168.40. IR: 666, 695, 711, 761, 812, 838, 927, 1009, 1063, 1090, 1307, 1346, 1380, 1427, 1467, 1571, 1595, 1686, 2874, 2920, 3001, 3065, 3429 cm$^{-1}$. LCMS (DMSO): RT=3.93 min (on 5 min column), m/z=511 ES$^-$. HPLC purity (as area %): >98. UV (in EtOH): λ max=203 nm. EI-MS: calculated mass of ion 512.0623 [M+H]$^+$, measured mass of ion 512.0620 [M+H]$^+$. Rf=0.36 (50% EtOAc/petrol).

Synthesis of 3-hydroxy-2-(4-nitrobenzyl)-3-phenyl-2,3-dihydroisoindol-1-one (AW403/NCL-00016655)

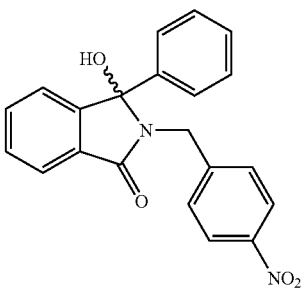 [SMILES: O=C1c2ccccc2C(O)(c2ccccc2)N1Cc1ccc([N+](=O)[O-])cc1]

The named compound was synthesised from 2-benzoylbenzoic acid (0.5 g, 2.21 mmol) and 4-nitrobenzylamine hydrochloride (0.46 g, 2.43 mmol) using General Procedure B, recrystallised from EtOAc/petrol and obtained as a yellow solid (0.56 g, 70%).

$^1$H NMR (300 MHz, CDCl$_3$) δ 3.36 (s, 1H, OH), 4.26-4.71 (dd AB, J=15.3 Hz, 2H, N—CH$_2$), 7.22-7.34 (m, 8H, Ar—H), 7.48-7.57 (m, 2H, Ar—H), 7.81-7.84 (m, 1H, CH=C—C(=O)), 7.96-8.01 (dd AB, J=8.8 Hz, 2H, C$_2$H$_2$C—NO$_2$). $^{13}$C NMR (CDCl$_3$, 75 MHz), δ 41.02, 91.09, 123.65, 124.05, 125.56, 126.65, 127.64, 128.93, 129.05, 129.82, 133.48, 138.08, 138.25, 142.31, 145.80, 148.57, 168.29. IR: 688, 756, 851, 934, 1055, 1105, 1192, 1283, 1337, 1398, 1468, 1514, 1605, 3083, 3181 cm$^{-1}$. LCMS (DMSO): RT=3.13 min (on 5 min column), m/z=359 ES$^-$. HPLC purity (as area %): >99. UV (in EtOH): λ max=269 nm. EI-MS: calculated mass of ion 361.1183 [M+H]$^+$, measured mass of ion 361.1186 [M+H]$^+$. Rf=0.35 (50% EtOAc/petrol). MP: 190-191° C.

Synthesis of 3-(1-hydroxymethylcyclopropylmethoxy)-2-(4-nitrobenzyl)-3-phenyl-2,3-dihydroisoindol-1-one (AW405/NCL-00016656)

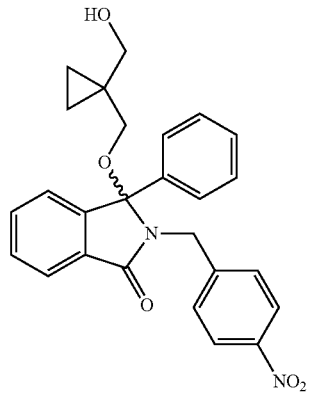

The named compound was synthesised from NCL-00016655 (300 mg, 0.83 mmol) and 1,1-bis(hydroxymethyl)cyclopropane (0.16 mL, 1.67 mmol) using General Procedure C, purified by chromatography (Biotage SP4; 10%-50% EtOAc/petrol) and obtained as pale yellow crystals (298 mg, 81%).

$^1$H NMR (300 MHz, CDCl$_3$) δ −0.02-0.01 (m, 2H, cyclopropane CH$_2$), 0.15-0.25 (m, 2H, cyclopropane CH$_2$), 2.05 (s, 1H, OH), 2.49-2.65 (m, 2H, C—O—CH$_2$), 3.20-3.40 (m, 2H, CH$_2$OH), 4.20-4.40 (m, 2H, N—CH$_2$), 6.80-7.10 (m, 8H, Ar—H), 7.25-7.35 (m, 2H, Ar—H), 7.70-7.90 (m, 3H, CH=C—C(=O) & C$_2$H$_2$C—NO$_2$)

$^{13}$C NMR (CDCl$_3$, 75 MHz), δ 8.59, 21.07, 42.08, 66.02, 66.13, 94.53, 123.34, 123.83, 126.54, 128.29, 128.81, 129.67, 130.13, 131.52, 133.04, 137.95, 138.03, 144.61, 145.46, 146.88, 168.36. IR: 696, 753, 796, 854, 910, 938, 1022, 1057, 1103, 1179, 1243, 1278, 1341, 1384, 1466, 1518, 1605, 1686, 2853, 2921, 3077, 3414 cm$^{-1}$. LCMS (DMSO): RT=3.22 min (on 5 min column). HPLC purity (as area %): >97. UV (in EtOH): λ max=267 nm. EI-MS: calculated mass of ion 445.1758 [M+H]$^+$, measured mass of ion 445.1757 [M+H]$^+$. Rf=0.27 (50% EtOAc/petrol). MP: 58-60° C.

Synthesis of succinic acid mono-{1-[7-chloro-1-(4-chloro-phenyl)-2-(4-nitrobenzyl)-3-oxo-2,3-dihydro-1H-isoindol-1-yloxymethyl]cyclopropylmethyl}ester (AW393/NCL-00016149)

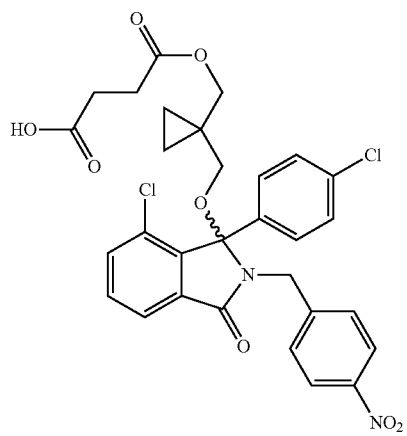 [SMILES: O=C(O)CCC(=O)OCC1(COC2(c3ccc(Cl)cc3)c3c(Cl)cccc3C(=O)N2Cc2ccc([N+](=O)[O-])cc2)CC1]

The named compound was synthesised from NU8406 (100 mg, 0.19 mmol), pyridine (0.03 mL, 0.39 mmol), 4-dimethylamino pyridine (5 mg, 0.04 mmol) and succinic anhydride (39 mg, 0.39 mmol) in anhydrous THF (10 mL) using General Procedure F, purified by chromatography (Biotage SP4; 50% EtOAc/petrol −20% MeOH/EtOAc) and obtained as white crystals (60 mg, 50%).

$^1$H NMR (300 MHz, CDCl$_3$) δ 0.20-0.42 (m, 2H, cyclopropane CH$_2$), 0.45-0.52 (m, 2H, cyclopropane CH$_2$), 2.45-2.52 (br m, 4H, —CH$_2$CH$_2$CO$_2$H), 2.62-2.93 (dd, AB, J=9.3 Hz, 2H, iso-C—O—CH$_2$—), 4.00-4.15 (m, 2H, CH$_2$OCOCH$_2$CH$_2$CO$_2$H), 4.30-4.60 (dd, AB, J=15.2 Hz, 2H, N—CH$_2$—), 7.01-7.31 (m, 6H, Ar—H), 7.42-7.57 (m, 2H, Ar—H), 7.80-8.10 (br m, 4H, ArH and CO$_2$H). $^{13}$C NMR (CDCl$_3$, 75 MHz), δ 9.38, 20.00, 29.20, 29.45, 42.50, 67.27, 68.58, 94.68, 122.67, 123.53, 128.51, 128.70, 128.86, 130.06, 130.56, 132.31, 134.37, 135.36, 141.10, 142.22, 144.50, 147.67, 167.32, 172.27, 176.16. IR: 594, 730, 819, 1076, 1165, 1344, 1521, 1707, 1708, 2882, 2929, 3079 cm$^{-1}$. LCMS (DMSO): RT=3.67 min (on 5 min column), m/z=612 ES$^-$ HPLC purity (as area %): >95. EI-MS: calculated mass of ion 613.1139 [M+H]$^+$, measured mass of ion 613.1139 [M+H]$^+$. Rf=0.06 (50% EtOAc/petrol). MP: 42-44° C.

Synthesis of succinic acid mono-{1-[7-chloro-1-(4-chlorophenyl)-2-(4-cyanobenzyl)-3-oxo-2,3-dihydro-1H-isoindol-1-yloxymethyl]cyclopropylmethyl}ester (AW417/NCL-00016659)

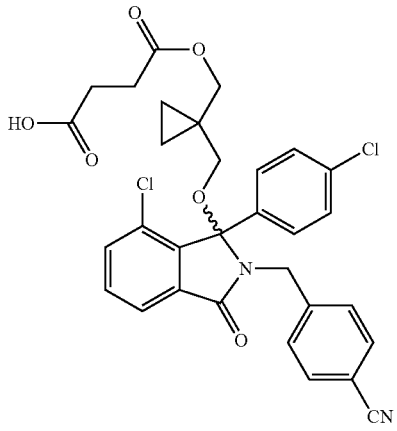 [SMILES: N#Cc1ccc(CN2C(=O)c3cccc(Cl)c3C2(OCC2(COC(=O)CCC(=O)O)CC2)c2ccc(Cl)cc2)cc1]

The named compound was synthesised from NCL-00010492 (110 mg, 0.22 mmol), pyridine (36 µL, 0.45 mmol), 4-dimethylamino pyridine (5 mg, 0.04 mmol) and succinic anhydride (45 mg, 0.45 mmol) in anhydrous THF (10 mL) using General Procedure F, purified by chromatography (Biotage SP4; 50% EtOAc/petrol −20% MeOH/EtOAc) and obtained as white crystals (20 mg, 15%).

$^1$H NMR (300 MHz, CDCl$_3$) δ −0.27-0.20 (m, 2H, cyclopropane CH$_2$), 0.29-0.36 (m, 2H, cyclopropane CH$_2$), 2.30-2.42 (br m, 4H, —CH$_2$CH$_2$CO$_2$H), 2.55-2.66 (dd, AB, J=9.3 Hz, 2H, iso-C—O—CH$_2$—), 3.85-3.90 (m, 2H, CH$_2$OCOCH$_2$CH$_2$CO$_2$H), 4.05-4.32 (dd, AB, J=15.2 Hz, 2H, N—CH$_2$—), 6.80-6.92 (br m, 5H, —C$_6$H$_4$CH and CO$_2$H), 6.93 (d AB, J=8.3 Hz, 2H, CC$_2$H$_2$C$_2$H$_2$CCN), 7.18 (d AB, J=8.3 Hz, 2H, CC$_2$H$_2$C$_2$H$_2$CCN), 7.23-7.25 (dd, J=8.0, 0.9 Hz, 1H, —CH—CH=C(Cl)—C—C(OCH$_2$—), 7.28-7.32 (m, 1H, —CH=C(Cl)—C—C(OCH$_2$—)), 7.62-7.65 (dd, J=7.4, 0.9 Hz, 1H, C(=O)—C=CH). $^{13}$C NMR (CDCl$_3$, 75 MHz), δ 9.01, 9.07, 19.49, 28.90, 28.99, 29.70, 42.28, 66.69, 68.23, 94.20, 111.07, 118.54, 122.37, 128.34, 129.58, 130.03, 131.88, 132.03, 133.86, 134.03, 134.71, 134.84, 140.60, 142.29, 167.08, 172.22, 176.80. IR: 728, 761, 814, 853, 928, 1009, 1074, 1161, 1207, 1373, 1458, 1719, 1730, 2227, 2857, 2926, 3005, 3071 cm$^{-1}$.

LCMS (DMSO): RT=3.41 min (on 5 min column), m/z=592 ES$^-$. HPLC purity (as area %): >96. UV (in EtOH): λ max=226.5 nm. EI-MS: calculated mass of ion 593.1241 [M+NH$_4$]$^+$, measured mass of ion 593.1240 [M+NH$_4$]$^+$. Rf=0.05 (50% EtOAc/petrol). MP: 72-74° C.

Synthesis of succinic acid mono-{1-[2-(4-bromobenzyl)-7-chloro-1-(4-chlorophenyl)-3-oxo-2,3-dihydro-1H-isoindol-1-yloxymethyl]cyclopropylmethyl}ester (AW436, NCL-00016653)

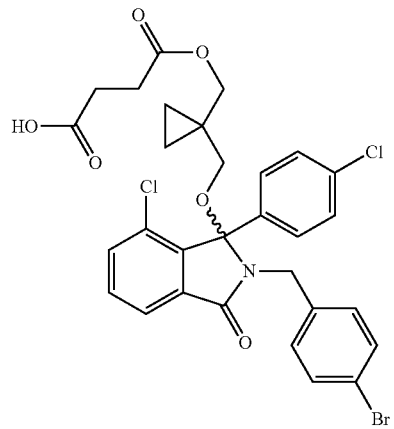 [SMILES: O=C(O)CCC(=O)OCC1(COC2(c3ccc(Cl)cc3)c3c(Cl)cccc3C(=O)N2Cc2ccc(Br)cc2)CC1]

The named compound was synthesised from NCL-00010493 (150 mg, 0.27 mmol), pyridine (44 µL, 0.55 mmol), 4-dimethylamino pyridine (7 mg, 0.05 mmol) and succinic anhydride (55 mg, 0.55 mmol) in anhydrous THF (10 mL) using General Procedure I, purified by chromatography (Biotage SP4; 50% EtOAc/petrol-EtOAc) and obtained as a brown oil (93 mg, 53%).

$^1$H NMR (300 MHz, CDCl$_3$) δ −0.04-0.18 (m, 2H, cyclopropane CH$_2$), 0.27-0.35 (m, 2H, cyclopropane CH$_2$), 2.37-2.46 (br m, 4H, —CH$_2$CH$_2$CO$_2$H), 2.52-2.69 (dd, AB, J=9.3 Hz, 2H, iso-C—O—CH$_2$—), 3.74-4.03 (dd AB, J=11.4 Hz, 2H, CH$_2$OCOCH$_2$CH$_2$CO$_2$H), 4.05-4.17 (dd, AB, J=14.9 Hz, 2H, N—CH$_2$—), 6.78 (d AB, J=8.4 Hz, 2H, —C$_2$H$_2$C$_2$H$_2$Br), 6.90-7.01, (m, 4H, CC$_2$H$_4$Cl), 7.06 (d AB, J=8.4 Hz, 2H C$_2$H$_2$—C(Br)), 7.25-7.27 (dd, J=7.9, 0.8 Hz, 1H, —CH—CH=C(Cl)—C—C(OCH$_2$—), 7.30-7.33 (m, 1H, —CH=C(Cl)—C—C(OCH$_2$—) 7.65-7.67 (dd, J=7.4, 0.8 Hz, 1H, C(=O)—C=CH) 9.00 (br s, 1H, COOH). $^{13}$C NMR (CDCl$_3$, 75 MHz), δ 8.92, 8.98, 19.34, 28.87, 28.90, 42.21, 66.60, 68.37, 94.45, 121.33, 122.28, 128.33, 128.43, 129.91, 130.78, 131.21, 131.88, 133.86, 134.02, 134.67, 134.84, 135.97, 140.75, 166.97, 172.14, 177.17. IR: 760, 817, 926, 1009, 1070, 1159, 1350, 1387, 1462, 1487, 1588, 1704, 1730, 2854, 2921 cm$^{-1}$. LCMS (DMSO): RT=3.64 min (on 5 min column), m/z=648 ES$^+$. HPLC purity (as area %): >96. UV (in EtOH): λ max=222.5 nm. EI-MS: calculated mass of ion 663.0659 [M+NH$_4$]$^+$, measured mass of ion 663.0653 [M+NH$_4$]$^+$ Rf=0.08 (50% EtOAc/petrol).

3-(4-chlorophenyl)-3-hydroxy-2-(4-methylbenzyl) isoindolin-1-one (tjb 14/02)

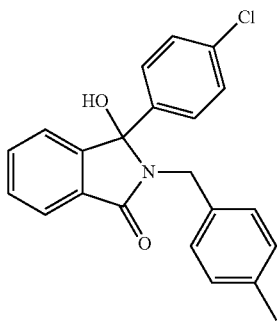 [SMILES: Cc1ccc(CN2C(=O)c3ccccc3C2(O)c2ccc(Cl)cc2)cc1]

The named compound was synthesised from 2-(4-chlorobenzoyl)-benzoic acid (2.0 g, 7.6 mmol) and 4-methyl benzylamine (1.07 mL, 8.4 mmol) using General Procedure B, purified by chromatography (Biotage SP4; 10-80% EtOAc/hexane) and obtained as a white solid (2.045 g, 72%).

$^1$H NMR (500 MHz, CDCl$_3$) δ 7.74-7.77 (1H, m, 7-H), 7.53-7.59 (2H, m, 5 & 6-H), 7.28-7.31, (3H, m, Ar—H), 7.24-7.26 (2H, m, Ar—B), 7.05 (2H, d, J=8.0, Ar—H), 6.96 (2H, d, J=8.0, Ar—H), 4.41 (1H, d, J=15.4, 2-CH), 4.20, (1H, d, J=15.4, 2-CH'), 2.22 (3H, s, CH$_3$). $^{13}$C NMR (125 MHz, CDCl$_3$) δ 166.7, 149.1, 139.0, 135.5, 135.0, 132.7, 132.6, 130.3, 129.4, 128.3, 128.2, 128.0, 127.9, 122.8, 122.6, 90.2, 42.1, 20.6. Found; 364.1101 [M+H]; C$_{22}$H$_{19}$NO$_2$Cl, requires 364.1099.

3-(4-chlorophenyl)-3-hydroxy-2-(4-methoxybenzyl) isoindolin-1-one (tjb 16/02)

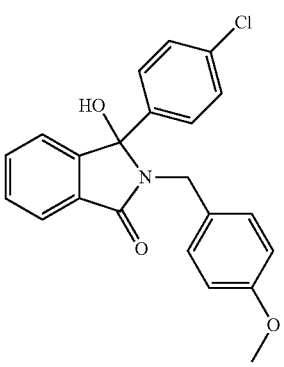 [SMILES: COc1ccc(CN2C(=O)c3ccccc3C2(O)c2ccc(Cl)cc2)cc1]

The named compound was synthesised from 2-(4-chlorobenzoyl)-benzoic acid (2.0 g, 7.6 mmol) and 4-methoxy benzylamine (0.542 mL, 4.18 mmol) using General Procedure B, purified by chromatography (Biotage SP4; 10-80% EtOAc/hexane) and obtained as a white solid (0.830 g, 57%).

$^1$H NMR (500 MHz, CDCl$_3$) δ 7.78-7.80 (1H, m, 7-H), 7.57-7.61 (2H, m, 5 & 6-H), 7.29-7.33 (3H, m, Ar—H), 7.25-7.27 (2H, m, Ar—H), 7.10-7.13 (2H, m, Ar—H), 6.73-6.76 (2H, m, Ar—H), 4.40 (1H, d, J=15.2, 2-CH), 4.26 (1H, d, J=15.2, 2-CH'), 3.72 (3H, s, CH$_3$). $^{13}$C NMR (125 MHz, CDCl$_3$) δ 166.7, 157.9, 149.1, 139.0, 132.6, 132.5, 130.3, 130.0, 129.4, 129.3, 128.2, 128.0, 122.8, 122.5, 113.190.1, 55.0, 41.72. Found; 380.1055 [M+H]; C$_{22}$H$_{19}$NO$_3$Cl, requires 380.1048.

3-(4-chlorophenyl)-3-(1'-hydroxy-2'-cyclopropyl-3'-methoxy)-2-(4-methylbenzyl)isoindolin-1-one (NCL-00016865)

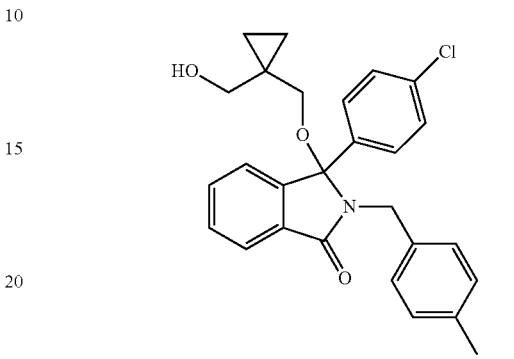

The named compound was synthesised from 3-(4-chlorophenyl)-3-hydroxy-2-(4-methylbenzyl)isoindolin-1-one (300 mg, 0.83 mmol) and 1,1-bis(hydroxymethyl)cyclopropane (0.16 mL, 1.67 mmol) using General Procedure C, purified by chromatography (Biotage SP4; 10%-80% EtOAc/n-hexane) and obtained as a glassy solid (187 mg, 54%).

$^1$H NMR (500 MHz, CDCl$_3$) δ 7.82-7.84 (1H, m, 7-H), 7.41-7.45 (2H, m, 5 & 6-H), 7.15 (4H, s, Ar—H), 7.04-7.07 (3H, m, 4 & Ar—H), 6.93 (2H, d, J=7.8, Ar—H), 4.60 (1H, d, J=14.8, 2-CH), 3.95 (1H, d, J=14.8, 2-CH'), 3.31 (1H, d, J=11.3, 1'-H), 3.25 (1H, d, J=11.3, 1'-H'), 2.64 (1H, d, J=9.5, 3'-H), 2.55 (1H, d, J=9.5, 3'-H'), 2.21 (3H, s, CH$_3$), 1.54 (1H, br s, 1'-OH), 0.27-0.30 (2H, m, H$_2$), −0.02-0.03 (2, m, H$_2$'). $^{13}$C NMR (125 MHz, CDCl$_3$) δ 168.2, 145.3, 137.3, 137.1, 134.5, 134.4, 132.8, 131.7, 129.9, 129.2, 128.9, 128.7, 127.9, 123.7, 122.8, 95.0, 68.0, 67.7, 42.9, 29.7, 22.1, 21.0, 8.6. Found; 448.1673 [M+H]; C$_{27}$H$_{27}$NO$_3$Cl, requires 448.1674.

3-(4-chlorophenyl)-3-(1'-hydroxy-2'-cyclopropyl-3'-methoxy)-2-(4-methoxybenzyl)isoindolin-1-one (NCL-00016866)

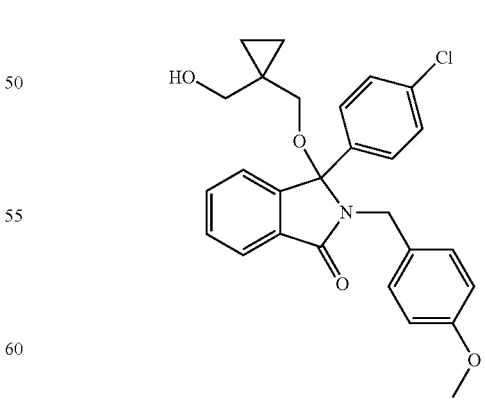

The named compound was synthesised from 3-(4-chlorophenyl)-3-hydroxy-2-(4-methoxybenzyl)isoindolin-1-one (300 mg, 0.79 mmol) and 1,1-bis(hydroxymethyl)cyclopropane (0.12 mL, 1.58 mmol) using General Procedure C, purified by chromatography (Biotage SP4; 10%-80% EtOAc/n-hexane) and obtained as a glassy solid (181 mg, 53%).

$^1$H NMR (500 MHz, CDCl$_3$) δ 7.75-7.86 (1H, m, 7-H), 7.35-7.39 (2H, m, 5 & 6-H), 7.08 (4H, m, Ar—H), 6.99-7.02 (3H, m, 4 & Ar—H), 6.57-6.60 (2H, m, Ar—H), 4.45 (1H, d, J=14.8, 2-CH), 3.97 (1H, d, J=14.8, 2-CH'), 3.62 (3H, s, CH$_3$), 3.32 (1H, d, J=11.3, 1'-H), 3.22 (1H, d, J=11.3, 1'-H'), 2.62 (1H, d, J=9.4, 3'-H), 2.53 (1H, d, J=9.4, 3'-H'), 1.53 (1H, br s, 1'-OH), 0.23-0.28 (2H, m, H$_2$), −0.02-0.02 (2H, m, H$_2$'). $^{13}$C NMR (125 MHz, CDCl$_3$) δ 168.1, 158.9, 145.3, 137.2, 134.4, 132.8, 131.7, 130.5, 129.9, 129.8, 128.6, 127.9, 123.6, 122.7, 113.6, 94.9, 68.0, 67.7, 55.3, 42.5, 22.1, 8.7, 8.6. Found; 464.1619 [M+H]; C$_{27}$H$_{27}$NO$_3$Cl, requires 464.1623.

3-(4-chlorophenyl)-3-(1'-hydroxy-2'-cyclopropyl-3'-methoxy)-2-(4-carboxamidebenzyl)isoindolin-1-one (NCL-00016867)

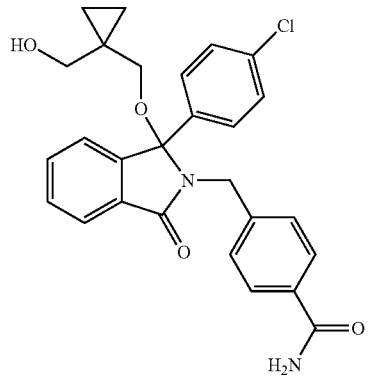 [SMILES: NC(=O)c1ccc(CN2C(=O)c3ccccc3C2(OCC2(CO)CC2)c2ccc(Cl)cc2)cc1]

To a solution of NCL-00010492 (200 mg, 0.436 mmol) in t-BuOH (8.48 mL) at 50° C. was added finely powdered KOH (647 mg). The resulting suspension was stirred at this temperature until TLC (10% MeOH/DCM) indicated the complete consumption of the starting material (3 h). The hot reaction mixture was filtered through Celite® and the pad rinsed with several portions of THF. The filtrate was partitioned between EtOAc (10 mL) and H$_2$O (10 mL) and the organic layer separated; the aqueous layer was extracted with EtOAc (2×10 mL). The combined organic layers were washed with brine (15 mL), dried (Na$_2$SO$_4$), filtered and concentrated in vacuo. The residue was dissolved in THF before the addition of a minimum amount of silica and the resulting suspension was concentrated in vacuo. Purification by flash column chromatography on silica gel, eluting with 2-10% MeOH in DCM afforded the title compound as a glassy solid (62 mg, 30%).

$^1$H NMR (500 MHz, CDCl$_3$) δ 7.77-7.80 (1H, m, 7-H), 7.51 (2H, d, J=8.2, Ar—H), 7.38-7.42 (2H, m, 5 & 6-H), 7.13-7.15 (2H, m, Ar—H), 7:06 (4H, m, Ar—H), 7.00-7.02 (1H, m, 4-H), 6.11, (1H, br s, N—H), 5.71 (1H, br s, N—H'), 4.48 (1H, d, J=15.0, 2-CH), 4.16 (1H, d, J=15.0, 2-CH'), 3.31 (1H, d, J=10, 1'-H), 3.25 (1H, d, J=10, 1'-H'), 2.62 (2H, s, 3'-H$_2$), 1.66 (1H, br s, 1'-OH) 0.24-0.34 (2H, m, H$_2$), −0.01-0.04 (2H, m, H$_2$). $^{13}$C NMR (125 MHz, CDCl$_3$) δ 169.2, 168.3, 145.1, 141.5, 137.0, 134.6, 133.1, 132.3, 131.4, 130.1, 129.3, 128.7, 127.9, 127.3, 123.8, 123.0, 94.8, 67.6, 67.4, 50.8, 42.7, 22.2, 8.6. Found; 499.1395 [M+Na]; C$_{27}$H$_{25}$N$_2$O$_4$ClNa, requires 499.1395.

Synthesis of 3-(4-chlorophenyl)-2-(4-fluorobenzyl)-3-hydroxy-2,3-dihydroisoindol-1-one (AW349, NCL-0014528)

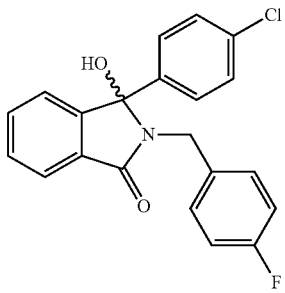

The named compound was synthesised from 2-(4-chlorobenzoyl)benzoic acid (2.24 g, 8.59 mmol) and 4-fluorobenzylamine (1.08 mL, 9.44 mmol) using General Procedure B, recrytsilised from EtOAc/petrol, purified by chromatography (Biotage SP4; Silica; 10%-30% EtOAc/petrol) and obtained as white crystals (1.57 g, 50%).

$^1$H NMR (300 MHz, CDCl$_3$) δ 4.40-4.53 (dd AB, J=15.2 Hz, 2H, N—CH$_2$), 4.58 (s, 1H, OH), 6.80-6.89 (m, 2H, CC$_2$H$_2$C$_2$H$_2$C(F)), 7.14-7.29 (m, 7H, ArH), 7.50-7.60 (m, 2H, ArH), 7.80-7.86 (m, 1H, —CH—C(C=O)). $^{13}$C NMR (CDCl$_3$, 75 MHz), δ 43.58, 92.63, 115.85, 116.13, 124.37, 124.52, 129.65, 129.82, 131.12, 131.91, 132.02, 134.55, 135.57, 135.70, 139.95, 151.19, 165.35, 170.25. IR: 696, 723, 766, 810, 835, 922, 1011, 1059, 1088, 1191, 1223, 12658, 1323, 1356, 1397, 1466, 1506, 1602, 1664, 2021, 2851, 2925, 3301 cm$^{-1}$. LCMS (DMSO): RT=3.71 min (on 5 min column), m/z=368 ES$^+$. HPLC purity (as area %): >98. UV (in EtOH): λ max=254 nm. EI-MS: calculated mass of ion 368.0848 [M+H]$^+$, measured mass of ion 368.0846 [M+H]$^+$. Rf=0.49 (50% EtOAc/petrol). MP: 149-150° C.

Synthesis of 3-(4-fluorophenyl)-3-hydroxy-2-(4-nitrobenzyl)-2,3-dihydroisoindol-1-one (AW408/NCL-00016657)

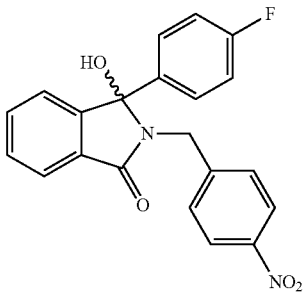 [SMILES: O=C1c2ccccc2C(O)(c2ccc(F)cc2)N1Cc1ccc([N+](=O)[O-])cc1]

The named compound was synthesised from 2-(4-fluorobenzoyl)-benzoic acid (2.10 g, 8.60 mmol) and 4-nitrobenzylamine hydrochloride (1.78 g, 9.46 mmol) using General Procedure B, recrystallised from EtOAc/petrol, purified by chromatography (Biotage; silica, 10%-40% EtOAc/petrol) and obtained as a yellow solid (1.01 g, 31%).

¹H NMR (300 MHz, CDCl₃) δ 4.21 (s, 1H, OH), 4.17-4.15 (dd AB, J=15.4 Hz, 2H, N—CH₂), 6.84-6.88 (m, 2H, ArH), 7.19-7.25 (m, 5H, Ar—H), 7.39-7.48 (m, 2H, Ar—H), 7.66-7.88 (m, 1H, CH=C—C(=O)), 7.88-7.91 (dd AB, J=8.8 Hz, 2H, C₂H₂C—NO₂). ¹³C NMR (CDCl₃, 75 MHz), δ 42.20, 91.07, 115.33, 115.51, 122.85, 123.28, 123.52, 128.28, 128.35, 129.42, 129.87, 133.27, 133.78, 145.30, 146.90, 148.72, 167.92. IR: 660, 692, 697, 760, 795, 814, 849, 892, 932, 1011, 1059, 1095, 1153, 1194, 1219, 1271, 1337, 1395, 1421, 1468, 1509, 1601, 1668, 3078, 3282 cm⁻¹. LCMS (DMSO): RT=3.18 min (on 5 min column), m/z=377 ES⁻¹. HPLC purity (as area %): >95. UV (in EtOH): λ max=266 nm EI-MS: calculated mass of ion 379.1089 [M+H]⁺, measured mass of ion 379.1084 [M+H]⁺. Rf=0.46 (50% EtOAc/petrol). MP: 183-185° C.

Synthesis of 3-(4-fluorophenyl)-3-(1-hydroxymethylcyclopropylmethoxy)-2-(4-nitrobenzyl)-2,3-dihydro-isoindol-1-one (AW413/NCL-00016896)

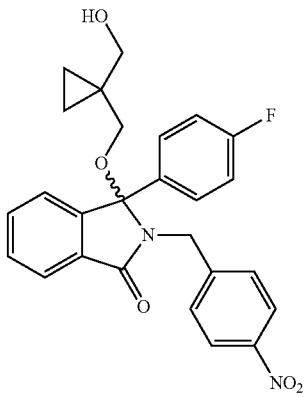 [SMILES: O=C1c2ccccc2C(OCC2(CO)CC2)(c2ccc(F)cc2)N1Cc1ccc([N+](=O)[O-])cc1]

The named compound was synthesised from NCL-00016657 (380 mg, 1.01 mmol) and 1,1-bis(hydroxymethyl)cyclopropane (0.19 mL, 2.03 mmol) using General Procedure C, purified by chromatography (Biotage SP4; silica; 25%-50% EtOAc/petrol) and obtained as a pale yellow oil (327 mg, 70%). Rf=0.29 (50:50 EtOAc:petrol). mp 57-58° C. λ$_{max}$ (CH₃OH)/nm=266. IR: 711, 727, 762, 802, 818, 853, 918, 1014, 1061, 1098, 1157, 1183, 1229, 1278, 1341, 1383, 1411, 1468, 1514, 1602, 1690, 2876, 2924, 3079, 3393 cm⁻¹. ¹H NMR: (300 MHz, CDCl₃) δ 0.14-0.31 (m, 2H, cyclopropane CH₂), 0.43-0.51 (m, 2H, cyclopropane CH₂), 2.17 (br s, 1H, OH), 2.82-2.91 (dd AB, J=9.4 Hz, 2H, CH₂O—C), 3.49-3.57 (dd AB, J=11.4 Hz, 2H, CH₂OH), 4.48-4.62 (dd AB, J=15.2 Hz, 2H, N—CH₂), 6.81-6.92 (m, 2H, ArH), 7.17-7.28 (m, 3H, ArH), 7.31-7.35 (dd AB, J=8.7 Hz, 2H, CC₂H₂C₂H₂C(NO₂)), 7.52-7.60 (m, 2H, ArH), 7.90-7.96 (m, 1H, CH=C—C(=O)), 7.98-8.02 (dd AB, J=8.7 Hz, 2H, CC₂H₂C₂H₂C(NO₂)). ¹³C NMR: (CDCl₃, 75 MHz) δ 8.85, 8.90, 22.66, 42.63, 67.65, 67.66, 94.92, 115.50, 123.54, 124.06, 128.74, 128.85, 130.16, 130.43, 131.81, 133.45, 134.67, 145.10, 145.71, 147.61, 161.51, 168.59. LCMS (DMSO): RT=3.46 min (on 5 min column), m/z=462 ES⁺. HPLC purity (as area %): >99. HRMS (EI): m/z Calcd. for ion: 463.1664 [M+H]⁺. Found: 463.1662 [M+H]⁺.

Synthesis of 3-chloro-2-(4-chlorobenzoyl)-4-fluorobenzoic acid (AW442)

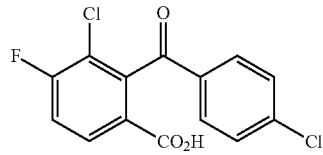 [SMILES: O=C(O)c1ccc(F)c(Cl)c1C(=O)c1ccc(Cl)cc1]

n-Butyl lithium (2.5M solution, 5.27 mL, 13.18 mmol) was added to a stirred solution of diisopropylamine (1.93 mL, 13.75 mmol) in anhydrous THF (25 mL) at −75° C. under a nitrogen atmosphere, and maintained at −30° C. for a further 1 h to produce lithium diisopropylamide (LDA). After re-cooling to −75° C., a solution of 3-chloro-4-fluorobenzoic acid (1 g, 5.73 mmol) in THF (20 mL) was added over 1 h, and stirring continued overnight at −75° C. under nitrogen. A solution of methyl 4-chlorobenzoate (1.95 g, 11.46 mmol) in THF (20 mL) was added over 10 min, stirring was continued at −70° C. for 2 h and then at RT for 4 h. Water (30 mL) was added and the aqueous layer was washed with ether (3×50 mL), acidified with 1M HCl, extracted with DCM (3×50 mL), dried over MgSO₄ and concentrated in vacuo to afford a yellow solid. Partial purification was attempted with chromatography (Biotage, silica, 50% EtOAc/petrol to 20% MeOH/EtOAc). The crude product (0.60 g, 34%) was used in the next step without further purification. Rf=0.05 (50:50 EtOAc: petrol). mp=188-190° C. λ$_{max}$ (CH₃OH)/nm=260. IR: 706, 749, 785, 843, 901, 958, 987, 1003, 1090, 1166, 1254, 1395, 1487, 1562, 1586, 1671, 1770, 2855, 2924, 3398 cm⁻¹.

¹H NMR: (300 MHz, MeOD) δ 7.27-7.32 (dd AB, J=8.5 Hz, 2H, CC₂H₂C₂H₂C(Cl)), 7.39-7.42 (m, 1H, CHC(F)C(Cl)), 7.60-7.66 (dd AB, J=8.5 Hz, 2H, CC₂H₂C₂H₂C(Cl)), 8.17 (d, J=8.30 Hz, 1H, CHCHC(F)C(Cl)), 13.60 (br s, 1H, CO₂H). ¹³C NMR (MeOD, 75 MHz), δ 119.90, 124.16, 132.022, 132.46, 133.89, 134.91, 135.87, 139.02, 163.04, 165.05, 197.46. LCMS (DMSO): RT=3.43 min (on 5 min column), m/z=311 ES⁻.

Synthesis of 4-chloro-3-(4-chlorophenyl)-5-fluoro-3-hydroxy-2-(4-nitrobenzyl)-2,3-dihydroisoindol-1-one (AW448/NCL-00016897)

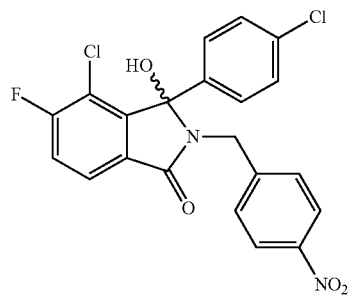 [SMILES: O=C1c2ccc(F)c(Cl)c2C(O)(c2ccc(Cl)cc2)N1Cc1ccc([N+](=O)[O-])cc1]

The named compound was synthesised from crude 3-chloro-2-(4-chlorobenzoyl)-4-fluorobenzoic acid (150 mg, 0.479 mmol) and 4-nitrobenzylamine hydrochloride (181 mg, 0.958 mmol) using General Procedure B, purified by chromatography (Biotage SP4; silica; 10-40% EtOAc/petrol), recrystallised from EtOAc/petrol and obtained as a white solid (0.04 mg, 2%). $R_f$=0.43 (50:50 EtOAc:petrol). mp=289-291° C. $\lambda_{max}$ (CH$_3$OH)/nm=265. IR: 672, 705, 738, 816, 853, 897, 959, 1012, 1090, 1148, 1204, 1256, 1345, 1401, 1423, 1516, 1585, 1676, 2859, 2974, 3210 cm$^{-1}$.

$^1$H NMR: (300 MHz, CDCl$_3$) δ 4.30 (br s, 1H, OH), 4.31-4.70 (dd, J=15.5 Hz, 2H, NCH$_2$), 6.90 (dd AB, J=8.1 Hz, 2H, —CC$_2$H$_2$C$_2$H$_2$C(Cl)), 7.22-7.26 (m, 2H, —CC$_2$H$_2$C$_2$H$_2$C(Cl)), 7.38 (dd AB, J=8.4 Hz, 2H, —CC$_2$H$_2$C$_2$H$_2$C(NO$_2$)), 7.64 (d, J=8.0 Hz, 1H, CHC(F)C(Cl)), 7.99 (d, J=8.4 Hz, 1H, CHCHC(F)C(Cl)), 8.05 (dd AB, J=8.4 Hz, 2H, —CC$_2$H$_2$C$_2$H$_2$C(NO$_2$)). $^{13}$C NMR: (CDCl$_3$, 75 MHz) δ 42.73, 90.17, 123.42, 123.54, 126.35, 128.08, 128.46, 128.93, 129.38, 130.55, 131.80, 131.80, 134.71, 141.26, 144.16, 144.57, 167.99, 168.46. LCMS (DMSO): RT=4.06 (on 5 min column), m/z=445 ES$^-$. HPLC purity (as area %): >95. HRMS (EI): m/z Calcd. for ion: 445.0164 [M–H]. Found: 445.0159 [M–H].

Synthesis of 4-chloro-3-(4-chlorophenyl)-3-((1-(hydroxymethyl)cyclopropyl)methoxy)-2-(4-nitrobenzyl)isoindolin-1-one (NU8406A/NCL-00013774 and NU8406B/NCL-00013775)

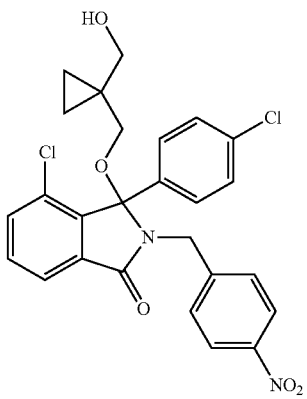 [SMILES: O=C1c2cccc(Cl)c2C(OCC2(CO)CC2)(c2ccc(Cl)cc2)N1Cc1ccc([N+](=O)[O-])cc1]

The named compound was synthesised from NU8398 (433 mg, 1.01 mmol) and 1,1-bis(hydroxymethyl)cyclopropane (0.19 mL, 2.03 mmol) using General Procedure C, purified by chromatography (Biotage SP4; silica; 20%-50% EtOAc/petrol) and obtained as yellow crystals (321 mg, 62%). $R_f$=0.30 (50:50 EtOAc:petrol). mp 76-77° C. $\lambda_{max}$ (CH$_3$OH)/nm=267. IR: 696, 759, 816, 853, 930, 1011, 1074, 1144, 1171, 1234, 1341, 1384, 1428, 1462, 1489, 1519, 1699, 2872, 2923, 3422 cm$^{-1}$.

$^1$H NMR: (300 MHz, CDCl$_3$) δ 0.21-0.42 (m, 2H, cyclopropane CH$_2$), 0.47-0.54 (m, 2H, cyclopropane CH$_2$), 2.12 (br s, 1H, OH), 2.89-3.05 (m, 2H, C—O—CH$_2$—), 3.52-3.61 (m, 2H, CH$_2$OH), 4.30-4.59 (dd, AB, J=15.2 Hz, N—CH$_2$—), 7.15-7.18 (m, 4H, ArH), 7.28-7.33 (m, 2H, ArH), 7.48-7.58 (m, 2H, ArH), 7.87-7.89 (dd, J=7.1, 1.1 Hz, 1H, —C(O)—C=CH—), 7.98-8.01 (m, 2H, —CH—NO$_2$). $^{13}$C NMR: (CDCl$_3$, 75 MHz) δ 8.84, 8.90, 22.59, 42.54, 67.58, 68.10, 94.71, 122.63, 123.56, 128.65, 128.77, 130.09, 130.40, 132.28, 134.37, 135.27, 135.55, 135.57, 141.10, 144.62, 147.64, 167.04. HPLC purity (as area %): >92. HRMS (EI): m/z Calcd. for ion: 530.1244 [M+NH$_4$]$^+$. Found: 530.1242 [M+NH$_4$]$^+$. Anal. Calcd. for C$_{26}$H$_{22}$Cl$_2$N$_2$O$_5$: C, 60.83; H, 4.32; N, 5.46%. Found: C, 60.68; H, 4.30; N, 5.40%.

Separation of enantiomers was achieved by chiral preparative HPLC (Daicel Chiralpak AD-H 250×10 mm; Hexane/Ethanol (4:1))

NU8406A/NCL-00013774 (white crystals)
Optical rotation: Specific rotation [α]=−4.98° (at 22.4° C., wavelength=589 nm, tube length=0.25 dm, concentration=0.402 g/100 mL).

NU8406B/NCL-00013775 (white crystals)
Optical Rotation: Specific rotation [α]=+4.85° (at 22.6° C., wavelength=589 nm, tube length=0.25 dm, concentration=0.412 g/100 mL).

Synthesis of 3-(4-chlorophenyl)-3-(2-hydroxymethylallyloxy)-2-(4-nitrobenzyl)-2,3-dihydroisoindol-1-one (AW468/NCL-00016895)

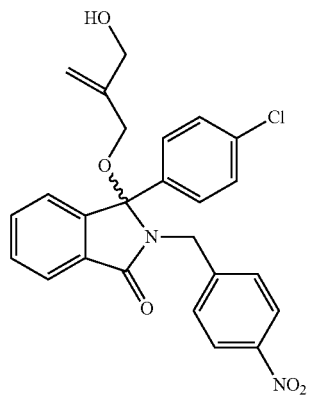 [SMILES: C=C(CO)COC1(c2ccc(Cl)cc2)c2ccccc2C(=O)N1Cc1ccc([N+](=O)[O-])cc1]

The named compound was synthesised from NU8260 (400 mg, 1.01 mmol) and 2-methylene-1,3-propanediol (0.17 mL, 2.03 mmol) using General Procedure C, purified by chromatography (Biotage SP4; silica; 10%-40% EtOAc/petrol) and obtained as a yellow oil (342 mg, 73%). $R_f$=0.24 (50:50 EtOAc:petrol). $\lambda_{max}$ (CH$_3$OH)/nm 268. IR: 702, 764, 808, 853, 922, 969, 1011, 1058, 1092, 1177, 1278, 1341, 1381, 1425, 1466, 1489, 1519, 1603, 1689, 2859, 2922, 3080, 3407 cm$^{-1}$.

$^1$H NMR (300 MHz, CDCl$_3$) δ 2.46 (br s, 1H, OH), 3.20-3.40 (dd, J=11.9 Hz, 2H, iso-OCH$_2$), 4.00 (s, 2H, CH$_2$OH), 4.31-4.61 (dd, J=15.1 Hz, 2H, NCH$_2$), 4.88 (s, 1H, C=CH), 5.04 (s, 1H, C=CH), 7.12-7.15 (m, 1H, ArH), 7.15-7.21 (dd AB, J=8.7 Hz, 4H, C$_6$H$_4$Cl), 7.33-7.36 (dd AB, J=8.7 Hz, 2H)), 7.49-7.53 (m, 2H, ArH), 7.87-7.91 (m, 1H, ArH), 7.95-7.98 (dd AB, 2H, CC$_2$H$_2$C$_2$H$_2$C(NO$_2$)). $^{13}$C NMR (CDCl$_3$, 75 MHz), δ 42.37, 63.63, 63.73, 94.80, 112.29, 123.27, 123.34, 123.86, 127.92, 128.69, 130.00, 130.29, 131.10, 133.23, 134.78, 136.74, 144.17, 144.57, 144.73, 147.03, 168.32. LCMS (DMSO): Rt=3.74 min (on 5 min column), m/z=465 (ES$^+$). HPLC purity (as area %): >98. HRMS (EI): m/z Calcd. for ion: 464.113900 [M]$^+$. Found: 464.115410 [M]$^+$.

It is, of course, to be understood that the invention is not intended to be restricted to the details of the above embodiments which are described by way of example only.

REFERENCES

1. Lane, D. P. *Nature* 1992, 358, 15-16.
2. Vousden, K. H.; Lu, X. *Nat. Rev. Cancer* 2002, 2, 594-604.
3. Momand, J.; Zambetti, G. P.; Olson, D. C.; George, D.; Levine, A. *Cell* 1992, 69, 1237-1245.

4. Fuchs, S. Y.; Adler, V.; Buschmann, T.; Wu, X. W.; Ronai, Z. *Oncogene* 1998, 17, 2543-2547.
5. Oliner, J. D.; Kinzler, K. W.; Meltzer, P. S.; George, D. L.; Vogelstein, B. *Nature* 1992, 358, 80-83.
6. Kussie, P. H.; Gorina, S.; Marechal, V.; Elenbaas, B.; Moreau, J.; Levine, A. J.; Pavletich, N. P. *Science* 1996, 274, 948-953.
7. Chene, P. *Nat. Rev. Cancer* 2003, 3, 102-109.
8. Chene, P.; Fuchs, J.; Bohn, J.; Garcia-Echeverria, C.; Furet, P.; Fabbro, D. *J. Molec. Biol.* 2000, 299, 245-253.
9. Duncan, S. J.; Gruschow, S.; Williams, D. H.; McNicolas, C.; Purewal, R.; Hajek, M.; Gerlitz, M.; Martin, S.; Wrigley, S. K.; Moore, M. *J. Am. Chem. Soc.* 2001, 123, 554-560.
10. Zhao, J. H.; Wang, M. J.; Chen, J.; Luo, A. P.; Wang, X. Q.; Wu, M.; Yin, D. L.; Liu, Z. H. *Cancer Lett* 2002, 183, 69-77.
11. Vassilev, L. T.; Vu, B. T.; Graves, B.; Carvajal, D.; Podlaski, F.; Filipovic, Z.; Kong, N.; Kammlott, U.; Lukacs, C.; Klein, C.; Fotouhi, N.; Liu, E. A. *Science* 2004, 303, 844-848.

The invention claimed is:

1. A compound of Formula I, or Formula II, or a pharmaceutically acceptable salt thereof,

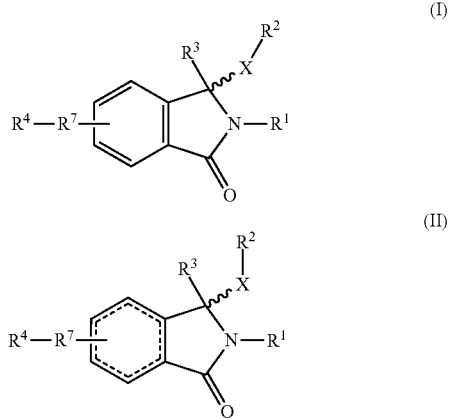

wherein in both formulae I and II:
X is selected from O or S;
$R^1$ is selected from substituted or unsubstituted aryl, and substituted or unsubstituted aralkyl;
$R^2$ is selected from:
(i) hydroxy-2,2-dimethylpropyl, hydroxy-2,2-cyclopropylpropyl, 2-hydroxymethyl allyl, and a succinic acid derivative,
(ii) hydroxycyclooctyl, hydroxymethylcyclohexylmethylene, and hydroxycyclohexyl, and
(iii) hydroxymethylbenzyl;
$R^3$ is selected from substituted or unsubstituted aryl, and substituted or unsubstituted aralkyl and
$R^4$-$R^7$ represents groups $R^4$, $R^5$, $R^6$ and $R^7$ which are independently selected from hydrogen, halo, hydroxy, substituted or unsubstituted alkyl, substituted or unsubstituted hydroxyalkyl, substituted or unsubstituted alkenyl, substituted or unsubstituted alkynyl, substituted or unsubstituted heteroaryl, substituted or unsubstituted heteroaralkyl, substituted or unsubstituted alkylamine, substituted or unsubstituted alkoxy, trifluoromethyl, amino, nitro, carboxyl, carbonyl, methylsulfone, trifluoromethylsulfone, cyano and substituted or unsubstituted sulfonamide.

2. A compound according to claim 1, wherein $R^1$ is substituted or unsubstituted aralkyl.
3. A compound according to claim 2, wherein $R^2$ is selected from hydroxy-2,2-dimethylpropyl, hydroxy-2,2-cyclopropylpropyl, 2-hydroxymethyl allyl, and a succinic acid derivative.
4. A compound according to claim 2, wherein $R^2$ is selected from hydroxycyclooctyl, hydroxymethylcyclohexylmethylene, and hydroxycyclohexyl.
5. A compound according to claim 2, wherein $R^2$ is hydroxymethylbenzyl.
6. A compound according to claim 1, wherein $R^1$ is substituted benzyl.
7. A compound according to claim 6, wherein $R^1$ is 4-nitrobenzyl, 4-chlorobenzyl, 4-bromobenzyl, cyanobenzyl, or 4-iodobenzyl.
8. A compound according to claim 1, wherein $R^3$ is substituted or unsubstituted phenyl.
9. A compound according to claim 8, wherein $R^3$ is 4-chlorophenyl or 4-fluorophenyl.
10. A compound according to claim 1, wherein $R^4$-$R^7$ are all hydrogen or at least one of $R^4$-$R^7$ is a chlorine atom.
11. A compound according to claim 1, wherein $R^3$ is substituted aryl.
12. A compound according to claim 1, wherein $R^1$ is substituted 1-ethylphenyl, 4-nitrobenzyl, 4-cyanobenzyl, 4-chlorobenzyl, 4-bromobenzyl or 4-iodobenzyl.
13. A compound according to claim 12, wherein the substituted 1-ethylphenyl is the S-enantiomer.
14. A compound according to claim 1, wherein $R^3$ is substituted phenyl.
15. A compound according to claim 1, wherein X is O.
16. A pharmaceutical composition comprising an effective amount of at least one compound according to claim 1 and a pharmaceutically acceptable carrier.
17. A compound according to claim 1 wherein the compound is a compound of Formula I, or a pharmaceutically acceptable salt thereof.
18. A compound according to claim 1, or a pharmaceutically acceptable salt thereof wherein the compound is

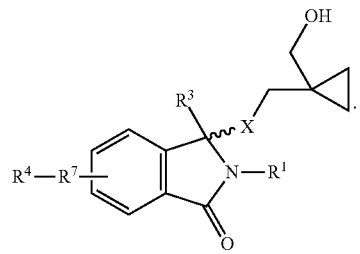

19. A compound according to claim 1, or a pharmaceutically acceptable salt thereof wherein the compound is

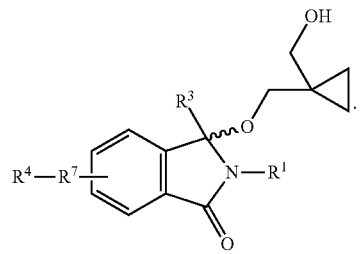

* * * * *

UNITED STATES PATENT AND TRADEMARK OFFICE
CERTIFICATE OF CORRECTION

| | | |
|---|---|---|
| PATENT NO. | : 8,618,158 B2 | Page 1 of 1 |
| APPLICATION NO. | : 13/001372 | |
| DATED | : December 31, 2013 | |
| INVENTOR(S) | : Bernard Thomas Golding et al. | |

It is certified that error appears in the above-identified patent and that said Letters Patent is hereby corrected as shown below:

In the Specification

Column 1, Line 45
  Replace "effect"
  with --effect$^7$.--

Column 10, Line 1
  Replace "chair-fauns"
  with --chair-forms--

Table 1, Formula NU8294
  Replace "389.13C$_{22}$H$_{22}$ClNO$_3$?"
  with --389.13C$_{22}$H$_{22}$ClNO$_3$.--

Table 1, Formula NU8298, IC50 ELISA data
  Replace "2.3 ± 0.3"
  with --4.7 ± 1.1--

Column 53, Line 55
  Replace "faun"
  with --form--

Column 56, Line 64
  Replace "TAR"
  with --JAR--

Column 58, Line 28
  Replace "PARD"
  with --PARP--

Signed and Sealed this
Fifth Day of August, 2014

Michelle K. Lee
*Deputy Director of the United States Patent and Trademark Office*